US012458354B2

(12) United States Patent
Shelton, IV et al.

(10) Patent No.: US 12,458,354 B2
(45) Date of Patent: Nov. 4, 2025

(54) STAPLE CARTRIDGE COMPRISING A SEATING CAM

(71) Applicant: Cilag GmbH International, Zug (CH)

(72) Inventors: Frederick E. Shelton, IV, Hillsboro, OH (US); Jason L. Harris, Lebanon, OH (US); Chester O. Baxter, III, Loveland, OH (US); Michael J. Stokes, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/422,195

(22) Filed: Jan. 25, 2024

(65) Prior Publication Data

US 2024/0156455 A1 May 16, 2024

Related U.S. Application Data

(63) Continuation of application No. 16/720,706, filed on Dec. 19, 2019, now Pat. No. 11,911,032.

(51) Int. Cl.
*A61B 17/072* (2006.01)
*A61B 17/00* (2006.01)

(52) U.S. Cl.
CPC .................. *A61B 17/07207* (2013.01); *A61B 2017/00367* (2013.01); *A61B 2017/0725* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC ...... A61B 17/07207; A61B 2017/0725; A61B 2017/07285; A61B 2017/07271; A61B 2017/07278; A61B 2017/00367; A61B 2017/07257
USPC .......... 227/175.1, 175.2, 175.3, 176.1–181.1
See application file for complete search history.

(56) References Cited

U.S. PATENT DOCUMENTS

| | | | | |
|---|---|---|---|---|
| 6,716,232 | B1 * | 4/2004 | Vidal | A61B 17/282 227/176.1 |
| 6,905,057 | B2 | 6/2005 | Swayze et al. | |
| 6,959,852 | B2 | 11/2005 | Shelton, IV et al. | |
| 6,978,921 | B2 | 12/2005 | Shelton, IV et al. | |
| 6,988,649 | B2 | 1/2006 | Shelton, IV et al. | |
| 7,000,818 | B2 | 2/2006 | Shelton, IV et al. | |
| 8,540,133 | B2 | 9/2013 | Bedi et al. | |
| 9,072,535 | B2 | 7/2015 | Shelton, IV et al. | |
| 9,351,726 | B2 | 5/2016 | Leimbach et al. | |

(Continued)

FOREIGN PATENT DOCUMENTS

| | | |
|---|---|---|
| EP | 2781195 A1 | 9/2014 |
| EP | 2997906 A1 | 3/2016 |

(Continued)

OTHER PUBLICATIONS

European Extended Search Report and Written Opinion dated Feb. 16, 2021, for Application No. 20215674.1, 10 pages.

(Continued)

*Primary Examiner* — Thanh K Truong
*Assistant Examiner* — Linda J. Hodge
(74) *Attorney, Agent, or Firm* — Frost Brown Todd LLP

(57) ABSTRACT

A replaceable staple cartridge is disclosed which is seatable in a jaw of a surgical stapling instrument. If the staple cartridge is not fully seated in the jaw, the closure of the surgical stapling instrument will fully seat the staple cartridge.

20 Claims, 103 Drawing Sheets

(56) References Cited

U.S. PATENT DOCUMENTS

| | | | | |
|---|---|---|---|---|
| 9,585,658 | B2 | 3/2017 | Shelton, IV | |
| 9,788,835 | B2 | 10/2017 | Morgan et al. | |
| 10,105,142 | B2 | 10/2018 | Baxter, III et al. | |
| 10,779,821 | B2 | 9/2020 | Harris et al. | |
| 11,376,098 | B2 | 7/2022 | Shelton, IV et al. | |
| 11,911,032 | B2 | 2/2024 | Shelton, IV et al. | |
| 2005/0222616 | A1* | 10/2005 | Rethy | A61B 17/105 606/215 |
| 2010/0137904 | A1 | 6/2010 | Wenchell | |
| 2010/0213241 | A1 | 8/2010 | Bedi | |
| 2012/0074198 | A1 | 3/2012 | Huitema et al. | |
| 2012/0312858 | A1 | 12/2012 | Patankar et al. | |
| 2013/0075448 | A1* | 3/2013 | Schmid | A61B 17/07207 227/176.1 |
| 2013/0256379 | A1 | 10/2013 | Schmid et al. | |
| 2015/0297222 | A1 | 10/2015 | Huitema et al. | |
| 2015/0297225 | A1* | 10/2015 | Huitema | A61B 17/105 227/176.1 |
| 2016/0000438 | A1 | 1/2016 | Swayze et al. | |
| 2016/0058440 | A1* | 3/2016 | Dinardo | A61B 17/07207 227/176.1 |
| 2016/0249928 | A1 | 9/2016 | Cappola et al. | |
| 2016/0270788 | A1 | 9/2016 | Czernik | |
| 2017/0086838 | A1* | 3/2017 | Harris | A61B 17/105 |
| 2018/0168641 | A1 | 6/2018 | Harris et al. | |
| 2018/0168650 | A1 | 6/2018 | Shelton, IV et al. | |
| 2019/0239885 | A1 | 8/2019 | Stokes et al. | |
| 2020/0305872 | A1 | 10/2020 | Weidner et al. | |

FOREIGN PATENT DOCUMENTS

| | | | |
|---|---|---|---|
| EP | 3122950 | A1 | 2/2017 |
| EP | 3123949 | A1 | 2/2017 |
| WO | WO 2003/094747 | A1 | 11/2003 |
| WO | WO 2015/153642 | A1 | 10/2015 |
| WO | WO 2018/071497 | A1 | 4/2018 |

OTHER PUBLICATIONS

International Search Report and Written Opinion dated Feb. 16, 2021, for International Application No. PCT/IB2020/061633, 13 pages.

Japanese First Office Action dated Jul. 30, 2024, for Application No. 2022-537541, 3 pages.

* cited by examiner

Knife is stowed
Continue retracting I-Beam

STAPLE CARTRIDGE COMPRISING A SEATING CAM

PRIORITY

This application is a continuation of U.S. patent application Ser. No. 16/720,706, entitled "Staple Cartridge Comprising A Seating Cam," filed Dec. 19, 2019, issued as U.S. Pat. No. 11,911,032 on Feb. 27, 2024, the disclosure of which is incorporated by reference herein in its entirety.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 113 is an exploded view of the staple firing system and the staple cartridge of FIG. 104;

FIG. 114 is a partial cross-sectional view of an end effector of a surgical instrument in accordance with at least one embodiment;

FIG. 115 is a partial cross-sectional view of the end effector of FIG. 114 illustrated in a closed configuration;

FIG. 116 is a partial cross-sectional view of the end effector of FIG. 114 illustrated in a partially-fired configuration;

FIG. 117 is a partial cross-sectional view of the end effector of FIG. 114 illustrated in a fired configuration;

FIG. 118 is a partial cross-sectional view of the end effector of FIG. 114 illustrating a firing system of the surgical instrument in a retraction mode;

FIG. 119 is a partial cross-sectional view of the end effector of FIG. 114 illustrating a portion of the firing system decoupled from a portion of the staple firing system that is being retracted;

FIG. 120 is a partial cross-sectional view of the end effector of FIG. 114 illustrating the end effector after it has been re-opened;

FIG. 121 is a partial exploded view of an end effector in accordance with at least embodiment illustrated with some components removed;

FIG. 122 is a partial cross-sectional view of an end effector of a surgical instrument in accordance with at least one embodiment comprising a staple cartridge in an unspent condition;

FIG. 123 is a partial cross-sectional view of the end effector of FIG. 122 illustrating a staple firing system of the surgical instrument in a pre-firing stroke configuration with a firing bar of the staple firing system being engaged with a sled/knife member of the staple firing system;

FIG. 124 is a partial cross-sectional view of the end effector of FIG. 122 in a partially-fired configuration with the staple firing system advanced just past a spent cartridge lockout of the stapling instrument;

Figure 122:
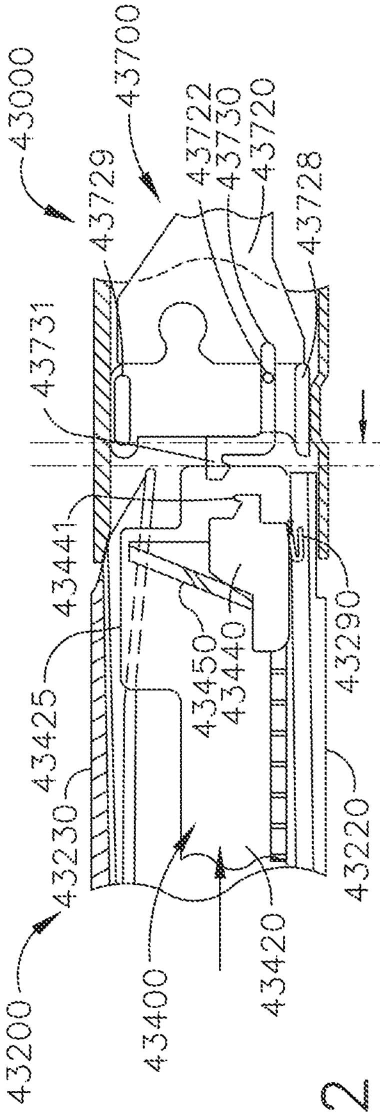
Figure 125:
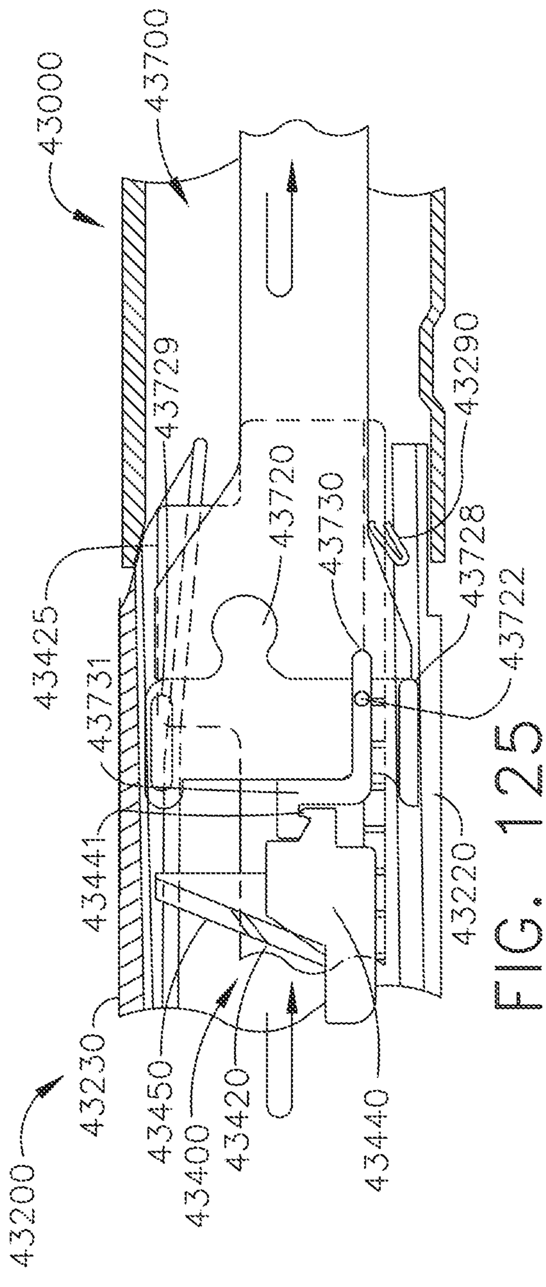
Figure 126:
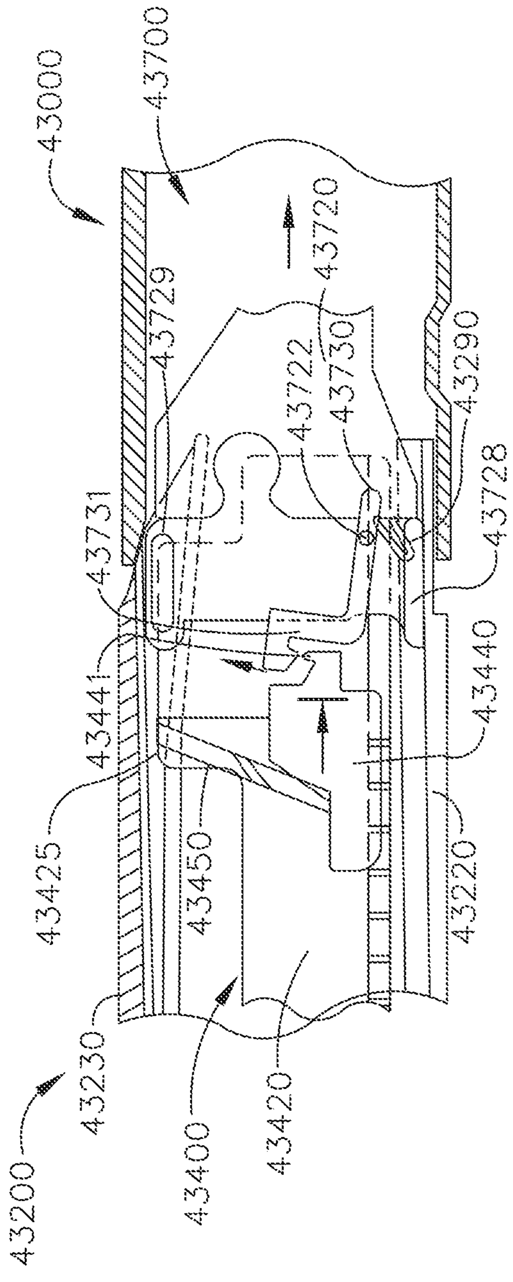
Figure 127:
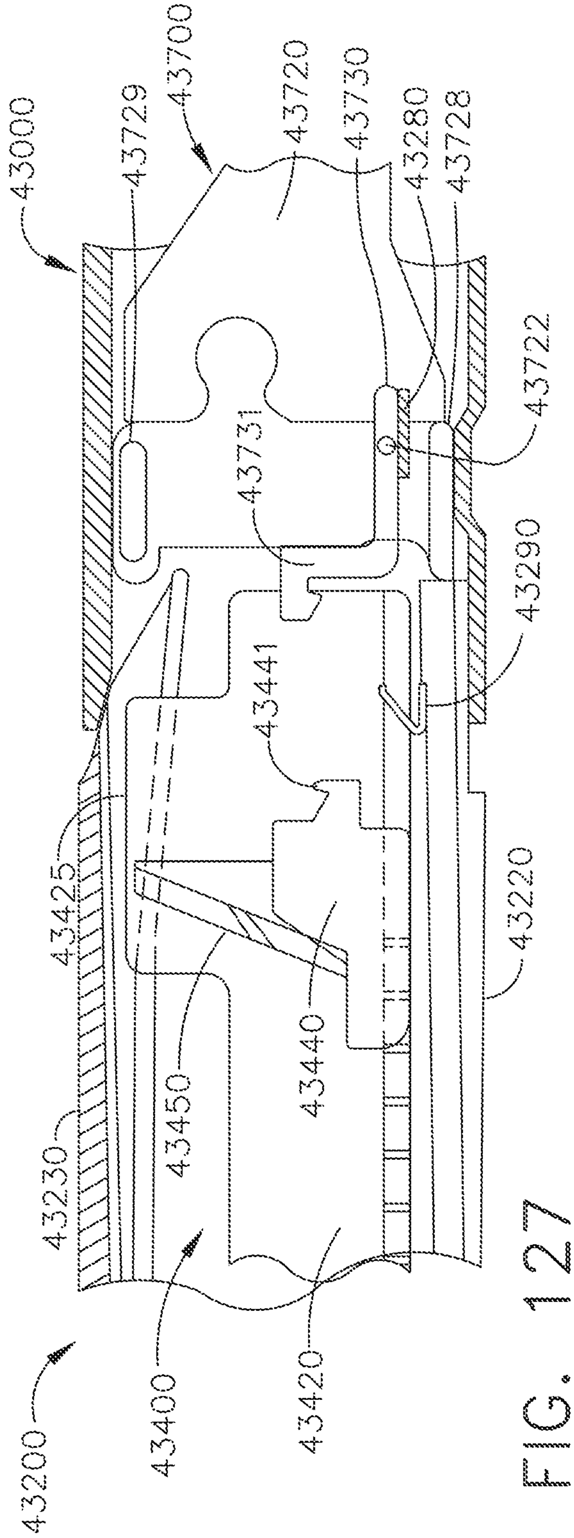
Figure 128:
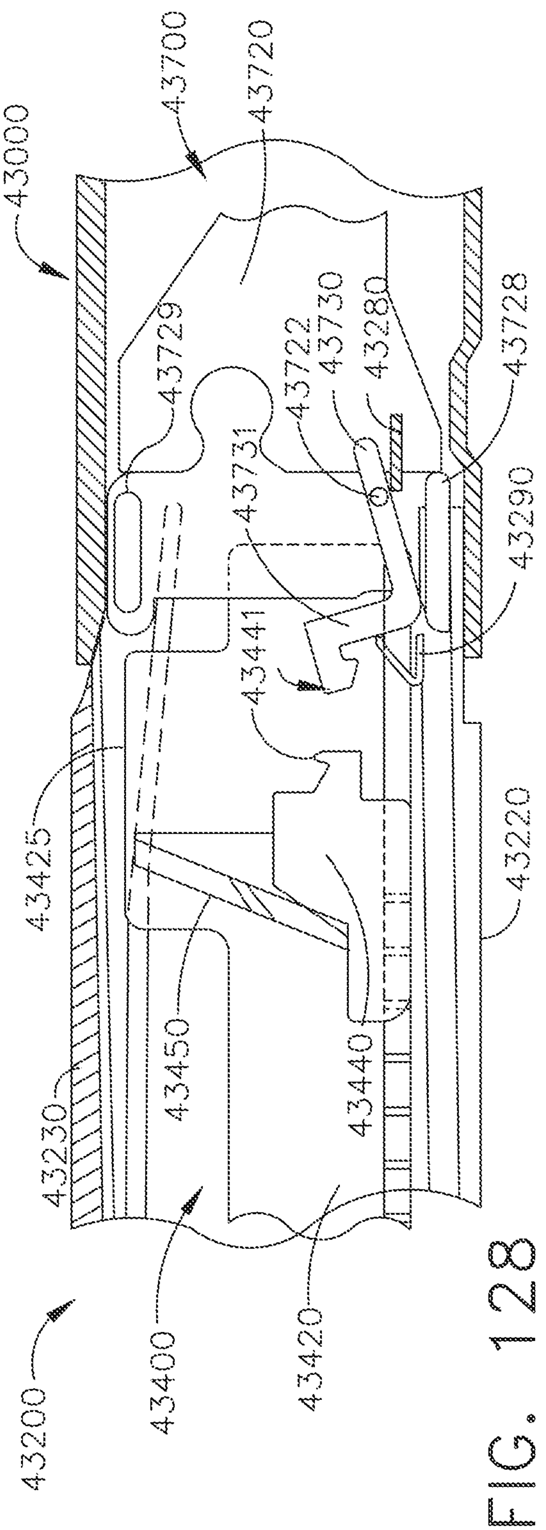
Figure 129:
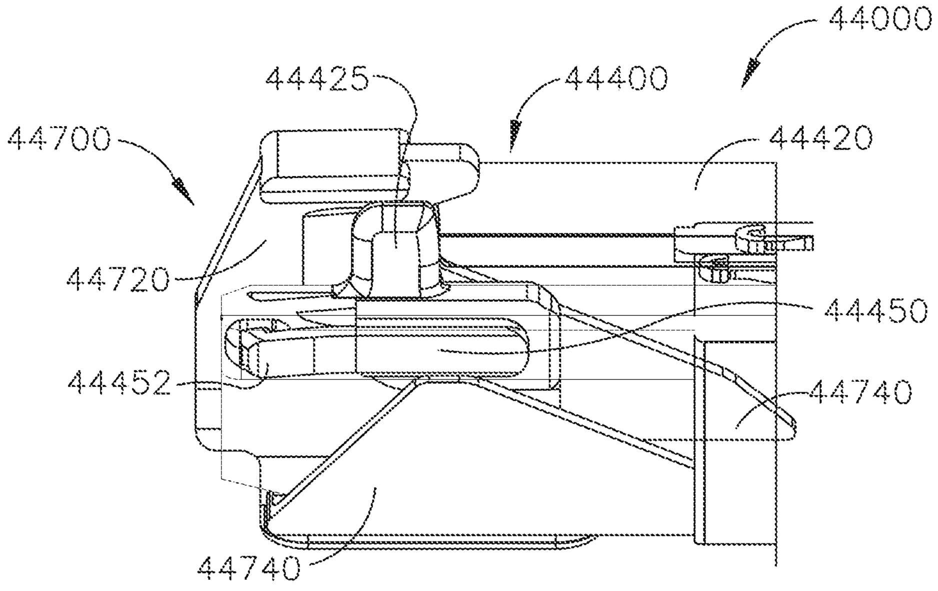
Figure 130:
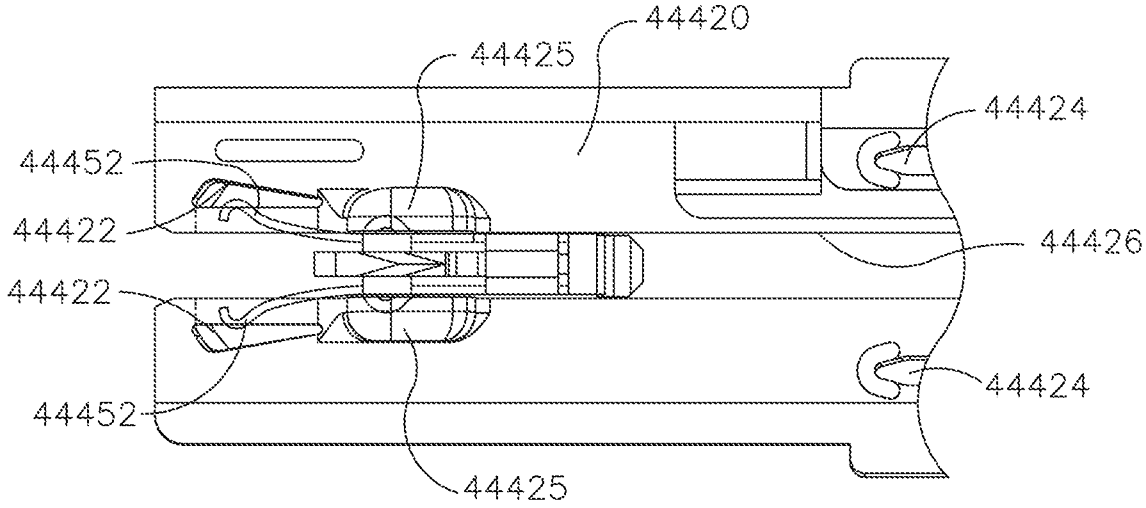
Figure 131:
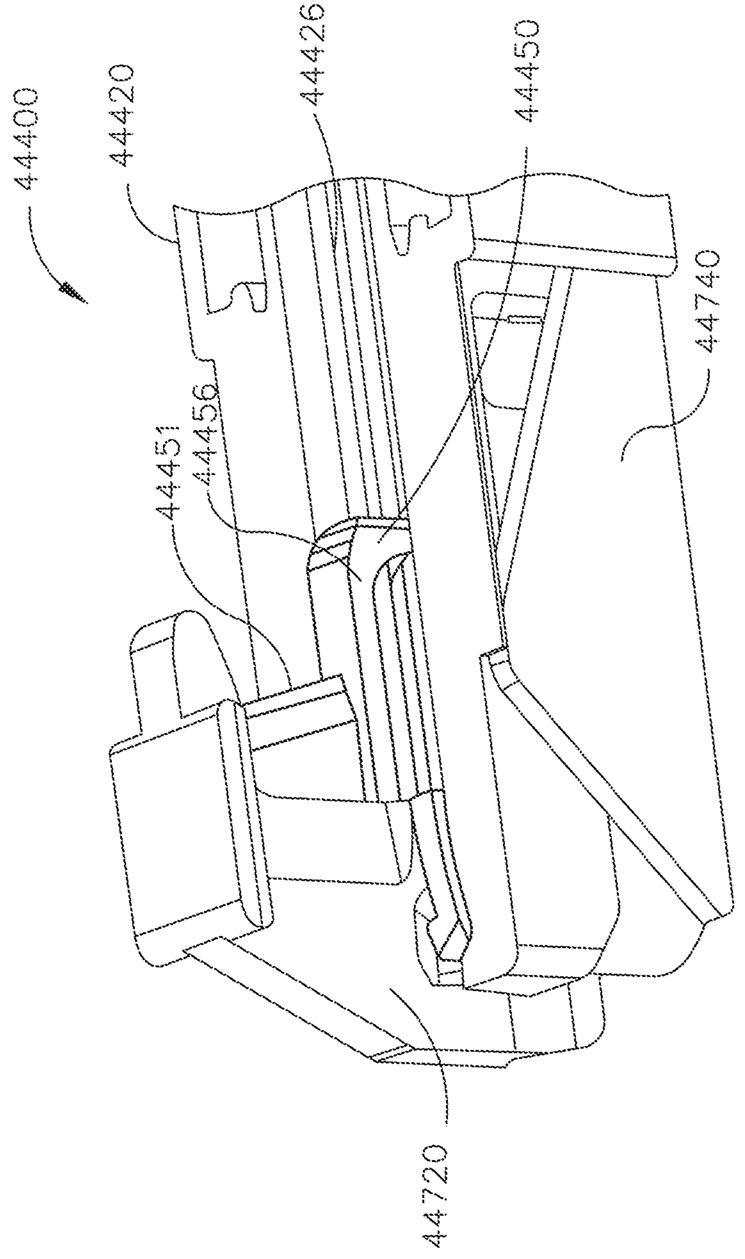
Figure 132:
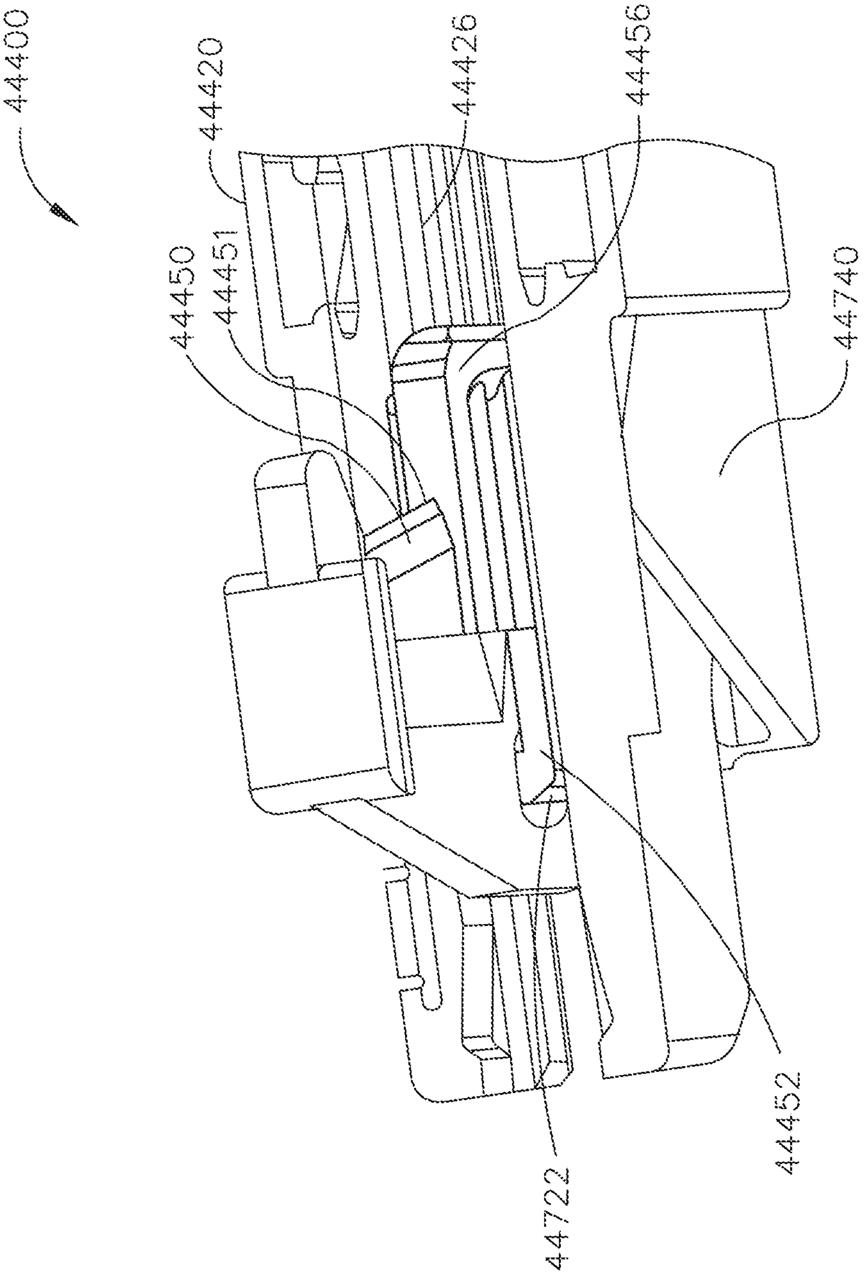
Figure 133:
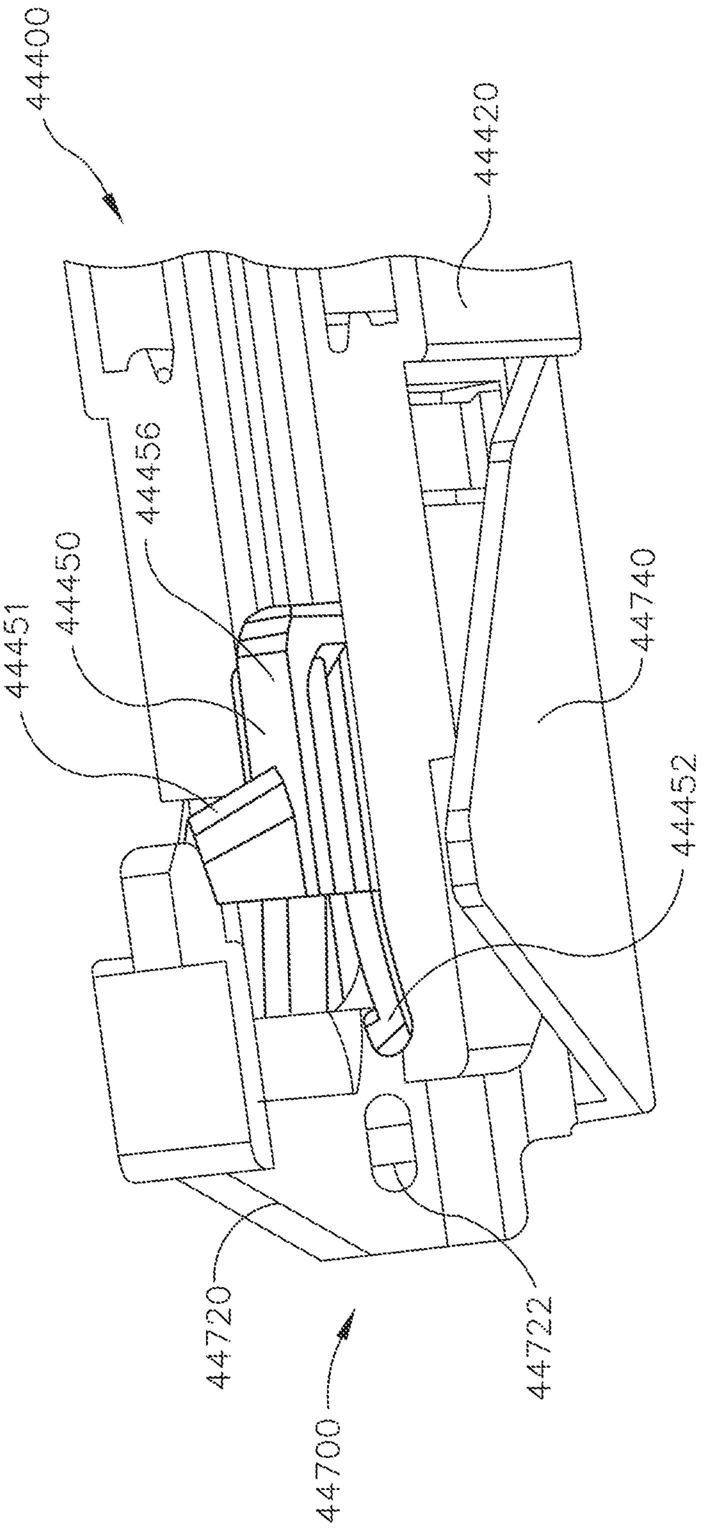
Figure 134:
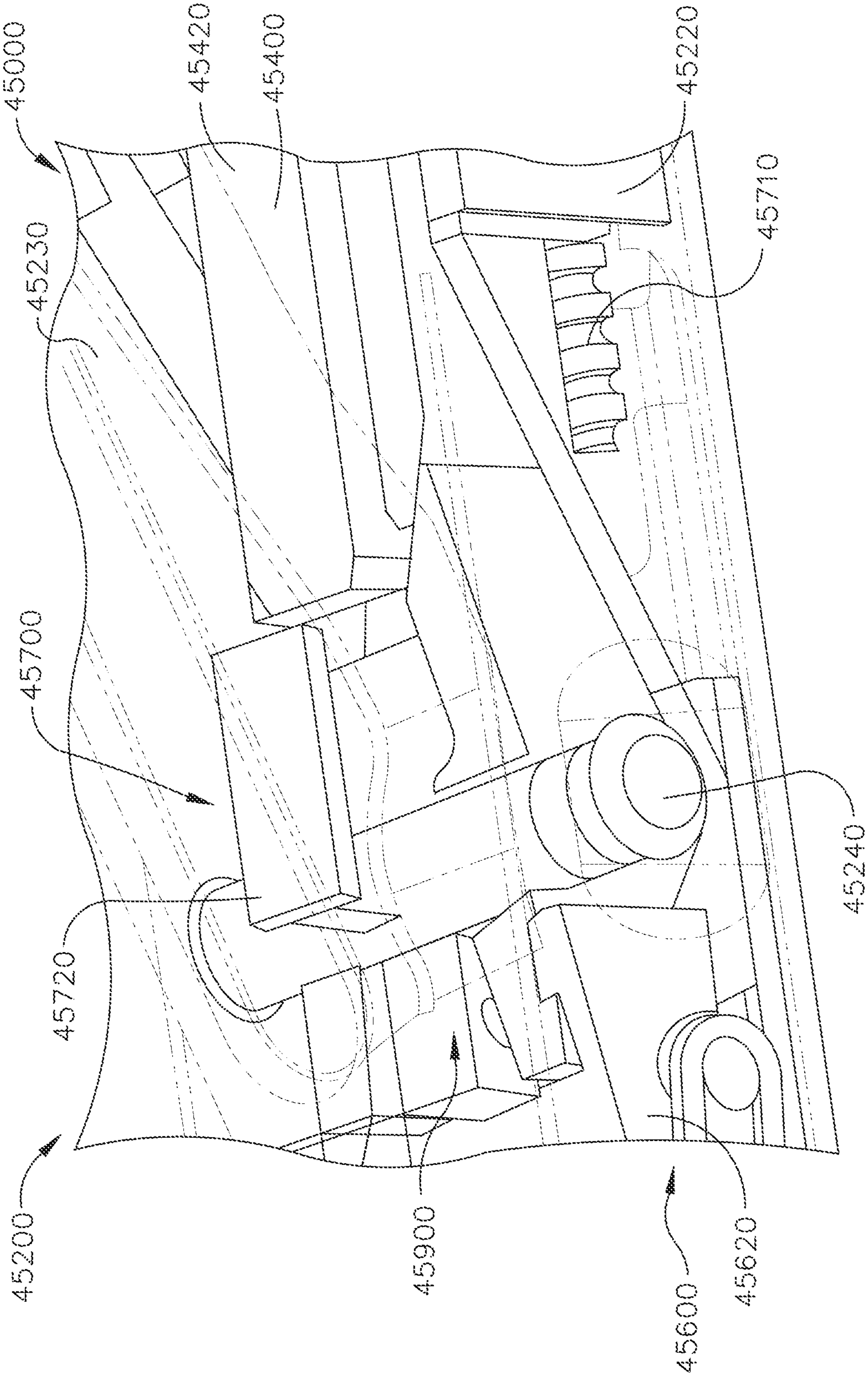
Figure 135:
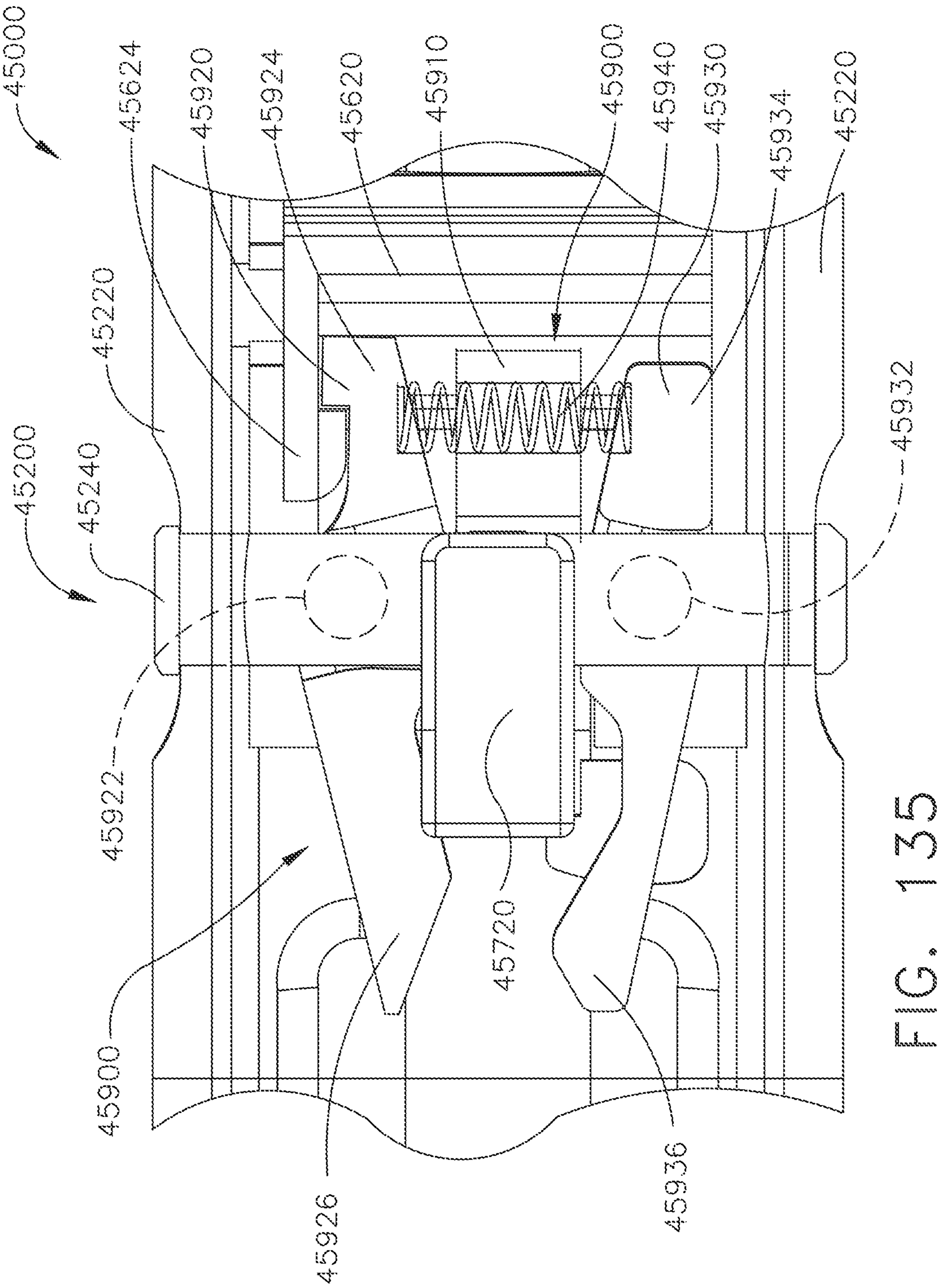
Figure 136:
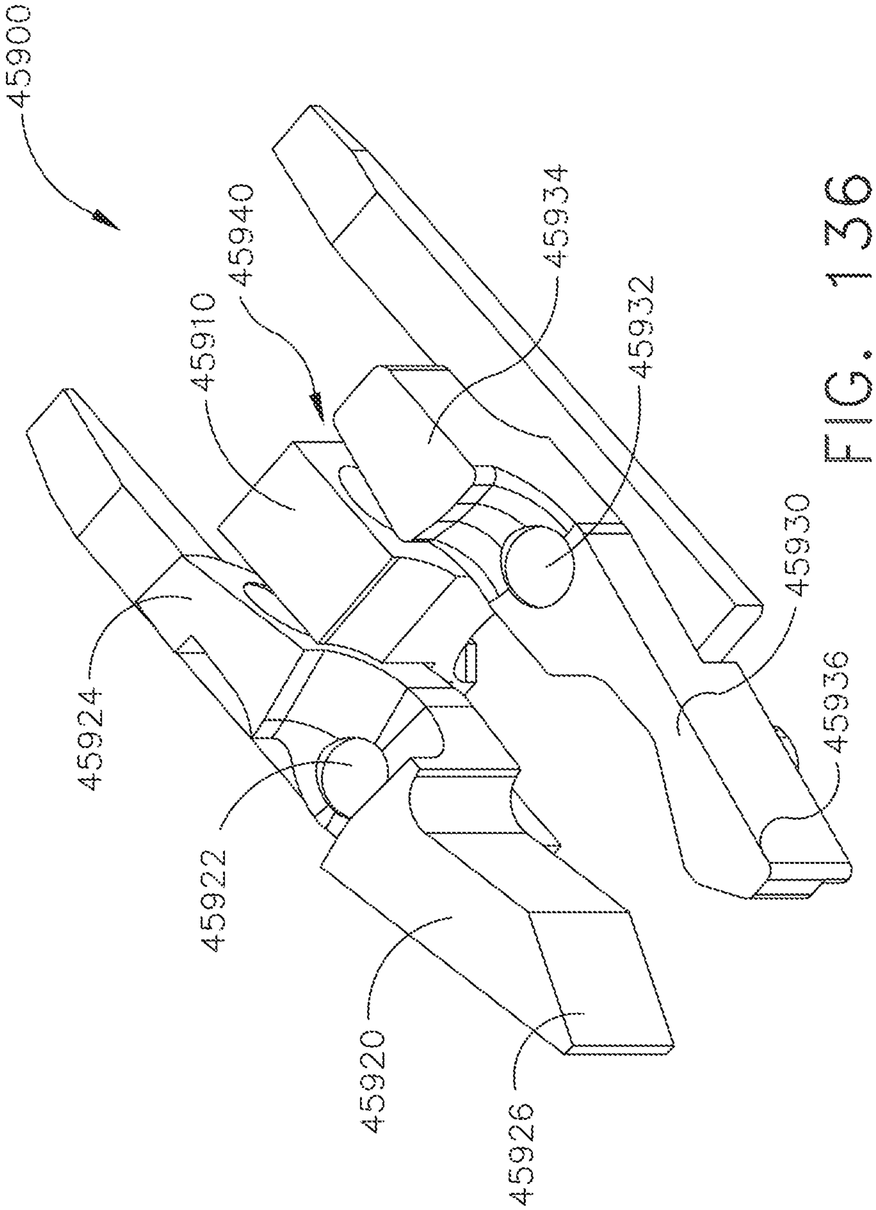
Figure 137:
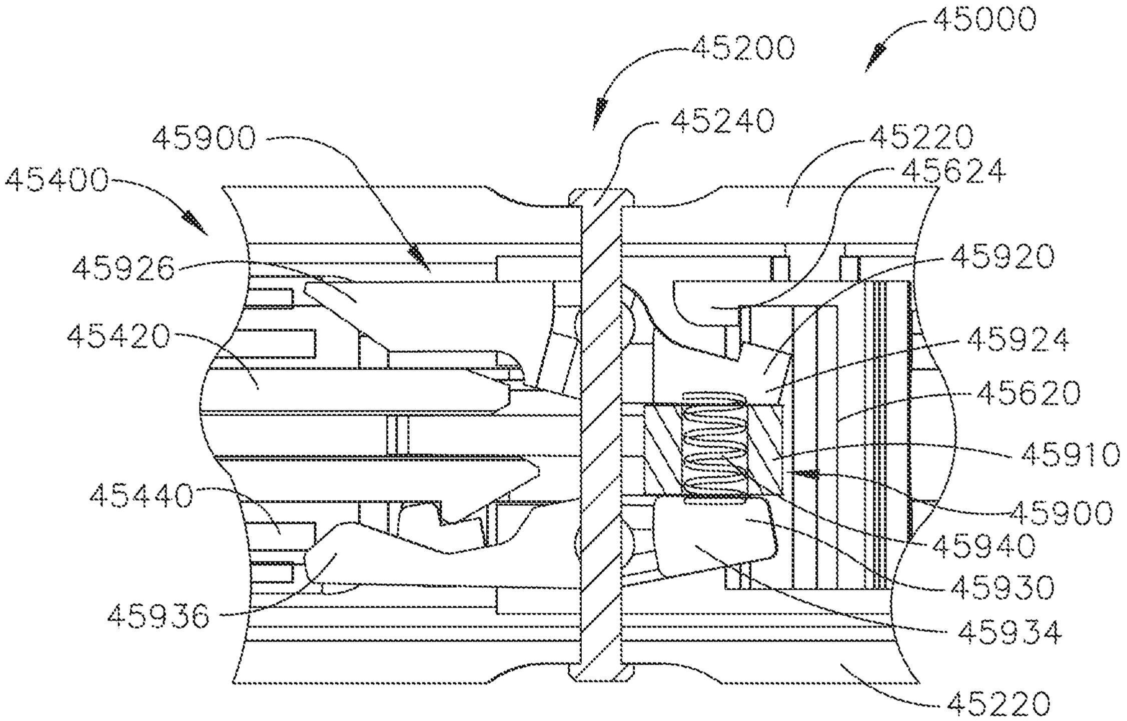
Figure 138:
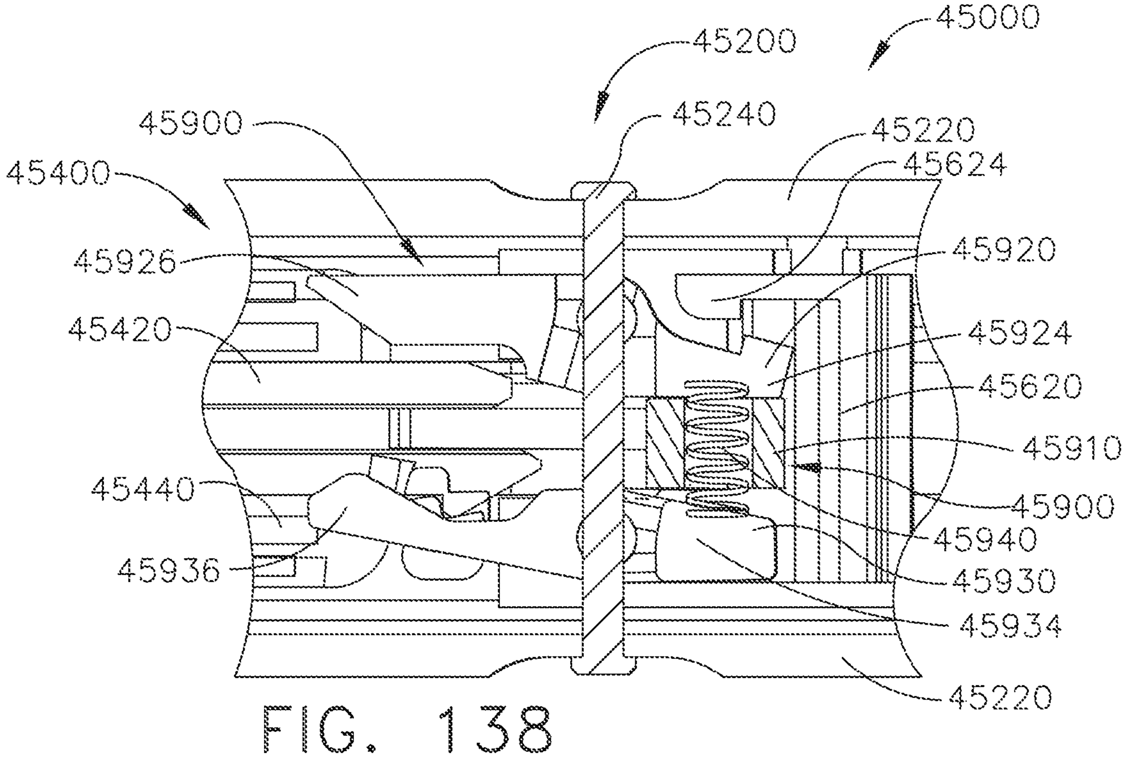
Figure 139:
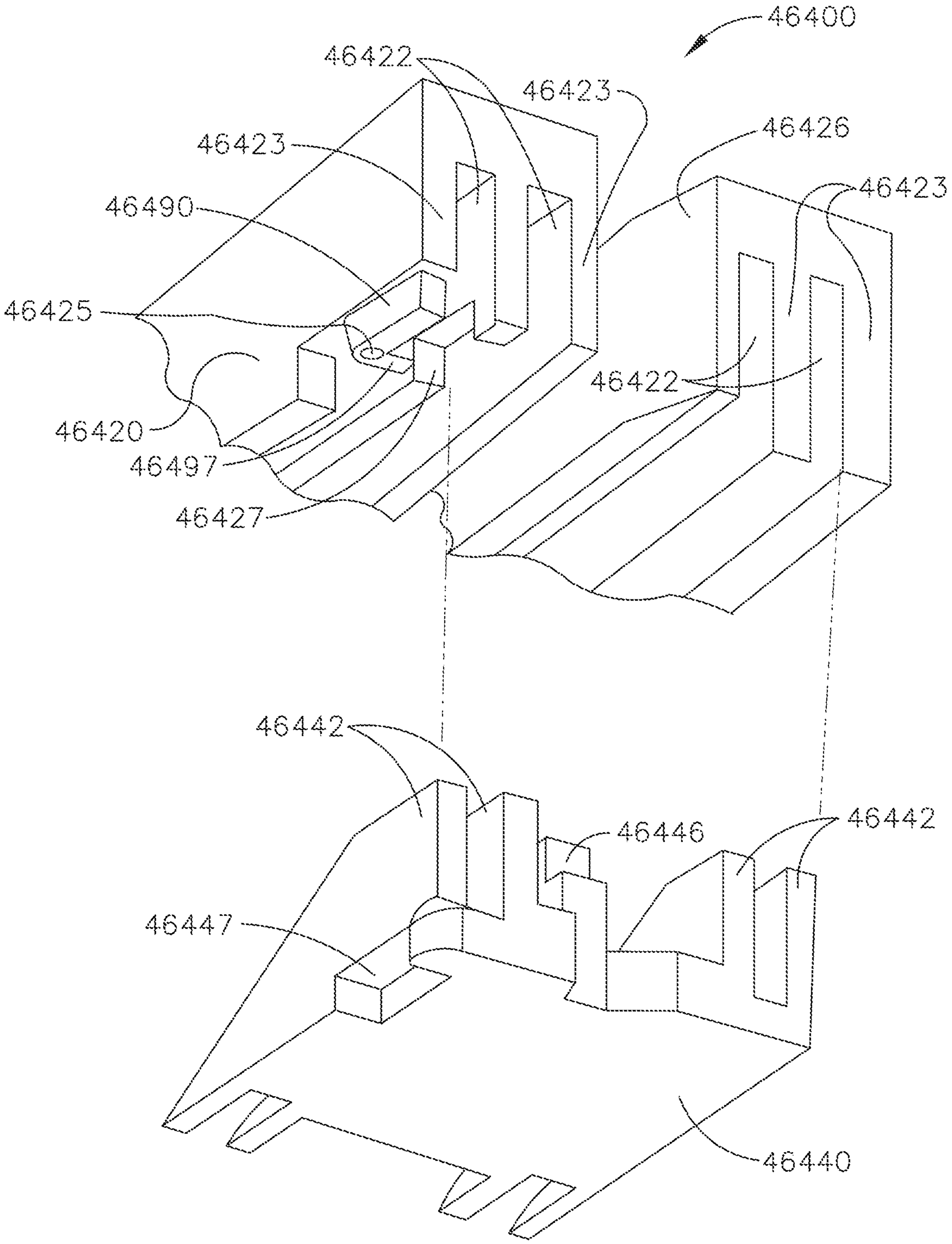
Figure 140:
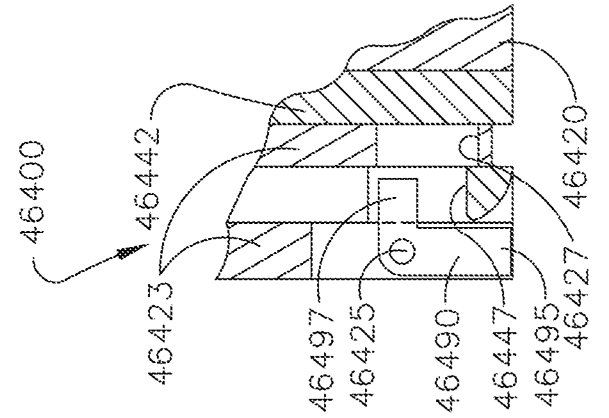
Figure 141:
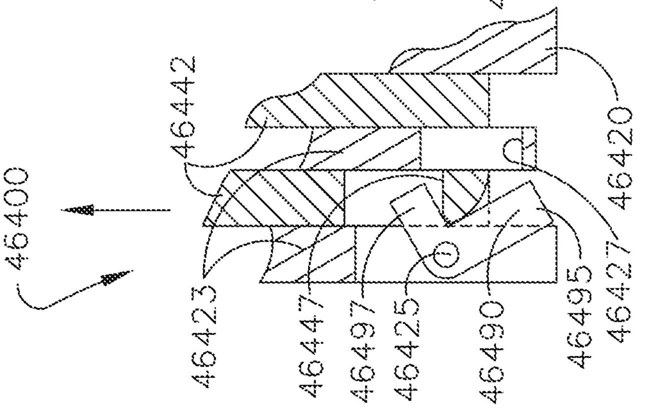
Figure 142:
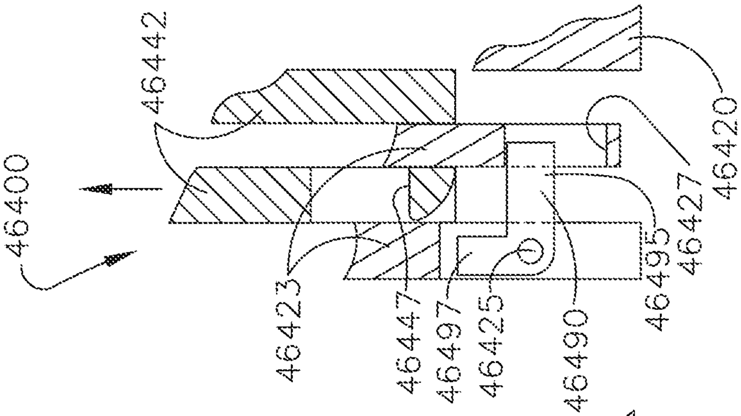
Figure 143:
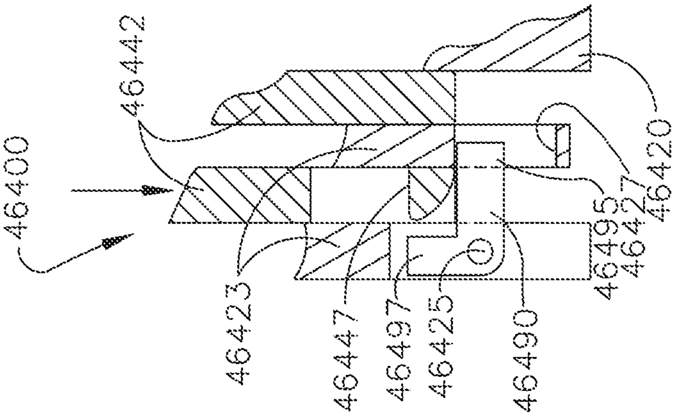
Figure 144:
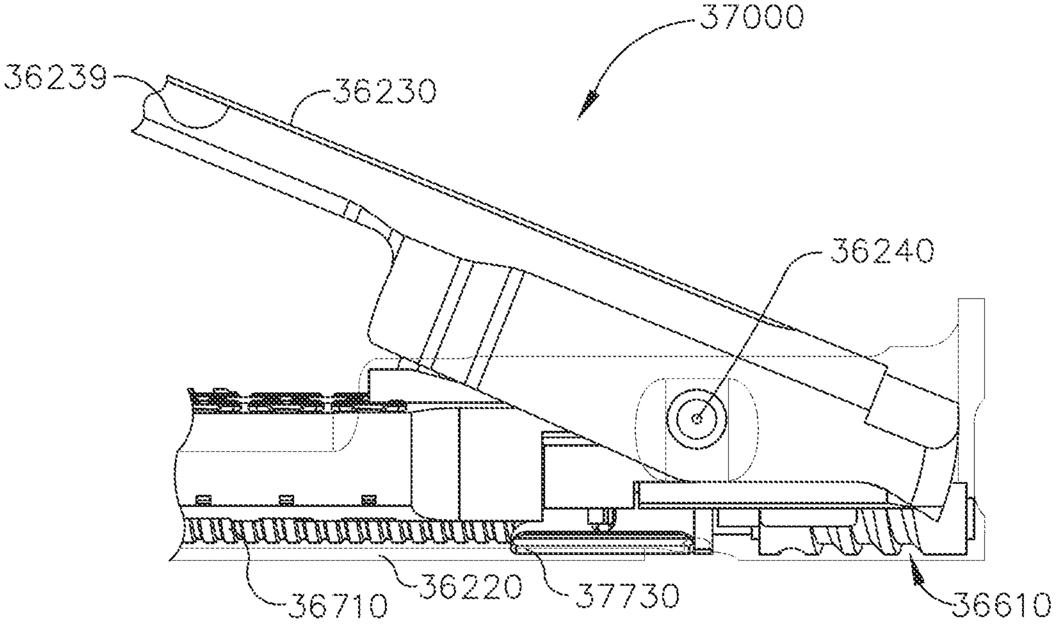
Figure 145:
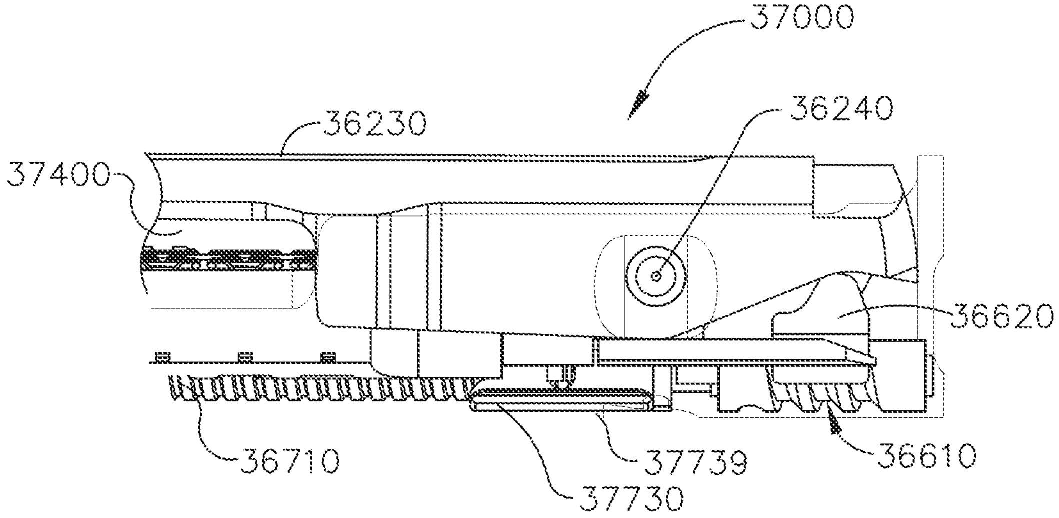
Figure 144A:
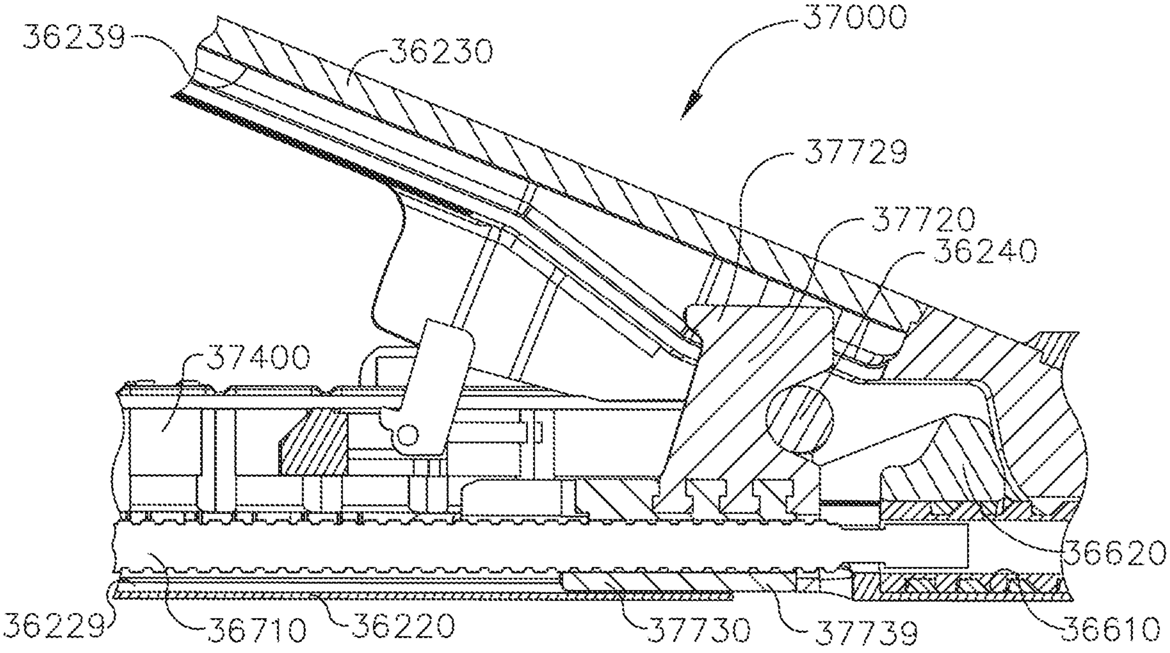
Figure 145A:
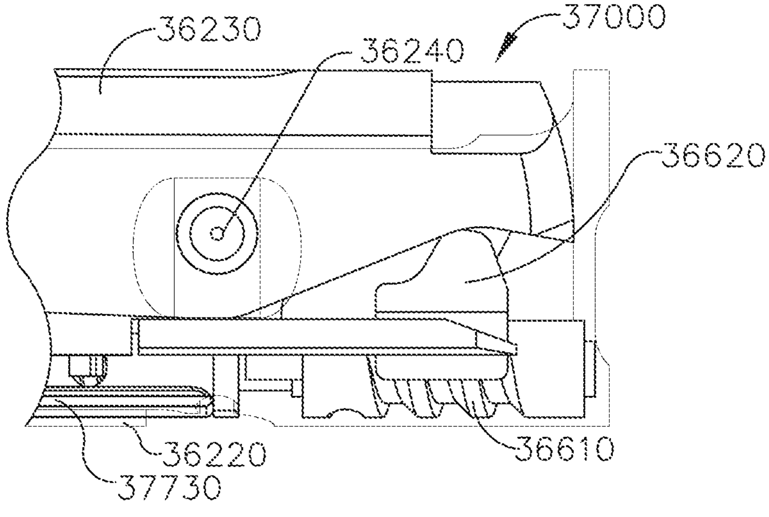
Figure 146:
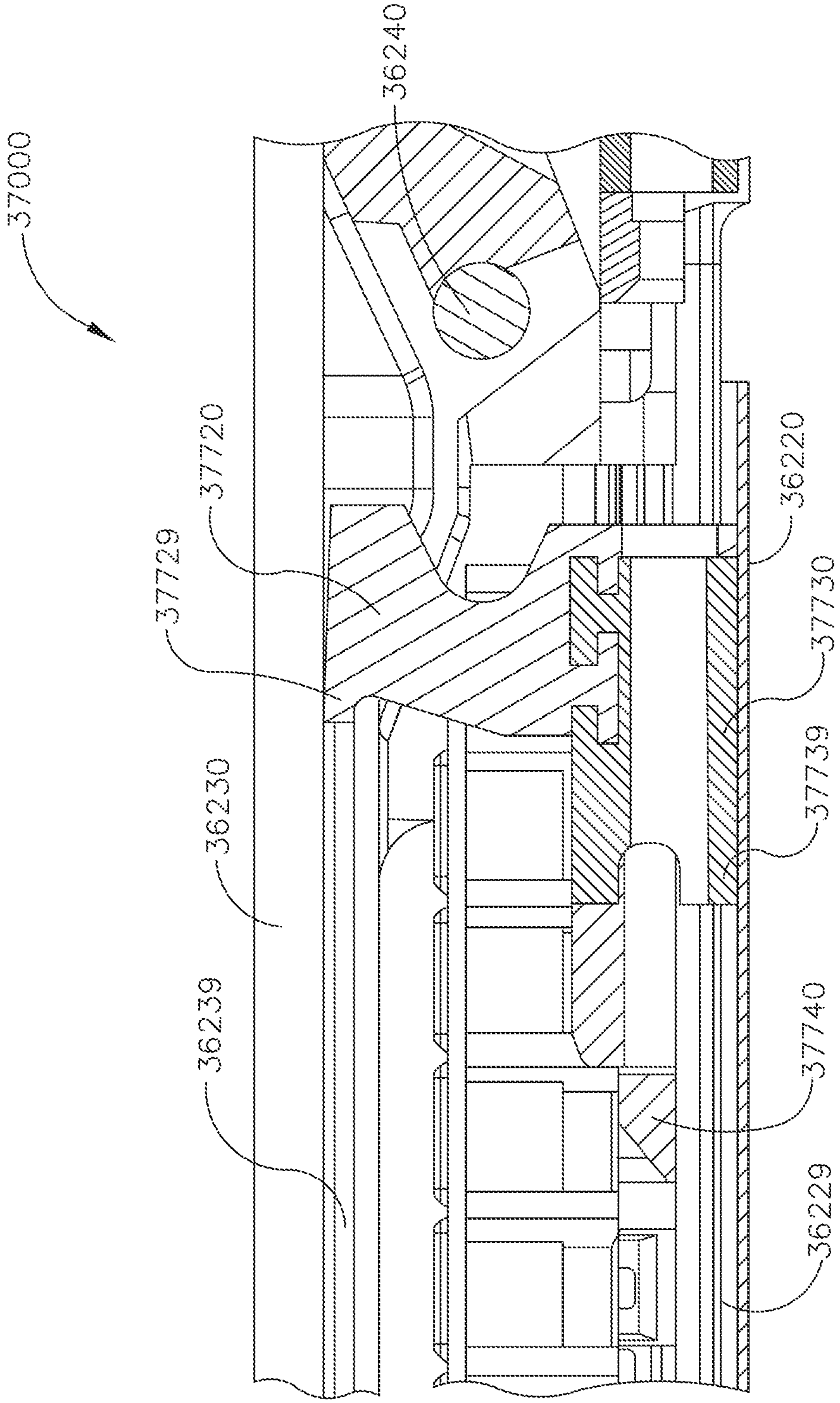
Figure 147:
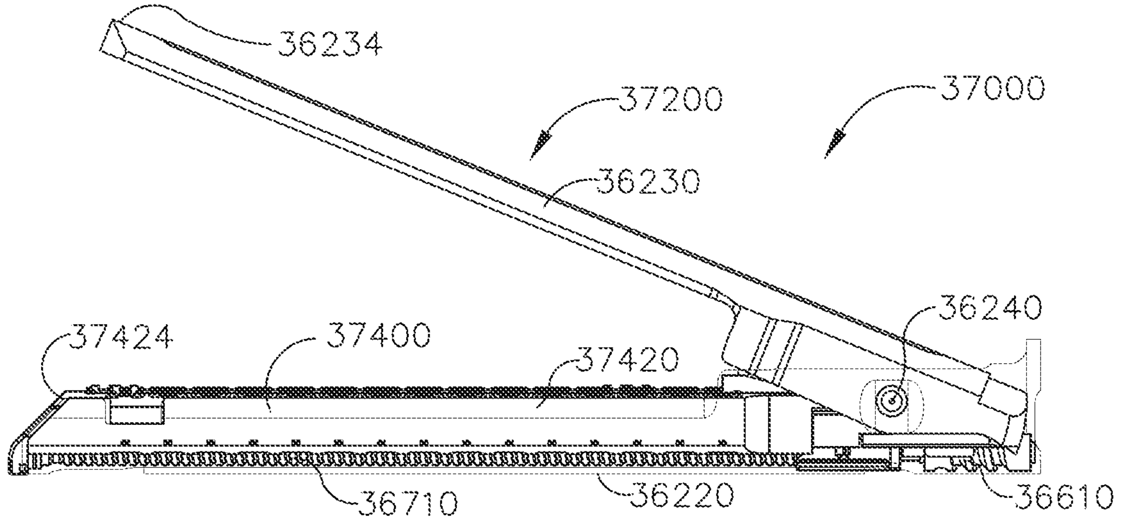
Figure 148:
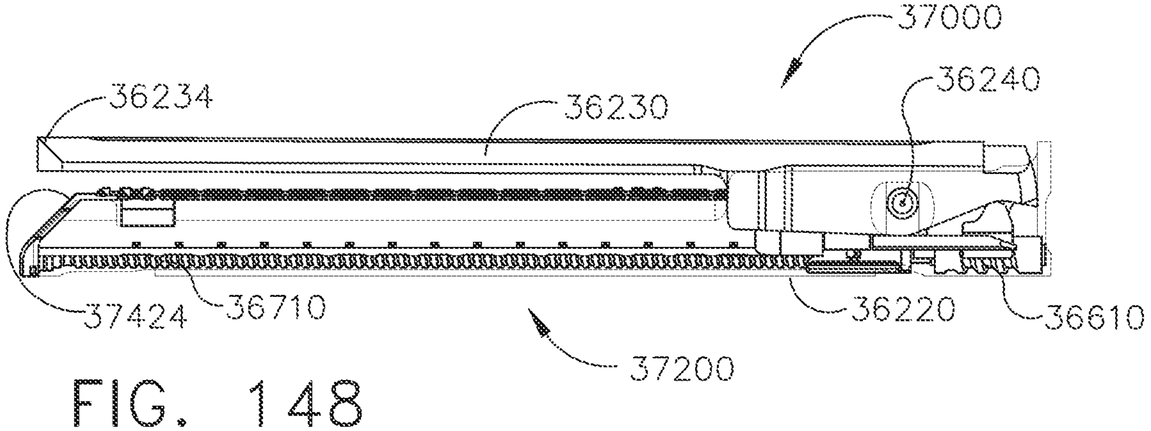
Figure 149:
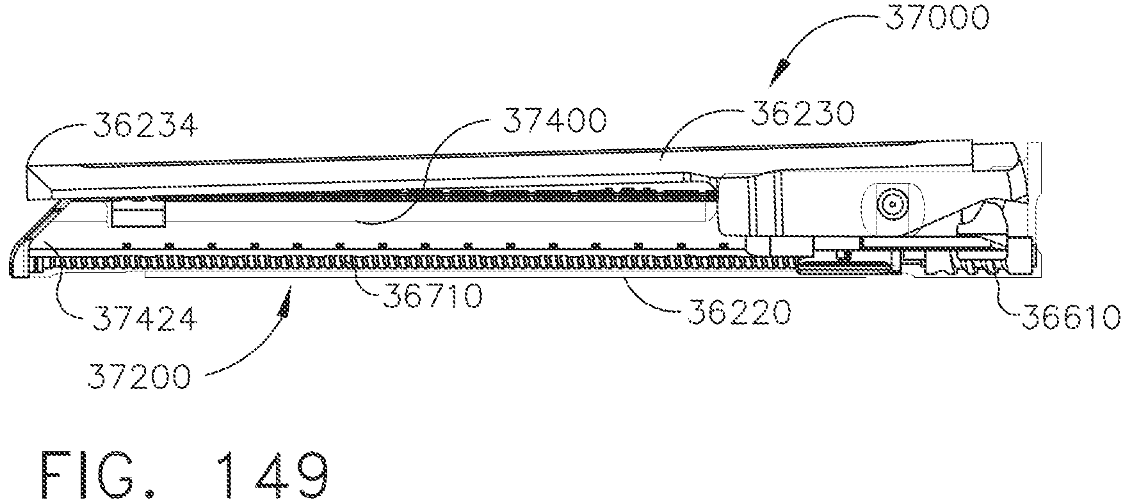
Figure 149A:
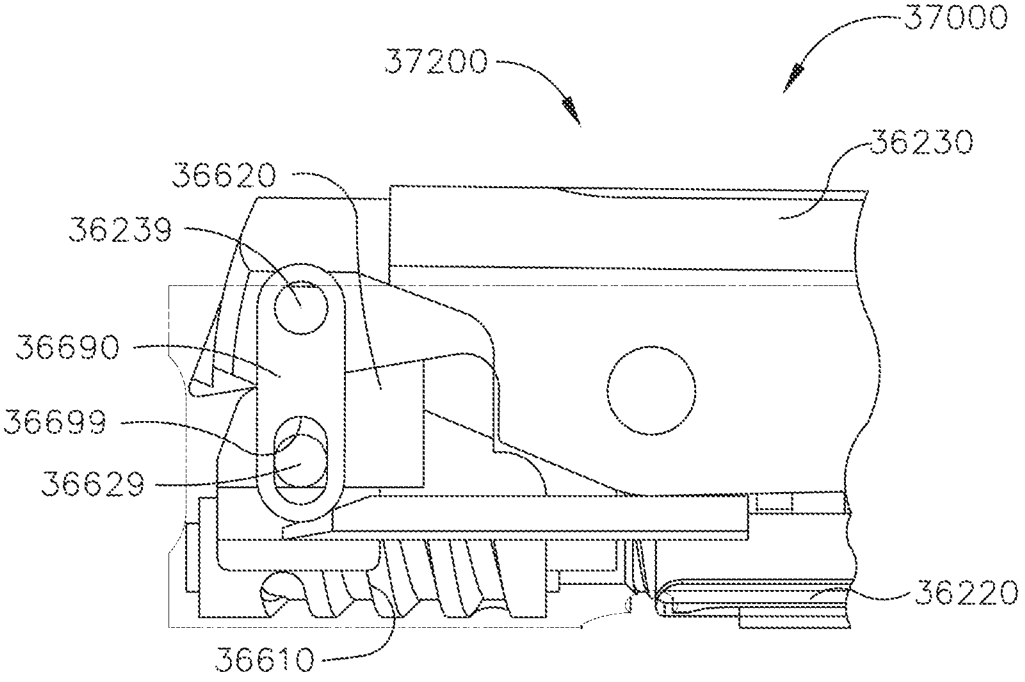
Figure 149B:
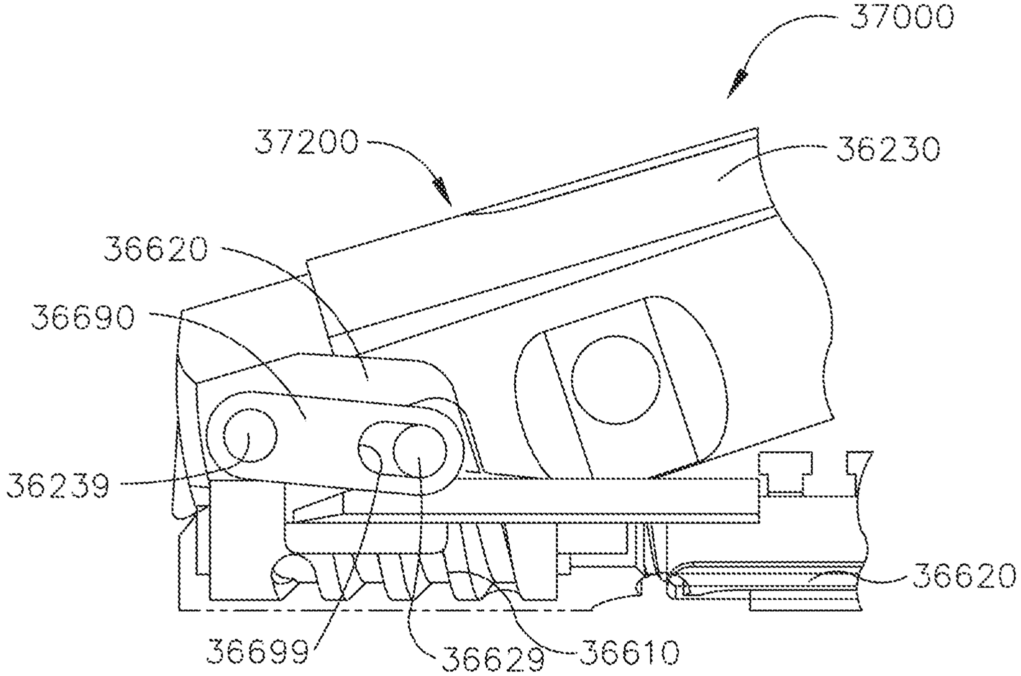
Figure 150:
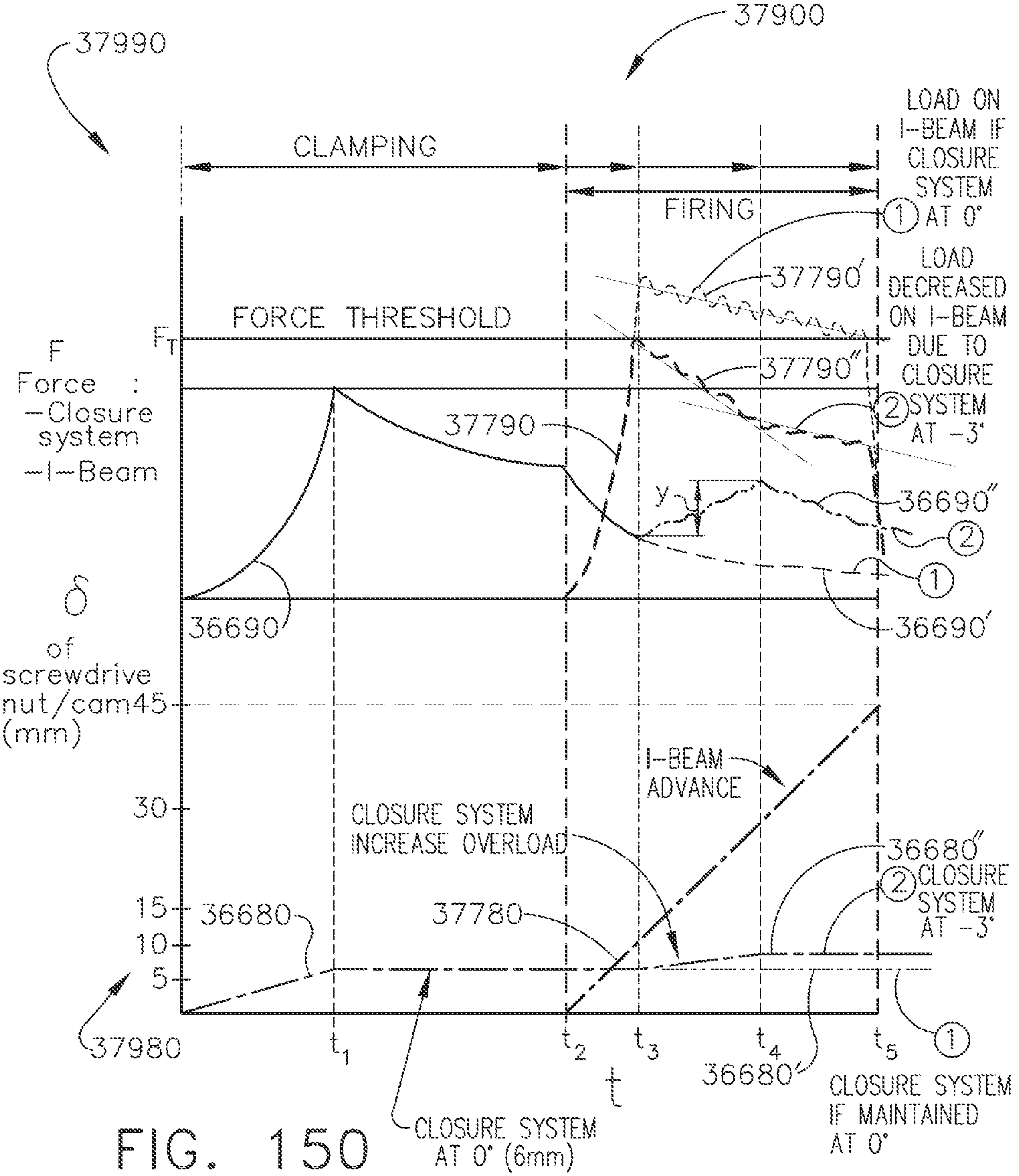
Figure 151:
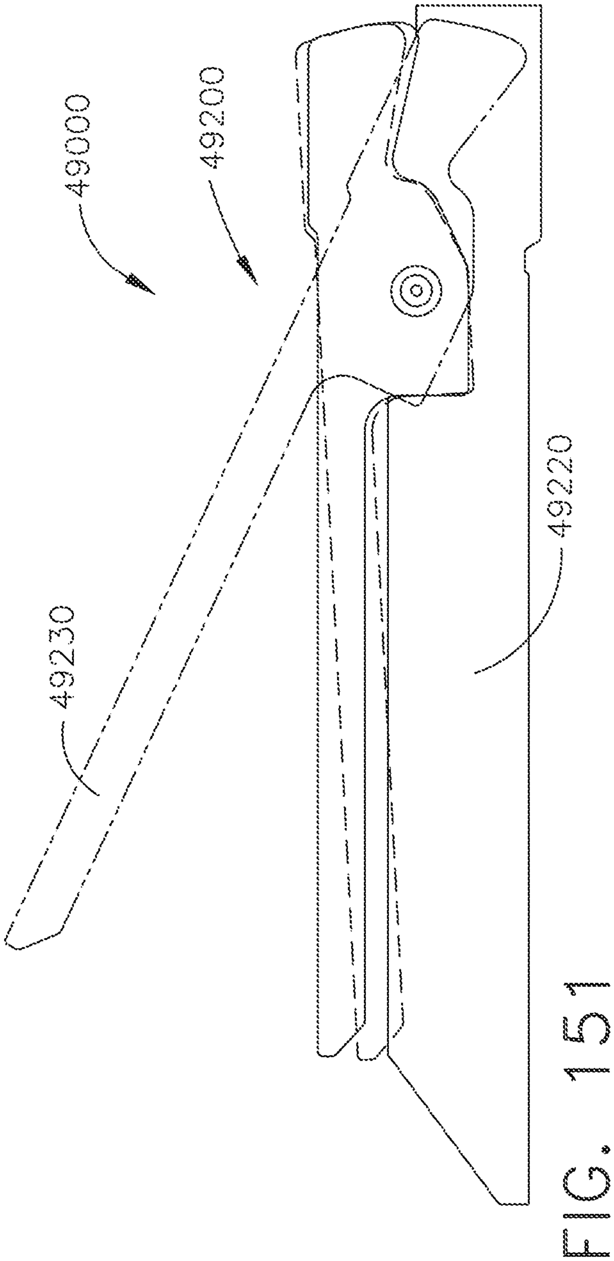
Figure 152:
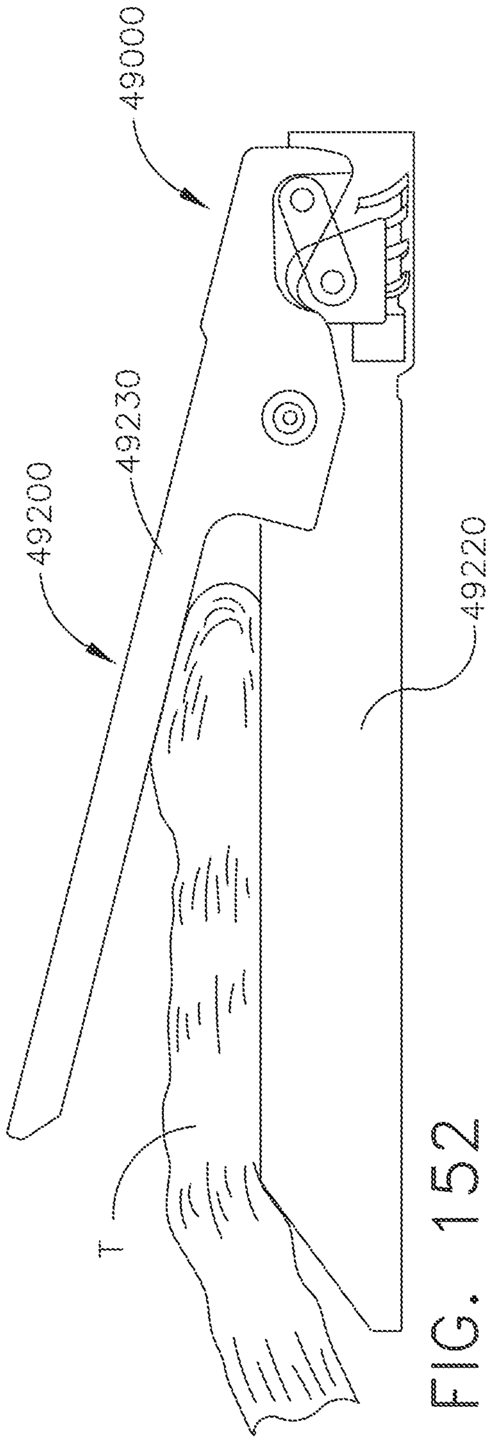
Figure 153:
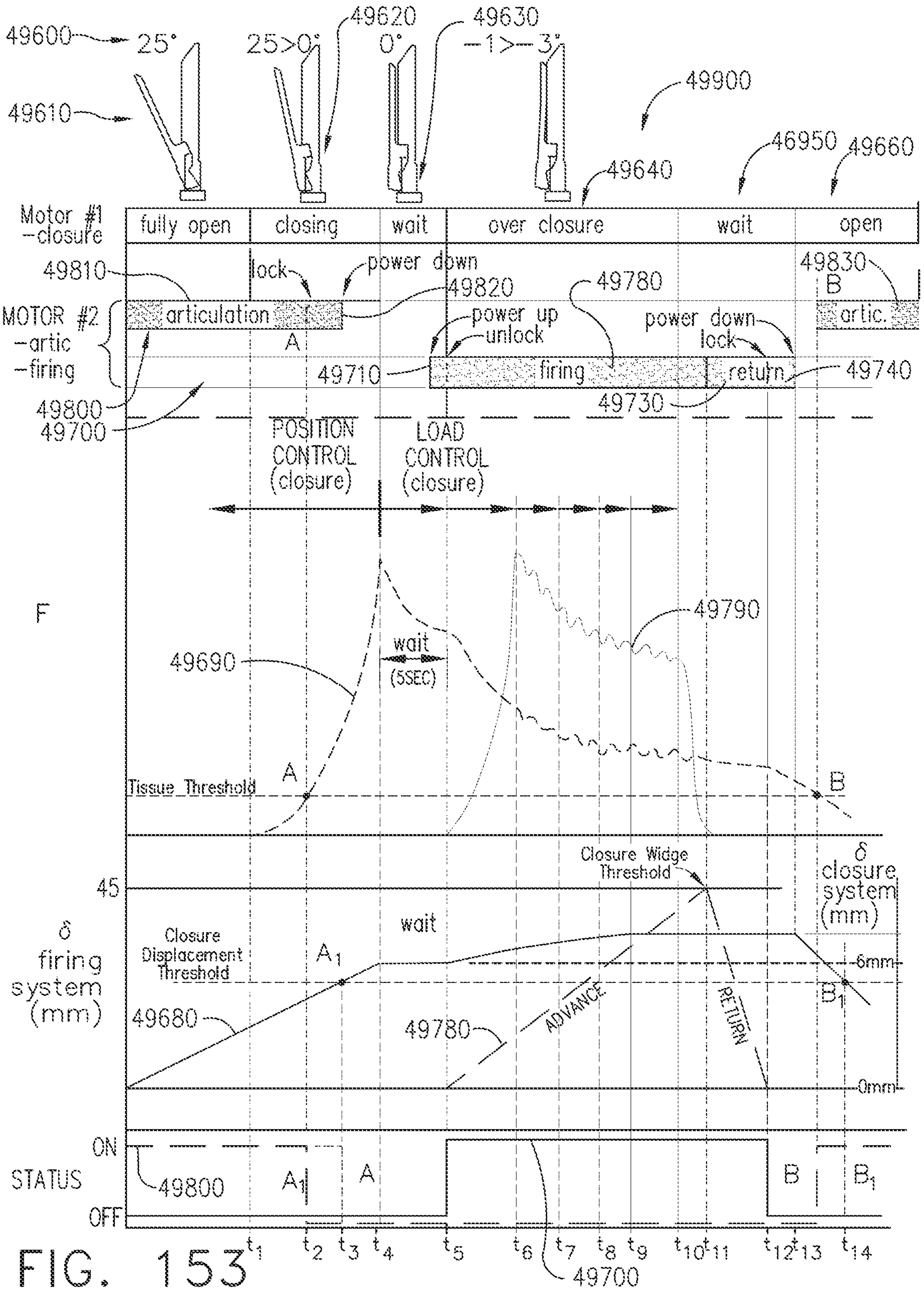
Figure 154:
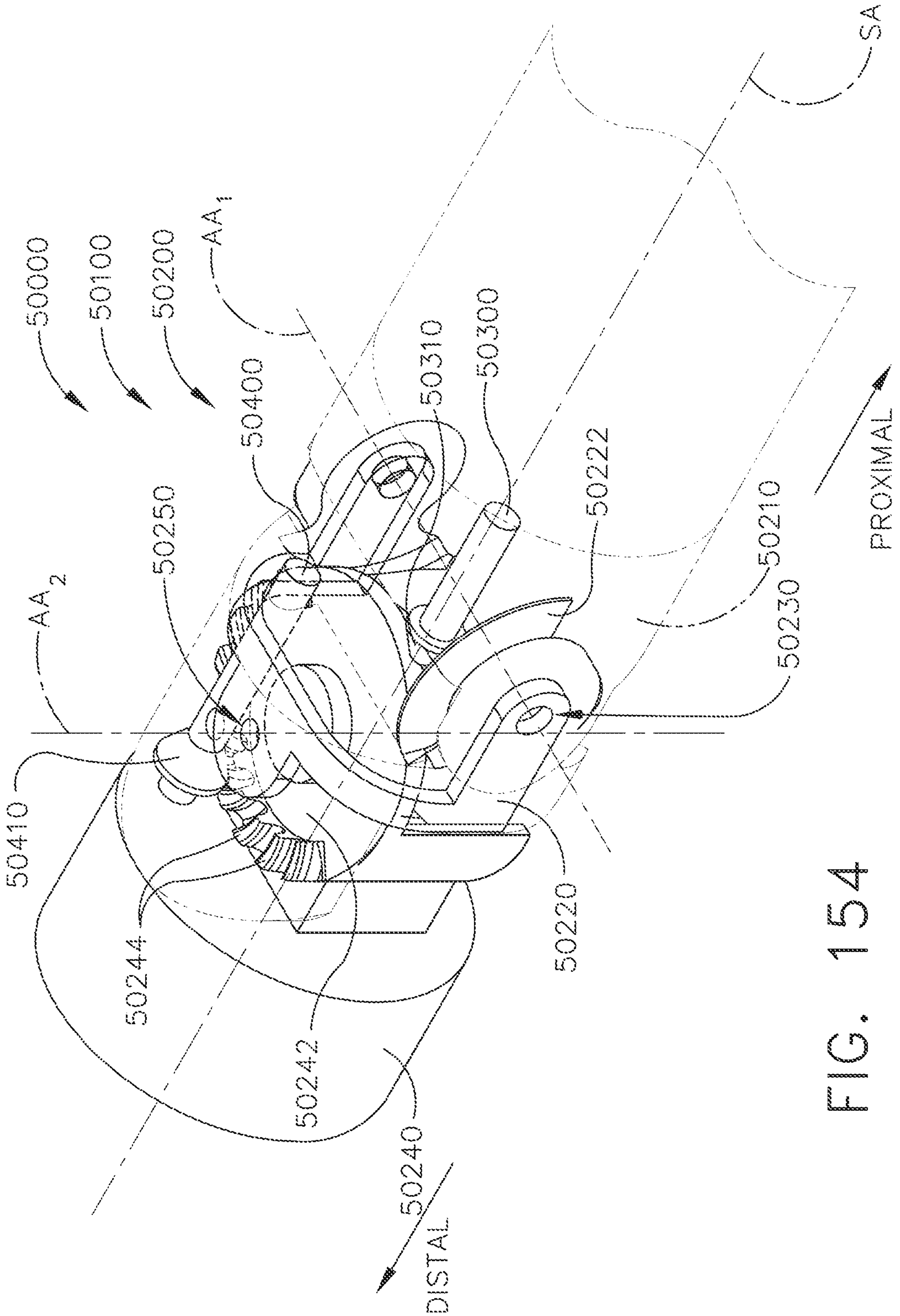
Figure 156:
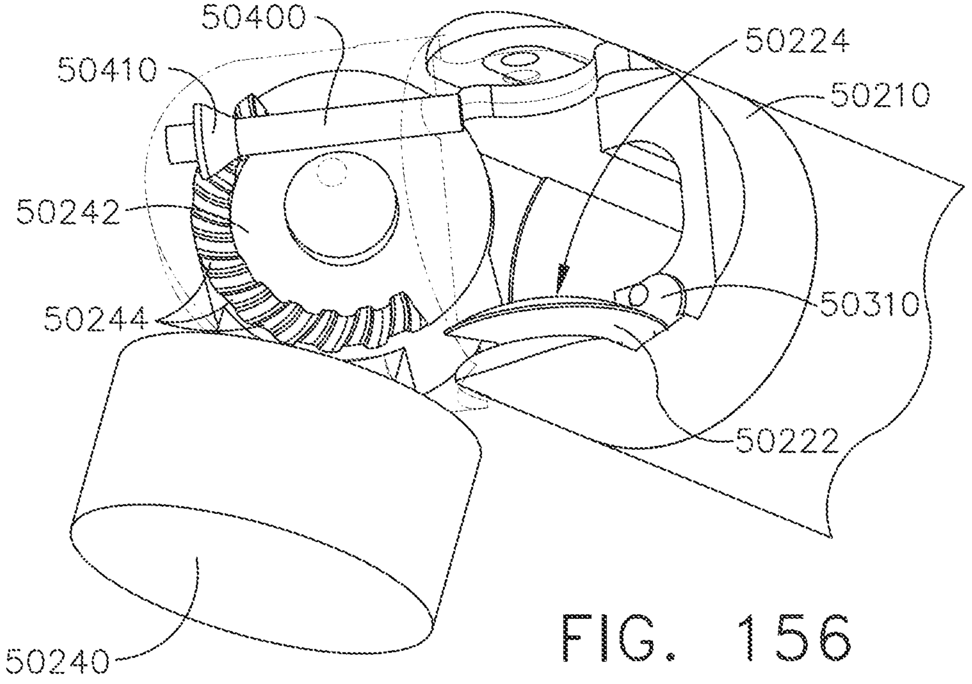
Figure 155:
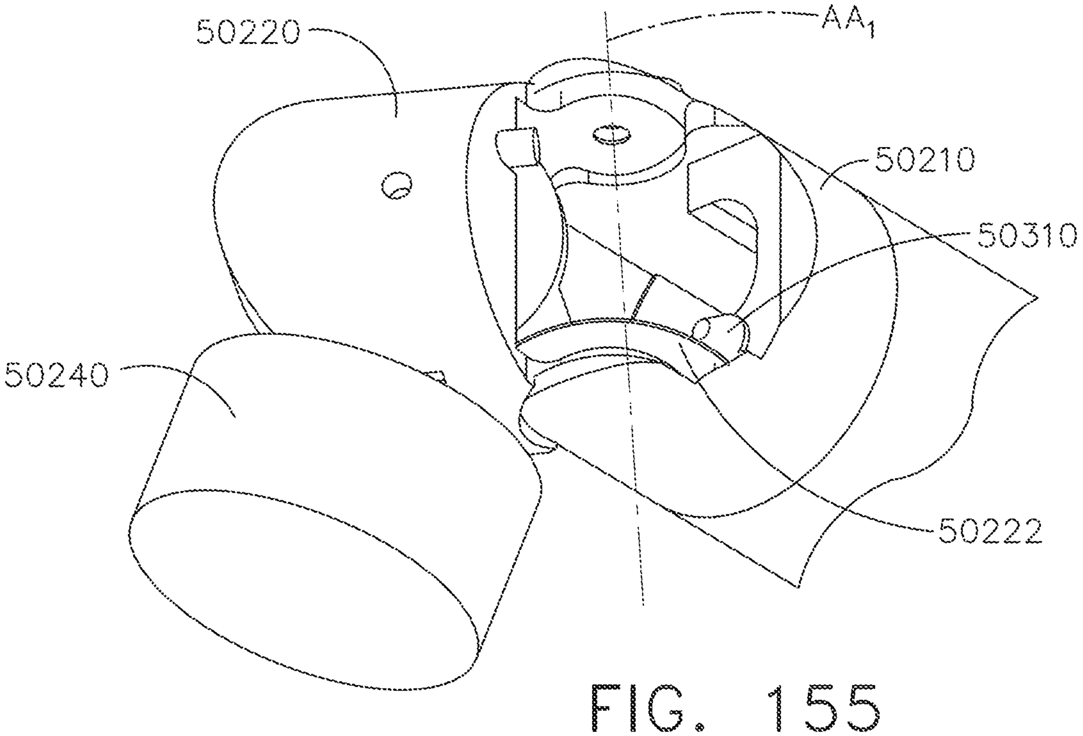
Figure 157:
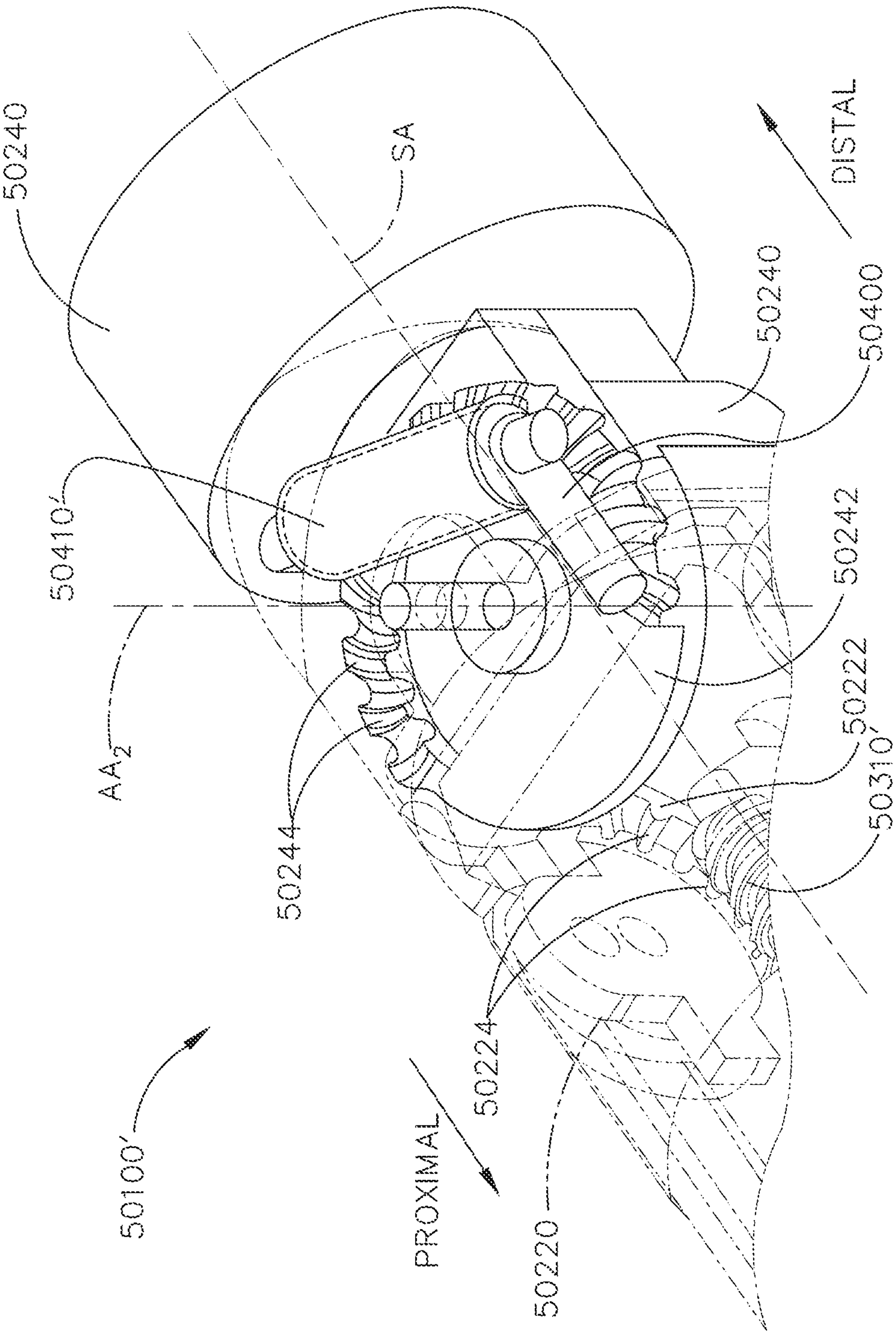
Figure 158:
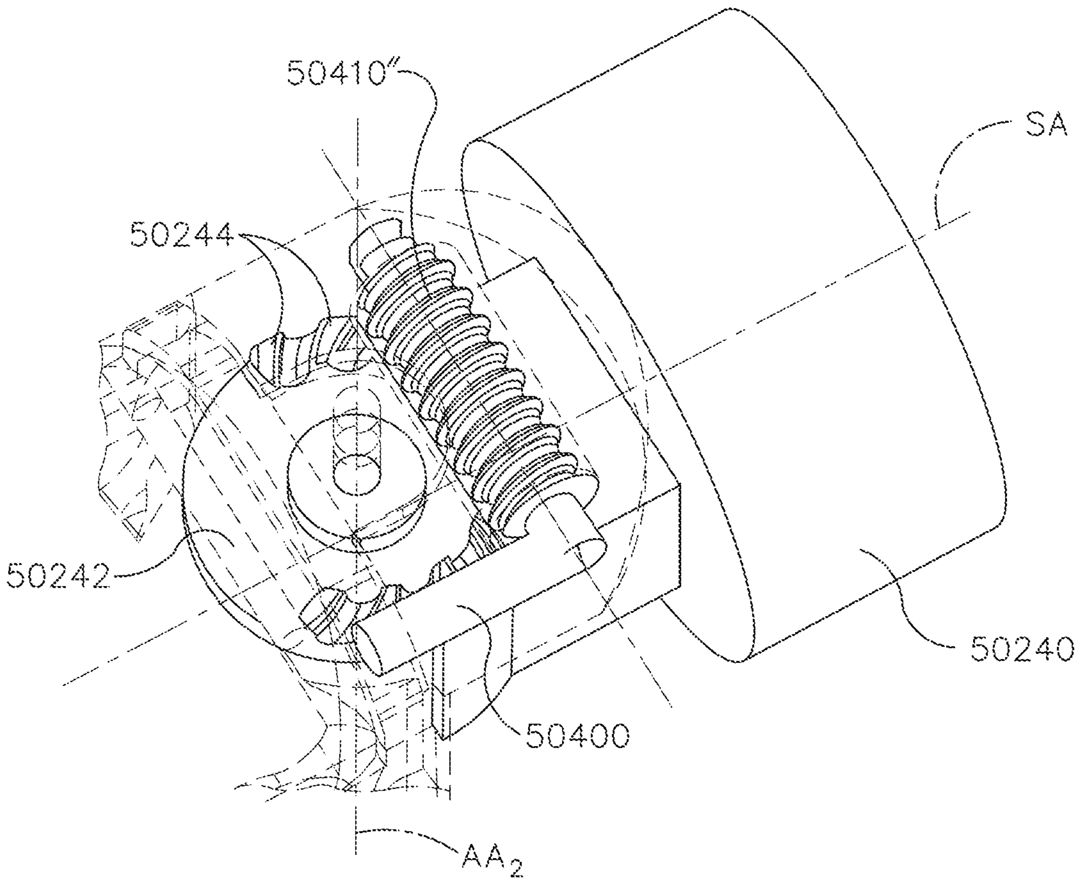
Figure 159:
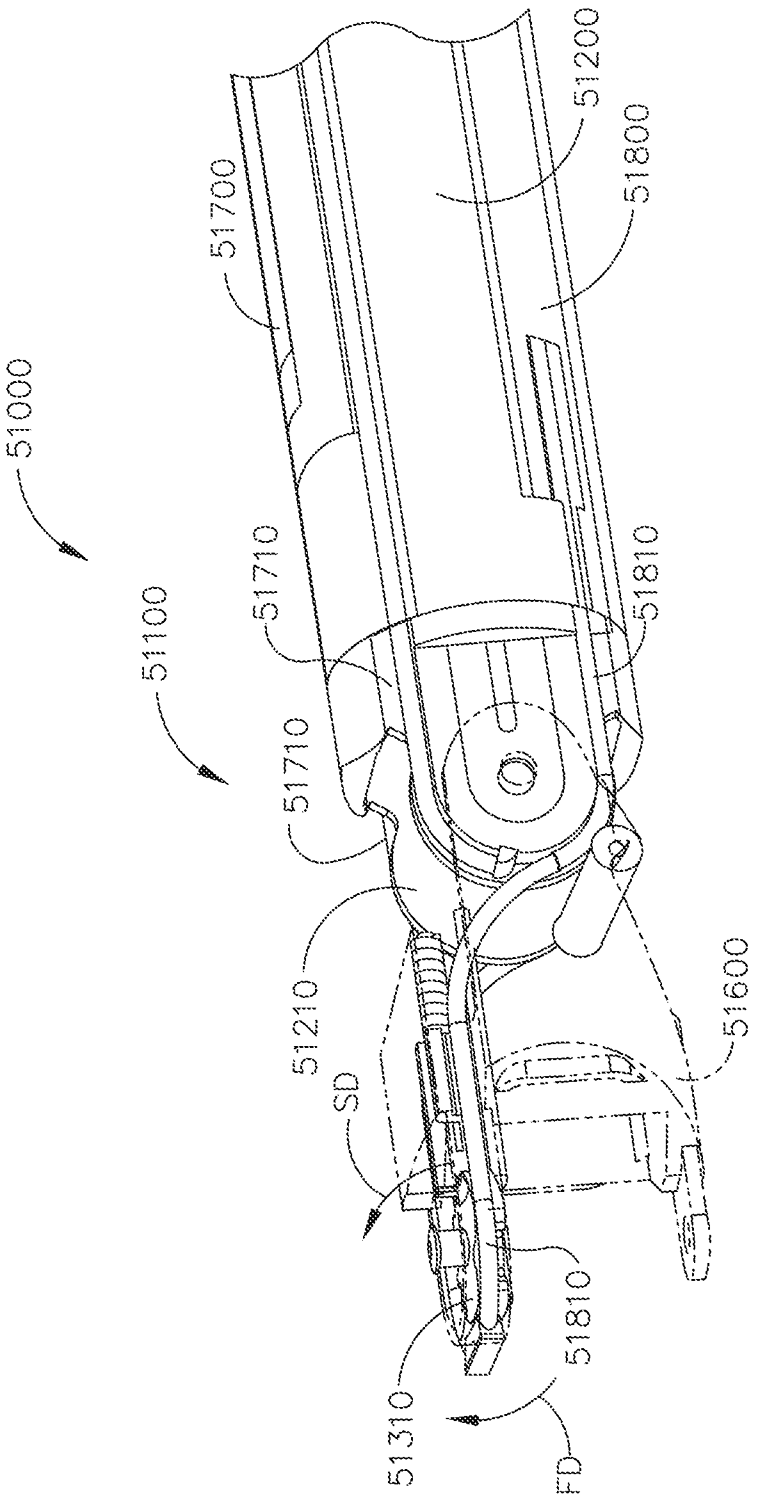
Figure 160:
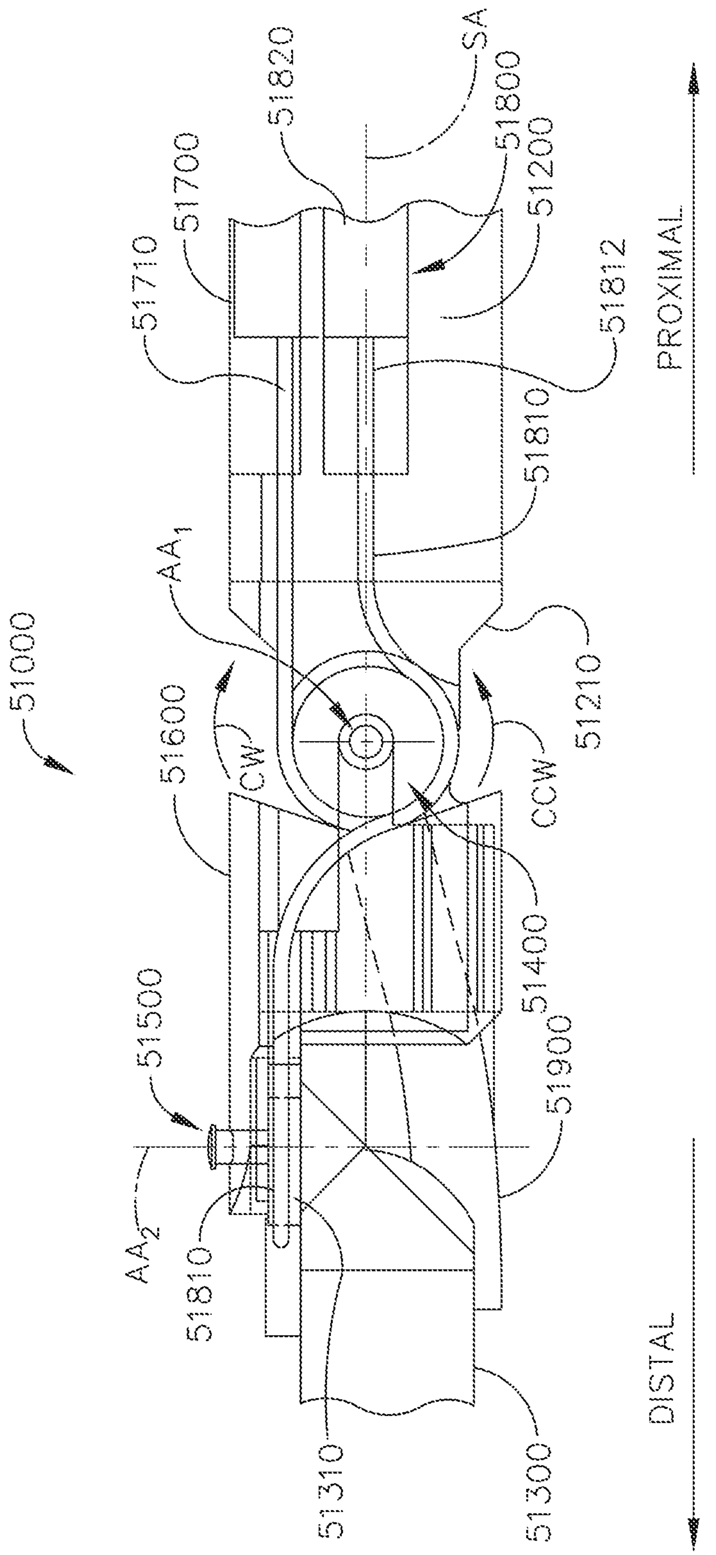
Figure 161:
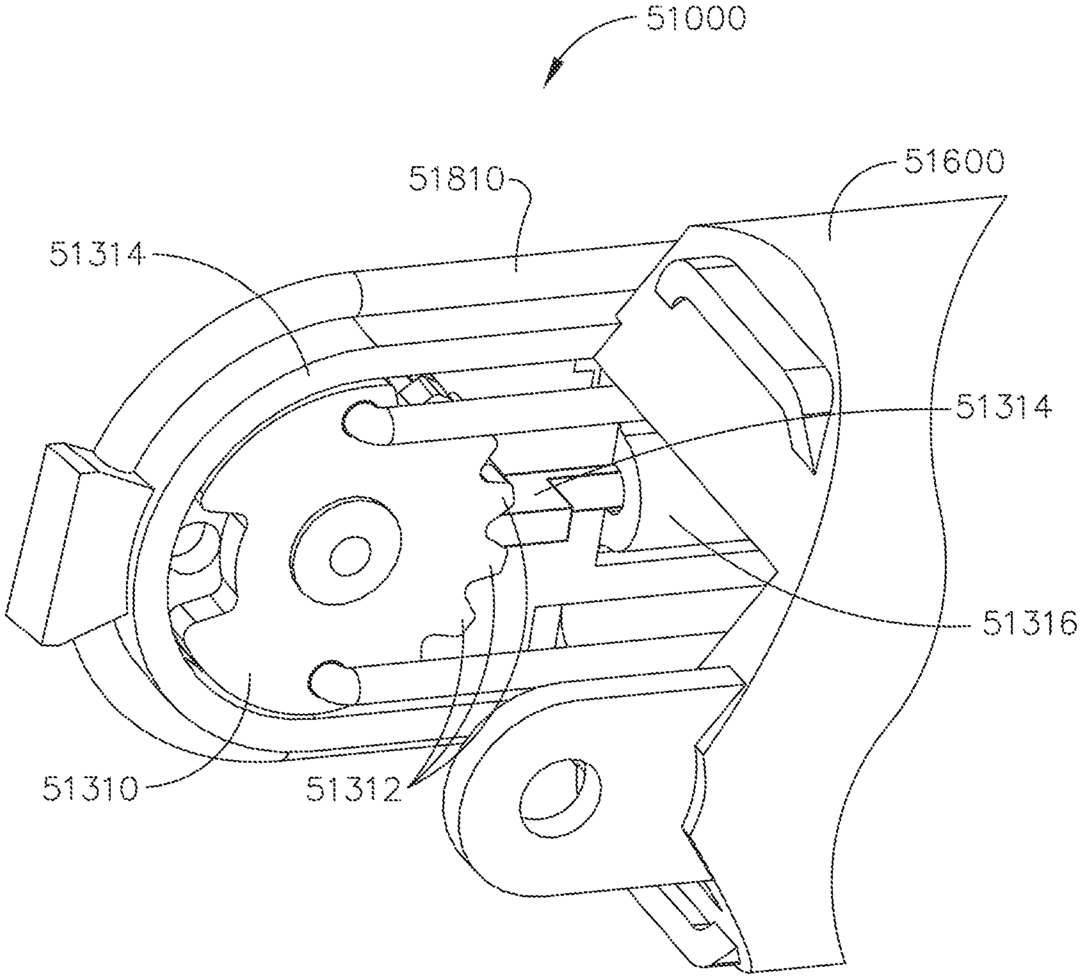
Figure 162:
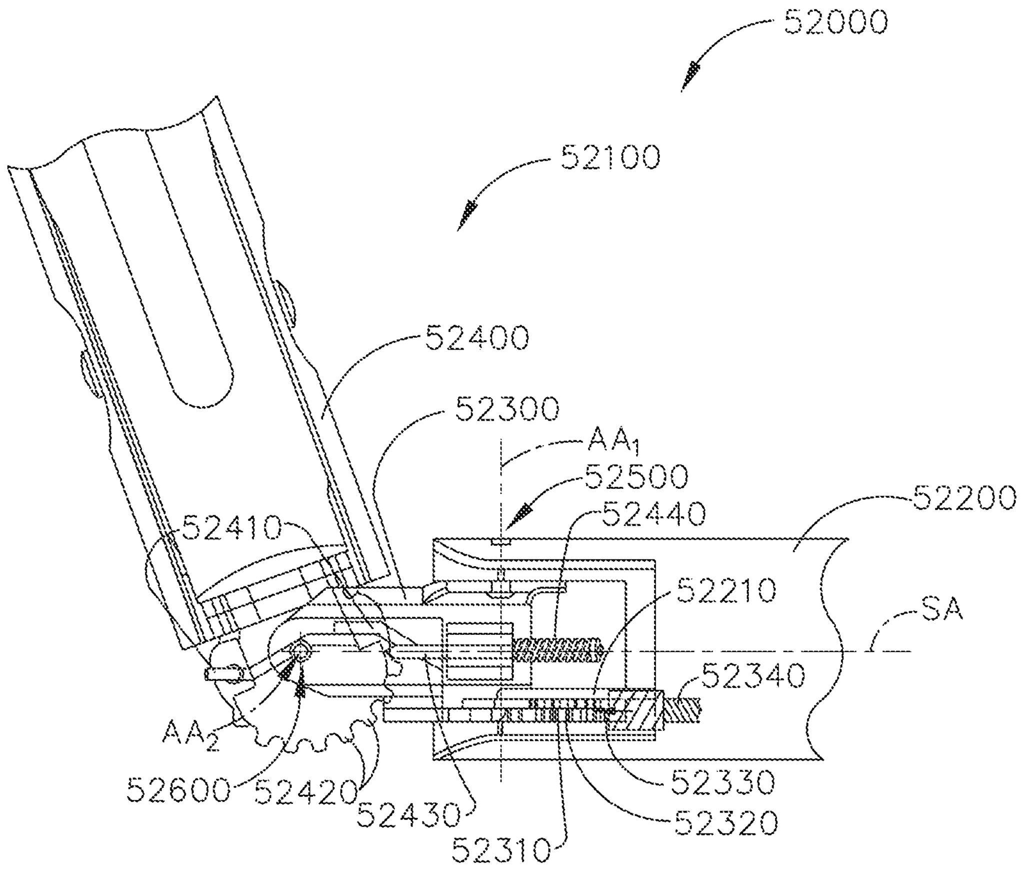
Figure 163:
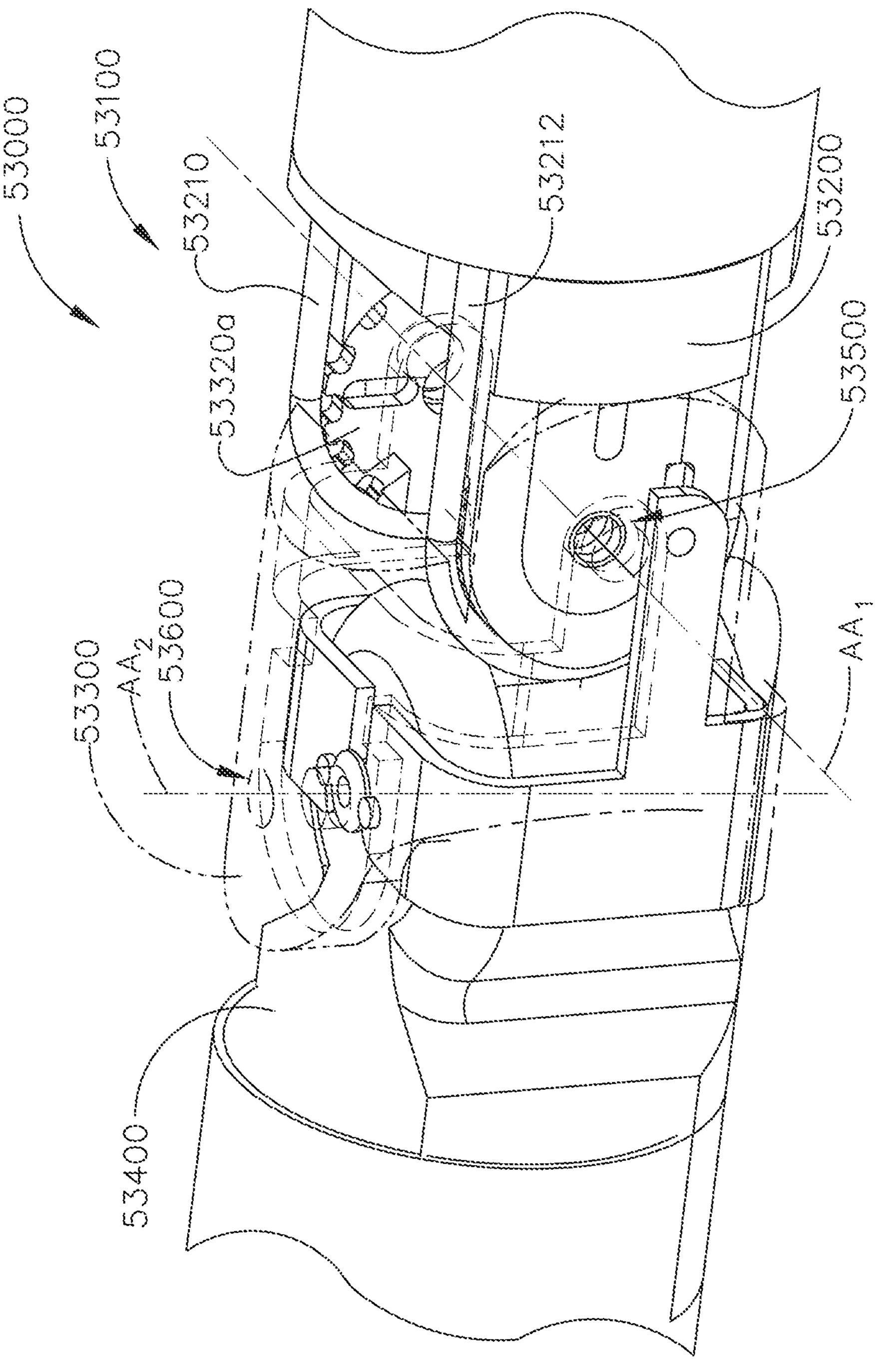
Figure 164:
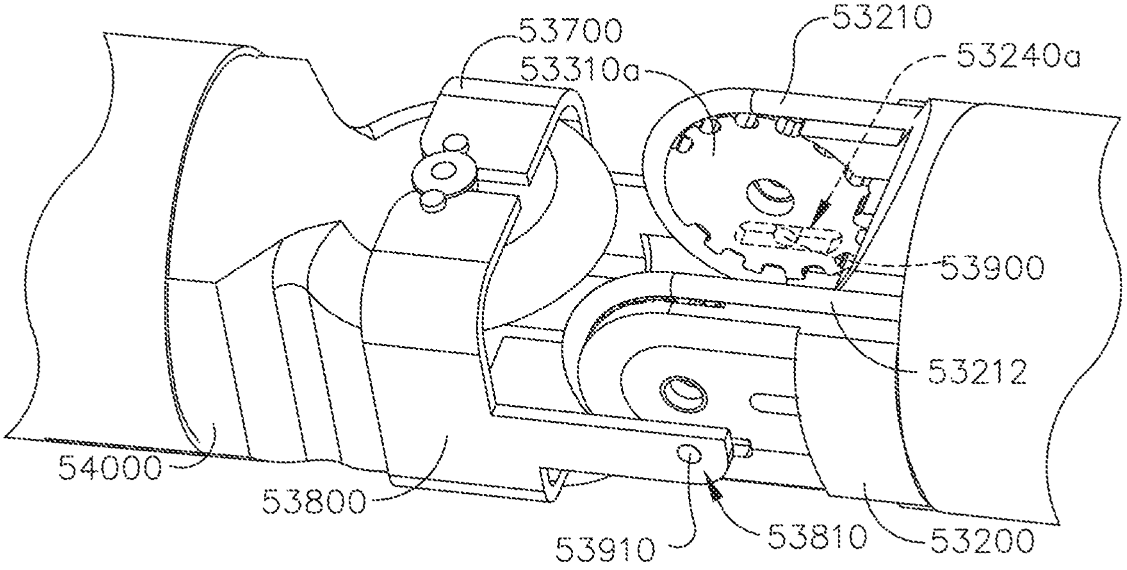
Figure 165:
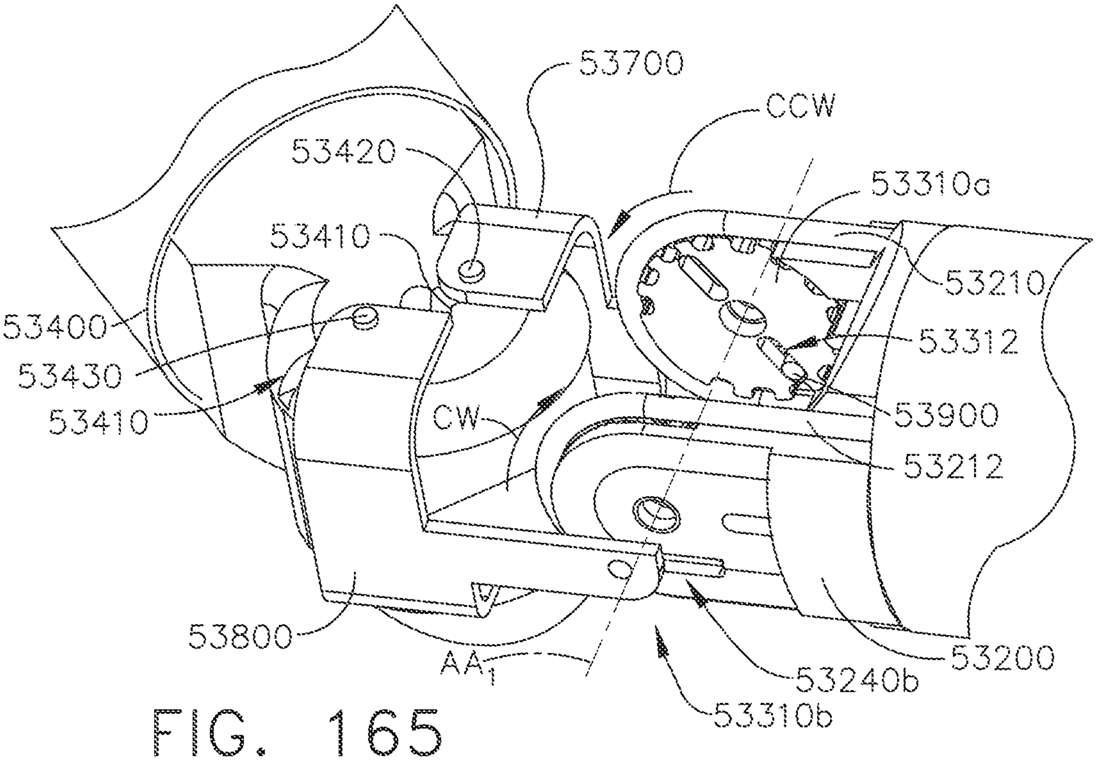
Figure 166:
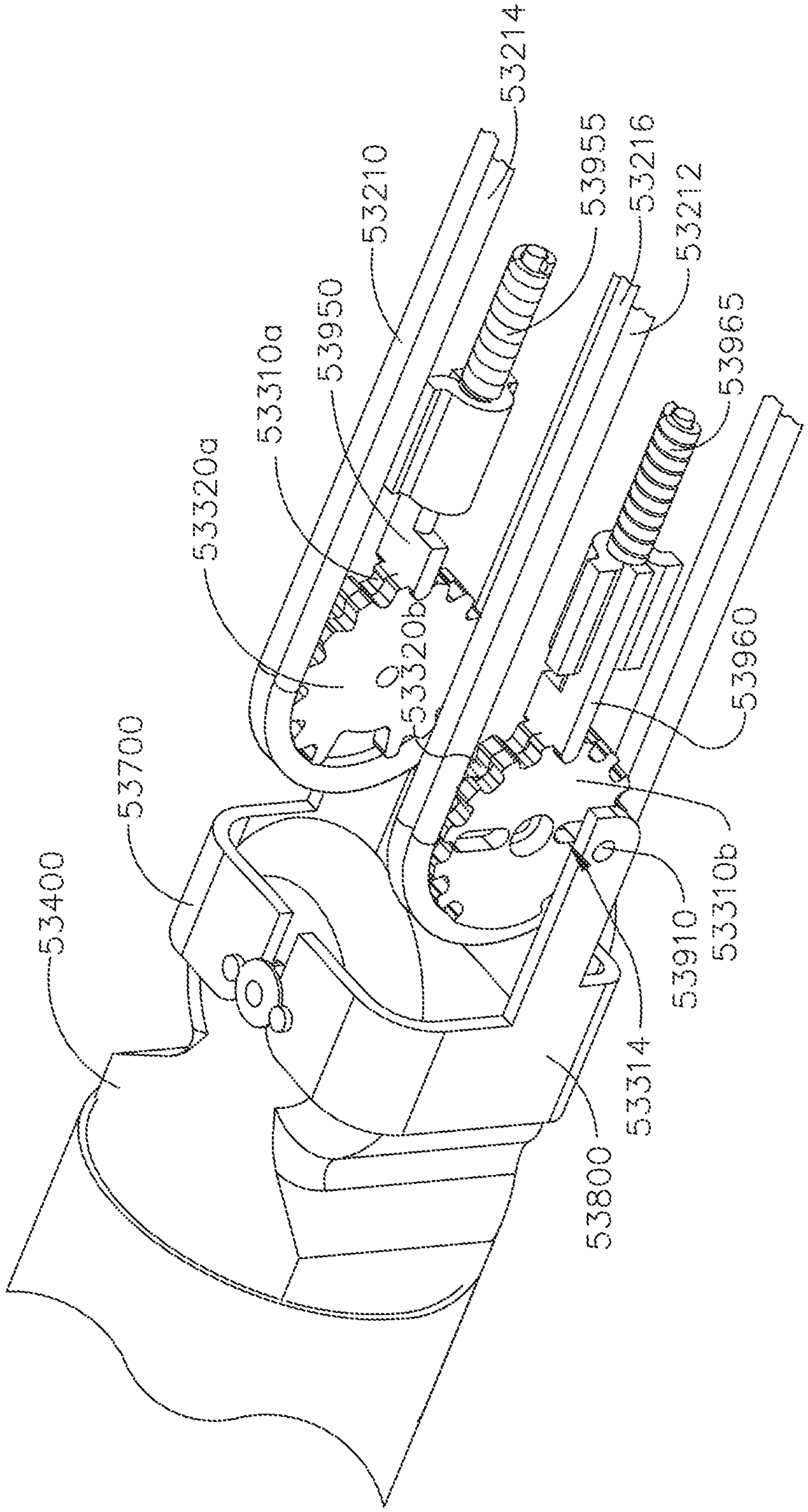
Figure 167:
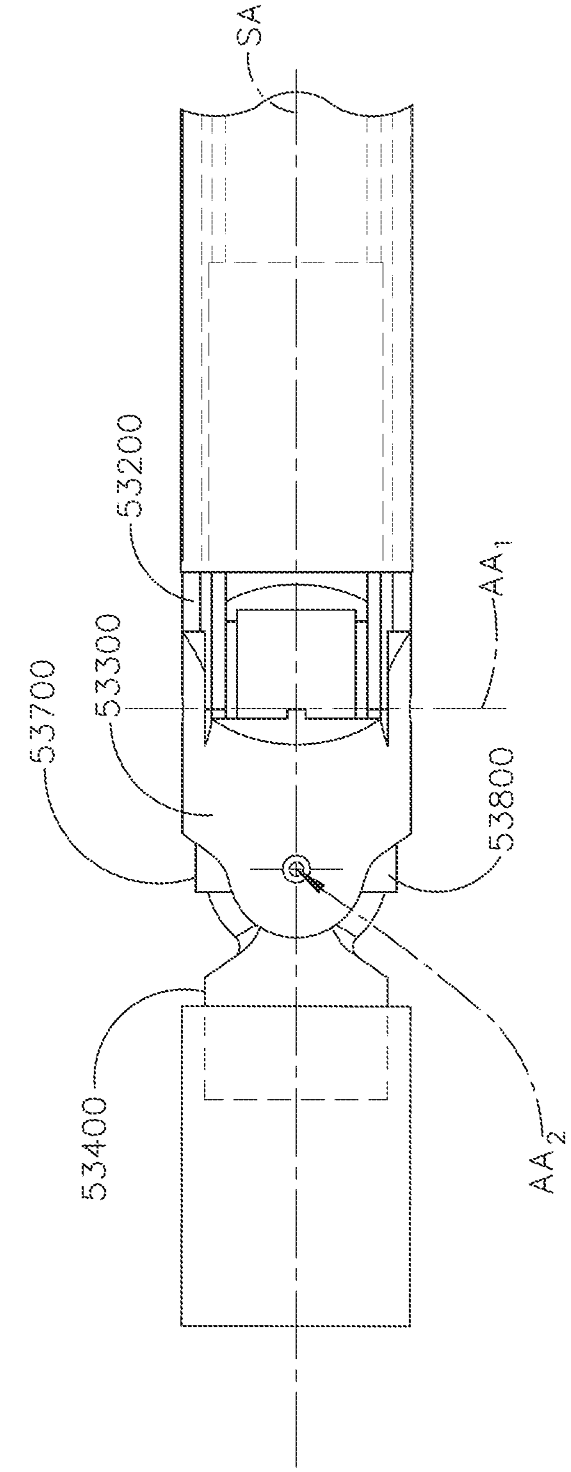

FIG. 125 is a partial cross-sectional view of the end effector of FIG. 122 illustrating the staple firing system being retracted;

FIG. 126 is a partial cross-sectional view of the end effector of FIG. 122 illustrating the firing bar of the staple firing system being decoupled from the sled by the spent cartridge lockout during the retraction of the staple firing system;

FIG. 127 is a partial cross-sectional view of the end effector of FIG. 122 illustrating the firing bar of the staple firing system in a fully-retracted position with the staple cartridge in a spent condition;

FIG. 128 is a partial cross-sectional view of the end effector of FIG. 122 illustrating the firing bar of the staple firing system being blocked by spent cartridge lockout because the spent staple cartridge has not been replaced with an unspent staple cartridge;

FIG. 129 is a partial perspective view of a staple cartridge including a staple firing drive;

FIG. 130 is a partial plan view of the staple cartridge of FIG. 129;

FIG. 131 is a partial perspective view of the staple firing drive of FIG. 129 in an unfired state;

FIG. 132 is a partial perspective view of the staple firing drive of FIG. 129 in a partially fired state;

FIG. 133 is a partial perspective view of the staple firing drive of FIG. 129 in a retracted state;

FIG. 134 is a partial perspective view of an end effector of a surgical instrument in accordance with at least one embodiment illustrated with a jaw of the end effector in an open position;

FIG. 135 is a partial elevational view of the end effector of FIG. 134 illustrating a jaw closure lockout in a locked state and a staple firing lockout in a locked state owing to the absence of an unfired staple cartridge seated in the end effector;

FIG. 136 is a perspective view of a lockout assembly including the jaw closure lockout and staple firing lockout of FIG. 135;

FIG. 137 is a partial elevational view of the end effector of FIG. 134 illustrating the jaw closure lockout in an unlocked state and the staple firing lockout in an unlocked state owing to the presence of an unfired staple cartridge seated in the end effector;

FIG. 138 is a partial elevational view of the end effector of FIG. 134 illustrating the staple cartridge of FIG. 137 in a partially fired state;

FIG. 139 is a partial exploded view of a staple cartridge comprising a cartridge body and a sled in accordance with at least one embodiment;

FIG. 140 is a partial cross-sectional view of the staple cartridge of FIG. 139 illustrating the sled in a proximal unfired position;

FIG. 141 is a partial cross-sectional view of the staple cartridge of FIG. 139 illustrating the sled being advanced distally during a staple firing stroke and activating a spent cartridge lockout in the staple cartridge;

FIG. 142 is a partial cross-sectional view of the staple cartridge of FIG. 139 illustrating the sled advanced distally during the staple firing stroke and the spent cartridge lockout in an activated state;

FIG. 143 is a partial cross-sectional view of the staple cartridge of FIG. 139 illustrating the sled being retracted after the staple firing stroke and the spent cartridge lockout in an activated state preventing the sled from being returned back into its proximal unfired position;

FIG. 144 is a partial elevational view of an end effector of a surgical instrument comprising an anvil jaw and a staple cartridge jaw in accordance with at least one embodiment illustrated in an open configuration;

FIG. 144A is a partial cross-sectional view of the end effector of FIG. 144;

FIG. 145 illustrates the end effector of FIG. 144 in a closed configuration;

FIG. 145A is a detail view of the end effector of FIG. 144 illustrated in the closed configuration of FIG. 145;

FIG. 146 is a partial cross-sectional view of the end effector of FIG. 144 illustrated in the closed configuration of FIG. 145;

FIG. 147 is an elevational view of the end effector of FIG. 144 illustrated with the anvil jaw in an open position relative to the staple cartridge jaw;

FIG. 148 is an elevational view of the end effector of FIG. 144 illustrated with the anvil jaw in a parallel position with respect to the staple cartridge jaw;

FIG. 149 is an elevational view of the end effector of FIG. 144 illustrated with the anvil jaw in an over clamped position with respect to the staple cartridge jaw;

FIG. 149A is a detail view of the end effector of FIG. 144 in the configuration of FIG. 149;

FIG. 149B is a detail view of the end effector of FIG. 144 illustrated in a re-opened configuration;

FIG. 150 is a chart depicting the displacement and loads experienced by the end effector clamping system and the staple firing system of the surgical instrument of FIG. 144;

FIG. 151 is an elevational view of an end effector in accordance with at least one embodiment;

FIG. 152 is an elevational view of the end effector of FIG. 151 being clamped onto patient tissue T;

FIG. 153 is a chart depicting the displacement and loads experienced by the end effector clamping system and the staple firing system of the surgical instrument of FIG. 151;

FIG. 154 is a perspective view of an articulation joint of a surgical instrument in accordance with at least one embodiment;

FIG. 155 is a perspective view of the articulation joint of the surgical instrument of FIG. 154 illustrated in an articulated configuration;

FIG. 156 is a partial perspective view of the articulation joint of the surgical instrument of FIG. 154 illustrated in an articulated configuration with a portion of the articulation joint hidden for the purpose of illustration;

FIG. 157 is a perspective view of an articulation joint of a surgical instrument in accordance with at least one embodiment;

FIG. 158 is a partial perspective view of an articulation joint of a surgical instrument in accordance with at least one embodiment;

FIG. 159 is a perspective view of an articulation joint of a surgical instrument in accordance with at least one embodiment;

FIG. 160 is a side elevation view of the articulation joint of the surgical instrument of FIG. 159 illustrating a firing member of the surgical instrument;

FIG. 161 is a perspective view of a portion of the articulation joint of the surgical instrument of FIG. 159 illustrating a distal articulation lock;

FIG. 162 is a plan view of an articulation joint of a surgical instrument in accordance with at least one embodiment;

FIG. 163 is a perspective view of an articulation joint of a surgical instrument in accordance with at least one embodiment;

FIG. 164 is a perspective view of the articulation joint of the surgical instrument of FIG. 163 illustrated with portions of the articulation joint hidden for clarity;

FIG. 165 is a perspective view of the articulation joint of the surgical instrument of FIG. 164 illustrating the articulation joint in an articulated configuration;

FIG. 166 is a perspective view of the articulation joint of the surgical instrument of FIG. 163 with portions of the articulation joint hidden for clarity; and FIG. 167 is a plan view of the articulation joint of the surgical instrument of FIG. 163.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Applicant of the present application owns the following U.S. Patent Applications that were filed on Dec. 19, 2019, even date herewith and which are each incorporated by reference in their respective entireties:

- U.S. application Ser. No. 16/720,766, entitled METHOD FOR OPERATING A SURGICAL INSTRUMENT, published as U.S. Pub. No. 2021/0186495 on Jun. 24, 2021;
- U.S. application Ser. No. 16/720,751, entitled SURGICAL INSTRUMENT COMPRISING A RAPID CLOSURE MECHANISM, published as U.S. Pub. No 2021/0186501 on Jun. 24, 2021;
- U.S. application Ser. No. 16/720,735, entitled SURGICAL INSTRUMENT COMPRISING A CLOSURE SYSTEM INCLUDING A CLOSURE MEMBER AND AN OPENING MEMBER DRIVEN BY A DRIVE SCREW, issued as U.S. Pat. No. 11,576,672 on Feb. 14, 2023;
- U.S. application Ser. No. 16/720,747, entitled SURGICAL INSTRUMENT COMPRISING A NESTED FIRING MEMBER, issued as U.S. Pat. No. 11,504,122 on Nov. 22, 2022;
- U.S. application Ser. No. 16/720,751, entitled STAPLE CARTRIDGE COMPRISING A DEPLOYABLE KNIFE, published as U.S. Pub. No. 2021/0186501 on Jun. 24, 2021;
- U.S. application Ser. No. 16/720,769, entitled STAPLE CARTRIDGE COMPRISING A DETACHABLE TISSUE CUTTING KNIFE, issued as U.S. Pat. No. 11,607,219 on Mar. 21, 2023;
- U.S. application Ser. No. 16/720,730, entitled STAPLING SYSTEM COMPRISING A CLAMP LOCKOUT AND A FIRING LOCKOUT, issued as U.S. Pat. No. 11,234,698 on Feb. 1, 2022; =U.S. application Ser. No. 16/720,742, entitled STAPLE CARTRIDGE COMPRISING A LATCH LOCKOUT, published as U.S. Pub. No. 2021/0186499 on Jun. 24, 2021;
- U.S. application Ser. No. 16/720,776, entitled SURGICAL INSTRUMENT COMPRISING A POWERED ARTICULATION SYSTEM, issued as U.S. Pat. No. 11,304,696 on Apr. 19, 2022;
- U.S. application Ser. No. 16/720,781, entitled MOTOR DRIVEN SURGICAL INSTRUMENT, issued as U.S. Pat. No. 11,529,139 on Dec. 20, 2022;
- U.S. application Ser. No. 16/720,789, entitled STAPLING INSTRUMENT COMPRISING INDEPENDENT JAW CLOSING AND STAPLE FIRING SYSTEMS, issued as U.S. Pat. No. 11,291,447 on Apr. 5, 2022;
- U.S. application Ser. No. 16/720,725, entitled STAPLE CARTRIDGE COMPRISING DRIVER RETENTION MEMBERS, published as U.S. Pub. No. 2021/0186492 on Jun. 24, 2021;
- U.S. application Ser. No. 16/720,740, entitled STAPLE CARTRIDGE COMPRISING DRIVER RETENTION MEMBERS, issued as U.S. Pat. No. 11,529,137 on Dec. 20, 2022;
- U.S. application Ser. No. 16/720,788, entitled STAPLE CARTRIDGE COMPRISING PROJECTIONS EXTENDING FROM A CURVED DECK SURFACE, issued as U.S. Pat. No. 11,446,029 on Sep. 20, 2022; and U.S. application Ser. No. 16/720,806, entitled STAPLE CARTRIDGE COMPRISING A CURVED DECK SURFACE, issued as U.S. Pat. No. 11,464,512 on Oct. 11, 2022.

Applicant of the present application owns the following U.S. Patent Applications that were filed on Mar. 25, 2019, and which are each herein incorporated by reference in their respective entireties:

- U.S. patent application Ser. No. 16/363,070, entitled FIRING DRIVE ARRANGEMENTS FOR SURGICAL SYSTEMS;
- U.S. patent application Ser. No. 16/363,051, entitled FIRING DRIVE ARRANGEMENTS FOR SURGICAL SYSTEMS;
- U.S. patent application Ser. No. 16/363,045, entitled ARTICULATION DRIVE ARRANGEMENTS FOR SURGICAL SYSTEMS; and
- U.S. patent application Ser. No. 16/363,062, entitled FIRING DRIVE ARRANGEMENTS FOR SURGICAL SYSTEMS.

Applicant of the present application owns the following U.S. Patent Applications that were filed on Jun. 30, 2019, and which are each herein incorporated by reference in their respective entireties:

- U.S. patent application Ser. No. 16/458,104, entitled METHOD FOR AUTHENTICATING THE COMPATIBILITY OF A STAPLE CARTRIDGE WITH A SURGICAL INSTRUMENT;
- U.S. patent application Ser. No. 16/458,108, entitled SURGICAL INSTRUMENT SYSTEM COMPRISING AN RFID SYSTEM;
- U.S. patent application Ser. No. 16/458,111, entitled SURGICAL INSTRUMENT COMPRISING AN RFID SYSTEM FOR TRACKING A MOVABLE COMPONENT;
- U.S. patent application Ser. No. 16/458,114, entitled SURGICAL INSTRUMENT COMPRISING AN ALIGNED RFID SENSOR;
- U.S. patent application Ser. No. 16/458,105, entitled SURGICAL STAPLING SYSTEM HAVING AN INFORMATION DECRYPTION PROTOCOL;
- U.S. patent application Ser. No. 16/458,110, entitled SURGICAL STAPLING SYSTEM HAVING AN INFORMATION ENCRYPTION PROTOCOL;
- U.S. patent application Ser. No. 16/458,120, entitled SURGICAL STAPLING SYSTEM HAVING A LOCKOUT MECHANISM FOR AN INCOMPATIBLE CARTRIDGE;
- U.S. patent application Ser. No. 16/458,125, entitled SURGICAL STAPLING SYSTEM HAVING A FRANGIBLE RFID TAG; and U.S. patent application Ser. No. 16/458,103, entitled PACKAGING FOR A REPLACEABLE COMPONENT OF A SURGICAL STAPLING SYSTEM.

Applicant of the present application owns the following U.S. Patent Applications that were filed on Jun. 30, 2019, and which are each herein incorporated by reference in their respective entireties:

- U.S. patent application Ser. No. 16/458,107, entitled METHOD OF USING MULTIPLE RFID CHIPS WITH A SURGICAL ASSEMBLY;
- U.S. patent application Ser. No. 16/458,109, entitled MECHANISMS FOR PROPER ANVIL ATTACHMENT SURGICAL STAPLING HEAD ASSEMBLY;
- U.S. patent application Ser. No. 16/458,119, entitled MECHANISMS FOR MOTOR CONTROL ADJUSTMENTS OF A MOTORIZED SURGICAL INSTRUMENT;
- U.S. patent application Ser. No. 16/458,115, entitled SURGICAL INSTRUMENT WITH BATTERY COMPATIBILITY VERIFICATION FUNCTIONALITY;
- U.S. patent application Ser. No. 16/458,117, entitled SURGICAL SYSTEM WITH RFID TAGS FOR UPDATING MOTOR ASSEMBLY PARAMETERS;
- U.S. patent application Ser. No. 16/458,121, entitled SURGICAL SYSTEMS WITH MULTIPLE RFID TAGS;
- U.S. patent application Ser. No. 16/458,122, entitled RFID IDENTIFICATION SYSTEMS FOR SURGICAL INSTRUMENTS;
- U.S. patent application Ser. No. 16/458,106, entitled RFID IDENTIFICATION SYSTEMS FOR SURGICAL INSTRUMENTS;
- U.S. patent application Ser. No. 16/458,112, entitled SURGICAL RFID ASSEMBLIES FOR DISPLAY AND COMMUNICATION;
- U.S. patent application Ser. No. 16/458,116, entitled SURGICAL RFID ASSEMBLIES FOR COMPATIBILITY DETECTION; and
- U.S. patent application Ser. No. 16/458,118, entitled SURGICAL RFID ASSEMBLIES FOR INSTRUMENT OPERATIONAL SETTING CONTROL.

Applicant of the present application owns the following U.S. Patent Applications, filed on Dec. 4, 2018, the disclosure of each of which is herein incorporated by reference in its entirety:

- U.S. patent application Ser. No. 16/209,385, entitled METHOD OF HUB COMMUNICATION, PROCESSING, STORAGE AND DISPLAY;
- U.S. patent application Ser. No. 16/209,395, entitled METHOD OF HUB COMMUNICATION;
- U.S. patent application Ser. No. 16/209,403, entitled METHOD OF CLOUD BASED DATA ANALYTICS FOR USE WITH THE HUB;
- U.S. patent application Ser. No. 16/209,407, entitled METHOD OF ROBOTIC HUB COMMUNICATION, DETECTION, AND CONTROL;
- U.S. patent application Ser. No. 16/209,416, entitled METHOD OF HUB COMMUNICATION, PROCESSING, DISPLAY, AND CLOUD ANALYTICS;
- U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS;
- U.S. patent application Ser. No. 16/209,427, entitled METHOD OF USING REINFORCED FLEXIBLE CIRCUITS WITH MULTIPLE SENSORS TO OPTIMIZE PERFORMANCE OF RADIO FREQUENCY DEVICES;
- U.S. patent application Ser. No. 16/209,433, entitled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;
- U.S. patent application Ser. No. 16/209,447, entitled METHOD FOR SMOKE EVACUATION FOR SURGICAL HUB;
- U.S. patent application Ser. No. 16/209,453, entitled METHOD FOR CONTROLLING SMART ENERGY DEVICES;
- U.S. patent application Ser. No. 16/209,458, entitled METHOD FOR SMART ENERGY DEVICE INFRASTRUCTURE;
- U.S. patent application Ser. No. 16/209,465, entitled METHOD FOR ADAPTIVE CONTROL SCHEMES FOR SURGICAL NETWORK CONTROL AND INTERACTION;
- U.S. patent application Ser. No. 16/209,478, entitled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;
- U.S. patent application Ser. No. 16/209,490, entitled METHOD FOR FACILITY DATA COLLECTION AND INTERPRETATION; and
- U.S. patent application Ser. No. 16/209,491, entitled METHOD FOR CIRCULAR STAPLER CONTROL ALGORITHM ADJUSTMENT BASED ON SITUATIONAL AWARENESS.

Applicant of the present application owns the following U.S. Patent Applications that were filed on Jun. 26, 2019 and which are each herein incorporated by reference in their respective entireties:

- U.S. patent application Ser. No. 16/453,273, entitled METHOD FOR PROVIDING AN AUTHENTICATION LOCKOUT IN A SURGICAL STAPLER WITH A REPLACEABLE CARTRIDGE;
- U.S. patent application Ser. No. 16/453,283, entitled SURGICAL STAPLING ASSEMBLY WITH CARTRIDGE BASED RETAINER CONFIGURED TO UNLOCK A FIRING LOCKOUT;
- U.S. patent application Ser. No. 16/453,289, entitled SURGICAL STAPLING ASSEMBLY WITH CARTRIDGE BASED RETAINER CONFIGURED TO UNLOCK A CLOSURE LOCKOUT;
- U.S. patent application Ser. No. 16/453,302 entitled UNIVERSAL CARTRIDGE BASED KEY FEATURE THAT UNLOCKS MULTIPLE LOCKOUT ARRANGEMENTS IN DIFFERENT SURGICAL STAPLERS;
- U.S. patent application Ser. No. 16/453,310, entitled STAPLE CARTRIDGE RETAINERS WITH FRANGIBLE RETENTION FEATURES AND METHODS OF USING SAME;
- U.S. patent application Ser. No. 16/453,330, entitled STAPLE CARTRIDGE RETAINER WITH FRANGIBLE AUTHENTICATION KEY;
- U.S. patent application Ser. No. 16/453,335, entitled STAPLE CARTRIDGE RETAINER WITH RETRACTABLE AUTHENTICATION KEY;

U.S. patent application Ser. No. 16/453,343, entitled STAPLE CARTRIDGE RETAINER SYSTEM WITH AUTHENTICATION KEYS;

U.S. patent application Ser. No. 16/453,355, entitled INSERTABLE DEACTIVATOR ELEMENT FOR SURGICAL STAPLER LOCKOUTS;

U.S. patent application Ser. No. 16/453,369, entitled DUAL CAM CARTRIDGE BASED FEATURE FOR UNLOCKING A SURGICAL STAPLER LOCKOUT;

U.S. patent application Ser. No. 16/453,391, entitled STAPLE CARTRIDGES WITH CAM SURFACES CONFIGURED TO ENGAGE PRIMARY AND SECONDARY PORTIONS OF A LOCKOUT OF A SURGICAL STAPLING DEVICE;

U.S. patent application Ser. No. 16/453,413, entitled SURGICAL STAPLE CARTRIDGES WITH MOVABLE AUTHENTICATION KEY ARRANGEMENTS;

U.S. patent application Ser. No. 16/453,423, entitled DEACTIVATOR ELEMENT FOR DEFEATING SURGICAL STAPLING DEVICE LOCKOUTS; and U.S. patent application Ser. No. 16/453,429 entitled SURGICAL STAPLE CARTRIDGES WITH INTEGRAL AUTHENTICATION KEYS.

Applicant of the present application owns the following U.S. Design Patent Applications that were filed on Jun. 25, 2019 which are each herein incorporated by reference in their respective entireties:

U.S. Design patent application Ser. No. 29/696,066, entitled SURGICAL STAPLE CARTRIDGE RETAINER WITH FIRING SYSTEM AUTHENTICATION KEY;

U.S. Design patent application Ser. No. 29/696,067, entitled SURGICAL STAPLE CARTRIDGE RETAINER WITH CLOSURE SYSTEM AUTHENTICATION KEY; and U.S. Design patent application Ser. No. 29/696,072, entitled SURGICAL STAPLE CARTRIDGE.

Applicant of the present application owns the following U.S. Patent Applications that were filed on Feb. 21, 2019 which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,670, entitled STAPLE CARTRIDGE COMPRISING A LOCKOUT KEY CONFIGURED TO LIFT A FIRING MEMBER;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled SURGICAL INSTRUMENT COMPRISING A DEACTIVATABLE LOCKOUT;

U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,660, entitled SURGICAL STAPLE CARTRIDGE WITH FIRING MEMBER DRIVEN CAMMING ASSEMBLY THAT HAS AN ONBOARD TISSUE CUTTING FEATURE;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND FRAME ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS

FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. Patent Applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design patent application Ser. No. 29/660,252, entitled SURGICAL STAPLER ANVILS.

Applicant of the present application owns the following U.S. Patent Applications that were filed on Aug. 3, 2017 and which are each herein incorporated by reference in their respective entireties:

U.S. patent application Ser. No. 15/668,324, entitled SURGICAL SYSTEM SHAFT INTERCONNECTION;

U.S. patent application Ser. No. 15/668,301, entitled SURGICAL SYSTEM BAILOUT; and U.S. patent application Ser. No. 15/668,319, entitled SURGICAL SYSTEM COMPRISING AN ARTICULATION BAILOUT.

Applicant of the present application owns the following U.S. Patent Applications that were filed on Jun. 28, 2017 and which are each herein incorporated by reference in their respective entireties:

U.S. patent application Ser. No. 15/635,693, entitled SURGICAL INSTRUMENT COMPRISING AN OFFSET ARTICULATION JOINT;

U.S. patent application Ser. No. 15/635,729, entitled SURGICAL INSTRUMENT COMPRISING AN ARTICULATION SYSTEM RATIO;

U.S. patent application Ser. No. 15/635,785, entitled SURGICAL INSTRUMENT COMPRISING AN ARTICULATION SYSTEM RATIO;

U.S. patent application Ser. No. 15/635,808, entitled SURGICAL INSTRUMENT COMPRISING FIRING MEMBER SUPPORTS;

U.S. patent application Ser. No. 15/635,837, entitled SURGICAL INSTRUMENT COMPRISING AN ARTICULATION SYSTEM LOCKABLE TO A FRAME;

U.S. patent application Ser. No. 15/635,941, entitled SURGICAL INSTRUMENT COMPRISING AN ARTICULATION SYSTEM LOCKABLE BY A CLOSURE SYSTEM;

U.S. patent application Ser. No. 15/636,029, entitled SURGICAL INSTRUMENT COMPRISING A SHAFT INCLUDING A HOUSING ARRANGEMENT;

U.S. patent application Ser. No. 15/635,958, entitled SURGICAL INSTRUMENT COMPRISING SELECTIVELY ACTUATABLE ROTATABLE COUPLERS;

U.S. patent application Ser. No. 15/635,981, entitled SURGICAL STAPLING INSTRUMENTS COMPRISING SHORTENED STAPLE CARTRIDGE NOSES;

U.S. patent application Ser. No. 15/636,009, entitled SURGICAL INSTRUMENT COMPRISING A SHAFT INCLUDING A CLOSURE TUBE PROFILE;

U.S. patent application Ser. No. 15/635,663, entitled METHOD FOR ARTICULATING A SURGICAL INSTRUMENT;

U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS;

U.S. patent application Ser. No. 15/635,549, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS;

U.S. patent application Ser. No. 15/635,578, entitled SURGICAL END EFFECTORS WITH IMPROVED JAW APERTURE ARRANGEMENTS;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT AXIS;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW;

U.S. patent application Ser. No. 15/635,621, entitled SURGICAL INSTRUMENT WITH POSITIVE JAW OPENING FEATURES;

U.S. patent application Ser. No. 15/635,631, entitled SURGICAL INSTRUMENT WITH AXIALLY MOVABLE CLOSURE MEMBER;

U.S. patent application Ser. No. 15/635,521, entitled SURGICAL INSTRUMENT LOCKOUT ARRANGEMENT;

U.S. Design patent application Ser. No. 29/609,083, entitled SURGICAL INSTRUMENT SHAFT;

U.S. Design patent application Ser. No. 29/609,087, entitled SURGICAL FORMING ANVIL;

U.S. Design patent application Ser. No. 29/609,093, entitled SURGICAL FASTENER CARTRIDGE;

U.S. Design patent application Ser. No. 29/609,121, entitled SURGICAL INSTRUMENT;

U.S. Design patent application Ser. No. 29/609,125, entitled SURGICAL INSTRUMENT;

U.S. Design patent application Ser. No. 29/609,128, entitled SURGICAL INSTRUMENT; and U.S. Design patent application Ser. No. 29/609,129, entitled DISPLAY SCREEN PORTION OF A SURGICAL INSTRUMENT HAVING A GRAPHICAL USER INTERFACE.

Applicant of the present application owns the following U.S. Patent Applications that were filed on Jun. 27, 2017 and which are each herein incorporated by reference in their respective entireties:

U.S. patent application Ser. No. 15/634,024, entitled SURGICAL ANVIL MANUFACTURING METHODS;

U.S. patent application Ser. No. 15/634,035, entitled SURGICAL ANVIL ARRANGEMENTS;

U.S. patent application Ser. No. 15/634,046, entitled SURGICAL ANVIL ARRANGEMENTS;

U.S. patent application Ser. No. 15/634,054, entitled SURGICAL ANVIL ARRANGEMENTS;

U.S. patent application Ser. No. 15/634,068, entitled SURGICAL FIRING MEMBER ARRANGEMENTS;

U.S. patent application Ser. No. 15/634,076, entitled STAPLE FORMING POCKET ARRANGEMENTS;

U.S. patent application Ser. No. 15/634,090, entitled STAPLE FORMING POCKET ARRANGEMENTS;

U.S. patent application Ser. No. 15/634,099, entitled SURGICAL END EFFECTORS AND ANVILS; and U.S. patent application Ser. No. 15/634,117, entitled ARTICULATION SYSTEMS FOR SURGICAL INSTRUMENTS.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,230, entitled ARTICULATABLE SURGICAL STAPLING INSTRUMENTS;

U.S. patent application Ser. No. 15/386,221, entitled LOCKOUT ARRANGEMENTS FOR SURGICAL END EFFECTORS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES;

U.S. patent application Ser. No. 15/386,240, entitled SURGICAL END EFFECTORS AND ADAPTABLE FIRING MEMBERS THEREFOR;

U.S. patent application Ser. No. 15/385,939, entitled STAPLE CARTRIDGES AND ARRANGEMENTS OF STAPLES AND STAPLE CAVITIES THEREIN;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TISSUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;
U.S. patent application Ser. No. 15/385,948, entitled SURGICAL STAPLING INSTRUMENTS AND STAPLE-FORMING ANVILS;
U.S. patent application Ser. No. 15/385,956, entitled SURGICAL INSTRUMENTS WITH POSITIVE JAW OPENING FEATURES;
U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT;
U.S. patent application Ser. No. 15/385,947, entitled STAPLE CARTRIDGES AND ARRANGEMENTS OF STAPLES AND STAPLE CAVITIES THEREIN;
U.S. patent application Ser. No. 15/385,896, entitled METHOD FOR RESETTING A FUSE OF A SURGICAL INSTRUMENT SHAFT;
U.S. patent application Ser. No. 15/385,898, entitled STAPLE FORMING POCKET ARRANGEMENT TO ACCOMMODATE DIFFERENT TYPES OF STAPLES;
U.S. patent application Ser. No. 15/385,899, entitled SURGICAL INSTRUMENT COMPRISING IMPROVED JAW CONTROL;
U.S. patent application Ser. No. 15/385,901, entitled STAPLE CARTRIDGE AND STAPLE CARTRIDGE CHANNEL COMPRISING WINDOWS DEFINED THEREIN;
U.S. patent application Ser. No. 15/385,902, entitled SURGICAL INSTRUMENT COMPRISING A CUTTING MEMBER;
U.S. patent application Ser. No. 15/385,904, entitled STAPLE FIRING MEMBER COMPRISING A MISSING CARTRIDGE AND/OR SPENT CARTRIDGE LOCKOUT;
U.S. patent application Ser. No. 15/385,905, entitled FIRING ASSEMBLY COMPRISING A LOCKOUT;
U.S. patent application Ser. No. 15/385,907, entitled SURGICAL INSTRUMENT SYSTEM COMPRISING AN END EFFECTOR LOCKOUT AND A FIRING ASSEMBLY LOCKOUT;
U.S. patent application Ser. No. 15/385,908, entitled FIRING ASSEMBLY COMPRISING A FUSE;
U.S. patent application Ser. No. 15/385,909, entitled FIRING ASSEMBLY COMPRISING A MULTIPLE FAILED-STATE FUSE;
U.S. patent application Ser. No. 15/385,920, entitled STAPLE FORMING POCKET ARRANGEMENTS;
U.S. patent application Ser. No. 15/385,913, entitled ANVIL ARRANGEMENTS FOR SURGICAL STAPLE/FASTENERS;
U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;
U.S. patent application Ser. No. 15/385,893, entitled BILATERALLY ASYMMETRIC STAPLE FORMING POCKET PAIRS;
U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;
U.S. patent application Ser. No. 15/385,911, entitled SURGICAL STAPLE/FASTENERS WITH INDEPENDENTLY ACTUATABLE CLOSING AND FIRING SYSTEMS;
U.S. patent application Ser. No. 15/385,927, entitled SURGICAL STAPLING INSTRUMENTS WITH SMART STAPLE CARTRIDGES;
U.S. patent application Ser. No. 15/385,917, entitled STAPLE CARTRIDGE COMPRISING STAPLES WITH DIFFERENT CLAMPING BREADTHS;
U.S. patent application Ser. No. 15/385,900, entitled STAPLE FORMING POCKET ARRANGEMENTS COMPRISING PRIMARY SIDEWALLS AND POCKET SIDEWALLS;
U.S. patent application Ser. No. 15/385,931, entitled NO-CARTRIDGE AND SPENT CARTRIDGE LOCKOUT ARRANGEMENTS FOR SURGICAL STAPLE/FASTENERS;
U.S. patent application Ser. No. 15/385,915, entitled FIRING MEMBER PIN ANGLE;
U.S. patent application Ser. No. 15/385,897, entitled STAPLE FORMING POCKET ARRANGEMENTS COMPRISING ZONED FORMING SURFACE GROOVES;
U.S. patent application Ser. No. 15/385,922, entitled SURGICAL INSTRUMENT WITH MULTIPLE FAILURE RESPONSE MODES;
U.S. patent application Ser. No. 15/385,924, entitled SURGICAL INSTRUMENT WITH PRIMARY AND SAFETY PROCESSORS;
U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;
U.S. patent application Ser. No. 15/385,910, entitled ANVIL HAVING A KNIFE SLOT WIDTH;
U.S. patent application Ser. No. 15/385,906, entitled FIRING MEMBER PIN CONFIGURATIONS;
U.S. patent application Ser. No. 15/386,188, entitled STEPPED STAPLE CARTRIDGE WITH ASYMMETRICAL STAPLES;
U.S. patent application Ser. No. 15/386,192, entitled STEPPED STAPLE CARTRIDGE WITH TISSUE RETENTION AND GAP SETTING FEATURES;
U.S. patent application Ser. No. 15/386,206, entitled STAPLE CARTRIDGE WITH DEFORMABLE DRIVER RETENTION FEATURES;
U.S. patent application Ser. No. 15/386,226, entitled DURABILITY FEATURES FOR END EFFECTORS AND FIRING ASSEMBLIES OF SURGICAL STAPLING INSTRUMENTS;
U.S. patent application Ser. No. 15/386,222, entitled SURGICAL STAPLING INSTRUMENTS HAVING END EFFECTORS WITH POSITIVE OPENING FEATURES;
U.S. patent application Ser. No. 15/386,236, entitled CONNECTION PORTIONS FOR DEPOSABLE LOADING UNITS FOR SURGICAL STAPLING INSTRUMENTS;
U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;
U.S. patent application Ser. No. 15/385,889, entitled SHAFT ASSEMBLY COMPRISING A MANUALLY- OPERABLE RETRACTION SYSTEM FOR USE WITH A MOTORIZED SURGICAL INSTRUMENT SYSTEM;
- U.S. patent application Ser. No. 15/385,890, entitled SHAFT ASSEMBLY COMPRISING SEPARATELY ACTUATABLE AND RETRACTABLE SYSTEMS;
- U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS;
- U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;
- U.S. patent application Ser. No. 15/385,894, entitled SHAFT ASSEMBLY COMPRISING A LOCKOUT;
- U.S. patent application Ser. No. 15/385,895, entitled SHAFT ASSEMBLY COMPRISING FIRST AND SECOND ARTICULATION LOCKOUTS;
- U.S. patent application Ser. No. 15/385,916, entitled SURGICAL STAPLING SYSTEMS;
- U.S. patent application Ser. No. 15/385,918, entitled SURGICAL STAPLING SYSTEMS;
- U.S. patent application Ser. No. 15/385,919, entitled SURGICAL STAPLING SYSTEMS;
- U.S. patent application Ser. No. 15/385,921, entitled SURGICAL STAPLE/FASTENER CARTRIDGE WITH MOVABLE CAMMING MEMBER CONFIGURED TO DISENGAGE FIRING MEMBER LOCKOUT FEATURES;
- U.S. patent application Ser. No. 15/385,923, entitled SURGICAL STAPLING SYSTEMS;
- U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;
- U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;
- U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;
- U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;
- U.S. patent application Ser. No. 15/385,932, entitled ARTICULATABLE SURGICAL END EFFECTOR WITH ASYMMETRIC SHAFT ARRANGEMENT;
- U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;
- U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;
- U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and
- U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. Patent Applications that were filed on Jun. 24, 2016 and which are each herein incorporated by reference in their respective entireties:
- U.S. patent application Ser. No. 15/191,775, entitled STAPLE CARTRIDGE COMPRISING WIRE STAPLES AND STAMPED STAPLES;
- U.S. patent application Ser. No. 15/191,807, entitled STAPLING SYSTEM FOR USE WITH WIRE STAPLES AND STAMPED STAPLES;
- U.S. patent application Ser. No. 15/191,834, entitled STAMPED STAPLES AND STAPLE CARTRIDGES USING THE SAME;
- U.S. patent application Ser. No. 15/191,788, entitled STAPLE CARTRIDGE COMPRISING OVERDRIVEN STAPLES; and
- U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:
- U.S. Design patent application Ser. No. 29/569,218, entitled SURGICAL FASTENER; U.S. Design patent application Ser. No. 29/569,227, entitled SURGICAL FASTENER;
- U.S. Design patent application Ser. No. 29/569,259, entitled SURGICAL FASTENER CARTRIDGE; and
- U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:
- U.S. patent application Ser. No. 15/089,325, entitled METHOD FOR OPERATING A SURGICAL STAPLING SYSTEM;
- U.S. patent application Ser. No. 15/089,321, entitled MODULAR SURGICAL STAPLING SYSTEM COMPRISING A DISPLAY;
- U.S. patent application Ser. No. 15/089,326, entitled SURGICAL STAPLING SYSTEM COMPRISING A DISPLAY INCLUDING A RE-ORIENTABLE DISPLAY FIELD;
- U.S. patent application Ser. No. 15/089,263, entitled SURGICAL INSTRUMENT HANDLE ASSEMBLY WITH RECONFIGURABLE GRIP PORTION;
- U.S. patent application Ser. No. 15/089,262, entitled ROTARY POWERED SURGICAL INSTRUMENT WITH MANUALLY ACTUATABLE BAILOUT SYSTEM;
- U.S. patent application Ser. No. 15/089,277, entitled SURGICAL CUTTING AND STAPLING END EFFECTOR WITH ANVIL CONCENTRIC DRIVE MEMBER;
- U.S. patent application Ser. No. 15/089,296, entitled INTERCHANGEABLE SURGICAL TOOL ASSEM- BLY WITH A SURGICAL END EFFECTOR THAT IS SELECTIVELY ROTATABLE ABOUT A SHAFT AXIS;
- U.S. patent application Ser. No. 15/089,258, entitled SURGICAL STAPLING SYSTEM COMPRISING A SHIFTABLE TRANSMISSION;
- U.S. patent application Ser. No. 15/089,278, entitled SURGICAL STAPLING SYSTEM CONFIGURED TO PROVIDE SELECTIVE CUTTING OF TISSUE;
- U.S. patent application Ser. No. 15/089,284, entitled SURGICAL STAPLING SYSTEM COMPRISING A CONTOURABLE SHAFT;
- U.S. patent application Ser. No. 15/089,295, entitled SURGICAL STAPLING SYSTEM COMPRISING A TISSUE COMPRESSION LOCKOUT;
- U.S. patent application Ser. No. 15/089,300, entitled SURGICAL STAPLING SYSTEM COMPRISING AN UNCLAMPING LOCKOUT;
- U.S. patent application Ser. No. 15/089,196, entitled SURGICAL STAPLING SYSTEM COMPRISING A JAW CLOSURE LOCKOUT;
- U.S. patent application Ser. No. 15/089,203, entitled SURGICAL STAPLING SYSTEM COMPRISING A JAW ATTACHMENT LOCKOUT;
- U.S. patent application Ser. No. 15/089,210, entitled SURGICAL STAPLING SYSTEM COMPRISING A SPENT CARTRIDGE LOCKOUT;
- U.S. patent application Ser. No. 15/089,324, entitled SURGICAL INSTRUMENT COMPRISING A SHIFTING MECHANISM;
- U.S. patent application Ser. No. 15/089,335, entitled SURGICAL STAPLING INSTRUMENT COMPRISING MULTIPLE LOCKOUTS;
- U.S. patent application Ser. No. 15/089,339, entitled SURGICAL STAPLING INSTRUMENT;
- U.S. patent application Ser. No. 15/089,253, entitled SURGICAL STAPLING SYSTEM CONFIGURED TO APPLY ANNULAR ROWS OF STAPLES HAVING DIFFERENT HEIGHTS;
- U.S. patent application Ser. No. 15/089,304, entitled SURGICAL STAPLING SYSTEM COMPRISING A GROOVED FORMING POCKET;
- U.S. patent application Ser. No. 15/089,331, entitled ANVIL MODIFICATION MEMBERS FOR SURGICAL STAPLE/FASTENERS;
- U.S. patent application Ser. No. 15/089,336, entitled STAPLE CARTRIDGES WITH ATRAUMATIC FEATURES;
- U.S. patent application Ser. No. 15/089,312, entitled CIRCULAR STAPLING SYSTEM COMPRISING AN INCISABLE TISSUE SUPPORT;
- U.S. patent application Ser. No. 15/089,309, entitled CIRCULAR STAPLING SYSTEM COMPRISING ROTARY FIRING SYSTEM; and
- U.S. patent application Ser. No. 15/089,349, entitled CIRCULAR STAPLING SYSTEM COMPRISING LOAD CONTROL.

Applicant of the present application also owns the U.S. Patent Applications identified below which were filed on Dec. 31, 2015 which are each herein incorporated by reference in their respective entirety:

- U.S. patent application Ser. No. 14/984,488, entitled MECHANISMS FOR COMPENSATING FOR BATTERY PACK FAILURE IN POWERED SURGICAL INSTRUMENTS;
- U.S. patent application Ser. No. 14/984,525, entitled MECHANISMS FOR COMPENSATING FOR DRIVETRAIN FAILURE IN POWERED SURGICAL INSTRUMENTS; and
- U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entirety:

- U.S. patent application Ser. No. 15/019,220, entitled SURGICAL INSTRUMENT WITH ARTICULATING AND AXIALLY TRANSLATABLE END EFFECTOR;
- U.S. patent application Ser. No. 15/019,228, entitled SURGICAL INSTRUMENTS WITH MULTIPLE LINK ARTICULATION ARRANGEMENTS;
- U.S. patent application Ser. No. 15/019,196, entitled SURGICAL INSTRUMENT ARTICULATION MECHANISM WITH SLOTTED SECONDARY CONSTRAINT;
- U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;
- U.S. patent application Ser. No. 15/019,215, entitled SURGICAL INSTRUMENTS WITH NON-SYMMETRICAL ARTICULATION ARRANGEMENTS;
- U.S. patent application Ser. No. 15/019,227, entitled ARTICULATABLE SURGICAL INSTRUMENTS WITH SINGLE ARTICULATION LINK ARRANGEMENTS;
- U.S. patent application Ser. No. 15/019,235, entitled SURGICAL INSTRUMENTS WITH TENSIONING ARRANGEMENTS FOR CABLE DRIVEN ARTICULATION SYSTEMS;
- U.S. patent application Ser. No. 15/019,230, entitled ARTICULATABLE SURGICAL INSTRUMENTS WITH OFF-AXIS FIRING BEAM ARRANGEMENTS; and
- U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entirety:

- U.S. patent application Ser. No. 15/043,254, entitled MECHANISMS FOR COMPENSATING FOR DRIVETRAIN FAILURE IN POWERED SURGICAL INSTRUMENTS;
- U.S. patent application Ser. No. 15/043,259, entitled MECHANISMS FOR COMPENSATING FOR DRIVETRAIN FAILURE IN POWERED SURGICAL INSTRUMENTS;
- U.S. patent application Ser. No. 15/043,275, entitled MECHANISMS FOR COMPENSATING FOR DRIVETRAIN FAILURE IN POWERED SURGICAL INSTRUMENTS; and
- U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entirety:

- U.S. patent application Ser. No. 14/742,925, entitled SURGICAL END EFFECTORS WITH POSITIVE JAW OPENING ARRANGEMENTS, now U.S. Pat. No. 10,182,818;
- U.S. patent application Ser. No. 14/742,941, entitled SURGICAL END EFFECTORS WITH DUAL CAM ACTUATED JAW CLOSING FEATURES, now U.S. Pat. No. 10,052,102;
- U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;
- U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;
- U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and
- U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

- U.S. patent application Ser. No. 14/640,746, entitled POWERED SURGICAL INSTRUMENT, now U.S. Pat. No. 9,808,246;
- U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;
- U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;
- U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;
- U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,985,148;
- U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;
- U.S. patent application Ser. No. 14/640,817, entitled INTERACTIVE FEEDBACK SYSTEM FOR POWERED SURGICAL INSTRUMENTS, now U.S. Pat. No. 9,924,961;
- U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;
- U.S. patent application Ser. No. 14/640,837, entitled SMART SENSORS WITH LOCAL SIGNAL PROCESSING, now U.S. Pat. No. 9,993,248;
- U.S. patent application Ser. No. 14/640,765, entitled SYSTEM FOR DETECTING THE MIS-INSERTION OF A STAPLE CARTRIDGE INTO A SURGICAL STAPLE/FASTENER, now U.S. Patent Application Publication No. 2016/0256160;
- U.S. patent application Ser. No. 14/640,799, entitled SIGNAL AND POWER COMMUNICATION SYSTEM POSITIONED ON A ROTATABLE SHAFT, now U.S. Pat. No. 9,901,342; and
- U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

- U.S. patent application Ser. No. 14/633,576, entitled SURGICAL INSTRUMENT SYSTEM COMPRISING AN INSPECTION STATION, now U.S. Pat. No. 10,045,779;
- U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;
- U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;
- U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;
- U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;
- U.S. patent application Ser. No. 14/633,542, entitled REINFORCED BATTERY FOR A SURGICAL INSTRUMENT, now U.S. Pat. No. 9,931,118;
- U.S. patent application Ser. No. 14/633,548, entitled POWER ADAPTER FOR A SURGICAL INSTRUMENT, now U.S. Pat. No. 10,245,028;
- U.S. patent application Ser. No. 14/633,526, entitled ADAPTABLE SURGICAL INSTRUMENT HANDLE, now U.S. Pat. No. 9,993,258;
- U.S. patent application Ser. No. 14/633,541, entitled MODULAR STAPLING ASSEMBLY, now U.S. Pat. No. 10,226,250; and
- U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

- U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;
- U.S. patent application Ser. No. 14/574,483, entitled SURGICAL INSTRUMENT ASSEMBLY COMPRISING LOCKABLE SYSTEMS, now U.S. Pat. No. 10,188,385;
- U.S. patent application Ser. No. 14/575,139, entitled DRIVE ARRANGEMENTS FOR ARTICULATABLE SURGICAL INSTRUMENTS, now U.S. Pat. No. 9,844,375;
- U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;
- U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;
- U.S. patent application Ser. No. 14/575,143, entitled SURGICAL INSTRUMENTS WITH IMPROVED CLOSURE ARRANGEMENTS, now U.S. Pat. No. 10,004,501;
- U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;
- U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;
- U.S. patent application Ser. No. 14/574,493, entitled SURGICAL INSTRUMENT ASSEMBLY COMPRISING A FLEXIBLE ARTICULATION SYSTEM, now U.S. Pat. No. 9,897,000; and
- U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

- U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;
- U.S. patent application Ser. No. 13/782,323, entitled ROTARY POWERED ARTICULATION JOINTS FOR SURGICAL INSTRUMENTS, now U.S. Pat. No. 9,782,169;
- U.S. patent application Ser. No. 13/782,338, entitled THUMBWHEEL SWITCH ARRANGEMENTS FOR SURGICAL INSTRUMENTS, now U.S. Patent Application Publication No. 2014/0249557;
- U.S. patent application Ser. No. 13/782,499, entitled ELECTROMECHANICAL SURGICAL DEVICE WITH SIGNAL RELAY ARRANGEMENT, now U.S. Pat. No. 9,358,003;
- U.S. patent application Ser. No. 13/782,460, entitled MULTIPLE PROCESSOR MOTOR CONTROL FOR MODULAR SURGICAL INSTRUMENTS, now U.S. Pat. No. 9,554,794;
- U.S. patent application Ser. No. 13/782,358, entitled JOYSTICK SWITCH ASSEMBLIES FOR SURGICAL INSTRUMENTS, now U.S. Pat. No. 9,326,767;
- U.S. patent application Ser. No. 13/782,481, entitled SENSOR STRAIGHTENED END EFFECTOR DURING REMOVAL THROUGH TROCAR, now U.S. Pat. No. 9,468,438;
- U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;
- U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and
- U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

- U.S. patent application Ser. No. 13/803,097, entitled ARTICULATABLE SURGICAL INSTRUMENT COMPRISING A FIRING DRIVE, now U.S. Pat. No. 9,687,230;
- U.S. patent application Ser. No. 13/803,193, entitled CONTROL ARRANGEMENTS FOR A DRIVE MEMBER OF A SURGICAL INSTRUMENT, now U.S. Pat. No. 9,332,987;
- U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;
- U.S. patent application Ser. No. 13/803,086, entitled ARTICULATABLE SURGICAL INSTRUMENT COMPRISING AN ARTICULATION LOCK, now U.S. Patent Application Publication No. 2014/0263541;
- U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;
- U.S. patent application Ser. No. 13/803,148, entitled MULTI-FUNCTION MOTOR FOR A SURGICAL INSTRUMENT, now U.S. Pat. No. 10,470,762;
- U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;
- U.S. patent application Ser. No. 13/803,117, entitled ARTICULATION CONTROL SYSTEM FOR ARTICULATABLE SURGICAL INSTRUMENTS, now U.S. Pat. No. 9,351,726;
- U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO DETECT MISLOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLE/FASTENER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLE/FASTENER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

A surgical stapling instrument 1000 is illustrated in FIGS. 1-17. The stapling instrument 1000 comprises a shaft 1100, an end effector 1200, and an articulation joint 1300 rotatably connecting the end effector 1200 to the shaft 1100. The articulation joint 1300 comprises an articulatable portion 1310 rotatably connected to a distal end 1110 of the shaft 1100 about a first articulation pivot 1320. The articulatable portion 1310 is also rotatably connected to a proximal end 1210 of the end effector about a second articulation pivot 1330. As a result, the articulatable portion 1310 is rotatable relative to a frame 1120 of the shaft 1100 about a first articulation axis AA1 and the end effector 1200 is rotatable relative to the articulatable portion 1310 about a second articulation axis AA2. The stapling instrument 1000 further comprises an articulation drive system 1500 configured to articulate the end effector 1200 about the articulation joint 1300.

Further to the above, the articulation drive system 1500 comprises first articulation drive cables 1520 attached to the first articulatable portion 1310 and second articulation drive cables 1530 attached to the proximal end 1210 of the end effector 1200. The first articulation drive cables 1520 are operably coupled to one or more electric motors such that, when one of the first articulation drive cables 1520 is pulled proximally, the articulatable portion 1310 articulates in a first direction about the first articulation pivot 1320 and, when the other articulation drive cable 1520 is pulled proximally, the articulatable portion 1310 articulates in a second, or opposite, direction about the first articulation pivot 1320. Similarly, the second articulation drive cables 1530 are operably coupled to one or more electric motors such that, when one of the second articulation drive cables 1530 is pulled proximally, the end effector 1200 articulates in a first direction about the second articulation pivot 1330 and, when the other articulation drive cable 1520 is pulled proximally, the end effector 1200 articulates in a second, or opposite, direction about the second articulation pivot 1330.

The end effector 1200 comprises a first jaw 1220 and a second jaw 1230 which is rotatable relative to the first jaw 1220 about an axis of rotation, or closure axis, CA defined by a pivot 1240. The first jaw 1220 comprises a channel configured to receive a staple cartridge 1400, or any other suitable staple cartridge. The staple cartridge 1400 comprises a cartridge body 1422 (FIG. 4) including staple cavities 1423 (FIG. 4) defined therein, staples removably stored in the staple cavities 1423, and staple drivers configured to support the staples and push the staples out of the cartridge body 1422 during a staple firing stroke. The second jaw 1230 comprises an anvil including staple forming pockets configured to deform the staples when the staples are ejected from the staple cartridge 1400 during the staple firing stroke. The staple cartridge 1400 comprises a tissue support surface 1421 and the second jaw 1230 comprises a tissue compression surface 1231 configured to compress the patient tissue between the jaws 1220 and 1230 when the second jaw 1230 is moved into its closed, or clamped, position. As described in greater detail below, the stapling instrument 1000 comprises a closure drive system 1600 configured to move the second jaw 1230 between an open, unclamped, position, and a closed, clamped, position.

Figure 1:
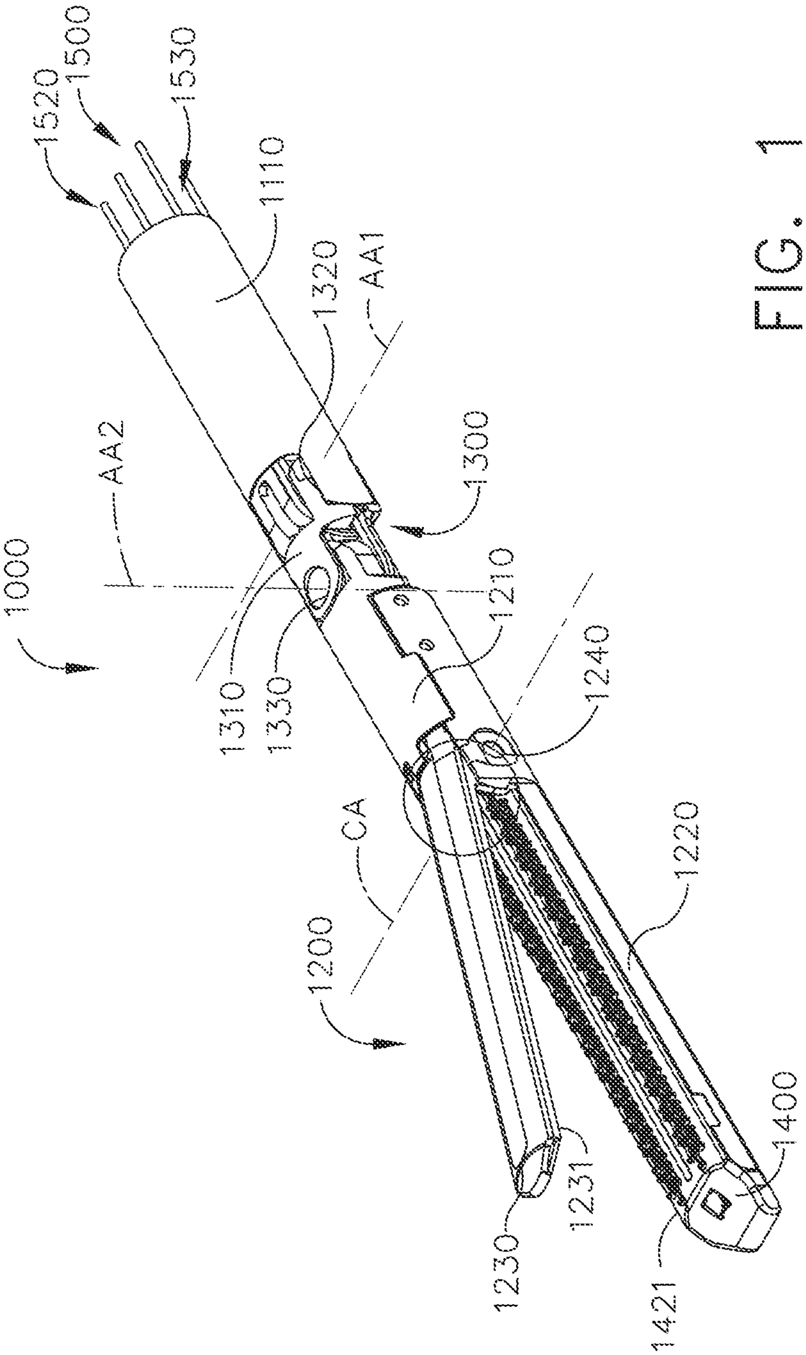
FIG. 1 is a perspective view of a distal end of a surgical stapling instrument in accordance with at least one embodiment.
Figure 2:
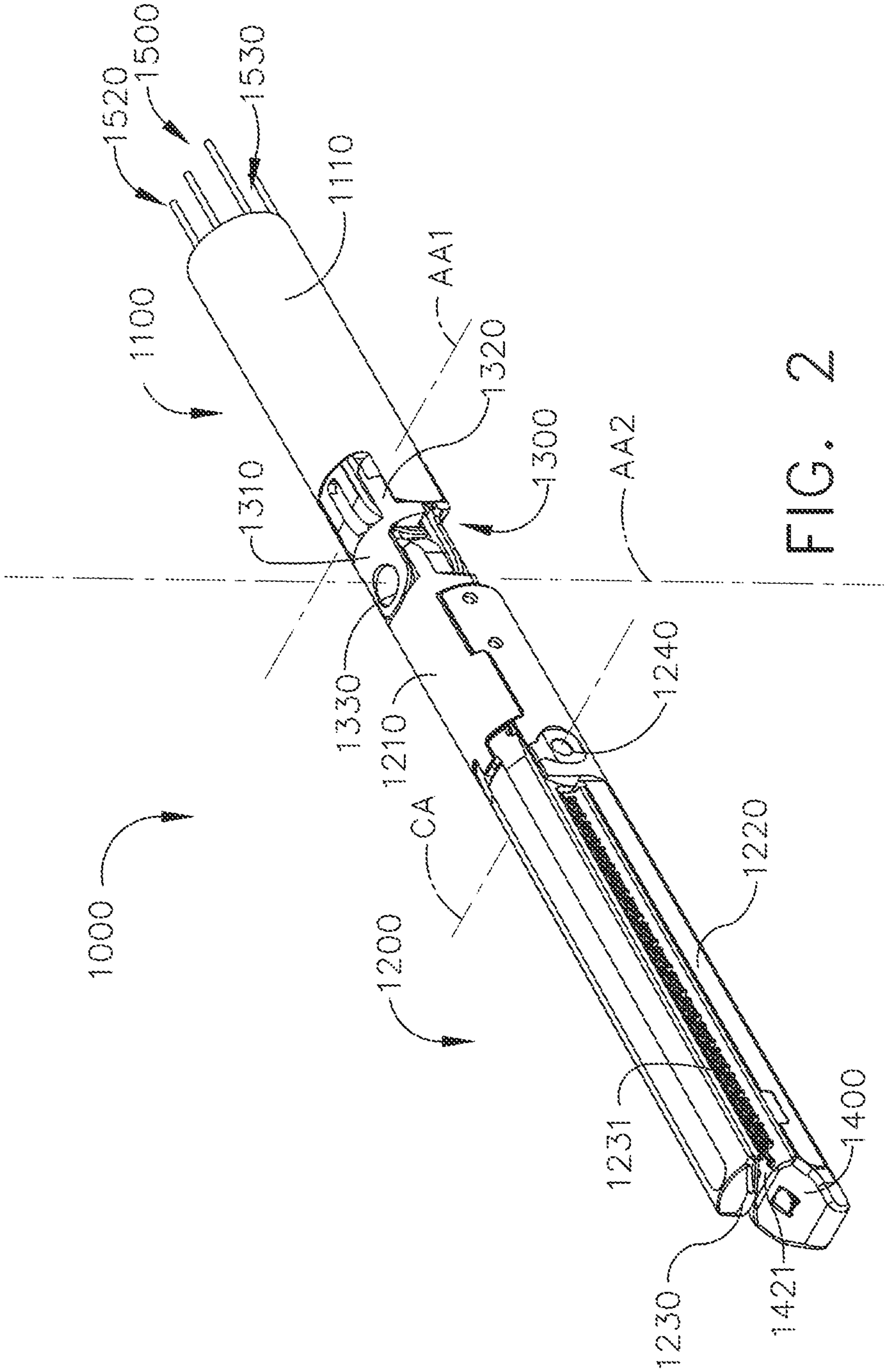
FIG. 2 is a perspective view of the distal end of the stapling instrument of FIG. 1 illustrated in a closed, or clamped, configuration.
Figure 3:
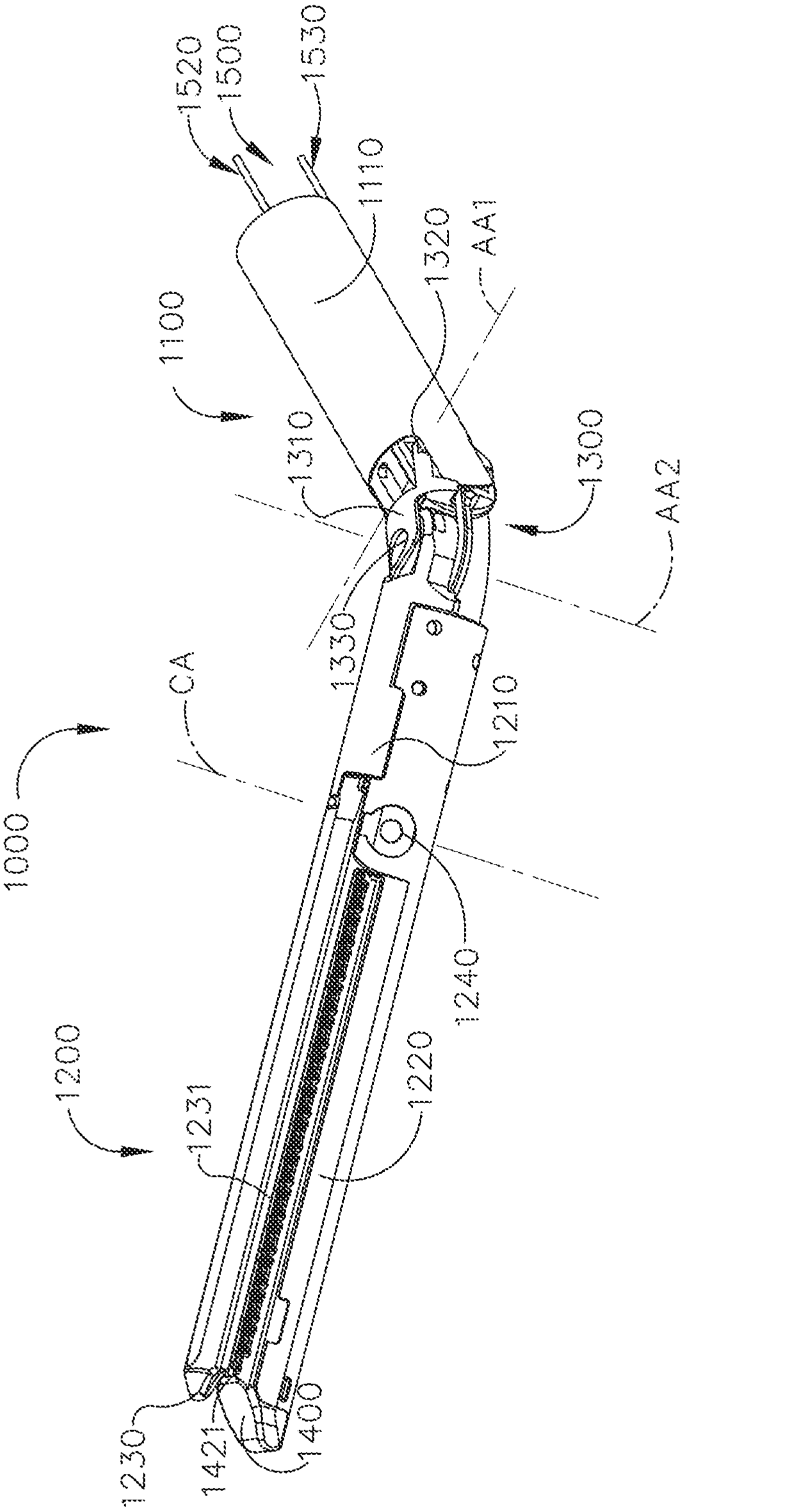
FIG. 3 is a perspective view of the distal end of the stapling instrument of FIG. 1 illustrated in an articulated configuration.
Figure 4:
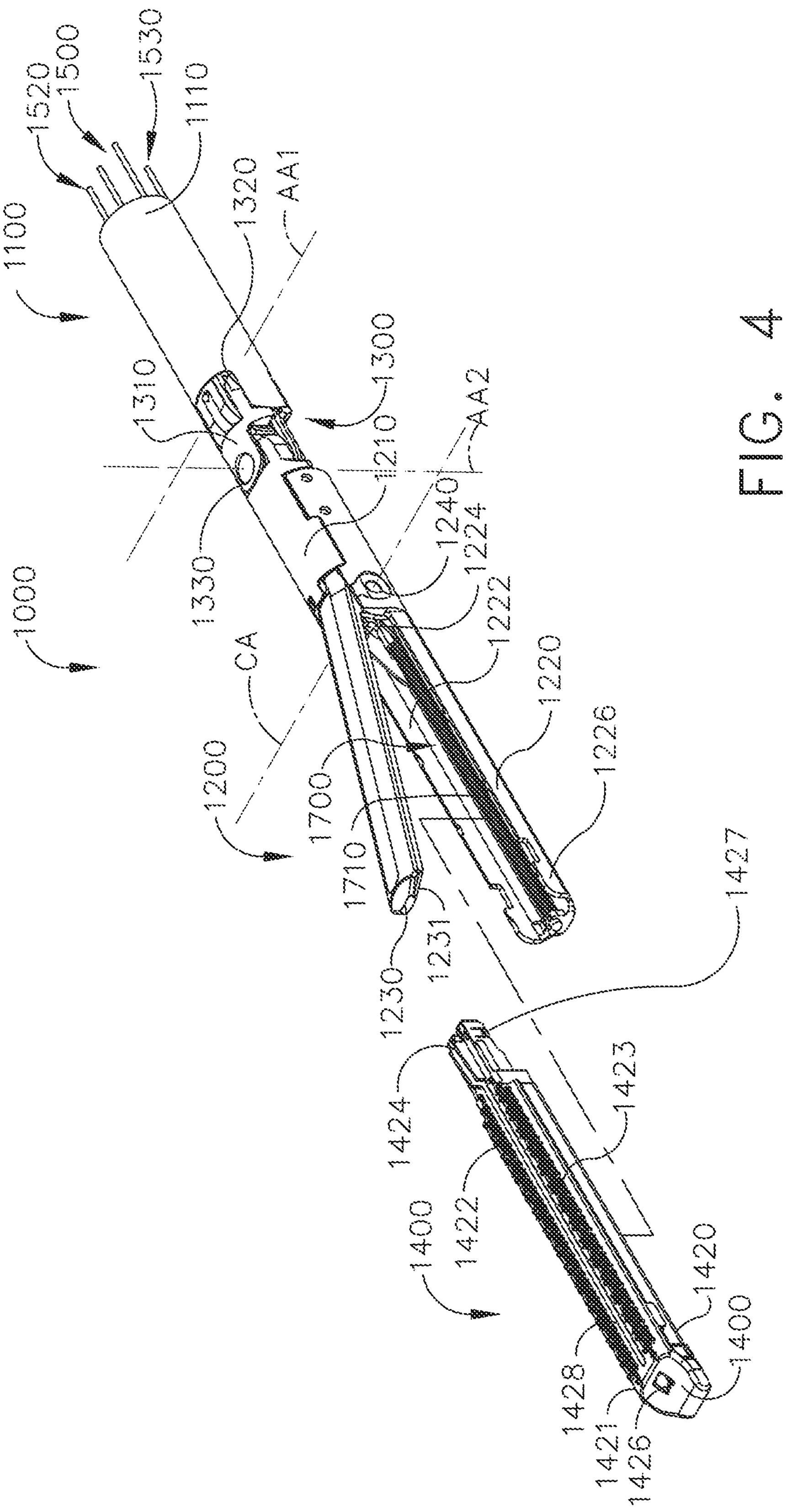
FIG. 4 is a perspective view of a staple cartridge removed from the stapling instrument of FIG. 1.
Figure 5:
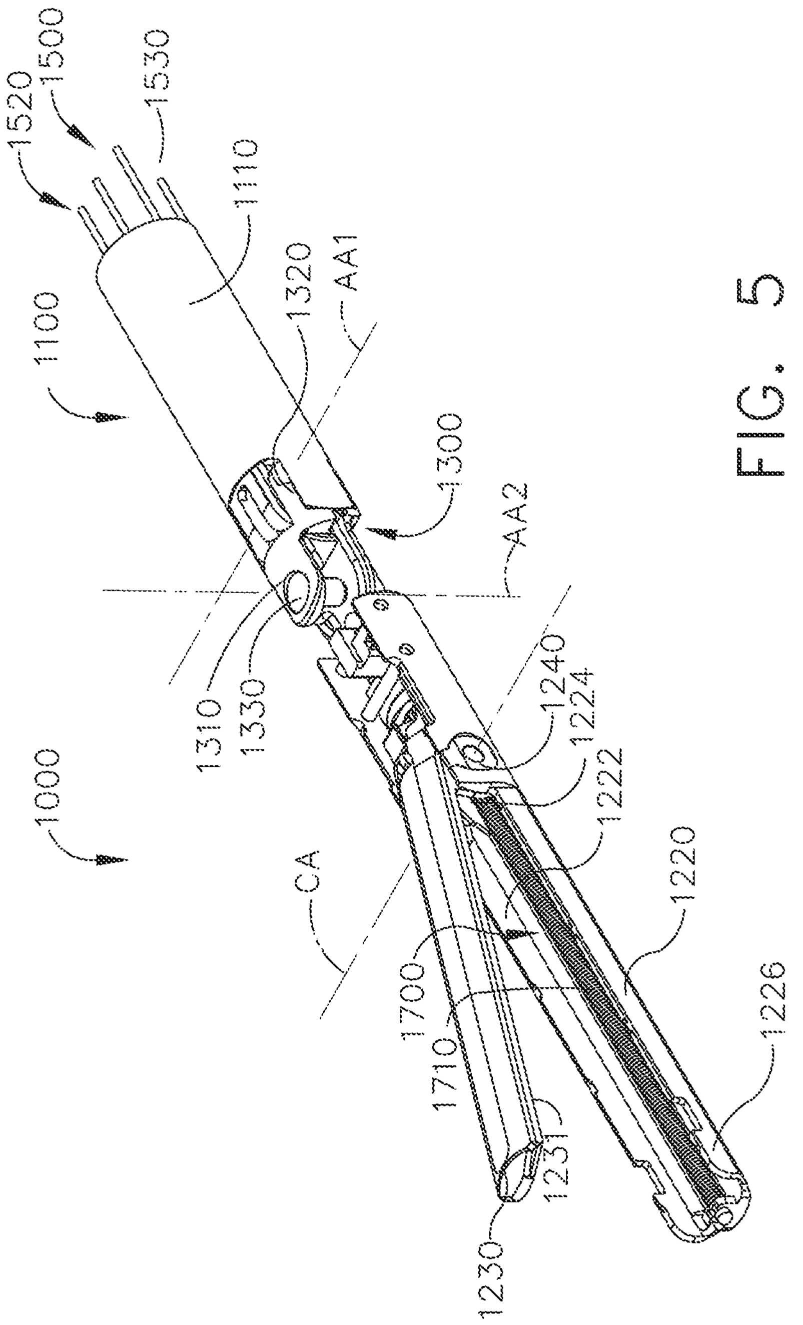
FIG. 5 is a perspective view of the distal end of the stapling instrument of FIG. 1 illustrated with some components removed.
Figure 6:
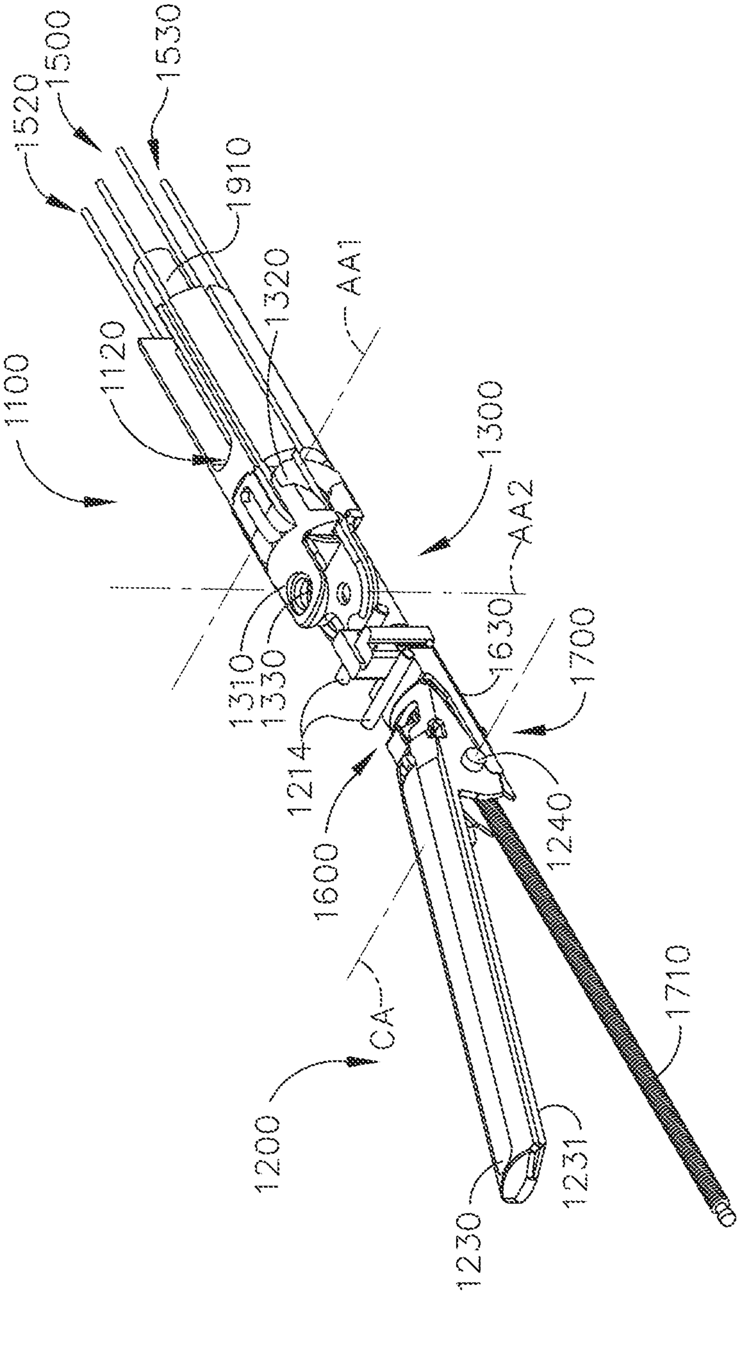
FIG. 6 is a perspective view of the distal end of the stapling instrument of FIG. 1 illustrated with additional components removed.
Figure 7:
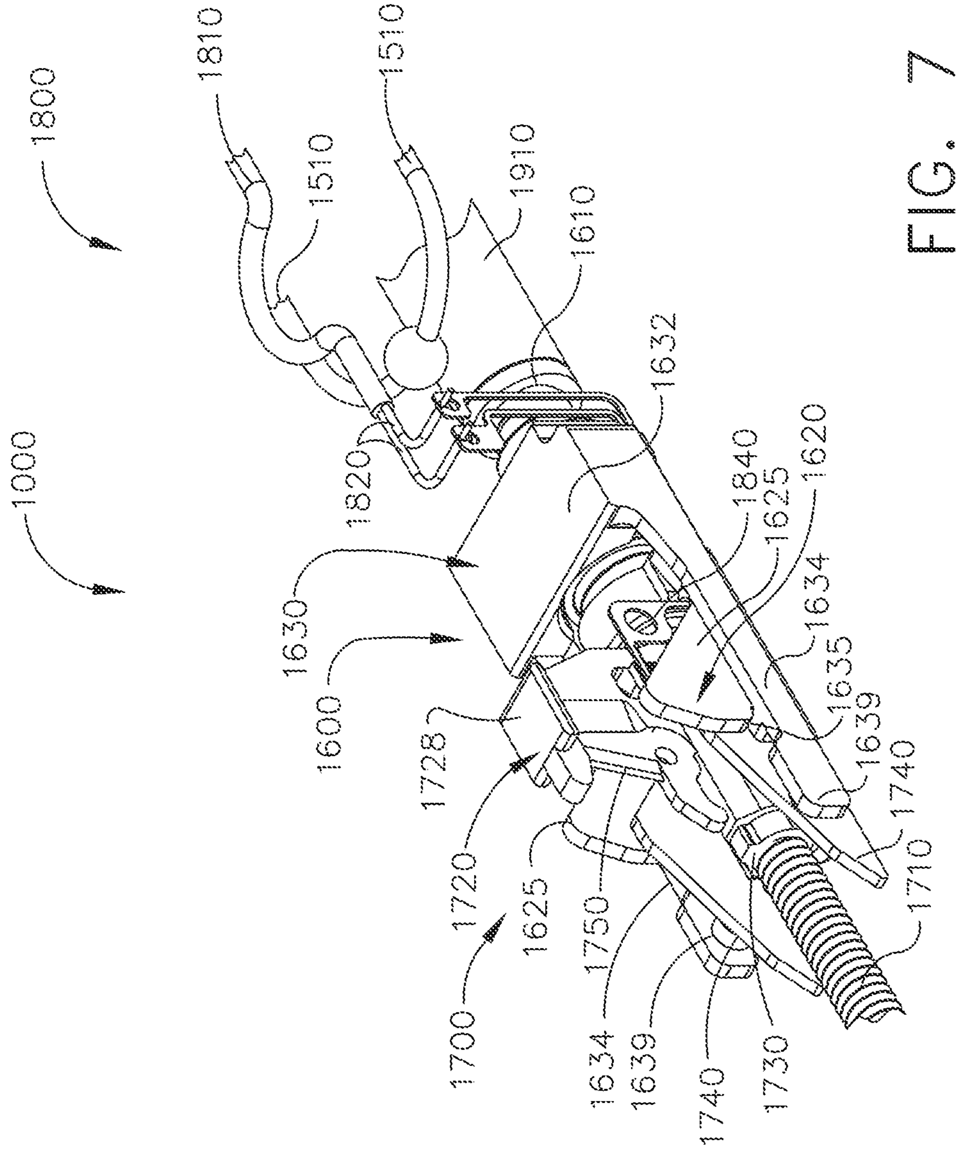
FIG. 7 is a perspective view of a drive system including a quick jaw closure system, a high-load jaw clamping system, and a staple firing system of the stapling instrument of FIG. 1.
Figure 8:
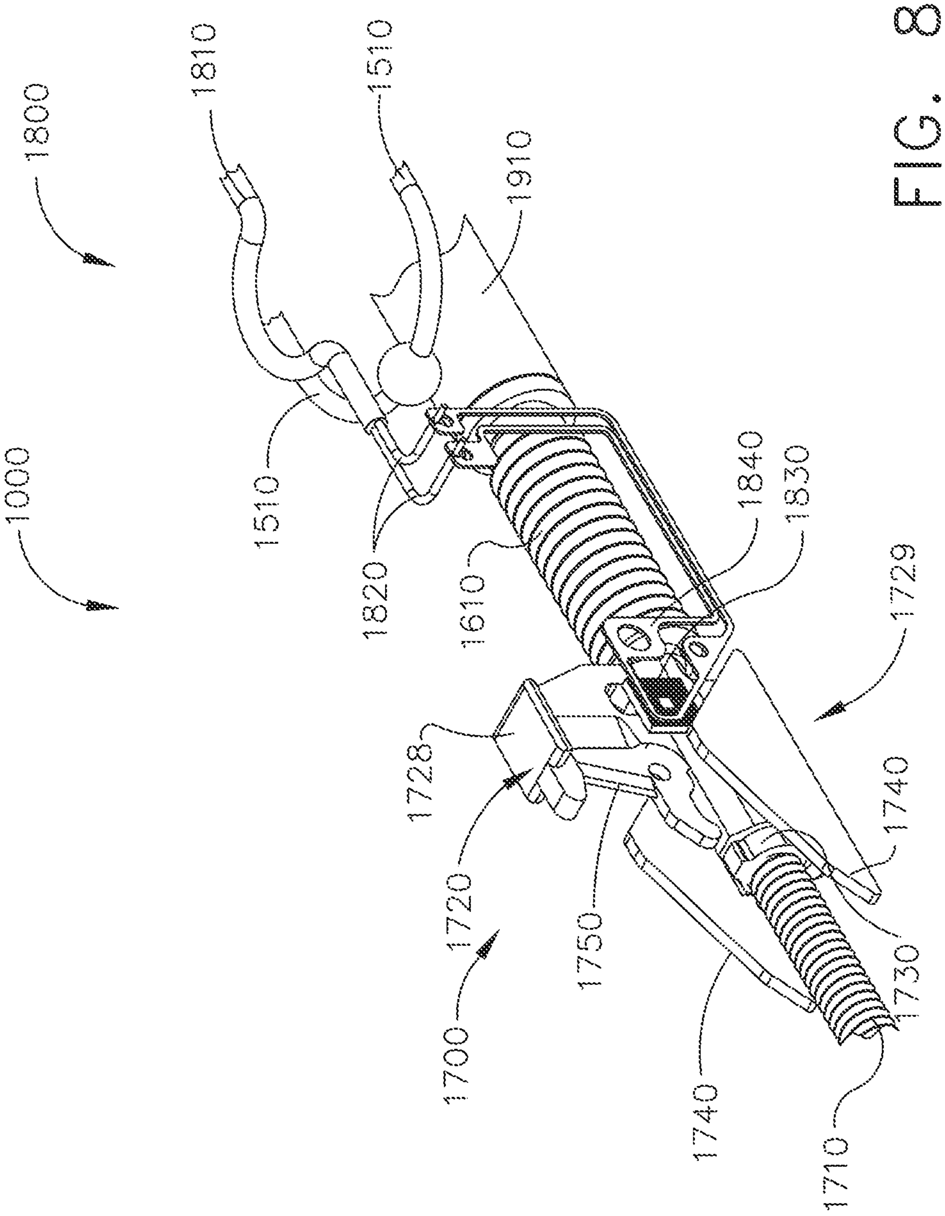
FIG. 8 is a perspective view of the staple firing system of FIG. 7.
Figure 9:
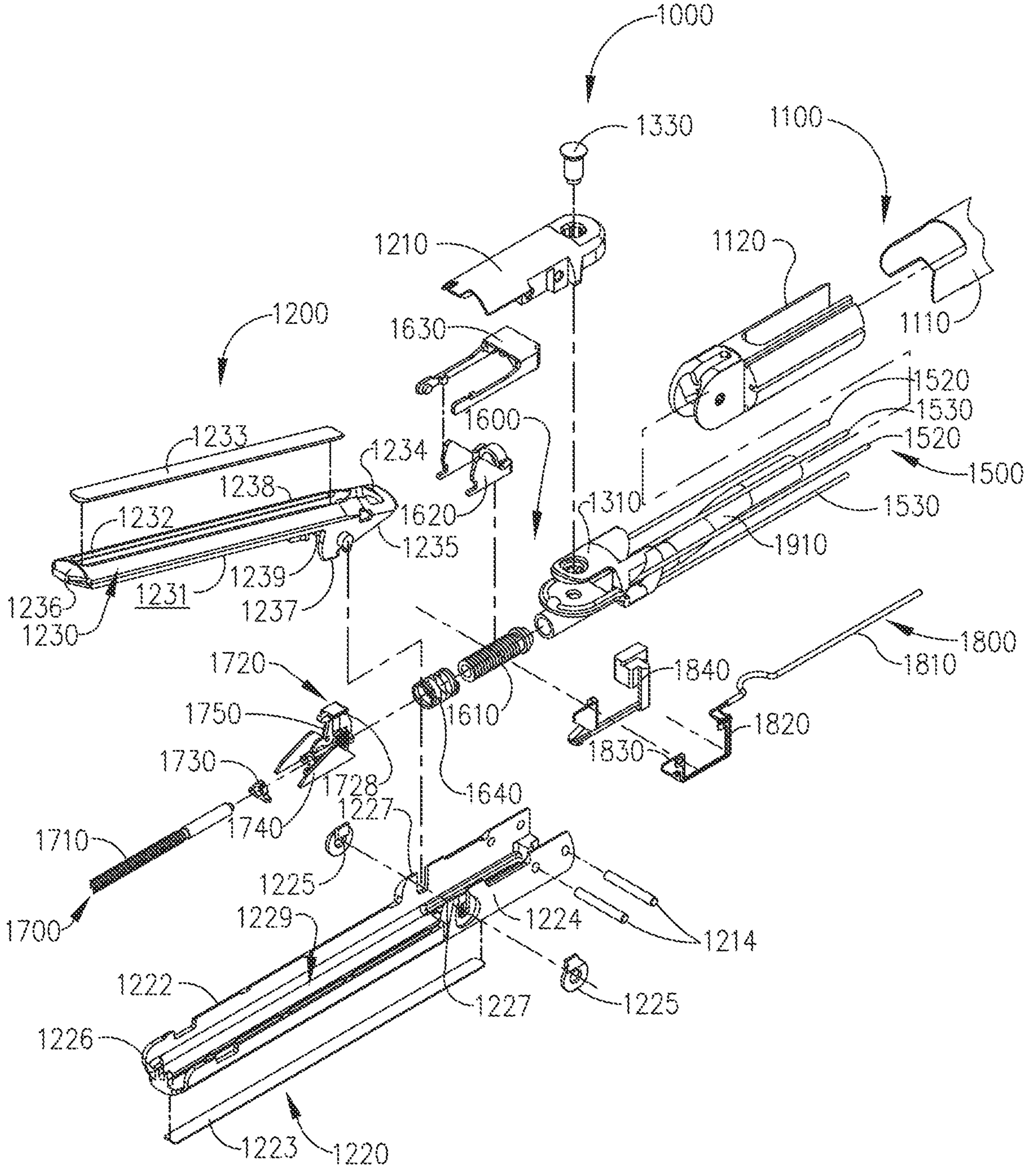
FIG. 9 is an exploded view of the distal end of the stapling instrument of FIG. 1.
Figure 10:
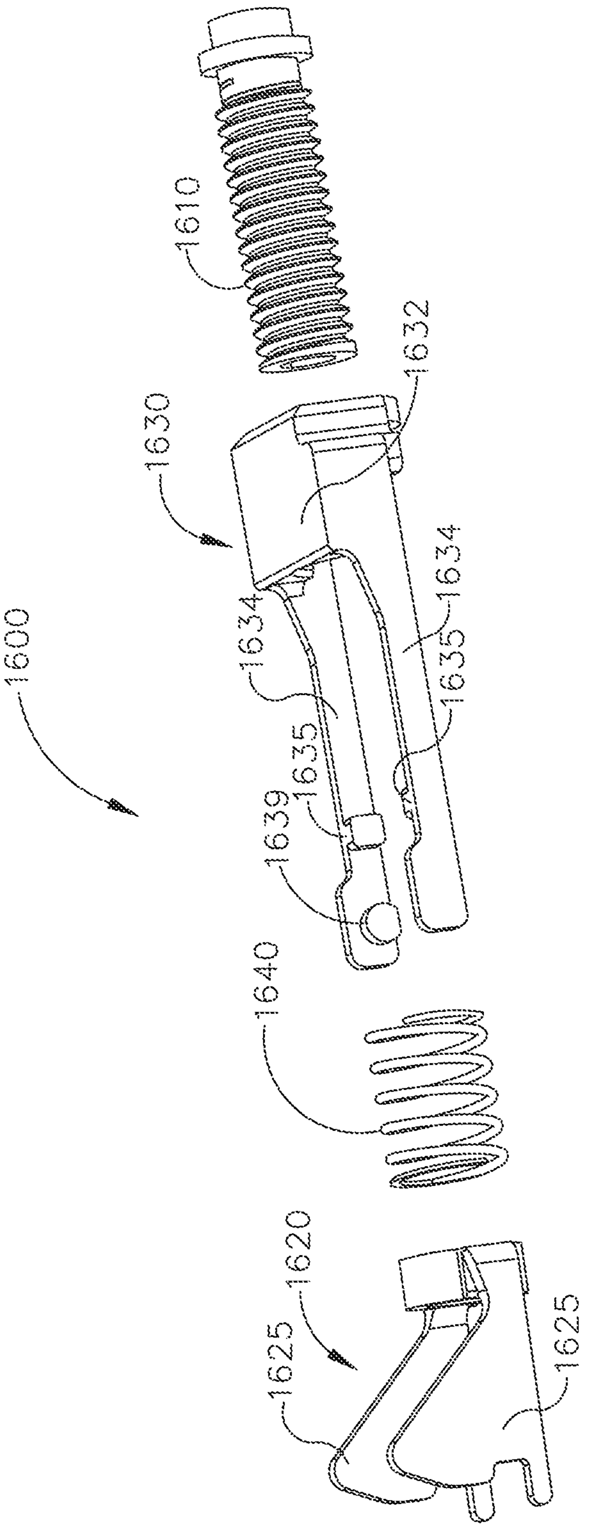
FIG. 10 is an exploded view of the quick jaw closure system and the high-load jaw clamping system of FIG. 7.
Figure 11:
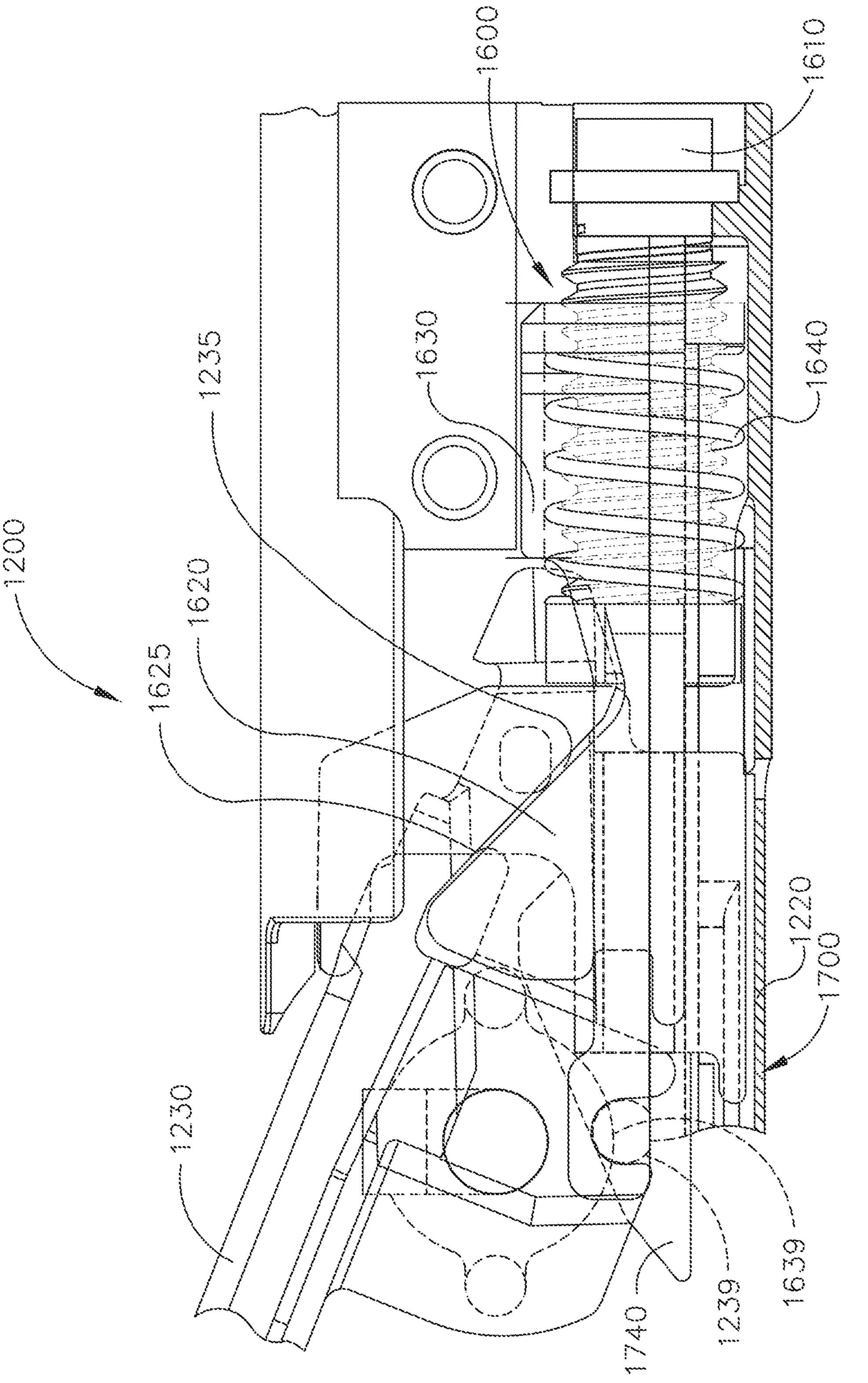
FIG. 11 illustrates an anvil jaw of the stapling instrument of FIG. 1 in an open position.
Figure 12:
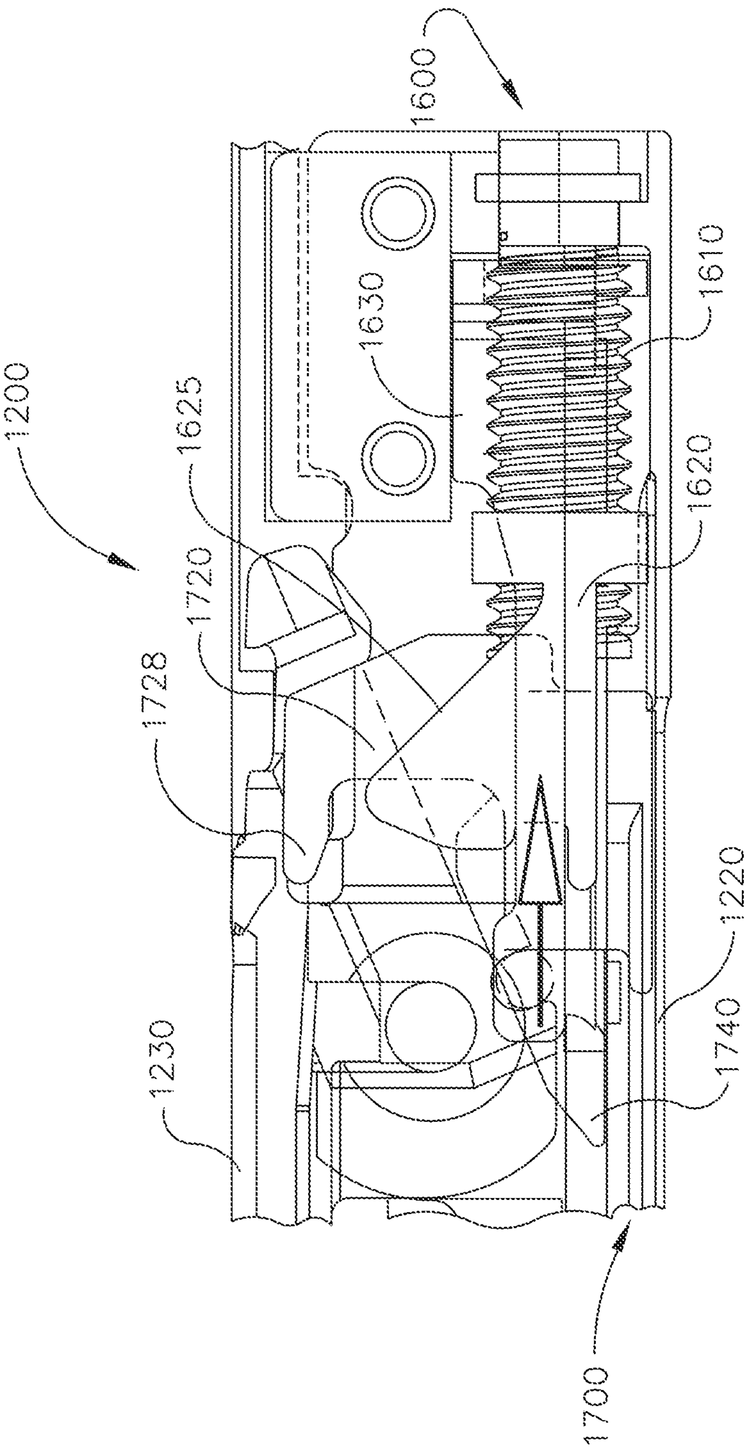
FIG. 12 illustrates the anvil jaw of FIG. 11 closed by the quick jaw closure system of FIG. 7.
Figure 13:
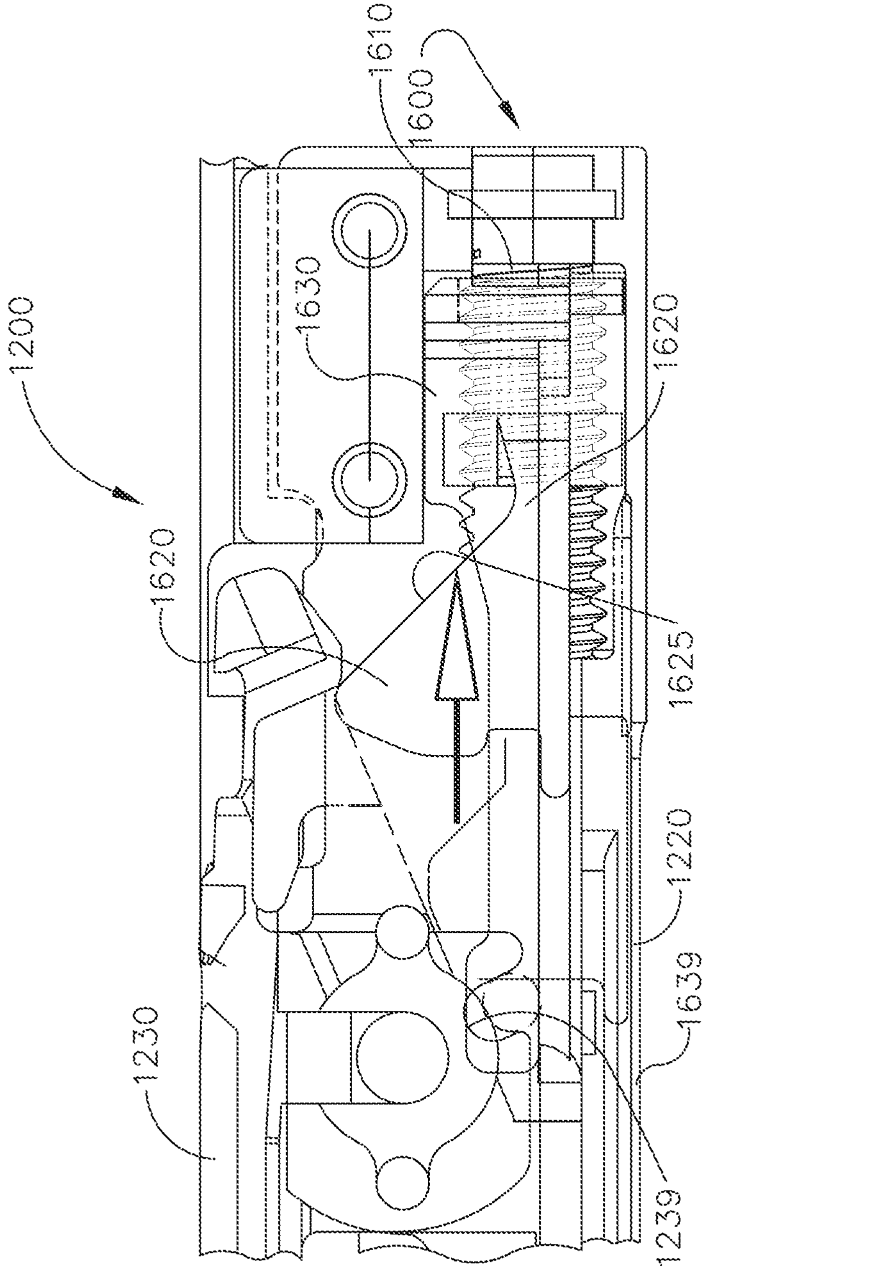
FIG. 13 illustrates the high-load jaw clamping system of FIG. 7 applying a high clamping load to the anvil jaw.
Figure 14:
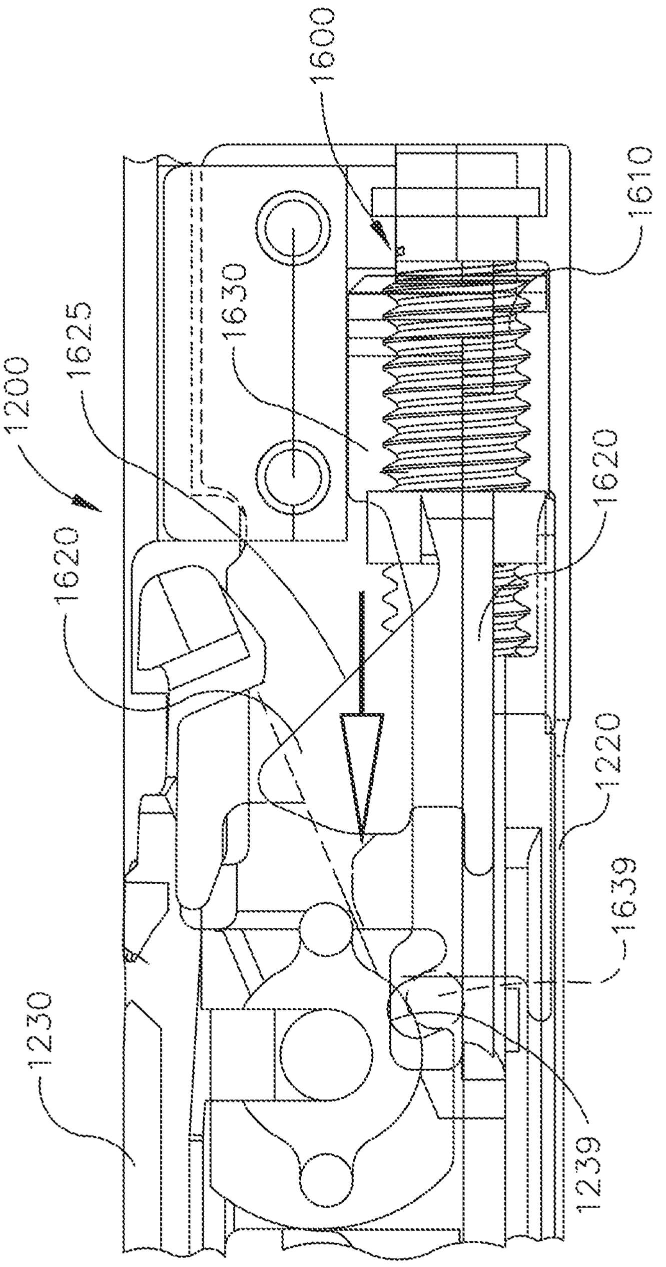
FIG. 14 illustrates the high-load jaw clamping system of FIG. 7 disengaged from the anvil jaw.
Figure 15:
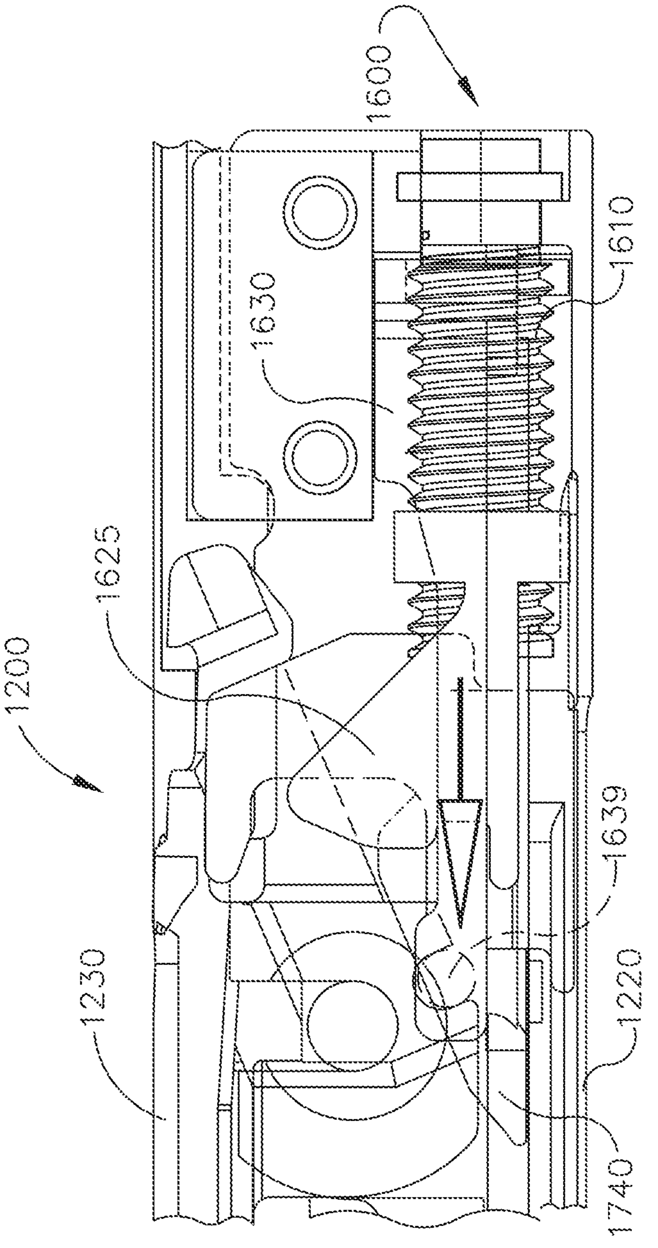
FIG. 15 illustrates the quick jaw closure system being disengaged from the anvil jaw.
Figure 16:
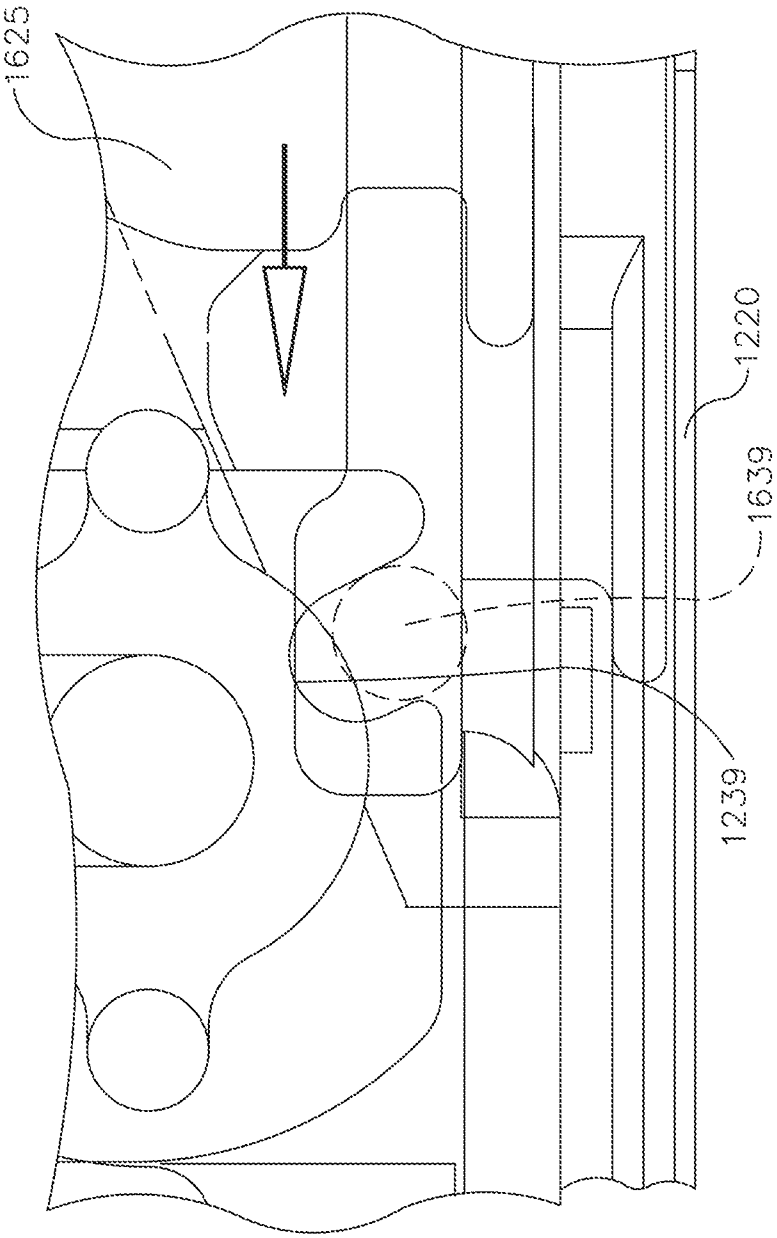
FIG. 16 is a detail view arising from FIG. 14.
Figure 17:
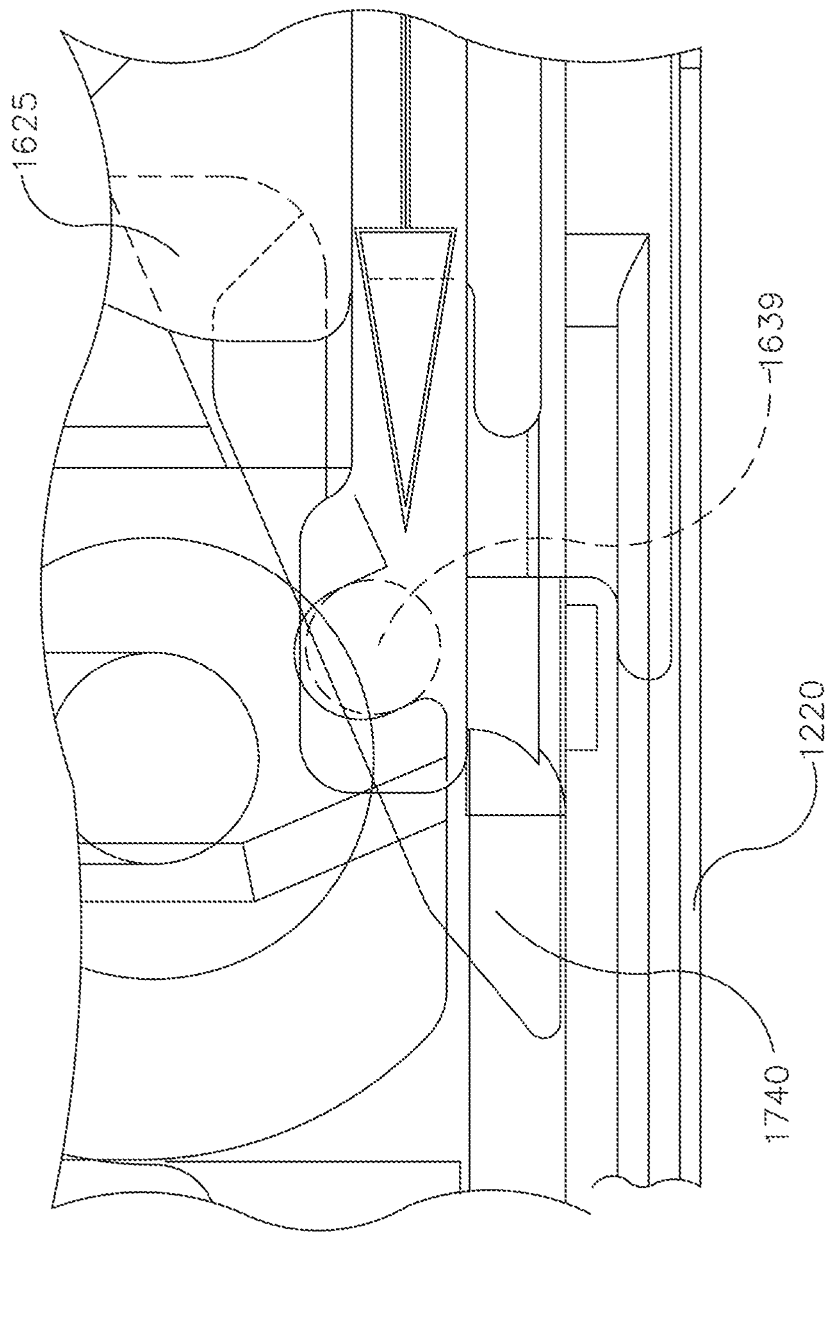
FIG. 17 is a detail view arising from FIG. 15.

Referring primarily to FIGS. 7-9, the closure drive system 1600 comprises a rotatable drive shaft 1610 which is driven by an electric motor operably coupled to the drive shaft 1610 by a flexible drive shaft 1910. The flexible drive shaft 1910 extends through the shaft 1100 and the articulation joint 1300 such that a distal end of the flexible drive shaft 1910 is coupled to the closure drive shaft 1610 at a location which is distal with respect to the articulation joint 1300, although the closure drive shaft 1610 can be coupled to the flexible drive shaft 1910 at any suitable location. The distal end of the flexible drive shaft 1910 comprises a hex-shaped recess which is configured to receive a hex-shaped lug extending proximally from the closure drive shaft 1610 such that the flexible drive shaft 1910 and the closure drive shaft 1610 rotate together; however, any suitable coupling between the shafts 1610 and 1910 could be used.

Further to the above, the closure drive system 1600 comprises a quick-closure system and a high-force closure system. Both the quick-closure system and the high-force closure system are configured to close the second jaw 1230, but in different ways. Referring primarily to FIG. 7, the closure drive system 1600 comprises a quick-closure member 1630 and high-force closure member 1620. The high-force closure member 1620 comprises a threaded aperture defined therein which is threadably engaged with the threads of the closure drive shaft 1610. When the drive shaft 1610 is turned in a first direction, the drive shaft 1610 drives the high-force closure member 1620 proximally. The quick-closure member 1630 is not threadably engaged with the drive shaft 1610 and, when the drive shaft 1610 is turned in the first direction, the quick-closure member 1630 is pushed proximally by the high-force closure member 1620 via a spring 1640 positioned intermediate the high-force closure member 1620 and the quick-closure member 1630. At the outset of the closing process, the quick-closure member 1630 is in direct contact with the second jaw 1230, but the high-force closure member 1620 is not in direct contact with the second jaw. The quick-closure member 1630 comprises a proximal end 1632 and drive arms 1634 extending distally therefrom. Each of the drive arms 1634 comprises a drive pin 1639 extending inwardly into a drive recess 1239 defined in the second jaw 1230 such that, when the quick-closure member 1630 is pushed proximally by the high-force closure member 1620, the quick-closure member 1630 rotates the second jaw 1230 into a closed position. As a result of this arrangement, the initial closing motion of the second jaw 1230 is caused by the quick-closure member 1630.

Notably, further to the above, the spring 1640 compresses between the high-force closure member 1620 and the quick-closure member 1630 when the high-force as the closure member 1620 is driven proximally. The amount of relative motion between the high-closure member 1620 and the quick-closure member 1630 is a function of the spring constant of the spring 1640 and, in addition, the clamping load, or resistance, being applied to the tissue by the second jaw 1230. As a result, the closed position of the second jaw 1230 at this stage of the closure stroke may vary depending on the thickness and/or density, for example, of the tissue positioned intermediate the second jaw 1230 and the staple cartridge 1400. If thicker tissue is positioned between the second jaw 1230 and the staple cartridge 1400, for instance, the tissue compression surface 1231 of the second jaw 1230 may not be parallel to the tissue support surface 1421 of the staple cartridge 1400. If thinner tissue is positioned between the second jaw 1230 and the staple cartridge 1400, the tissue compression surface 1231 of the second jaw 1230 may be parallel to, or past parallel with respect to, the tissue support surface 1421 of the staple cartridge 1400. This variability is not concerning at this stage as the quick-closure system of the closure system 1600 is designed to give a rough approximation of the position of the second jaw 1230 on the patient tissue before the tissue is fully clamped by the high-load closure system and before the staples are fired by the staple firing system 1700.

If the clinician desires to re-open the second jaw 1230, further to the above, the clinician controls the electric motor to operate the electric motor in an opposite direction to rotate the closure drive shaft 1610 in an opposite direction. In such instances, the closure drive shaft 1610 drives the high-force closure member 1620 distally which relaxes, or lowers, the force within the spring 1640 to allow the second jaw 1230 to open, at least slightly. Moreover, in such instances, the high-force closure member 1620 can push the quick-closure member 1630 distally to push the second jaw 1230 into an open, or unclamped, position. More specifically, each of the drive arms 1634 of the quick-closure member 1630 comprises an inwardly extending tab 1635 which is contacted by the high-force closure member 1620 when the high-force closure member 1620 is retracted distally such that the high-force closure member 1620 directly, or positively, pushes the quick-closure member 1630 distally during an opening stroke. The clinician can open and close the second jaw 1230 as many times as desired in order to properly position the jaws of the stapling instrument 1000 on the patient tissue. Compared to the high-force closure system, which is discussed in greater detail below, the quick-closure system moves the second jaw 1230 quickly without having to apply large compressive, or clamping, loads to the patient tissue.

As outlined above, the closure drive shaft 1610 is rotated to drive the high-force closure member 1620 proximally to push the quick-closure member 1630 proximally and quickly close the second jaw 1230. At this point, the high-force closure member 1620 is not in direct contact with the second jaw 1230. Continued rotation of the closure drive shaft 1610, however, brings the high-force closure member 1620 into contact with the second jaw 1230. More specifically, the high-force closure member 1620 comprises cams 1625 defined thereon which are brought into contact with cam surfaces 1235 defined on the bottom of the second jaw 1230 and drive the second jaw 1230 into its closed position. Owing to the direct contact between the cams 1625 and the second jaw 1230, the second jaw 1230 is positively positioned in its closed position. In such instances, as a result, the staple forming pockets defined in the second jaw 1230 are properly aligned with the staples in the staple cartridge 1400. Also, as a result, a high clamping force is applied to the tissue clamped between the second jaw 1230 and the staple cartridge 1400. At such point, the staple firing system 1700 can be operated to fire the staples from the staple cartridge 1400. If, however, the clinician desires to re-open the second jaw 1230 instead, the closure drive shaft 1610 can be operated in the reverse direction to drive the high-force closure member 1620 distally to disengage the cams 1625 from the second jaw 1230 and, to fully open the second jaw 1230, drive the quick-closure member 1240 distally as described above. The entire disclosure of U.S. Pat. No. 9,585,658, entitled STAPLING SYSTEMS, which issued on Mar. 7, 2017, is incorporated by reference herein.

The staple firing system 1700 of the stapling instrument 1000 comprises a firing drive shaft 1710. The proximal end of the firing drive shaft 1710 comprises a hex-shaped lug extending proximally that is operably engaged with a flexible rotatable firing drive shaft extending through the closure drive shaft 1610; however, any suitable coupling between the shafts 1610 and 1710 could be used. The flexible drive shaft is operably coupled to an electric motor which is operable independently of the closure motor such that the firing drive shaft 1710 is operable independently of the closure drive shaft 1610. The staple firing system 1700 further comprises a firing member 1720 which includes a threaded nut 1730 threadably engaged with a threaded portion of the firing drive shaft 1710. When the firing drive shaft 1710 is rotated in a first direction, the firing member 1720 is driven distally to perform the staple firing stroke. The firing member 1720 further comprises ramps 1740 which are configured to engage the drivers in the staple cartridge 1400 and eject the staples from the staple cartridge 1400 during the staple firing stroke. The firing member 1720 also comprises a tissue cutting knife 1750 which cuts the stapled tissue during the staple firing stroke. When the firing drive shaft 1710 is rotated in a second, or opposite, direction, the firing member 1720 is driven proximally.

As described above, referring primarily to FIGS. 4 and 9, the first jaw 1220 comprises a channel 1222 configured to receive the staple cartridge 1400. The first jaw 1220 is pinned to the proximal end 1210 of the end effector 1200 by two pins 1214 such that there is no relative movement, or at least substantial relative movement, between the first jaw 1220 and the proximal end 1210. The first jaw 1220 comprises a proximal end 1224 configured to receive a proximal end 1424 of the staple cartridge 1400 and a distal end 1226 configured to receive a distal end 1426 of the staple cartridge 1400. In this embodiment, the distal end 1426 of the staple cartridge 1400 hangs over the distal end 1226 of the first jaw 1220 which provides a datum for properly positioning the distal end 1426 of the staple cartridge 1400 relative to the channel 1222. The staple cartridge 1400 comprises a longitudinal slot 1428 defined in the cartridge body 1422 which is configured to receive a portion of the firing member 1420 therein. The first jaw 1220 further comprises a longitudinal slot 1229 defined therein which is aligned with the longitudinal slot 1428 when the staple cartridge 1400 is seated in the channel 1222. The longitudinal slot 1228 is an internal slot defined in the bottom portion of the channel 1222 which is configured to receive a bottom cam 1729 of the firing member 1720 during the staple firing stroke. The first jaw 1220 further comprises a cap 1223 attached to the channel 1222 by welds, for example, which enclose the internal longitudinal slot 1228 of the channel 1222.

As described above, the second jaw 1230 is rotatably mounted to the first jaw 1220 about a pivot 1240. Referring primarily to FIG. 9, the second jaw 1230 comprises outwardly-extending pins 1237 which are closely received in slots 1227 defined in the first jaw 1220. The pins 1237 are captured in the slots 1227 by retaining members 1225 press-fit onto the pins 1237 such that the pins 1237 can pivot within the slots 1227 but not translate within the slots 1227. The second jaw 1230 further comprises an anvil body 1232, a proximal end 1234, and a distal end 1236. Similar to the first jaw 1220, the second jaw 1230 comprises an internal slot 1238 defined therein which is configured to receive a top cam 1728 of the firing member 1720 during the staple firing stroke. The second jaw 1230 further comprises a cap 1233 attached to the anvil body 1232 by welds, for example, which enclose the internal longitudinal slot 1238 of the anvil body 1232. During the staple firing stroke, the top cam 1728 of the firing member 1720 engages the second jaw 1230 and the bottom cam 1729 engages the first jaw 1220. As a result, the cams 1728 and 1729 co-operate to hold the second jaw 1230 in position relative to the first jaw 1220.

Referring primarily to FIG. 8, the stapling instrument 1000 further comprises a sensor system 1800 configured to assess the position of the firing member 1720. The sensor system 1800 comprises a cable 1810 extending through the shaft 1100 which sheaths at least two conductors, or wires, 1820. The wires 1820 form a circuit with a sensor 1830, such as an RFID antenna, for example, which is in signal communication with a controller of the stapling instrument. The firing member 1720 comprises a detectable member, such as an RFID tag, for example, which is detectable by the sensor system 1800 when the firing member 1720 is in its proximal, unfired position. When the firing member 1720 is advanced distally during the staple firing stroke, the RFID tag is no longer detectable by the sensor system 1800 and the controller can determine that the staple firing stroke is in process or at least that the staple cartridge 1400 has been at least partially fired. The end effector 1200 further comprises a sensor support 1840 which supports the sensor 1830.

Figure 73:
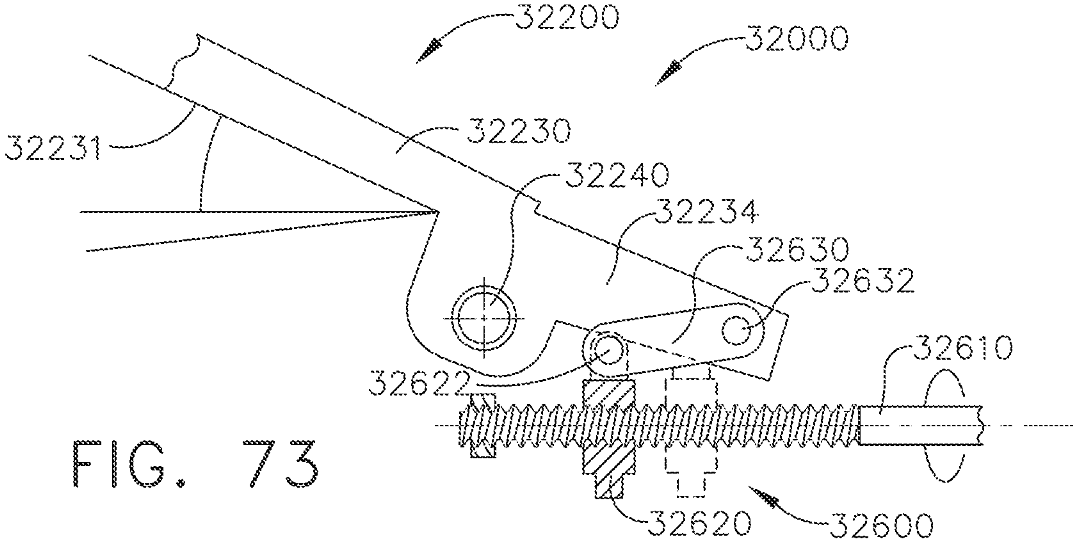
FIG. 73 is a partial elevational view of an end effector of a stapling instrument in accordance with at least one embodiment.
Figure 74:
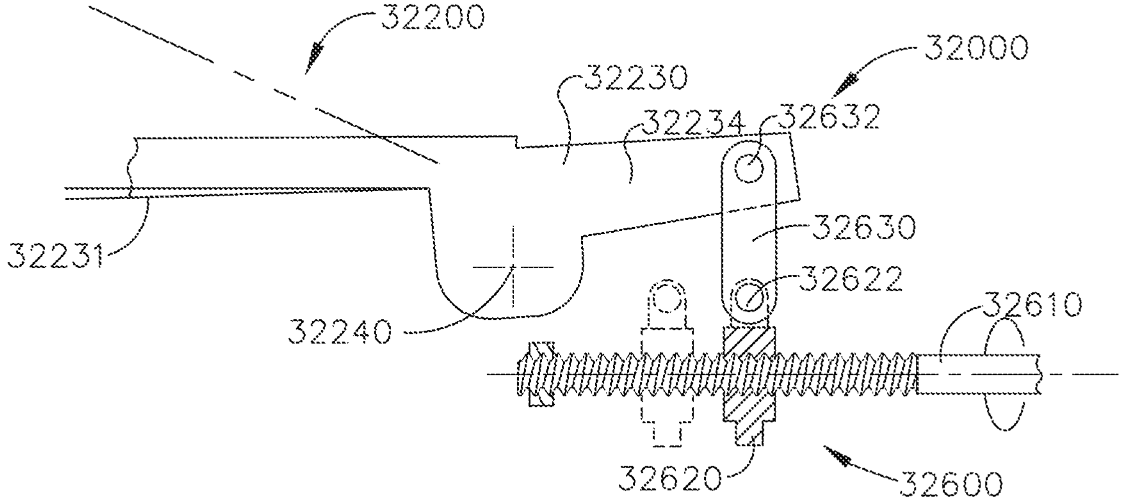
FIG. 74 is a partial elevational view of the end effector of FIG. 73 illustrated in a clamped configuration.

A surgical instrument 32000 is illustrated in FIGS. 73 and 74. Similar to the above, the surgical instrument 32000 comprises an end effector 32200 and a closure system 32600. The surgical instrument 32000 also comprises an end effector articulation system and a staple firing system, but these systems are not described herein for the sake of brevity. The end effector 32200 comprises a first jaw configured to receive a staple cartridge and, in addition, a second jaw 32230 comprising an anvil rotatably coupled to the first jaw about a pivot 32240. The second jaw 32230 is movable from an open, or unclamped, position (FIG. 73) to a closed, or clamped, position (FIG. 74) by the closure system 32600. The closure system 32600 comprises a rotatable drive shaft 32610 including a distal end rotatably supported within the first jaw by a bearing. The closure system 32600 further comprises a closure member, or nut, 32620 threadably engaged with a threaded portion of the rotatable drive shaft 32610. When the drive shaft 32610 is rotated in a first direction, the closure member 32620 is driven proximally to close the end effector 32200 and, when the drive shaft 32610 is rotated in a second, or opposite, direction, the closure member 32620 is driven distally to open the end effector 32200. The closure system 32600 further comprises a closure link 32630 which is pivotally mounted to the closure member 32620 about a pivot 32622 and pivotally mounted to the second jaw 32230 about a pivot 32632. When the closure member 32620 is driven proximally, the closure link 32630 drives the proximal end 32234 of the second jaw 32230 upwardly to rotate the second jaw 32230 into its closed position, as illustrated in FIG. 74. Notably, the closure link 32630 is driven into an upright position in which the pivot 32632 is in-line with the pivot 32622 and, as a result, the closure link 32630 is locked in-phase providing a large amount of clamping force to the tissue captured between the second jaw 32230 and the first jaw. In this position, the tissue compression surface 32231 of the second jaw 32230 is parallel to the tissue support surface of the staple cartridge; however, this system can be arranged to overclamp the tissue by orienting the compression surface 32231 toward the staple cartridge when the second jaw 32230 is driven closed by the closure drive system 32600. In any event, the link 32630 rotates quickly at the outset of the closure stroke as compared to the end of the closure stroke for a given speed of the closure drive shaft 32610. This is due to the initial orientation of the closure link 32630 being relatively flat, or substantially in-line with the motion of the closure member 32620, and the final orientation of the closure link 32630 being orthogonal, or at least substantially perpendicular, to the motion of the closure member 32620. As a result, the initial motion of the second jaw 32230 toward the first jaw is fast as compared to the end of the closure stroke for a given speed of the closure drive shaft 32610. When the closure member 32620 is driven distally, the closure member 32620 pulls the proximal end 32234 downwardly via the link 32640 to open the second jaw 32230.

Figure 75:
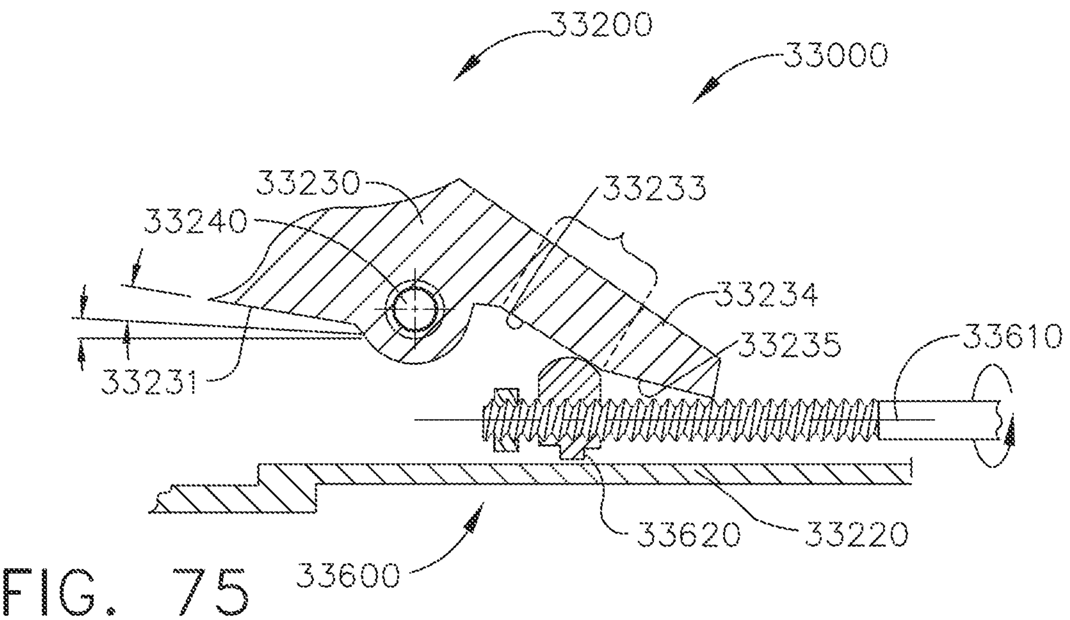
FIG. 75 is a partial elevational view of an end effector of a stapling instrument in accordance with at least one embodiment.
Figure 76:
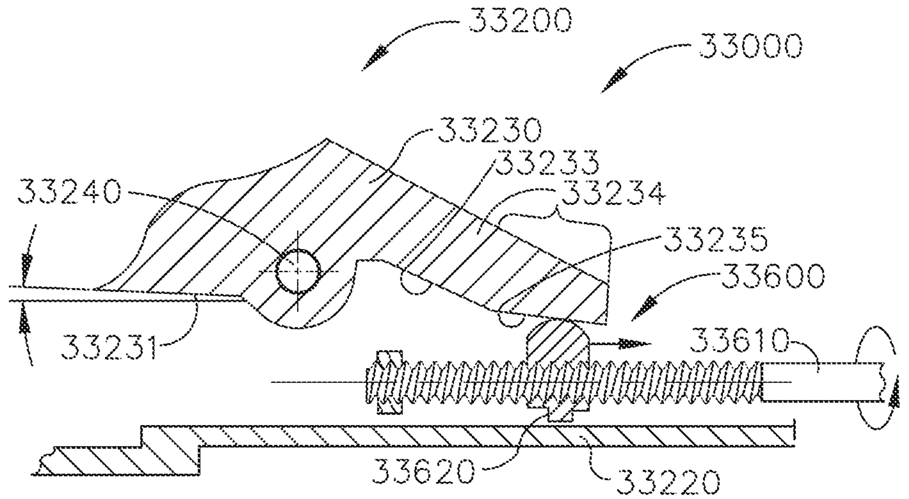
FIG. 76 is a partial elevational view of the end effector of FIG. 75 illustrated in a clamped configuration.

A surgical instrument 33000 is illustrated in FIGS. 75 and 76. The surgical instrument 33000 comprises an end effector 33200 and a closure system 33600. The surgical instrument 33000 also comprises an end effector articulation system and a staple firing system, but these systems are not described herein for the sake of brevity. The end effector 33200 comprises a first jaw configured to receive a staple cartridge and, in addition, a second jaw 33230 comprising an anvil rotatably coupled to the first jaw about a pivot 33240. The second jaw 33230 is movable from an open, or unclamped, position (FIG. 75) to a closed, or clamped, position (FIG. 76) by the closure system 33600. The closure system 33600 comprises a rotatable drive shaft 33610 including a distal end rotatably supported by the first jaw by a bearing. The closure system 33600 further comprises a closure member, or nut, 33620 threadably engaged with a threaded portion of the rotatable drive shaft 33610. When the drive shaft 33610 is rotated in a first direction, the closure member 33620 is driven proximally to close the end effector 33200 and, when the drive shaft 33610 is rotated in a second, or opposite, direction, the closure member 33620 is driven distally to allow the end effector 32200 to be opened. The proximal end 33234 of the second jaw 33230 comprises a distal cam surface 33233 and a proximal cam surface 33235 which are sequentially engaged by the closure member 33620 during the closing stroke. Notably, the distal cam surface 33233 comprises a linear, or an at least substantially linear, angled surface. When the closure member 33620 contacts the distal cam surface 33233, the closure member 33620 rotates the second jaw 33230 downwardly at a first rate. Similarly, the proximal cam surface 33235 comprises a linear, or an at least substantially linear, angled surface. When the closure member 33620 contacts the proximal cam surface 33235, the closure member 33620 rotates the second jaw 33230 downwardly at a second rate which is faster than the first rate. As a result, the initial clamping motion of the second jaw 33230 is fast while the final clamping motion of the second jaw 33230 is slower. Moreover, the shallower cam angle of the proximal cam surface 33235 allows the second jaw 33230 to apply a large clamping force to the tissue during the final clamping motion of the second jaw 33230. When the closure member 33620 is driven distally, the closure member 33620 is disengaged from the proximal cam surface 33235 and the distal cam surface 33233 such that the second jaw 33230 can be opened. In at least one embodiment, the second jaw 33230 is opened by a spring, for example, and/or by the staple firing system when the firing member is retracted.

Figure 79:
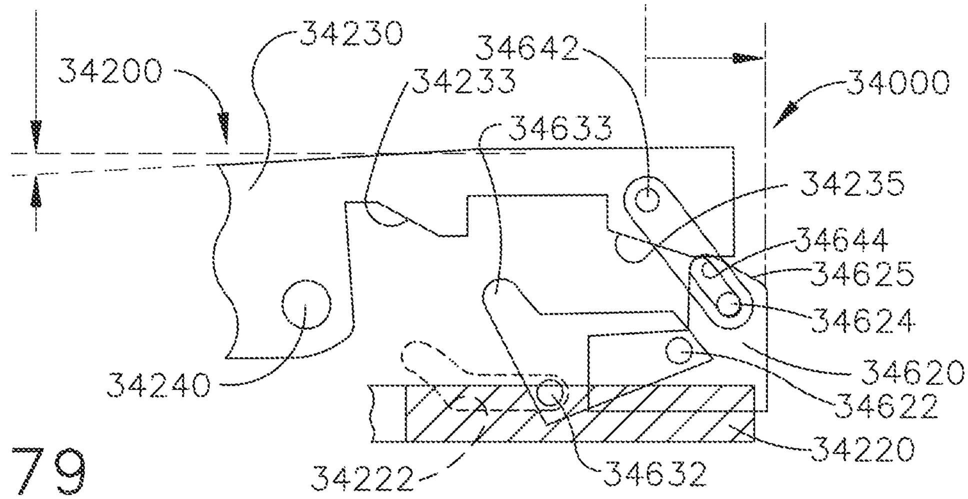
FIG. 79 is a partial elevational view of the end effector of FIG. 77 illustrated in an overclamped configuration.
Figure 80:
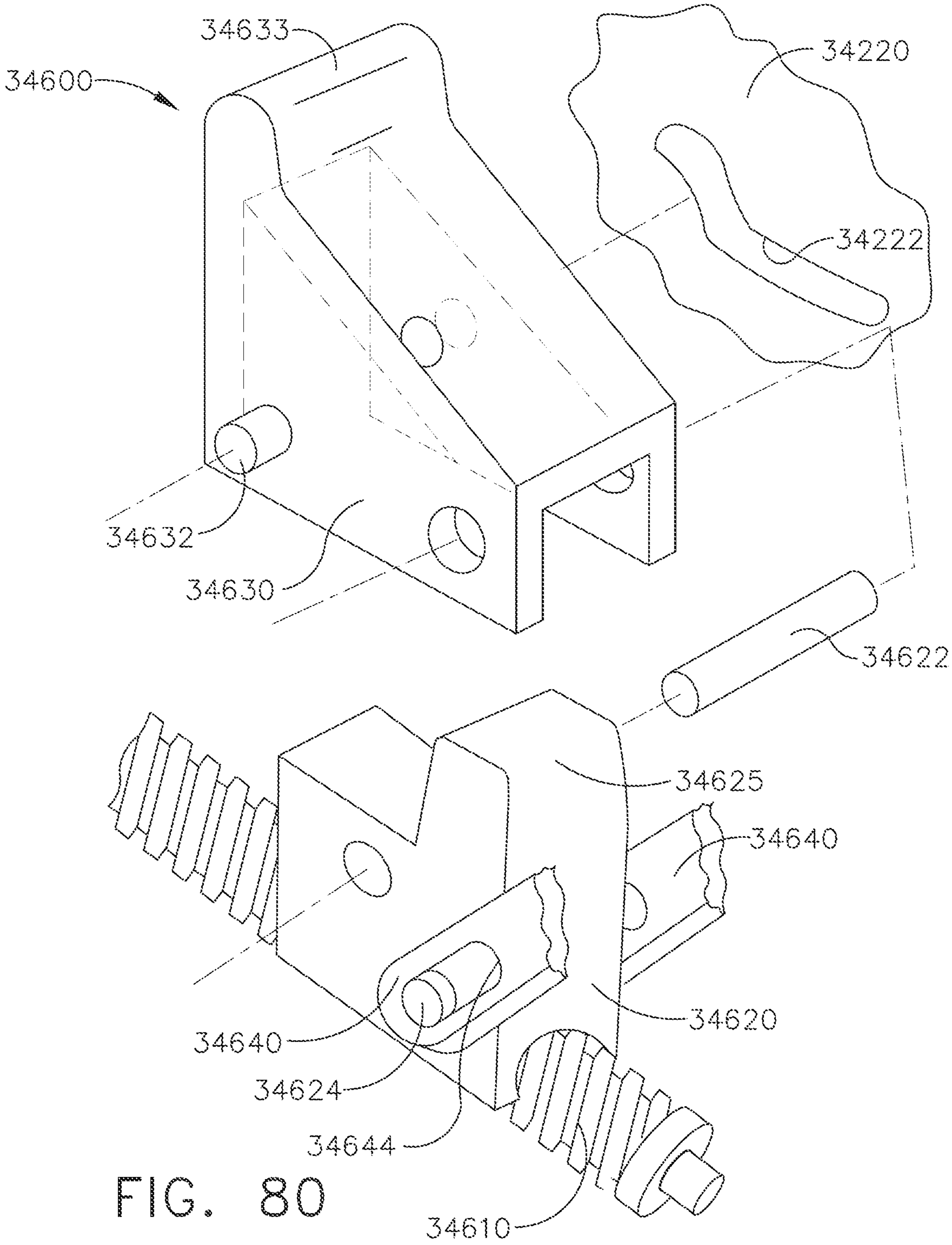
FIG. 80 is an exploded view of an end effector closure system of the stapling instrument of FIG. 77.

A surgical instrument 34000 is illustrated in FIGS. 77-80. The surgical instrument 34000 comprises an end effector 34200 and a closure system 34600. The surgical instrument 34000 also comprises an end effector articulation system and a staple firing system, but these systems are not described herein for the sake of brevity. The end effector 34200 comprises a first jaw 34220 configured to receive a staple cartridge and, in addition, a second jaw 34230 comprising an anvil rotatably coupled to the first jaw 34220 about a pivot 34240. The second jaw 34230 is movable from an open, or unclamped, position (FIG. 77) to a closed, or clamped, position (FIG. 78) to an overclamped position (FIG. 79) by the closure system 34600. The closure system 34600 comprises a rotatable drive shaft 42610 (FIG. 80) including a distal end rotatably supported by a bearing in the first jaw. The closure system 34600 further comprises a closure member, or nut, 34620 threadably engaged with a threaded portion of the rotatable drive shaft 34610 and a pivotable cam 34630 rotatably mounted to the closure member 34620 about a pin 34622. When the drive shaft 34610 is rotated in a first direction, the closure member 34620 is driven proximally such that a cam surface 34633 defined on the cam 34630 and a cam surface 34625 defined on the closure member 34620 sequentially engage the second jaw 34230 to close the end effector 34200. The second jaw 34230 comprises a first cam surface 34233 and a second cam surface 34235 defined thereon which are engaged by the cam surface 34633 and the cam surface 34625, respectively. At the outset of the closure stroke, referring to FIG. 78, the cam 34630 engages the first cam surface 34233 on the second jaw 34230 to quickly pivot the second jaw 34230 into a closed, or clamped, position. At this point, however, the cam surface 34625 defined on the closure member 34620 is not yet in contact with the second cam surface 34235 defined on the second jaw 34230. Further rotation of the closure drive shaft 34610 in the same direction, however, drives the closure member 34620 proximally to place the cam surface 34625 into contact with the cam surface 34235 on the second jaw 34230. Concurrently, the cam 34630 is cammed downwardly out of contact with the second jaw 34230. More specifically, referring primarily to FIG. 80, the cam 34630 comprises pins 34632 extending laterally therefrom which travel in slots 34222 defined in the first jaw 34220 and, owing to the contour of the slots 34222, the cam 34630 is pulled downwardly out of contact with the second jaw 34230 as the closure member 34620 comes into contact with the second jaw 34230. At such point, further rotation of the closure drive shaft 34610 in the same direction causes the closure member 34620 to drive the second jaw 34230 into its overclamped orientation as illustrated in FIG. 79. In this condition, the closure member 34620 is wedged between the first jaw 34220 and the second jaw 34230 and the position of the second jaw 34230 is positively set by the closure member 34620.

Figure 77:
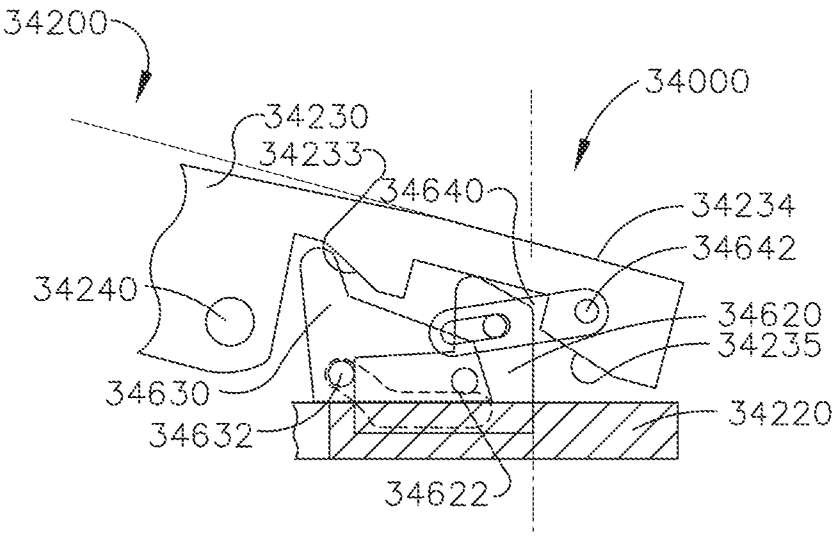
FIG. 77 is a partial elevational view of an end effector of a stapling instrument in accordance with at least one embodiment.
Figure 78:
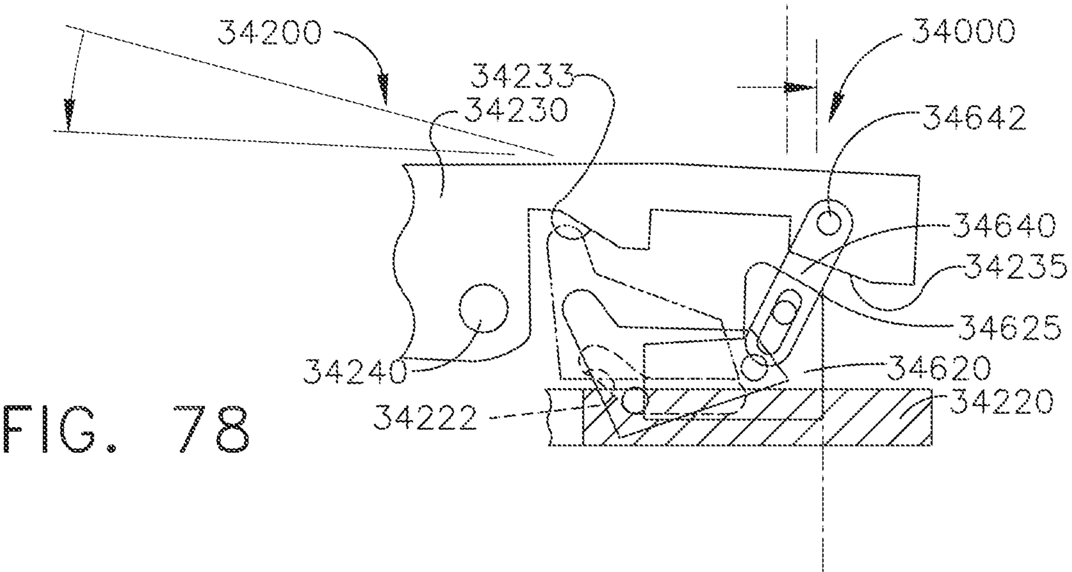
FIG. 78 is a partial elevational view of the end effector of FIG. 77 illustrated in a partially clamped configuration.

When the closure drive shaft 34610 is rotated in a second, or opposite, direction, the closure member 34620 is driven distally to disengage the closure member 34620 from the second jaw 34230. Moreover, in such instances, the pivotable cam 34630 is pivoted upwardly back into position owing to the interaction between the pins 34632 and the sidewalls of the slots 34222 in order to reset the cam 34630. The closure system 34600 further comprises opening links 34640 which are pivotally mounted to the closure member 34620 about pivot pins 34624 and pivotally mounted to the second jaw 34230 about a pivot 34632. When the closure member 34620 is driven distally, the opening links 34640 drive the proximal end 34234 of the second jaw 34230 downwardly to rotate the second jaw 34230 into its open position (FIG. 77). Notably, the opening links 34640 each comprise a slot 34644 defined therein which permit the pivot pins 34624 to slide within the links 34640 and permit the relative movement between the opening links 34640 and the closure member 34620 during the closure stroke, discussed above.

Figure 81:
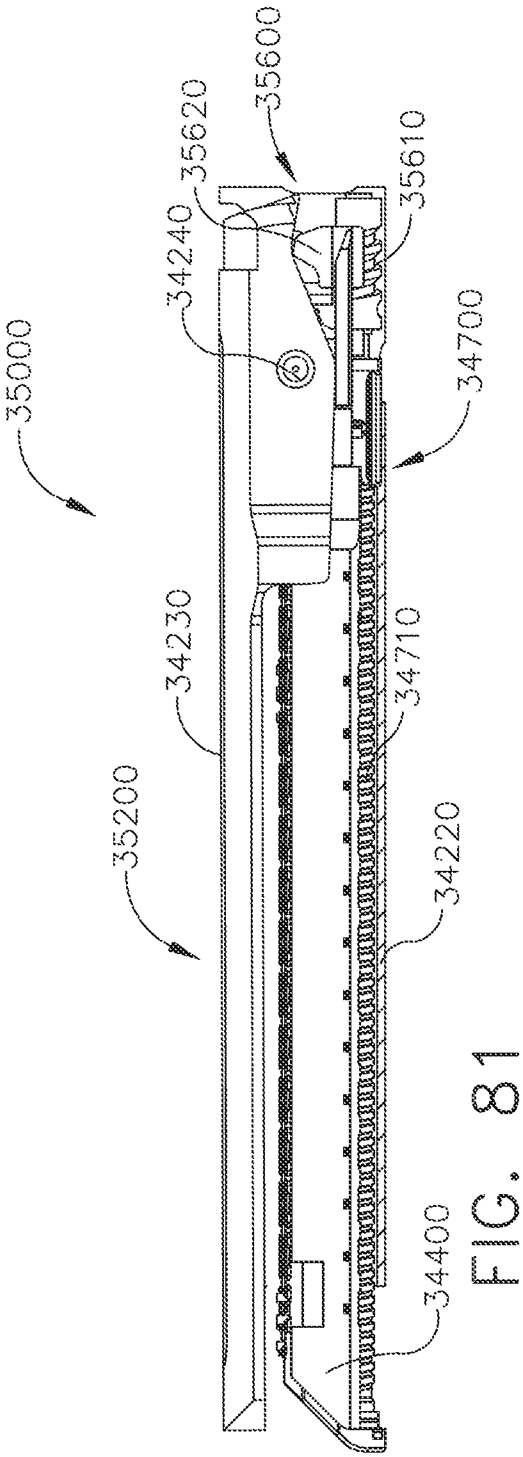
FIG. 81 is a partial elevational view of an end effector of a surgical instrument in accordance with at least one embodiment.
Figure 82:
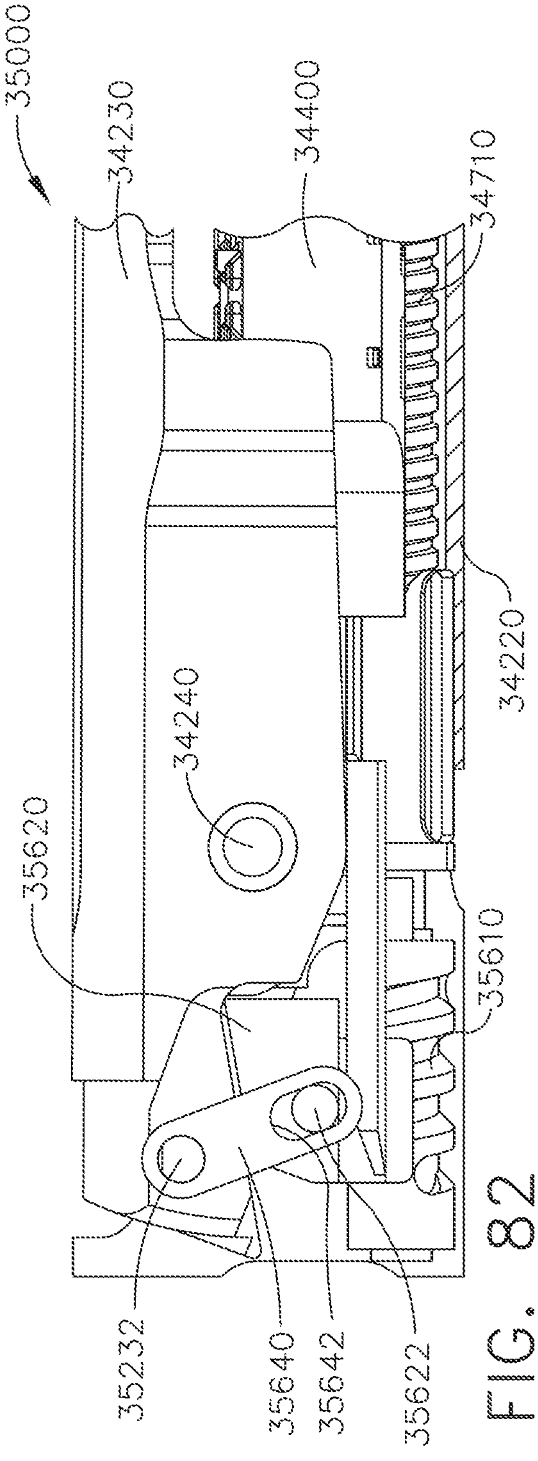
FIG. 82 is another partial elevational view of the end effector of FIG. 81.

A surgical instrument 35000 is illustrated in FIGS. 81 and 82. The surgical instrument 35000 comprises an end effector 35200, a closure system 35600, a staple firing system 34700, and an end effector articulation system. Similar to the end effector 34200, the end effector 35200 comprises a first jaw 34220 and a second jaw 34230. The first jaw 34220 is configured to receive a staple cartridge 34400, or any other suitable staple cartridge. The second jaw 34230 is pivotable relative to the first jaw 34220 about a pivot 34240 between an open position and a closed position by the closure system 35600. The closure system 35600 comprises a rotatable drive shaft 35610 and a closure member, or nut, 35620 threadably engaged with a threaded portion of the drive shaft 35610. When the drive shaft 35610 is rotated in a first direction, the closure member 35620 is driven proximally into contact with the second jaw 34230 to close the second jaw 34230. The closure system 35600 further comprises an opening link 35460 rotatably mounted to the closure member 35620 about a pin 35622 extending into a slot 35642 defined in the opening link 35460. The opening link 35460 is also pivotably mounted to the second jaw 35230 about a pin 25232 such that, when the drive shaft 35610 is rotated in an opposite direction and the closure member 35620 is driven distally, the closure member 35630 pulls the second jaw 35230 into an open position by pulling on the opening link 35460. Notably, the closure member 35630 applies an opening force to the second jaw 34230 at a different location than which it applies the closing force. Once the second jaw 35230 has been closed, or at least suitably closed, a rotatable drive shaft 34710 of the staple firing system 34700 that is driven to perform a staple firing stroke in accordance with a manner described elsewhere herein.

Figure 84:
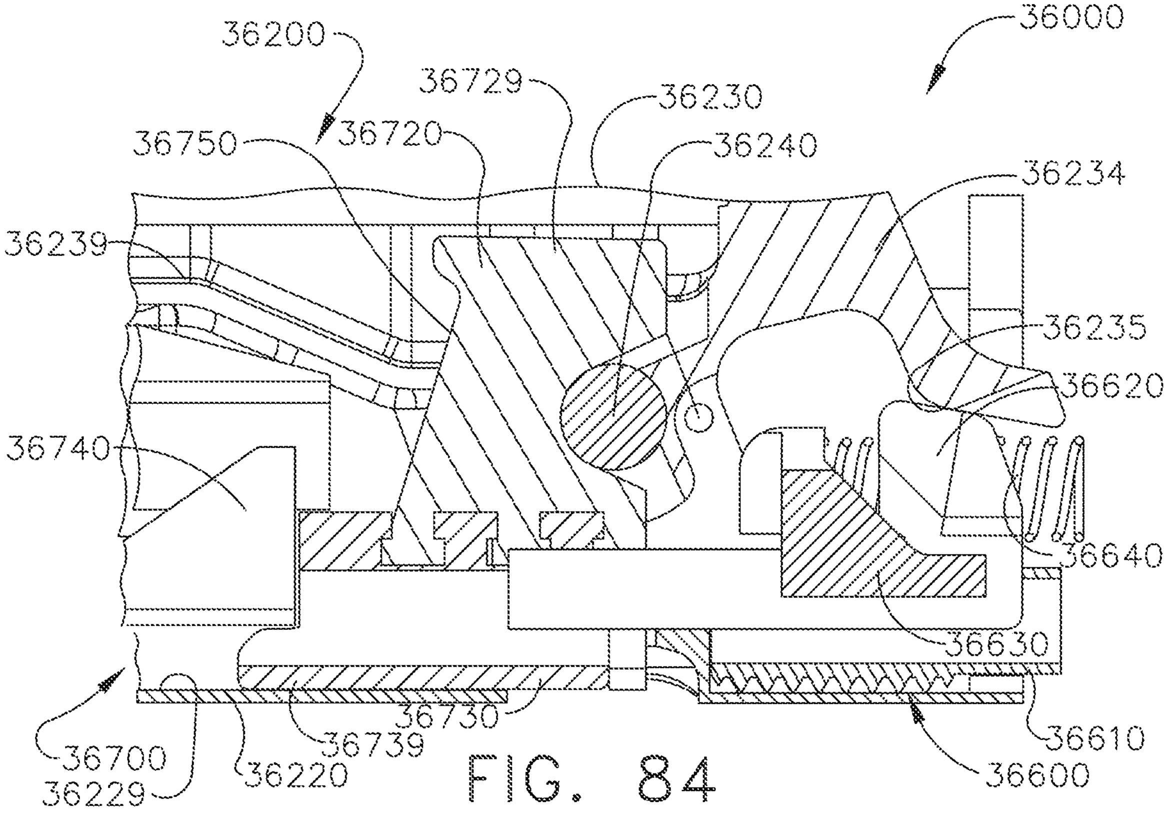
FIG. 84 is a partial cross-sectional view of the end effector of FIG. 83 illustrated in a closed configuration.
Figure 83:
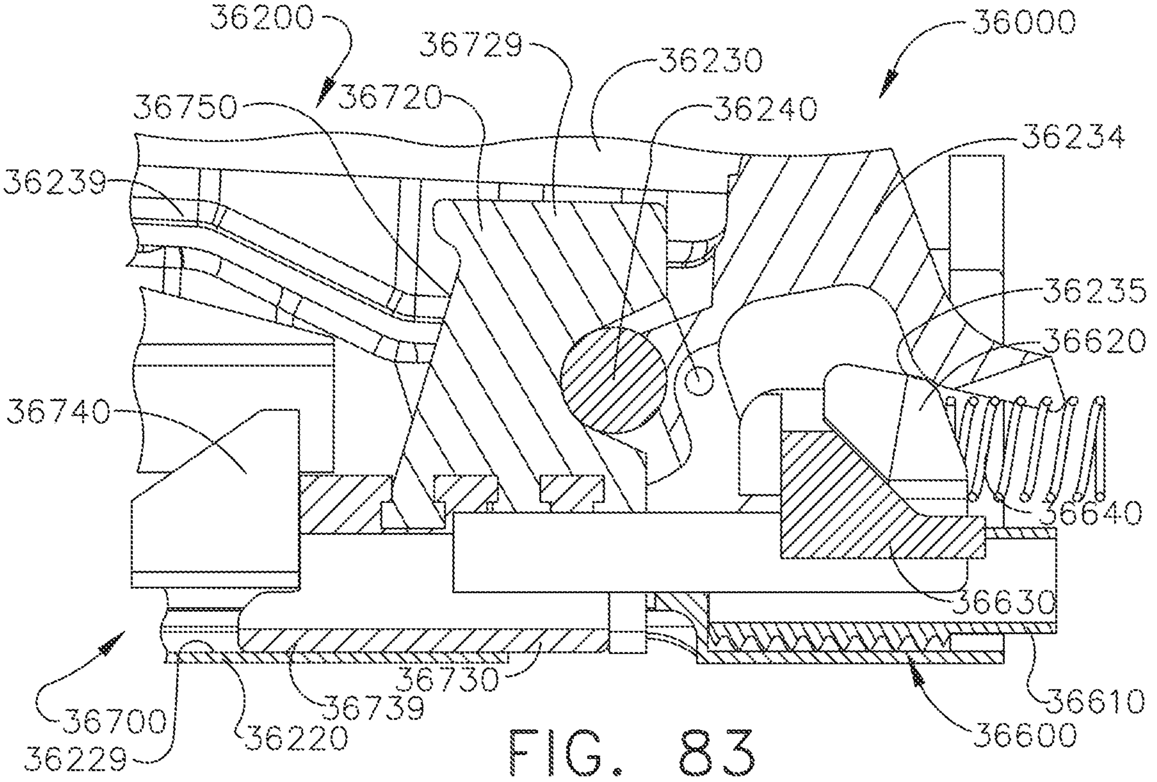
FIG. 83 is a partial cross-sectional view of an end effector of a surgical instrument in accordance with at least one embodiment illustrating the end effector in a partially closed configuration.
Figure 85:
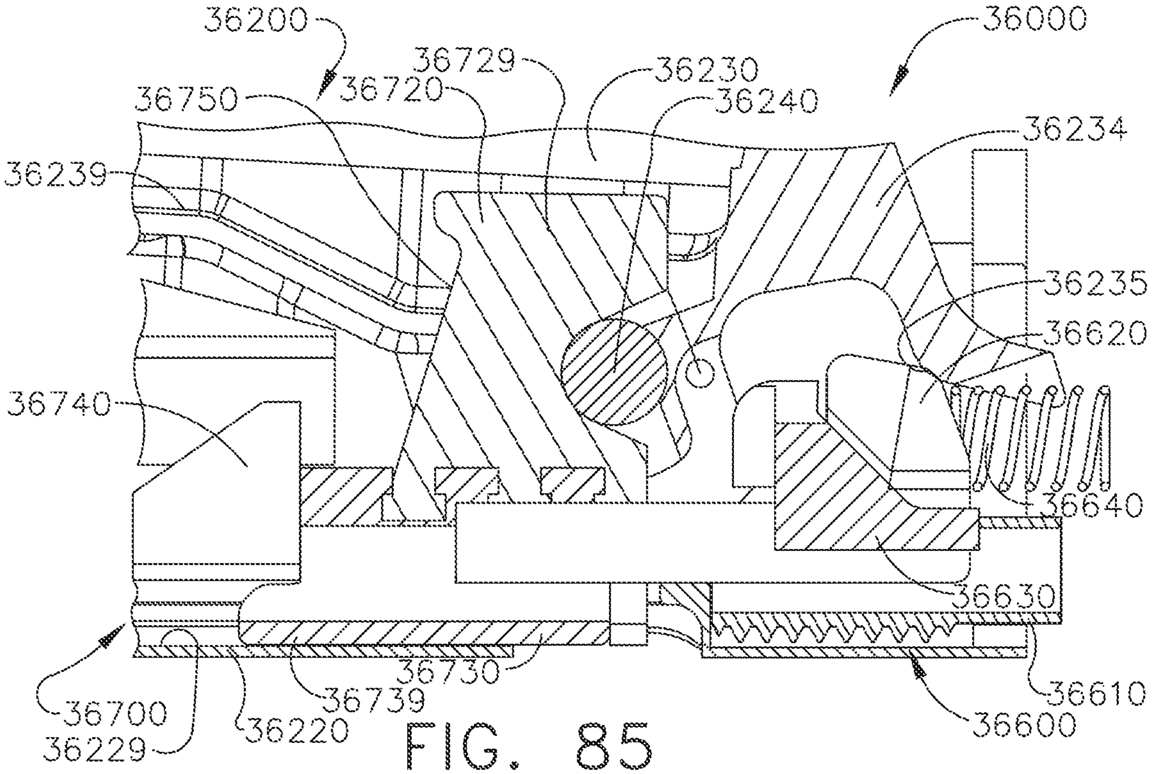
FIG. 85 is a partial cross-sectional view of the end effector of FIG. 83 illustrated in a partially open configuration.
Figure 86:
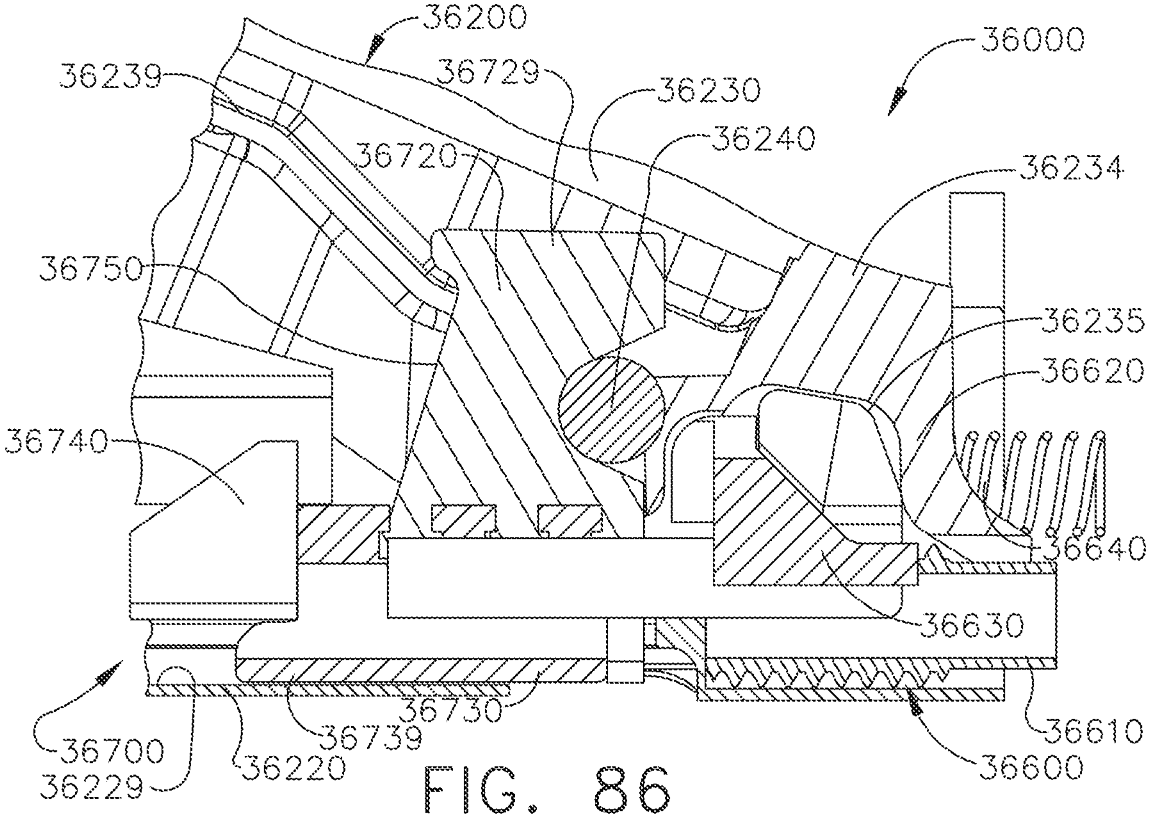
FIG. 86 is a partial cross-sectional view of the end effector of FIG. 83 illustrated in a fully open configuration.

A surgical instrument 36000 is illustrated in FIGS. 83-86. The surgical instrument 36000 comprises an end effector 36200, a closure system 36600, a staple firing system 36700, and an end effector articulation system. The end effector 36200 comprises a first jaw 36220 and a second jaw 36230. The first jaw 36220 is configured to receive a staple cartridge while the second jaw 36230 is pivotable relative to the first jaw 36220 about a pivot 36240 between an open position and a closed position by the closure system 36600. The closure system 36600 comprises a rotatable drive shaft 36610 and a closure member, or nut, 36620 threadably engaged with a threaded portion of the drive shaft 36610. When the drive shaft 36610 is rotated in a first direction, the closure member 36620 is driven proximally into contact with a cam surface 36235 defined on the second jaw 36230 to close the second jaw 36230, as illustrated in FIGS. 83 and 84. The surgical instrument 36000 further comprises an opening member 36630 configured to bias the second jaw 36230 into an open position. The opening member 36630 is pushed against the second jaw 36320 by an opening spring 36640 positioned intermediate the opening member 36630 and the frame of the end effector 36200. As a result, the proximal motion of the closure member 36620 opposes, and overcomes, the opening force being applied to the second jaw 36320 by the opening member 36630 as the closure member 36620 closes the second jaw 36230. When the closure member 36620 is driven distally, however, the opening force being applied to the second jaw 36320 by the opening member 36630 can push the second jaw 36230 open. In some instances, however, the opening force being applied by the opening member 36630 may not be sufficient to open, or at least sufficiently open, the second jaw 36230, as illustrated in FIG. 85. Such instances can arise when the spring constant of the opening spring 36640 is low. In any event, referring to FIG. 86, the continued distal movement of the closure member 36320 brings the closure member 36320 into contact with the opening member 36630 and drives the opening member 36630 to positively open the second jaw 36230. As a result, the retraction of the closure member 36620 can unstick the second jaw 36230 when the opening spring 36640 isn't strong enough to push the second jaw 36230 open.

Referring again to FIGS. 83-86, the staple firing system 36700 comprises a rotatable drive shaft. The staple firing system 36700 comprises an I-beam portion 36720, a threaded portion 36730, and a sled portion 36740. The threaded portion 36730 is threadably coupled to the firing drive shaft and the I-beam portion 36720 is fixedly mounted to the threaded portion 36730. As a result, the I-beam portion 36720 moves with the threaded portion 36730 when the threaded portion 36730 is driven proximally and distally by the firing drive shaft. Moreover, the I-beam portion 36720 and the threaded portion 36730 co-operate to hold the first jaw 36220 and the second jaw 36230 in position relative to one another during the staple firing stroke. More specifically, the threaded portion 36730 comprises a first cam 36739 which engages the first jaw 36220 and the I-beam portion 36720 comprises a second cam 36729 which engages the second jaw 36230 during the staple firing stroke. The first jaw 36220 comprises an internal slot 36229 defined therein configured to receive the first cam 36739 and, similarly, the second jaw 36230 comprises an internal slot 36239 defined therein configured to receive the second cam 36729. The staple firing system 36700 further comprises a sled 36740 which is pushed distally by the threaded portion 36730. The sled 36740 is configured to engage the staple drivers contained within a staple cartridge and drive the staples out of the staple cartridge during the staple firing stroke. The I-beam portion 36720 comprises a knife edge 36750 which is configured to cut the tissue being stapled. Notably, the knife edge 36750 is positioned proximally behind the sled 36740 such that the knife edge 36750 does not cut unstapled tissue. In any event, the sled 36740 is not attached to the threaded portion 36730 and, as a result, the sled 36740 does not return proximally with the I-beam portion 36720 and the threaded portion 36370 when the threaded portion 36370 is driven proximally after the staple firing stroke. Instead, the sled 36740 is left behind wherever the staple firing stroke ends.

Figure 89:
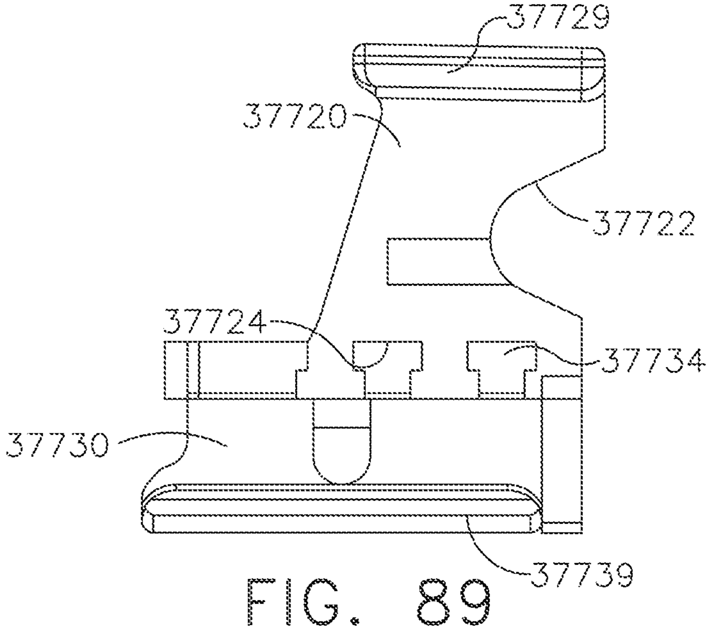
FIG. 89 is an elevational view of a firing member of the end effector of FIG. 88.
Figure 90:
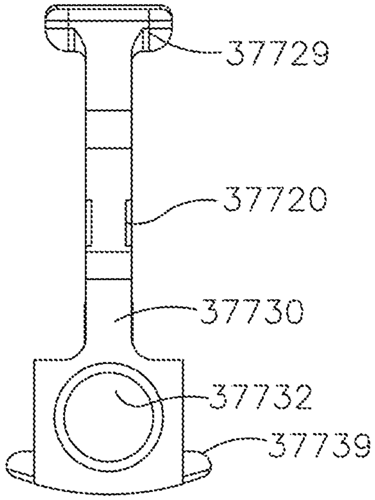
FIG. 90 is another elevational view of the firing member of FIG. 88.

A staple firing system 37700 of a stapling instrument 37000 is illustrated in FIGS. 87-90. Similar to the staple firing system 36700, the staple firing system 37700 comprises an I-beam portion 37720, a threaded portion 37730, and a sled portion 37740. The threaded portion 37730 is threadably coupled to the firing drive shaft via a threaded aperture 37732 and the I-beam portion 37720 is fixedly mounted to the threaded portion 37730. Referring primarily to FIG. 89, the I-beam portion 37720 and the threaded portion 37730 comprise interlocking tabs 37724 and 37734, respectively, which secure the I-beam portion 33720 to the threaded portion 37730. In at least one instance, the interlocking tabs 37724 and 37734 are press-fit into an interlocking relationship. As a result, the I-beam portion 37720 moves with the threaded portion 37730 when the threaded portion 37730 is driven proximally and distally by the firing drive shaft.

Similar to the above, the I-beam portion 37720 and the threaded portion 37730 co-operate to hold the first jaw 36220 and the second jaw 36230 in position relative to one another during the staple firing stroke. More specifically, the threaded portion 37730 comprises a first cam 37739 which engages the first jaw 36220 and the I-beam portion 37720 comprises a second cam 37729 which engages the second jaw 36230 during the staple firing stroke. The first jaw 36220 comprises an internal slot 36229 defined therein configured to receive the first cam 37739 and, similarly, the second jaw 36230 comprises an internal slot 36239 defined therein configured to receive the second cam 37729. When the assembly comprising the I-beam portion 37720 and the threaded portion 37730 is in its proximal, unfired position (FIG. 87), the first cam 37739 is at least partially positioned in the first internal slot 36229 and the second cam 37729 is positioned in an enlarged chamber 36237 defined in the second jaw 36230 that leads into the second internal slot 36239. The enlarged chamber 36237 permits the second jaw 36230 to be opened and closed without interference from the I-beam portion 37720. Moreover, the I-beam portion 37720 comprises a notch, or recess, 37722 defined therein which is configured to receive a pivot pin 36242 connecting the second jaw 36230 to the first jaw 36220 when the I-beam portion 37720 is in its proximal-most position. The notch 37722 permits the I-beam portion 37720 to be in a very proximal position which can, as described above, provide clearance for the pivotable second jaw 36230 and also allow the end effector 37200 to be shorter thereby allowing the end effector 37200 to be inserted into smaller spaces. In fact, the sidewall of the notch 37722 can be in contact with the pivot pin 36242 when the I-beam portion 37720 is in its proximal unfired position.

Figure 87:
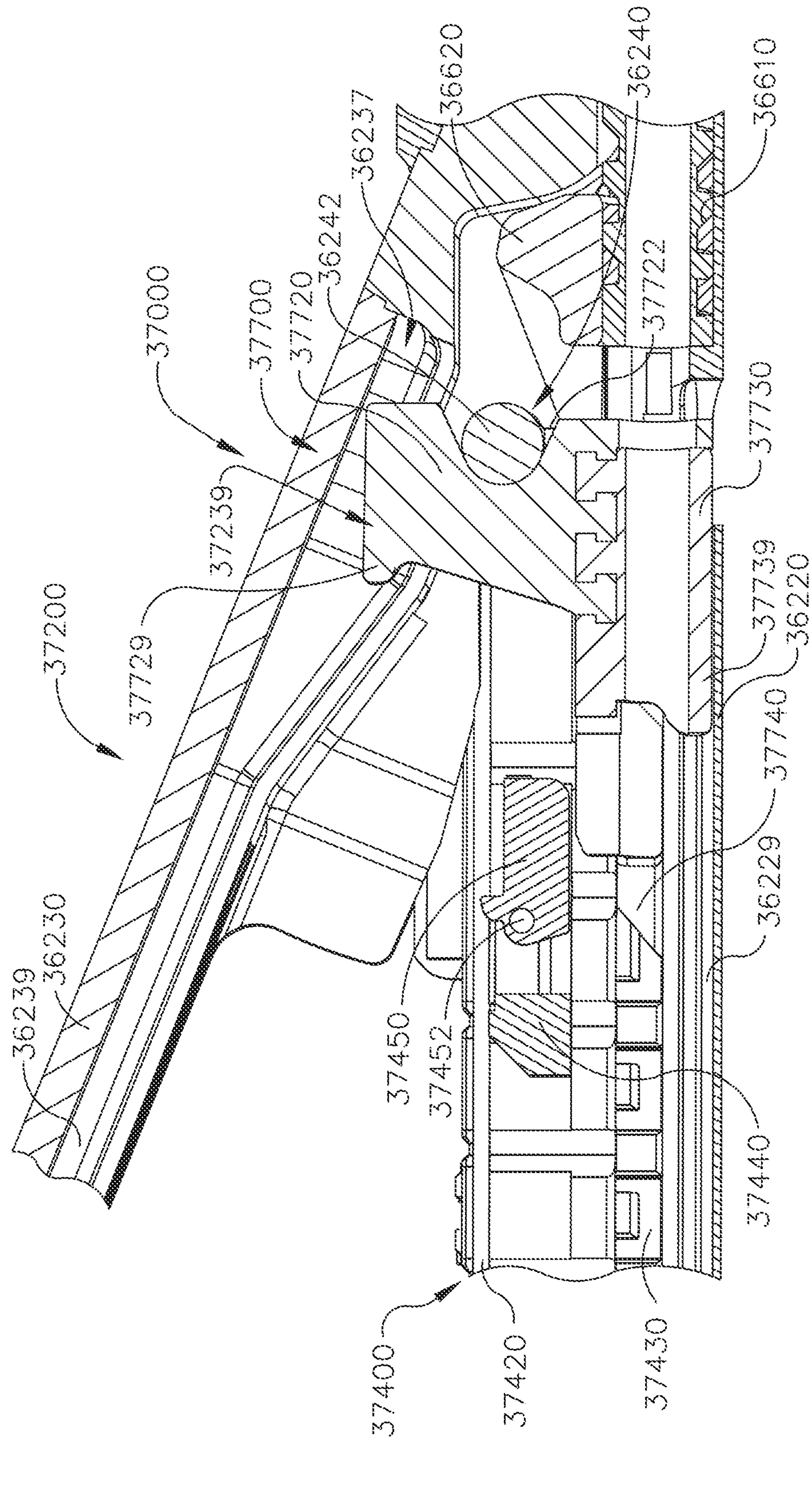
FIG. 87 is a partial cross-sectional view of an end effector of a surgical instrument in accordance with at least one embodiment.
Figure 88:
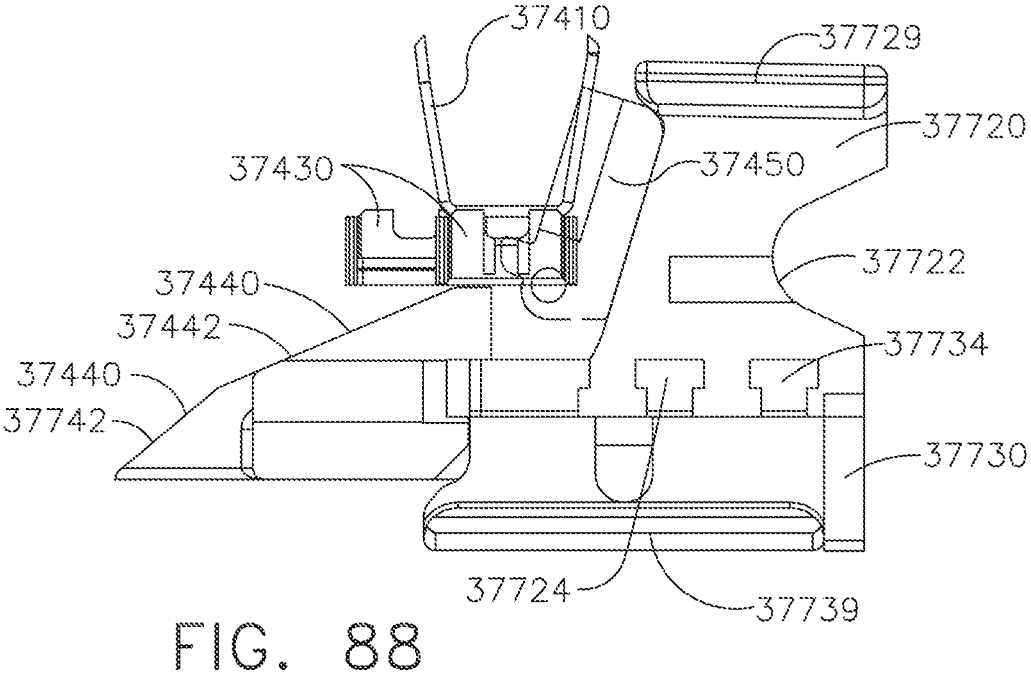
FIG. 88 is an elevational view of a firing assembly including a firing member.
Figure 92:
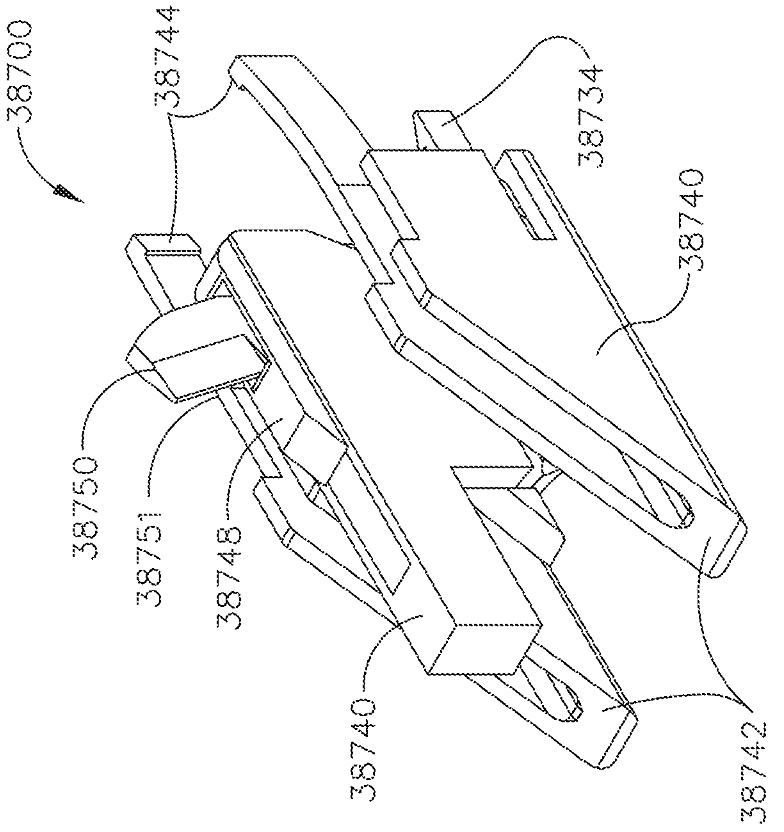
FIG. 92 is another perspective view of the firing assembly of FIG. 91.
Figure 91:
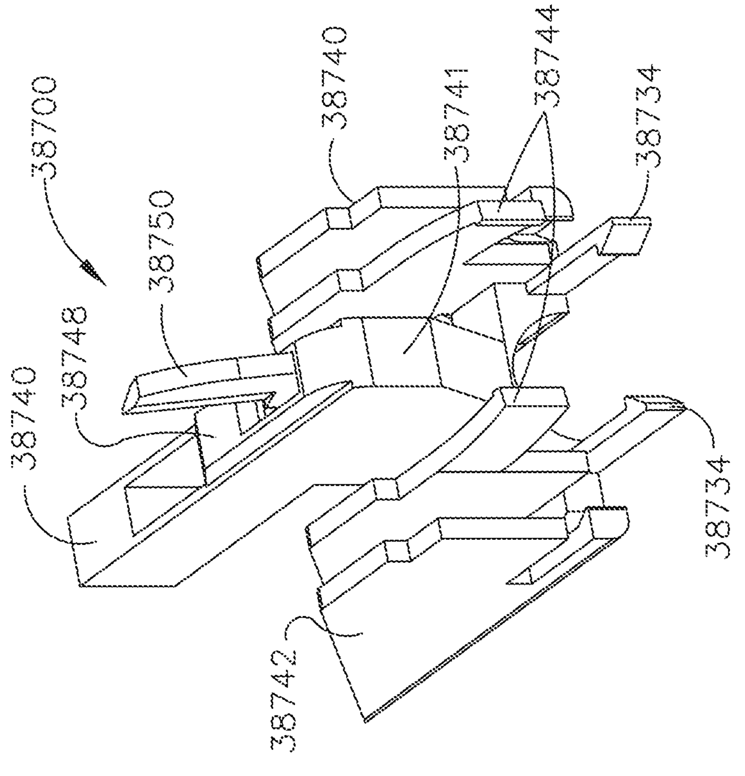
FIG. 91 is a perspective view of a firing assembly of a surgical instrument in accordance with at least one embodiment.

Further to the above, referring primarily to FIG. 88, the staple firing system 37700 further comprises a sled 37740 which is mounted to the threaded portion 37730 such that the sled 37740 travels distally and proximally with the threaded portion 37730 during the staple firing stroke and the retraction stroke, respectively. In use, referring primarily to FIG. 87, a replaceable staple cartridge, such as staple cartridge 37400, for example is positioned over the sled 37740 when the staple cartridge 37400 is seated in the first jaw 36220. The staple cartridge 37400 comprises a cartridge body 37420 (FIG. 87), staples 37410 (FIG. 88) removably stored in the cartridge body 37420, and staple drivers 37430 positioned within the cartridge body 37420 which support and drive the staples 37410 toward the anvil portion of the second jaw 36230 during the staple firing stroke. The sled 37740 comprises ramps 37742 defined thereon which engage the staple drivers 37430 to lift the staples 37410 toward the second jaw 36230. Notably, the staple cartridge 37400 further comprises a sled portion 37440 which is stored within the cartridge body 37420 and pushed distally by the I-beam portion 37720 during the staple firing stroke. The sled portion 37440 comprises ramps 37442 which align with the ramps 37742 on the sled 37740 at the outset of the staple firing stroke and co-operate with the ramps 37742 to fully drive the staple drivers 37430 and fully form, or fire, the staples 37410 during the staple firing stroke. As will be described in greater detail below in connection with different embodiments, the sled portion 37440 comprises a tissue cutting knife 37452 that rotates between an undeployed position in which the knife edge of the tissue cutting knife 37452 is positioned below the deck, or top surface, of the cartridge body 37420—as illustrated in FIG. 87, and a deployed position in which the knife edge extends above the deck. The tissue cutting knife is rotated about a pivot 37452 by the firing assembly when the firing assembly contacts, or picks up, the sled portion 37440 at the outset of the staple firing stroke. Notably, the sled portion 37440 in the staple cartridge 37400 is not retracted with the sled 37740 during the retraction stroke. Instead, the sled portion 37440 is left behind at the end of the staple firing stroke. The entire disclosures of U.S. Pat. No. 10,105,142, entitled SURGICAL STAPLER WITH PLURALITY OF CUTTING ELEMENTS, which issued on Oct. 23, 2018, and U.S. Pat. No. 9,788,835, entitled DEVICES AND METHODS FOR FACILITATING EJECTION OF SURGICAL FASTENERS FROM CARTRIDGES, which issued on Oct. 17, 2017, are incorporated by reference herein.

As described above in connection with FIGS. 83 and 84, and now in connection with FIGS. 144,144A, 145, and 145A, the closure member 36620 of the closure drive 36600 is driven proximally into contact with a cam surface 36235 defined on the second jaw 36230 to close the second jaw 36230. As also described above, and referring to FIG. 146, a firing assembly including the I-beam portion 37720 and the threaded portion 37730 is driven distally during the staple firing stroke such that the cam 37739 travels within the longitudinal slot 36229 defined in the first jaw 36220 and the cam 37729 travels within the longitudinal slot 36239. In various instances, the second jaw 36230 is closed by the closure system 36600 and then the staple firing system 37700 is actuated. In such instances, the end effector closing operation and the staple firing operation are performed sequentially. In other instances, both the end effector closing system and the staple firing system are operated at the same time. In at least one such instance, the end effector closing system is used to close the second jaw 36230 and then the staple firing system is used to fire the staples from the staple cartridge 37400. During the staple firing stroke, however, the end effector closing system is also actuated to decrease and/or maintain the distance, or tissue gap, between the second jaw 36230 and the staple cartridge 37400 during the staple firing stroke. In at least one instance, the end effector jaw closure system 37600 is used to move the second jaw 36320 into an overclamped position, i.e., an orientation in which the second jaw 36320 is tipped toward, or past parallel with respect to, the staple cartridge 36400 during the staple firing stroke. FIGS. 147-149 illustrate the progression of the second jaw 36230 from an open position (FIG. 147), a parallel clamped position (FIG. 148), and an overclamped position (FIG. 149). In FIG. 148, the tissue gap between the bottom, or tissue compression surface, of the second jaw 36230 and the top surface, or deck, of the staple cartridge 36400 is the same, or at least substantially the same, between the proximal end and the distal end of the end effector 37200. In this instance, the tissue gap distance is approximately 6 mm, for example, but any suitable tissue gap distance could be used. In FIG. 149, it can be seen that the distal end 36234 of the second jaw 36230 is closer to the distal end 37424 than the parallel position of FIG. 148 indicating an overclamped position. In this instance, the second jaw 36230 is overclamped by approximately 3 degrees, for example, but any suitable amount of overclamping could be used. Placing the second jaw 36230 in an overclamped position can allow the second jaw 36230 to resist opening forces created by the staple deformation and/or compensate for internal deflection of the second jaw 36230 during the staple firing stroke.

The above-provided discussion is graphically depicted in the graph 37900 of FIG. 150. The graph 37900 comprises a bottom portion 37980 which depicts the motion of the closure drive 36600 and the staple firing drive 37700 and a top portion 37990 which depicts the force loads experienced by the closure drive 36600 and the staple firing drive 37700. With regard to the top portion 37990 of the graph 37900, the force load within the closure drive 36600 is depicted by trace 36690 and the force load within the firing drive 37700 is depicted by trace 37790. In fact, the trace 36690 splits into a first portion 36690' to depict the scenario when the closure drive 36600 is not actuated during the staple firing stroke and a second portion 36690" to depict the scenario when the closure drive 36600 is actuated during the staple firing stroke. These two different operational scenarios of the closure drive 36600 are reflected in two different operational scenarios within the trace 37790 of the staple firing drive 37700. More specifically, the trace 37790 splits into a first portion 37790' which corresponds to the first portion 36690' of the closure drive and a second portion 37790" which corresponds to the second portion 37790". The first portion 37790' depicts that the staple firing load is higher when the closure drive 36600 is not actuated during the staple firing stroke and the second portion 37790" depicts that the staple firing load is lower when the closure drive 36600 is actuated during the staple firing stroke. To this end, operating the closure drive 36600 during the staple firing stroke is also reflected in the bottom portion 37980 of the graph 37900. The motion of the second jaw 36230 is depicted by the motion trace 36680 which, similar to the above, splits into a first portion 36680' which corresponds to the force traces 36690' and 37790', discussed above, and a second portion 36680" which corresponds to the force traces 36690" and 37790", also discussed above. When the closure drive 36600 is not operated during the staple firing stroke, the second jaw 36230 is maintained in a parallel, or an at least substantially parallel, orientation as depicted by the motion trace 36680'. When the closure drive 36600 is operated during the staple firing stroke, the second jaw 36230 is moved into an overclamped orientation as depicted by the motion trace 36680". Notably, these two operational possibilities are not reflected in the motion trace 37780 of the staple firing drive 37700. Stated another way, the motion of the staple firing drive 37700 can be independent of the operation of the closure drive 36600.

In various instances, further to the above, the staple firing drive 37700 can be used to close the second jaw 36230. In at least one such instance, the staple firing drive 37700 can be used to advance the firing assembly distally such that the cams 37729 and 37739 co-operate to pull the second jaw 36230 toward its closed position at the same time that the closure drive 36600 is being operated to close the second jaw 36230. In at least one other instance, the staple firing drive 37700 can be used to advance the firing assembly distally to close the second jaw 36230 without the assistance of the closure drive 36600. Given that the closure drive 36600 and the staple firing drive 37700 can be operated sequentially and/or at the same time, the closure drive 36600 and the staple firing drive 37700 are each operated by a separate electric motor. In at least one instance, the stapling instrument 37000 is attached to a robotic surgical instrument comprising a first electric motor for driving the closure drive 36600 and a second electric motor for driving the staple firing drive 37700. In at least one other instance, the stapling instrument 37000 comprises a handheld stapling instrument including a handle comprising a first electric motor operably engaged with the closure drive 36600 and a second electric motor operably engaged with the staple firing drive 37700.

An end effector 49200 of a surgical instrument 49000 is illustrated in FIGS. 151 and 152. The end effector 49200 comprises a first jaw 49220 and a second jaw 49230 pivotably attached to the first jaw 49220. The surgical instrument 49000 further comprises an articulation joint about which the end effector 49200 can be rotated. Various articulation joints are described elsewhere herein. The various configurations, or closure states, of the end effector 49200 are depicted at the top of FIG. 153. The second jaw 49230 is movable between an open position by a closure drive 49600 in which there is an approximately 30 degree angle, or jaw aperture, for example, between the jaws 49220 and 49230, a partially closed position, a parallel position, and an overclamped position in which there is approximately −1 to −3 degree angle, for example, between the jaws 49220 and 49230. The fully-open position of the second jaw 49220 establishes an operating condition 49610, the closing of the second jaw 49220 establishes an operating condition 49620, the parallel position of the second jaw 49230 establishes an operating condition 49630, and the overclamped position of the second jaw 49220 establishes an operating condition 49640. The closure drive 49600 comprises an electric motor which is controlled by a control system of the surgical instrument 49000. The closure drive 49600 comprises a closure member which, similar to the above, is retracted proximally by the closure motor to close the second jaw 49230. The distance in which the closure member is retracted is depicted by the trace 49680 and the motion of the closure member corresponds to the closure states of the end effector 49200 depicted at the top of FIG. 153. Notably, the closure system 49600 enters into a wait period, or dwell, once the second jaw 49230 has reached its parallel position during the operating condition 49630. Similarly, the closure system 49600 enters into a wait period, or dwell, in operating condition 49650. The second jaw 49230 is then opened during operating condition 49660.

The surgical instrument 49000 further comprises a staple firing system 49700 and an articulation drive system 49800. The staple firing system 49700 and the articulation drive system 49800 are operated by the same electric motor which is shifted between a first operating state to drive the articulation drive system 49800 and a second operating state to drive the staple firing system 49700. In various instances, the electric motor comprises a transmission which is electronically shifted and/or mechanically shifted to place the electric motor in its first operating state and its second operating state. During the operating conditions 49610 and 49620, the electric motor is in its first operating state and, as a result, the end effector 49200 is articulatable while it is open and/or while it is being closed. Once the end effector 49200 is closed in operating condition 49630, however, the electric motor is shifted into its second operating state. In such instances, the end effector 49200 is locked into its articulated position, whatever that may be, and then the electric motor is powered down. By locking the end effector 49200 into position before powering down the electric motor, sudden jerking movements of the end effector 49200 can be prevented. Stated another way, if the end effector 49200 is experiencing resistance to its articulation from the tissue T, for example, and the electric motor is powered down before the end effector 49200 is locked in position, the end effector 49200 may unexpectedly articulate, or de-articulate. The full-powered condition of the articulation system 49800 is depicted by condition 49810 in FIG. 153 and the ramp-down condition of the articulation system 49800 is depicted by condition 49820.

Once the electric motor is shifted into its second condition, the staple firing drive 49700 is actuatable to perform a staple firing stroke. The staple firing drive 49700 comprises a firing member which is advanced distally during the staple firing stroke and then retracted proximally after the staple firing stroke. The motion of the firing member is depicted by the motion trace 49780 in FIG. 153. Moreover, FIG. 153 depicts that the electric motor is powered up during operating condition 49710 before the staple firing system 49700 is unlocked and then powered to perform the staple firing stroke during operating condition 49730. The force load experienced by the firing member is depicted by the force trace 49790 which shows that the firing member experiences a high load during the staple firing stroke and then a much lower load as the firing member is being retracted during operating condition 49730. After the firing member has been retracted, the staple firing system 49700 is locked and the electric motor is then powered down during the operating condition 49740. Similar to the above, locking the firing drive before de-powering the electric motor reduces the possibility of sudden jerks within the staple firing system 49700. At such point, the electric motor is switched back into its first operating state, the electric motor is re-powered, and the articulation drive system 49800 is unlocked during an operating state 49830. Notably, the operating state 49830 in which the end effector 49200 can be articulated and the operating state 49660 in which the end effector 49200 can be opened overlap.

Further to the above, the surgical instrument 49000 comprises one or more position sensors to determine the position of the closure member of the closure system 49600 and/or the position of the second jaw 49230. The surgical instrument 49000 further comprises one or more position sensors to determine the position of the firing member of the staple firing system 49700. The surgical instrument 49000 comprises an electric circuit configured to assess the current drawn by the electric motor of the closure drive system 49600 to evaluate the force load experienced by the closure member of the closure drive system 49600. The surgical instrument 49000 further comprises an electric circuit configured to assess the current drawn by the second electric motor used to drive the staple firing system 49700 to assess the firing load experienced by the firing member of the staple firing system 49700. All of these sensors and circuits are in communication with the control system of the surgical instrument 49000. With this information, the control system can determine when certain operational states have been reached. For instance, when the control system determines that the second jaw 49230 has reached its parallel position, the control system can stop the closure motor as part of the operational state 49630. At such point, the control system can monitor the force load within the closure drive system 49600 until the force load falls below a threshold and, at that point, determine that the operational state 49630 is over and signal to the user of the surgical instrument 49000 that an optimal condition for performing the staple firing stroke has been reached.

As discussed above, the electric motor used to drive the articulation drive system 49800 and the firing drive system 49700 is shiftable between a first operating state and a second operating state. In at least one embodiment, the closure drive 49600 can be used to shift this electric motor between its first and second operating states. The entire disclosures of International Patent Publication WO2015/153642, entitled SURGICAL INSTRUMENT WITH SHIFTABLE TRANSMISSION, which published on Oct. 8, 2015, and U.S. Pat. No. 9,351,726, entitled ARTICULATION CONTROL SYSTEM FOR ARTICULATABLE SURGICAL INSTRUMENTS, which issued on May 31, 2016, are incorporated by reference herein.

A staple firing system 38700 is illustrated in FIGS. 91-96. The staple firing system 38700 comprises a rotatable drive shaft and a firing member threadably engaged with the drive shaft. The staple firing system 38700 further comprises a drive portion 38730 and a sled portion 38740. The sled portion 38740 comprises at least one push surface 38741 defined on the proximal side thereof which is contacted by the firing member when the firing member is advanced distally during a staple firing stroke. The sled portion 38740 also becomes attached to the firing member by lock arms 38734 when the firing member is moved distally into contact with the sled portion 38740. At least initially, the sled portion 38740 moves relative to the drive portion 38370. At such point, as described in greater detail below, the sled portion 38740 and the drive portion 38370 are advanced distally together such that ramps 38742 defined on the sled portion 38740 fire the staples from the staple cartridge during the staple firing stroke. The staple firing system 38700 further comprises a tissue cutting knife 38750 rotatably mounted to the drive portion 38730 about a pivot pin 38752.

Figure 93:
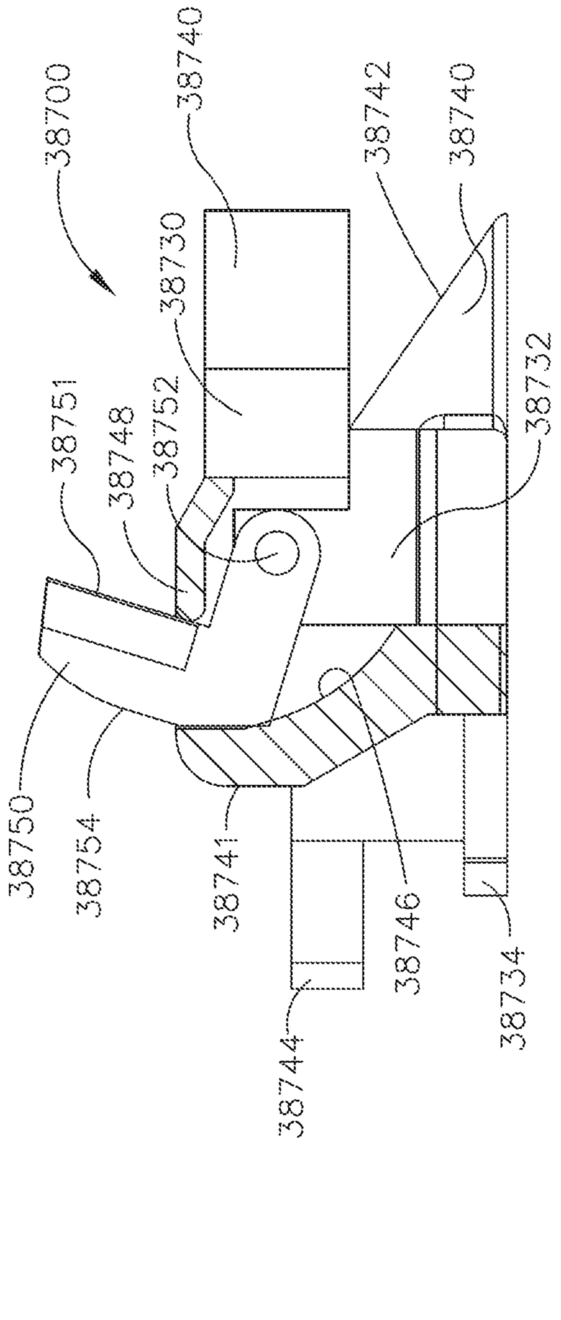
FIG. 93 is a cross-sectional elevational view of the firing assembly of FIG. 91 illustrating a tissue cutting knife of the firing assembly in a deployed configuration.
Figure 94:
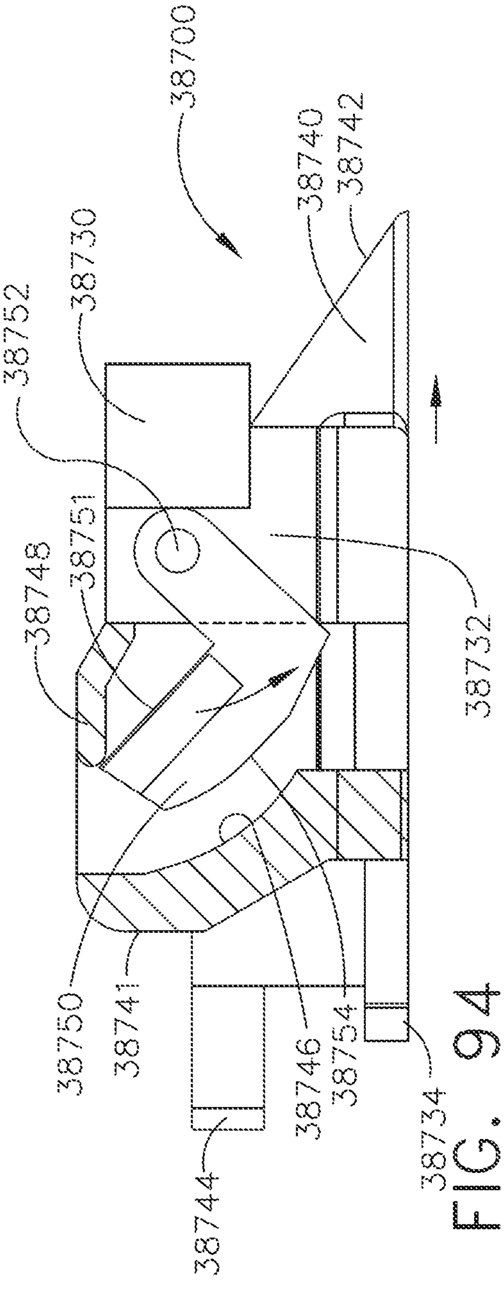
FIG. 94 is a cross-sectional elevational view of the firing assembly of FIG. 91 in an undeployed configuration.
Figure 96:
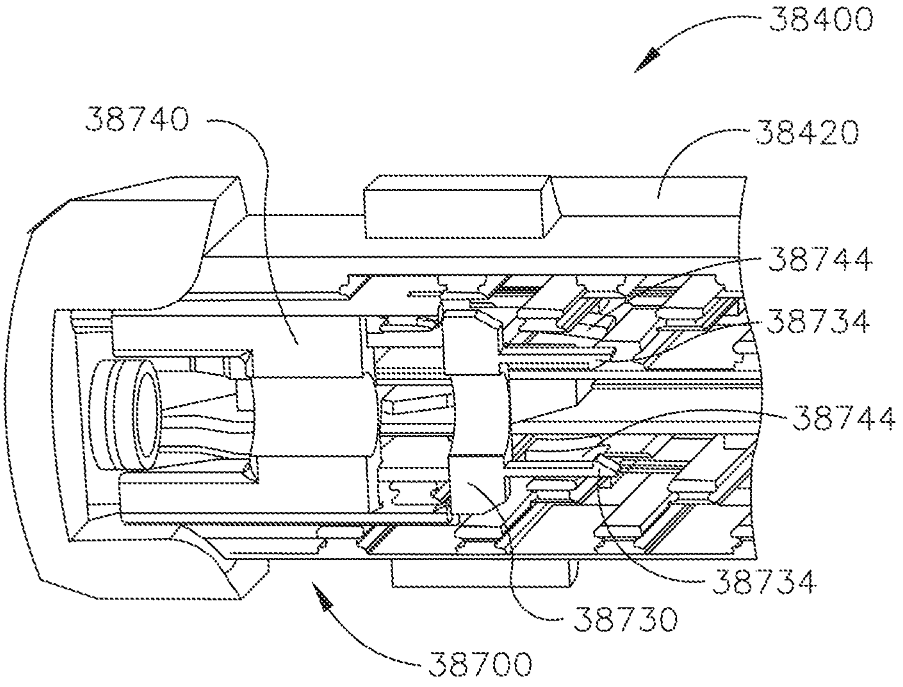
FIG. 96 is a partial perspective view of the staple cartridge of FIG. 95.
Figure 95:
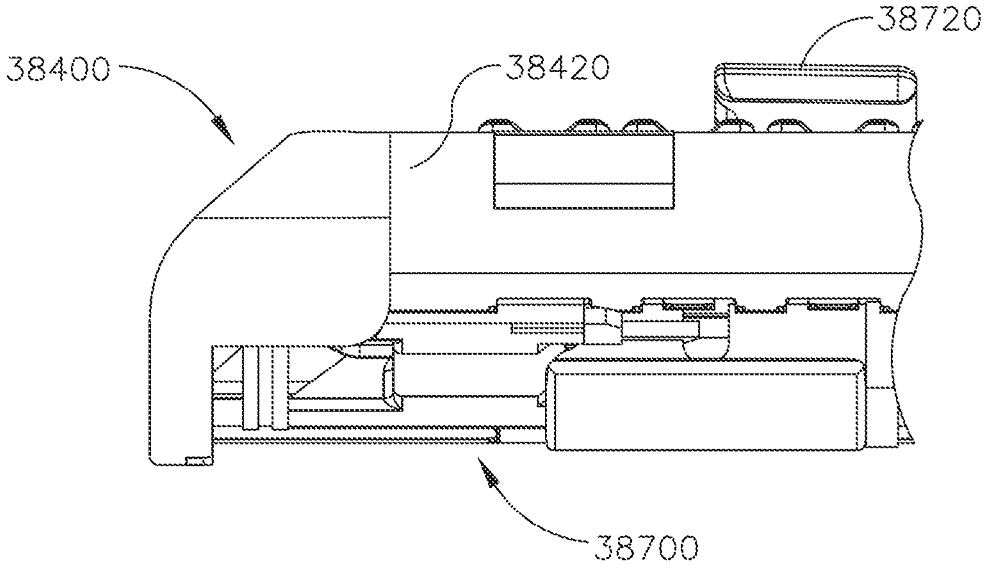
FIG. 95 is a partial elevational view of a staple cartridge comprising the firing assembly of FIG. 91.
Figure 97:
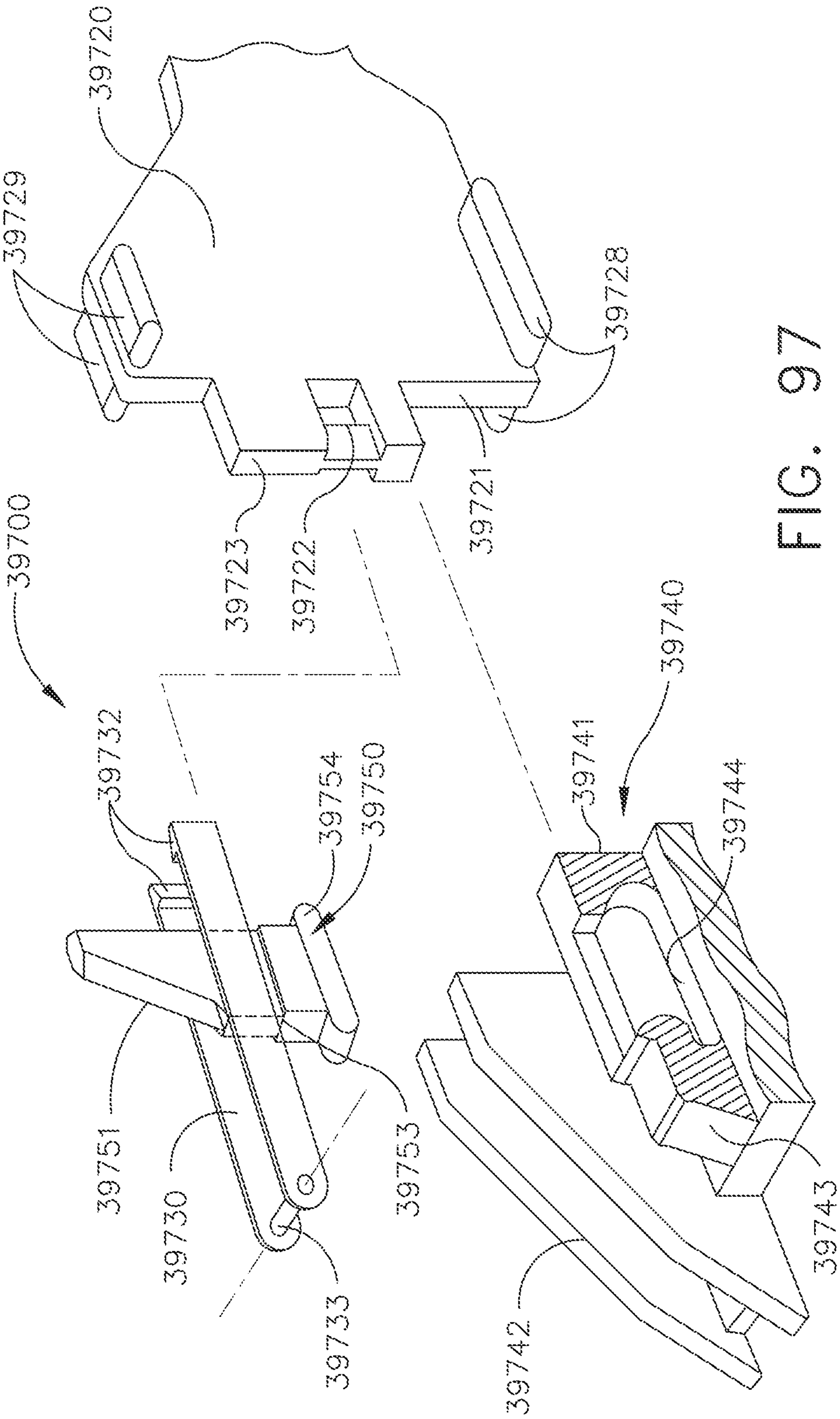
FIG. 97 is a partial exploded view of a firing assembly of a surgical instrument in accordance with at least one embodiment.

The tissue cutting knife 38750 is rotatable between an undeployed position (FIG. 94) and a deployed position (FIG. 93) at the outset of the staple firing stroke. The sled portion 38740 is movable distally relative to the drive portion 38730, at least initially, until a cam surface 38746 defined in the sled portion 38740 contacts the tissue cutting knife 38750, as illustrated in FIG. 93, and rotates the tissue cutting knife 38750 upwardly into its deployed position. The cam surface 38746 is curved, or arcuate, to facilitate the rotation of the tissue cutting knife 38750 about the pivot pin 38752, although any suitable configuration could be used. When the tissue cutting knife 38750 contacts a shoulder 38748 defined on the sled portion 38740, the tissue cutting knife 38750 stops rotating and, instead, the distal motion of the sled portion 38740 is transferred to the drive portion 38730 through the tissue cutting knife 38750. At such point, the drive portion 38730 and the sled portion 38740 translate distally together to perform the staple firing stroke with the tissue cutting knife 38750 in its deployed position. In fact, the sled portion 38740 holds the tissue cutting knife 38750 in its deployed position during the staple firing stroke. Notably, a knife edge 38751 of the tissue cutting knife 38750 extends above the sled portion 38740 when the tissue cutting knife 38750 is in its deployed position (FIG. 93) and does not extend above the sled portion 38740 when the tissue cutting knife 38750 is in its undeployed position (FIG. 94).

At the end of the staple firing stroke, or after the staple firing stroke has been stopped, further to the above, the rotatable drive shaft is rotated in the opposite direction and the firing member of the staple firing system 38700 is driven in the opposite direction. When the firing member is retracted, the firing member pulls the sled portion 38740 proximally owing to the lock arms 38734 attaching the sled portion 38740 to the firing member. That said, the initial retraction motion of the firing member and the sled portion 38740 does not translate the drive portion 38730 proximally. Instead, the initial retraction motion of the sled portion 38740 rotates the tissue cutting knife 38750 back down into its undeployed position, as illustrated in FIG. 94. Thereafter, referring to FIGS. 95 and 96, the proximal movement of sled portion 38740 stops owing to the detachment of the sled portion 38740 from the firing member. More specifically, the proximal-extending stop arms 38744 of the sled portion 38740 engage the cartridge body 38420 and prevent the sled portion 38740 from being retracted with the firing member. At such point, the lock arms 38734 of the sled portion 38740 decouple from the firing member leaving the sled portion 38740 and the drive portion 38730 in their fired positions. Such an arrangement prevents the spent staple cartridge 38400 from being used again. As a result, the spent staple cartridge 38400 must be replaced with an unspent staple cartridge in order to use the surgical instrument once again. That said, other spent cartridge lockout systems could be used which could permit the return of the sled portion 38740 after the staple firing stroke so long as a spent staple cartridge could not be re-fired.

A staple firing system 39700 is illustrated in FIGS. 97-103. The staple firing system 39700 comprises a firing bar 39720 which is translatable distally through a staple cartridge, such as staple cartridge 39400, for example, to perform a staple firing stroke. The firing bar 39720 comprises a first cam 39278 which engages a first jaw and a second cam 39279 which engages a second jaw during the staple firing stroke to hold the first and second jaws together. The staple firing system 39700 further comprises a sled 39740 which is pushed distally by the firing bar 39720 during the staple firing stroke. The sled 39740 comprises a proximal push surface 39741 which is contacted by a distal push surface 39271 on the firing bar 39720. The sled 39740 further comprises a central body 39743 and ramps 39742 extending from the central body 39743.

Figure 98:
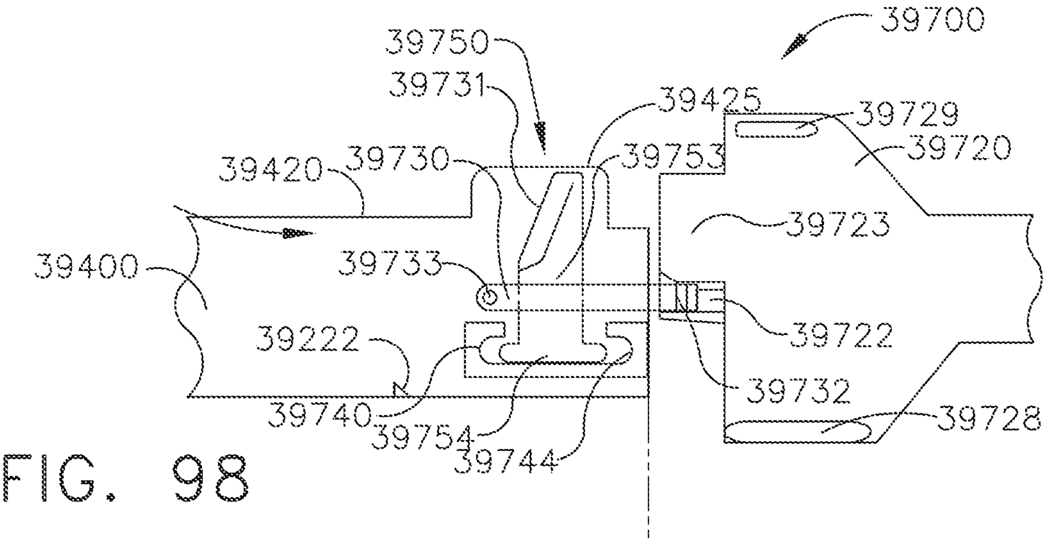
FIG. 98 is a partial elevational view of the firing assembly of FIG. 97 and a staple cartridge illustrating the firing assembly in an unfired position.

Further to the above, the staple firing system 39700 further comprises a tissue cutting knife 39750 and a knife retractor 39730. The tissue cutting knife 39750 comprises a base 39754 positioned within a recess 39744 defined in the sled 39740 and a knife body 39753 including a knife edge 39751. The knife retractor 39730 comprises lock arms 39732 which engage shoulders 39722 defined in the firing bar 39720 and a cross-bar 39733 connecting the distal ends of the lock arms 39732. Referring to FIG. 98, the sled 39740, the tissue cutting knife 39750, and the knife retractor 39730 are stored in a cartridge body 39420 of the staple cartridge 39400 such that, when the staple cartridge 39400 is inserted into the first jaw, the lock arms 39732 of the knife retractor 39730 attach to the firing bar 39720 and the knife body 39753 of the tissue cutting knife 39750 abuts a distal push surface 39723 (FIG. 97) defined on the firing bar 39720. At this point, the knife edge 39731 extends above the top surface, or deck, of the cartridge body 39420, but is covered by rails 39425 extending upwardly from the cartridge body 39420 such that the knife edge 39731 is not exposed when the staple firing system 39700 is in its unfired condition.

Figure 99:
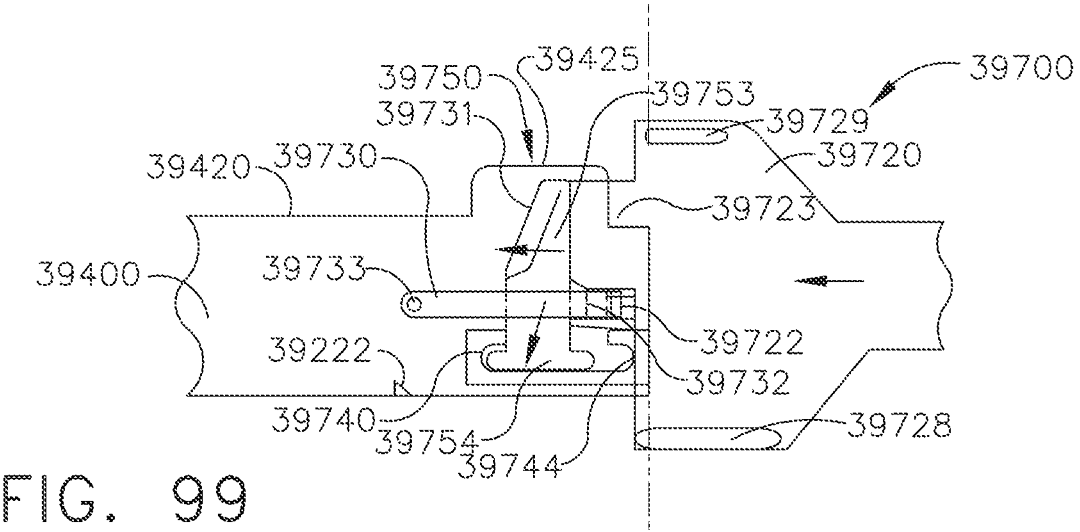
FIG. 99 is a partial elevational view of the firing assembly of FIG. 97 and the staple cartridge of FIG. 98 illustrating the firing assembly in a partially fired position.
Figure 100:
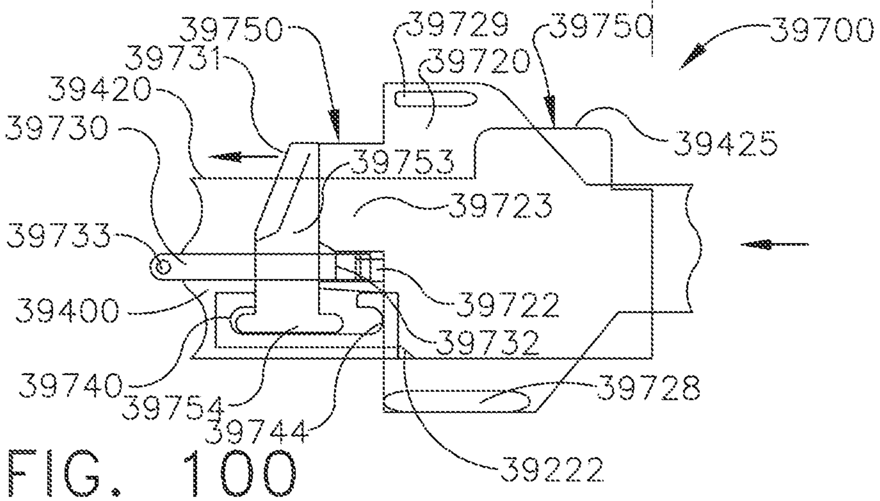
FIG. 100 is a partial elevational view of the firing assembly of FIG. 97 and the staple cartridge of FIG. 98 illustrating the firing assembly in a fired position.
Figure 101:
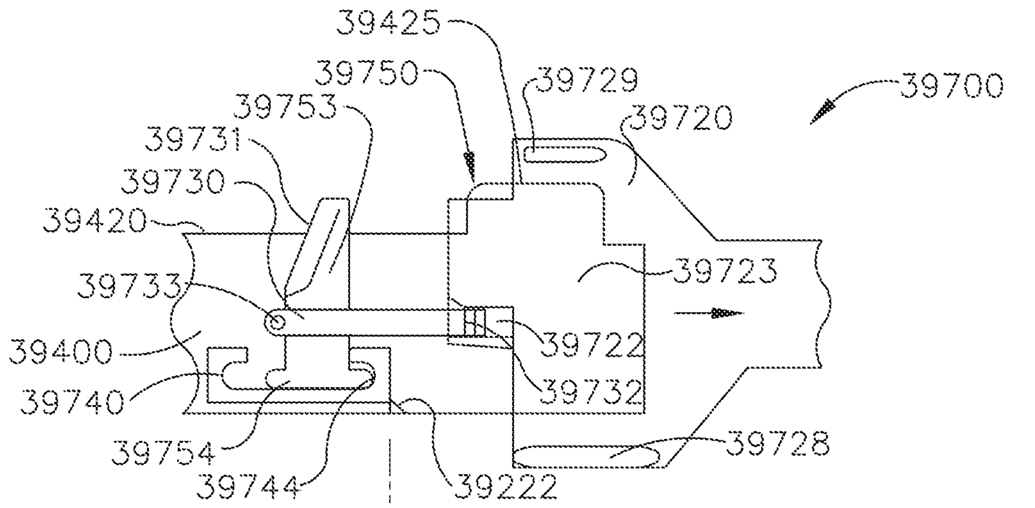
FIG. 101 is a partial elevational view of the firing assembly of FIG. 97 and the staple cartridge of FIG. 98 illustrating the firing assembly at the end of the staple firing stroke.
Figure 102:
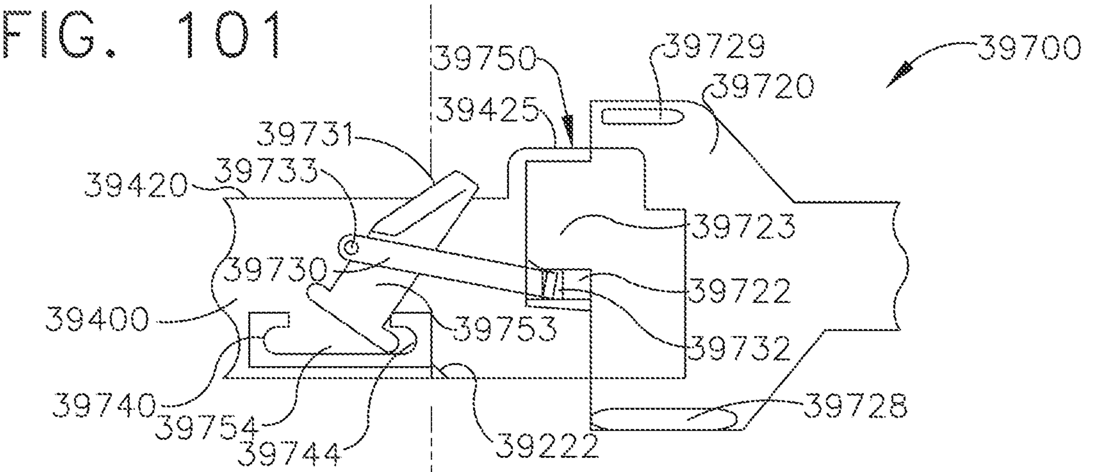
FIG. 102 is a partial elevational view of the firing assembly of FIG. 97 and the staple cartridge of FIG. 98 illustrating the firing assembly being retracted after the staple firing stroke.
Figure 103:
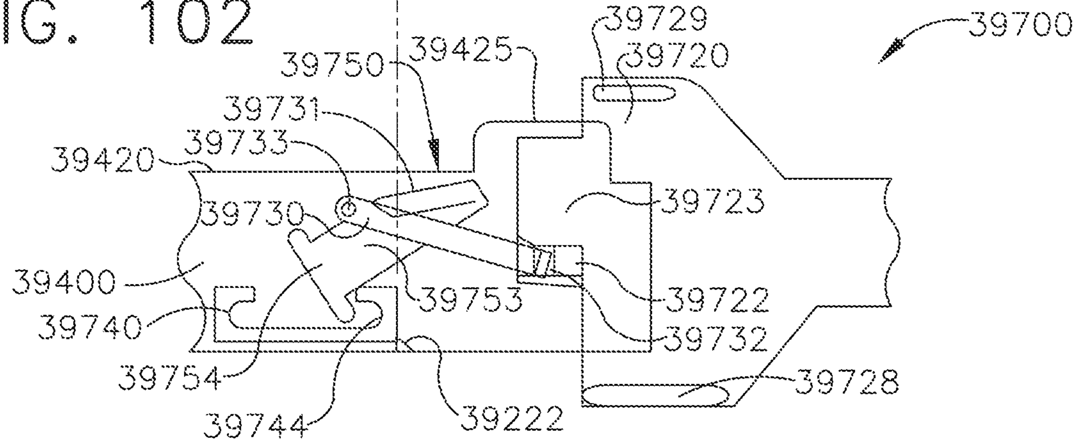
FIG. 103 is a partial elevational view of the firing assembly of FIG. 97 and the staple cartridge of FIG. 98 illustrating the firing assembly in a retracted position.

When the staple firing system 39700 is advanced distally to perform the staple firing stroke, referring to FIG. 99, the firing bar 39720 contacts and pushes the sled 39740 and the tissue cutting knife 39750 distally. Notably, referring to FIG. 100, the sled 39740 passes over a projection 39222 extending from the first jaw at the outset of the staple firing stroke. The projection 39222 comprises a proximal-facing ramp that permits the sled 39740 to pass thereover. Throughout the staple firing stroke, the knife retractor 39730 extends in front of the tissue cutting knife 39750. After the staple firing stroke has been completed, or is otherwise stopped, referring to FIG. 101, the firing bar 39720 is retracted to its unfired position. In such instances, the knife retractor 39730 contacts the tissue cutting knife 39750 to pull the tissue cutting knife 39750 and the sled 39740 proximally. Notably, the base 39754 of the tissue cutting knife 39750 initially slides within the sled recess 39744 when the tissue cutting knife 39750 is pulled proximally, i.e., until the knife base 39754 contacts the proximal end of the sled recess 39744. At such point, the tissue cutting knife 39750 and the sled 39740 move proximally together until the sled 39740 reaches the projection 39222 extending from the first jaw, as illustrated in FIG. 102. The projection 39222 stops the proximal movement of the sled 39740 and, as a result, the continued proximal retraction of the firing bar 39720 rotates the tissue cutting knife 39750 proximally until the tissue cutting knife 39750 is completely retracted below the deck of the cartridge body 39420. At such point, the spent staple cartridge 39400 can be safely removed from the first jaw and replaced with another staple cartridge.

Figure 104:
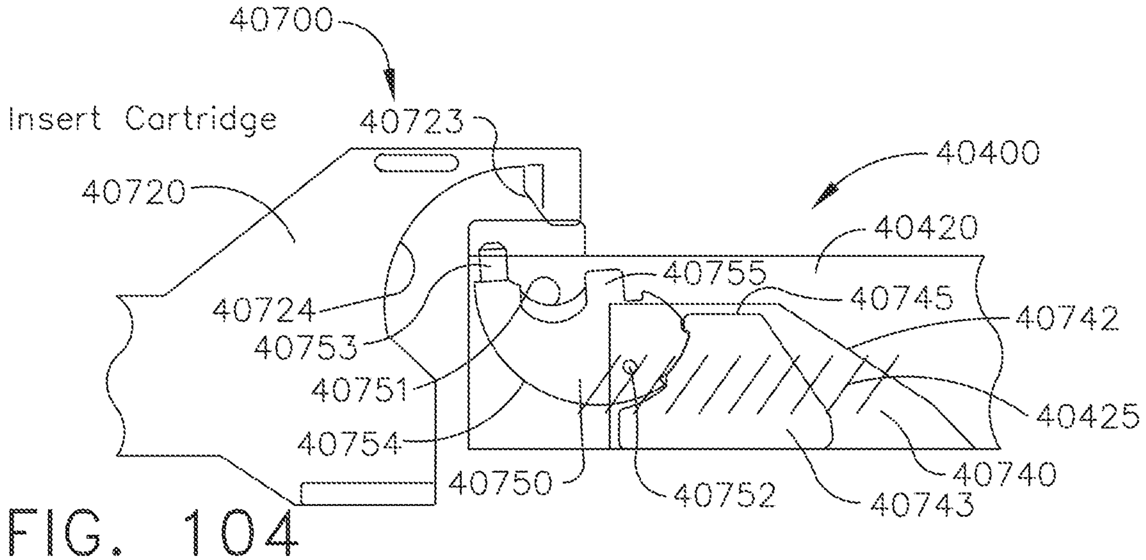
FIG. 104 illustrates a staple firing system and a staple cartridge in accordance with at least one embodiment.
Figure 105:
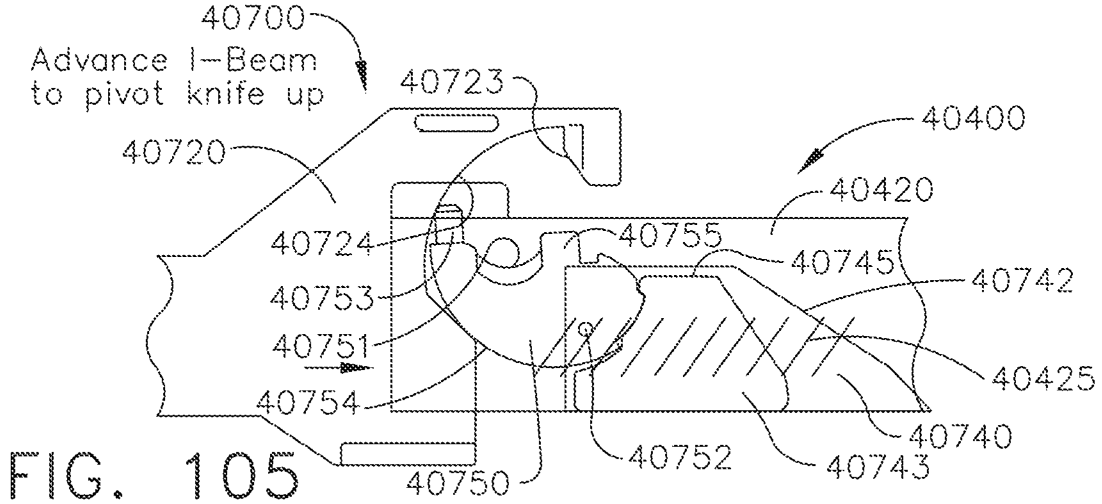
FIG. 105 illustrates a firing member of the staple firing system of FIG. 104 being advanced distally during a staple firing stroke.
Figure 106:
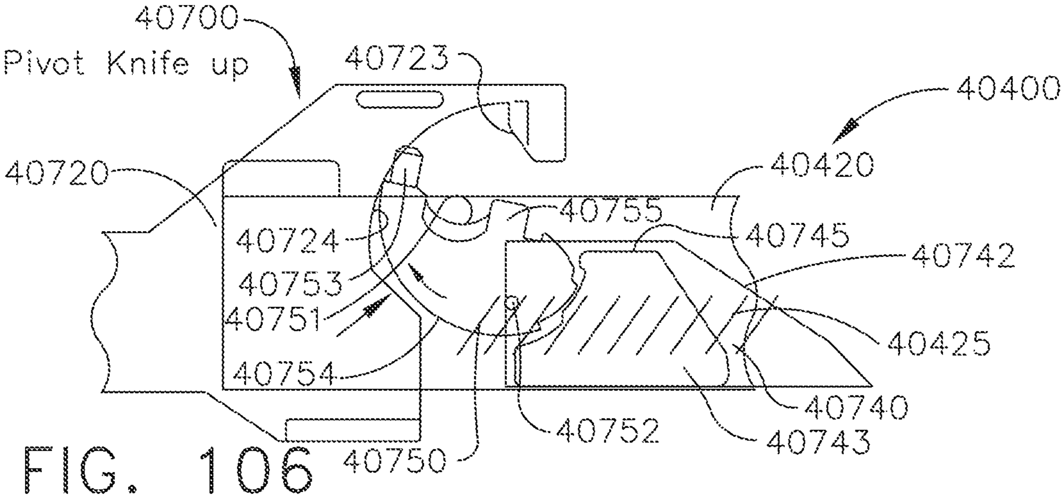
FIG. 106 illustrates the firing member of FIG. 105 rotating a tissue cutting knife of the staple firing system from an undeployed position to a deployed position.
Figure 107:
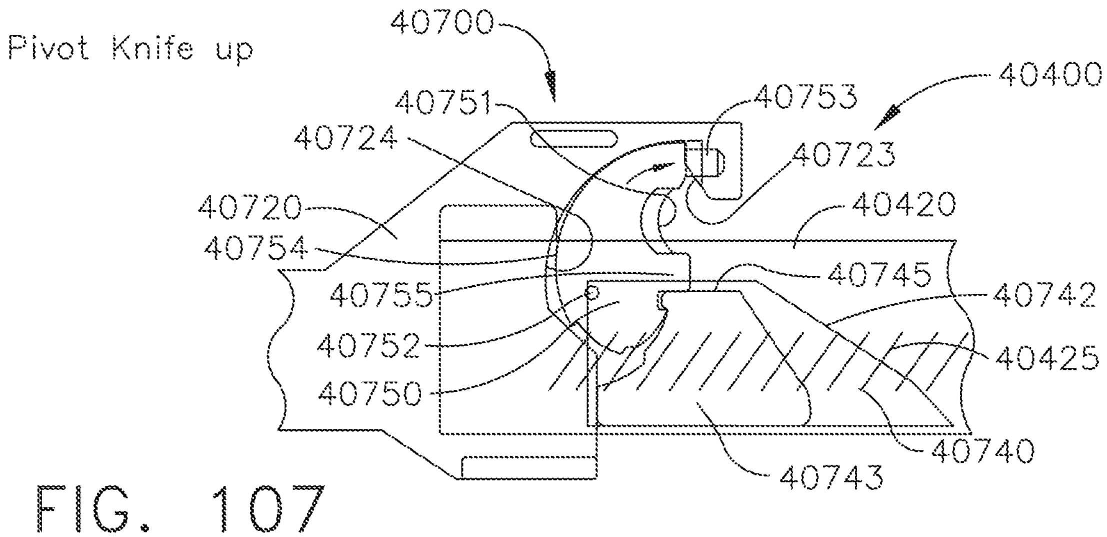
FIG. 107 illustrates the tissue cutting knife of FIG. 106 in a fully-deployed position.
Figure 108:
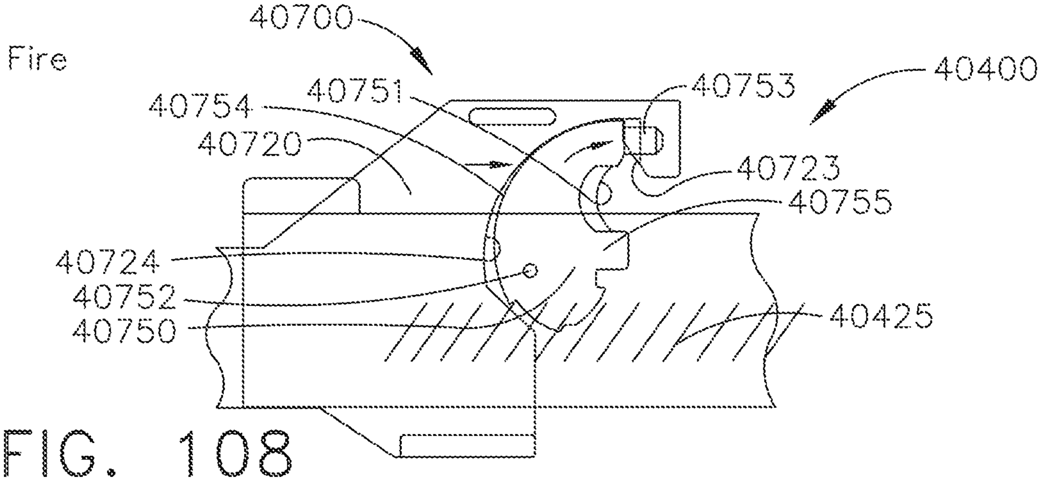
FIG. 108 illustrates the staple firing system of FIG. 104 being advanced distally during a staple firing stroke.
Figure 109:
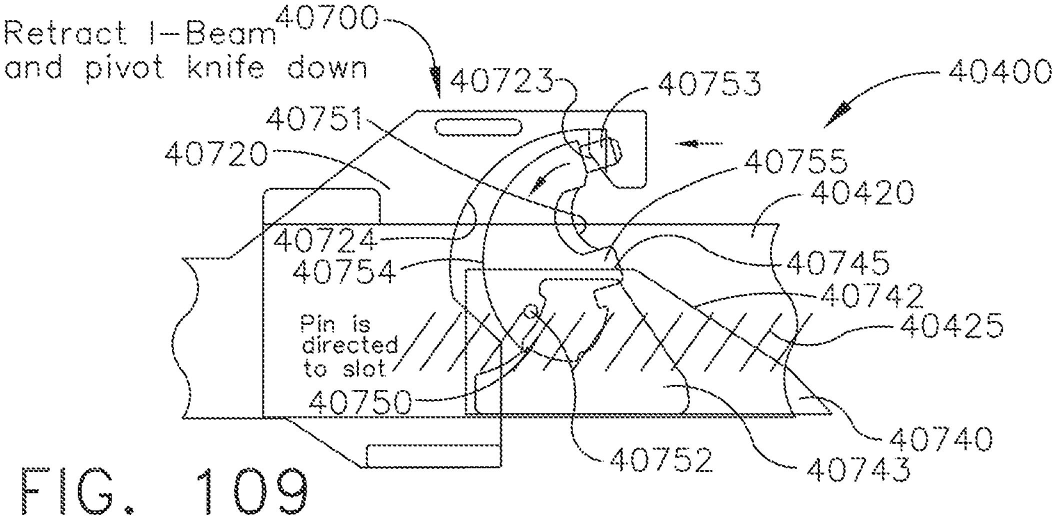
FIG. 109 illustrates the firing member of FIG. 105 being retracted after the staple firing stroke.
Figure 110:
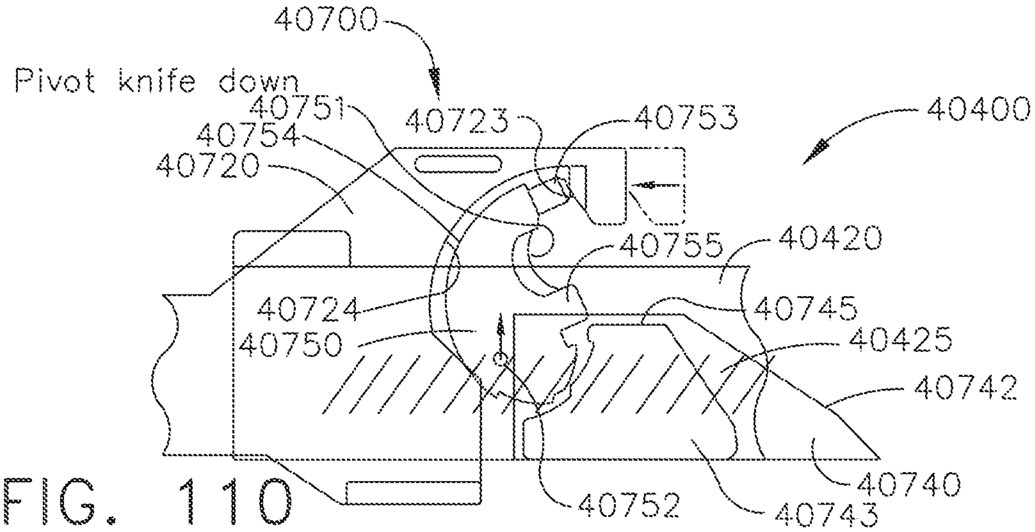
FIG. 110 illustrates the tissue cutting knife of FIG. 106 being rotated toward its undeployed position by the firing member of FIG. 105 as the firing member is being retracted.
Figure 111:
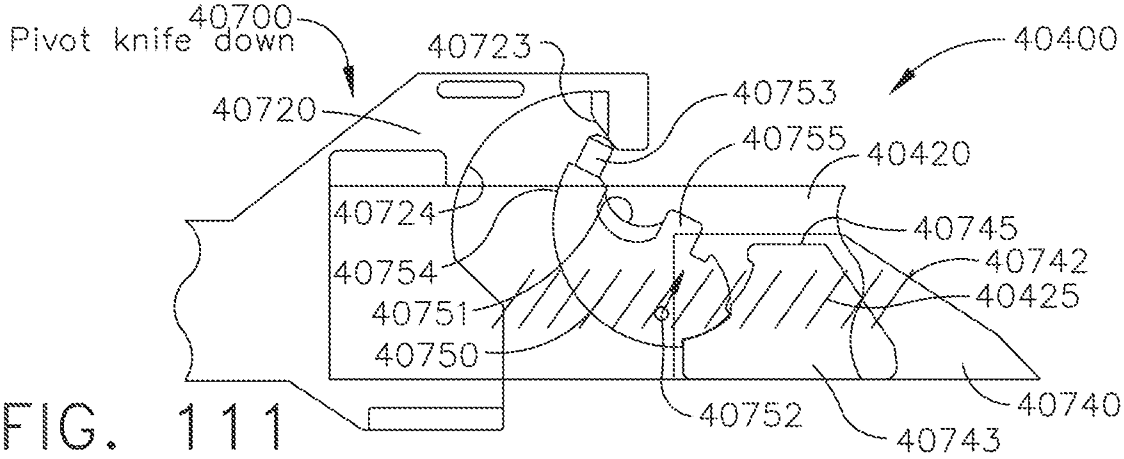
FIG. 111 illustrates a knife edge of the tissue cutting knife of FIG. 106 retracted below the deck of the staple cartridge.
Figure 112:
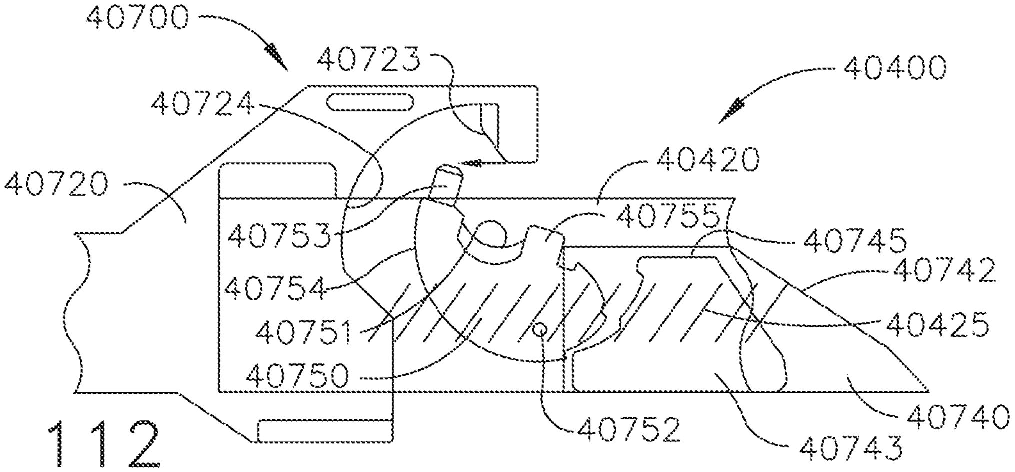
FIG. 112 illustrates the firing member of FIG. 105 decoupled from the tissue cutting knife of FIG. 106.
Figure 113:
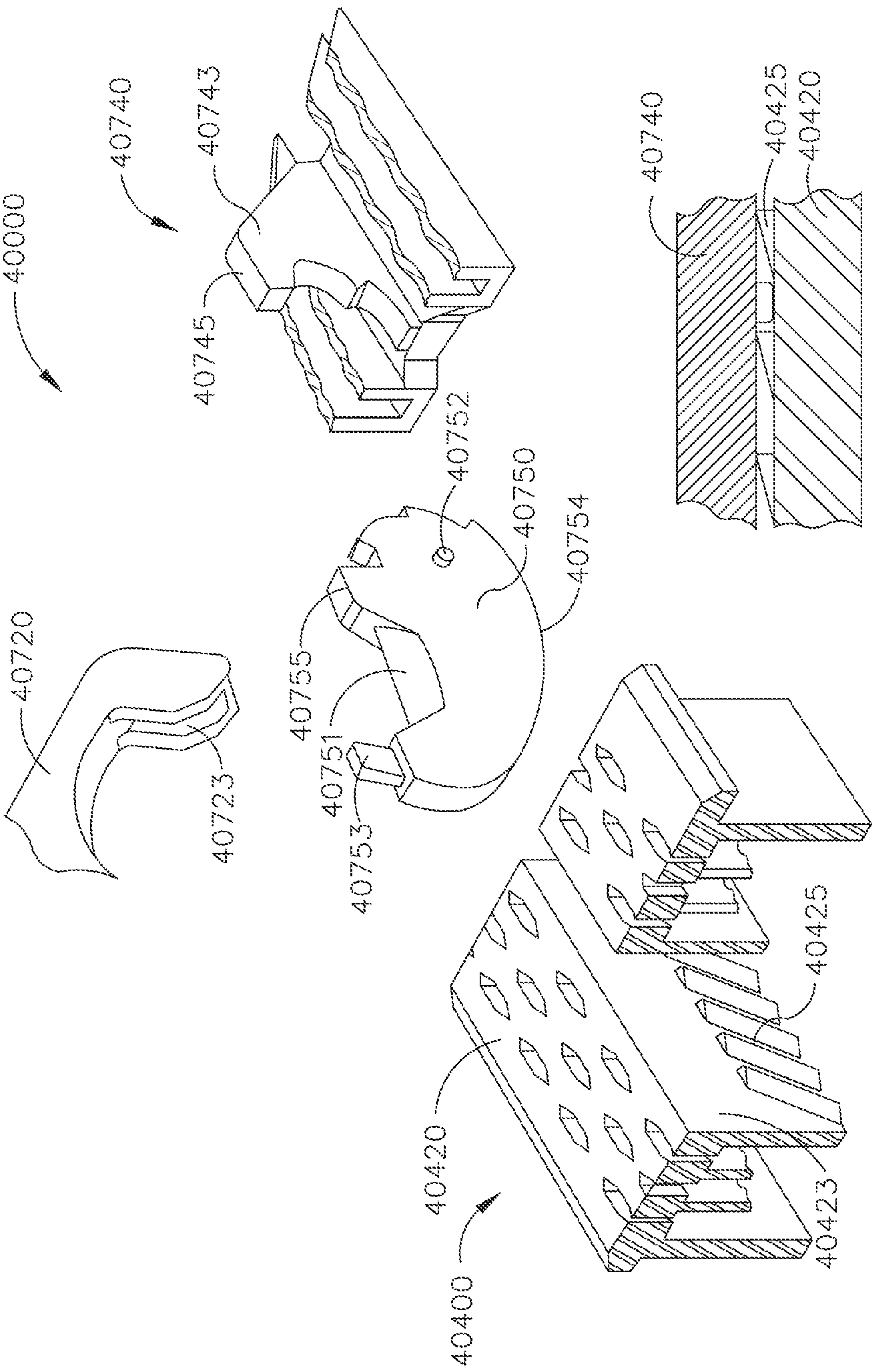

A stapling instrument 40000 comprising a staple cartridge 40400 and a staple firing system 40700 is illustrated in FIGS. 104-113. Referring primarily to FIG. 104, the staple firing system 40700 comprises a firing bar 40720, a sled 40740 movable distally by the firing bar 40720 during a staple firing stroke, and a tissue cutting knife 40750 rotatably mounted to the sled 40740 about a pivot 40752. That said, the sled 40740 and the tissue cutting knife 40750 are positioned in the staple cartridge 40400 and are presented in front of the firing bar 40720 when the staple cartridge 40400 is seated in the stapling instrument 40000. When the firing bar 40720 is advanced distally to perform a staple firing stroke, as illustrated in FIG. 105, the firing bar 40720 contacts the tissue cutting knife 40750. As the firing bar 40720 is moved further distally, referring to FIGS. 106 and 107, the firing bar 40720 rotates the tissue cutting knife 40750 from an undeployed position (FIGS. 104 and 105) to a deployed position in which the knife edge 40751 of the tissue cutting knife 40750 is exposed above the top, or deck, of a cartridge body 40420 of the staple cartridge 40400. The tissue cutting knife 40750 comprises an arcuate cam surface 40754 defined on the proximal side thereof which is contacted by an arcuate cam recess 40724 defined in the firing bar 40720 which rotates the tissue cutting knife 40750 into its deployed position. When the tissue cutting knife 40750 is in its deployed position, as illustrated in FIG. 107, a lock tab 40753 extending from the tissue cutting knife 40750 is received in a lock recess, or catch, 40723 defined in the firing bar 40720 which stops the rotation of the tissue cutting knife 40750 in its deployed position. Moreover, a stop tab 40755 extending from the tissue cutting knife 40750 is seated on a top surface 40745 of the sled 40740 when the tissue cutting knife 40750 is in its deployed position. In any event, at such point, referring to FIG. 108, the firing bar 40720 can push the tissue cutting knife 40740 and the sled 40750 through the staple firing stroke. Referring to FIG. 113, a center portion 40743 of the sled 40740 and a bottom portion of the tissue cutting knife 40750 travel within a longitudinal slot 40423 defined in the cartridge body 40420 of the staple cartridge 40400.

After the staple firing stroke, or after the staple firing stroke has been stopped, referring to FIGS. 109-112, the firing bar 40720 can be retracted into its unfired position. In such instances, the firing bar 40720 pulls proximally on the lock tab 40753 of the tissue cutting knife 40750 which causes the tissue cutting knife 40750 to rotate toward its undeployed position. The cartridge body 40420 of the staple cartridge 40400 comprises angled ridges 40425 extending into the longitudinal slot 40423 which are configured to guide the tissue cutting knife 40750 back into its retracted position when the firing bar 40720 is retracted proximally. The tissue cutting knife 40750 comprises pins 40752 extending from the lateral sides thereof which engage the ridges 40425 when the tissue cutting knife 40750 is rotated backwards into the longitudinal slot 40423. Moreover, in various embodiments, the engagement between the pins 40752 and the ridges 40425 can prevent the tissue cutting knife 40750 from being retracted proximally altogether. In such instances, referring to FIG. 112, the firing bar 40720 becomes decoupled from the tissue cutting knife 40750 and, as a result, the firing bar 40720 does not retract the tissue cutting knife 40750 and the sled 40740. Instead, the tissue cutting knife 40750 and the sled 40740 remain in their fired position, but with the tissue cutting knife 40750 in its undeployed position which permits the spent staple cartridge 40400 to be safely removed from the stapling instrument 40000.

Figure 114:
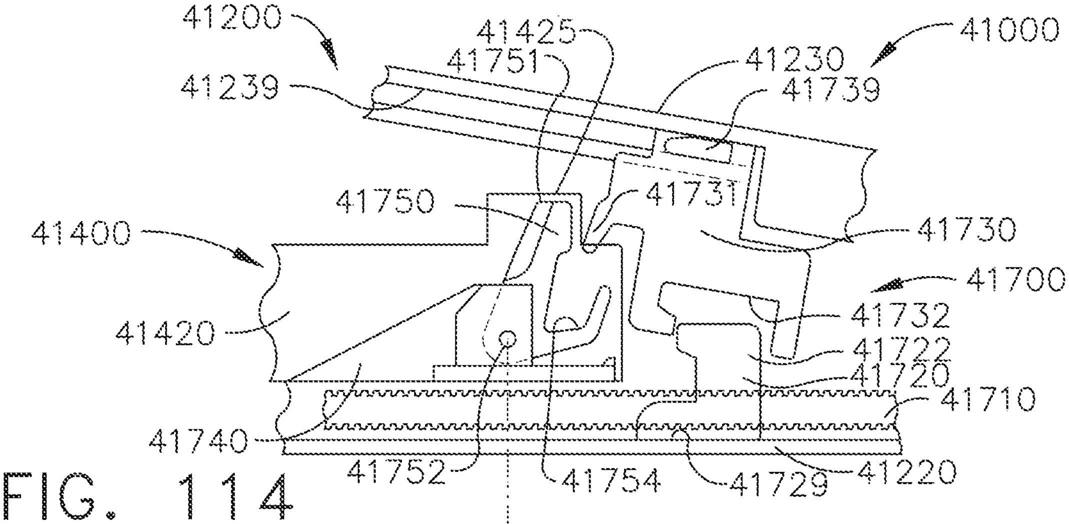

A stapling instrument 41000 comprising an end effector 41200 and a staple firing system 41700 is illustrated in FIGS. 114-120. Referring primarily to FIG. 114, the end effector 41200 comprises a first jaw 41220 and, in addition, a second jaw 41230 rotatably mounted to the first jaw 41220. The second jaw 41230 is rotatable between an open, unclamped position (FIG. 114) and a closed, clamped position (FIG. 115) by a closure system of the stapling instrument 41000. The first jaw 41220 comprises a longitudinal slot defined therein which is configured to receive a portion of the staple firing system 41700. Similarly, the second jaw 41230 comprises a longitudinal slot 41239 defined therein which is configured to receive a portion of the staple firing system 41700. The first jaw 41220 is configured to receive a staple cartridge 41400 therein which comprises a cartridge body 41420, staples removably stored in staple cavities defined in the cartridge body 41420, and staple drivers movably positioned in the cartridge body 41420 which are configured to eject the staples out of the cartridge body 41420 during a staple firing stroke.

Figure 115:
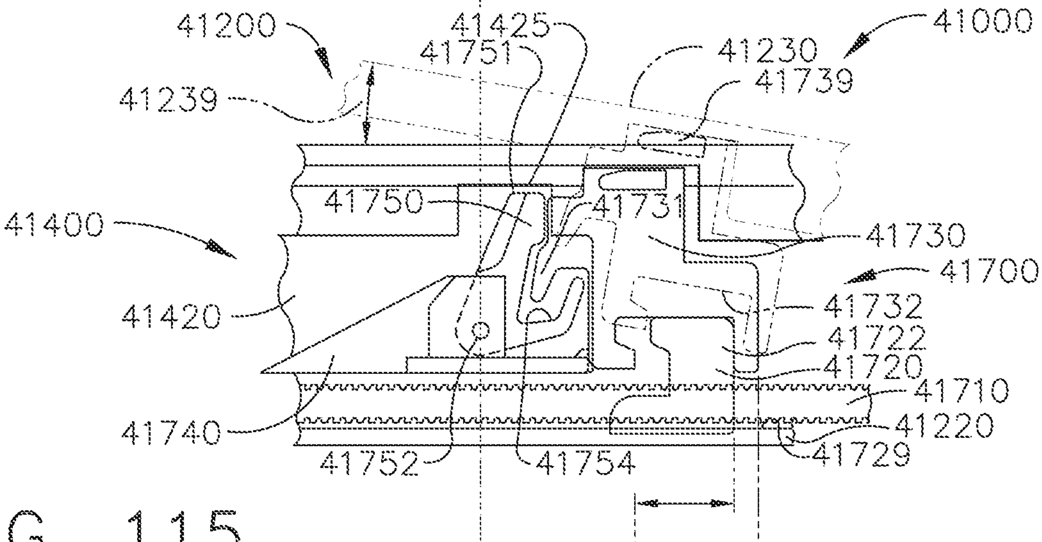
Figure 116:
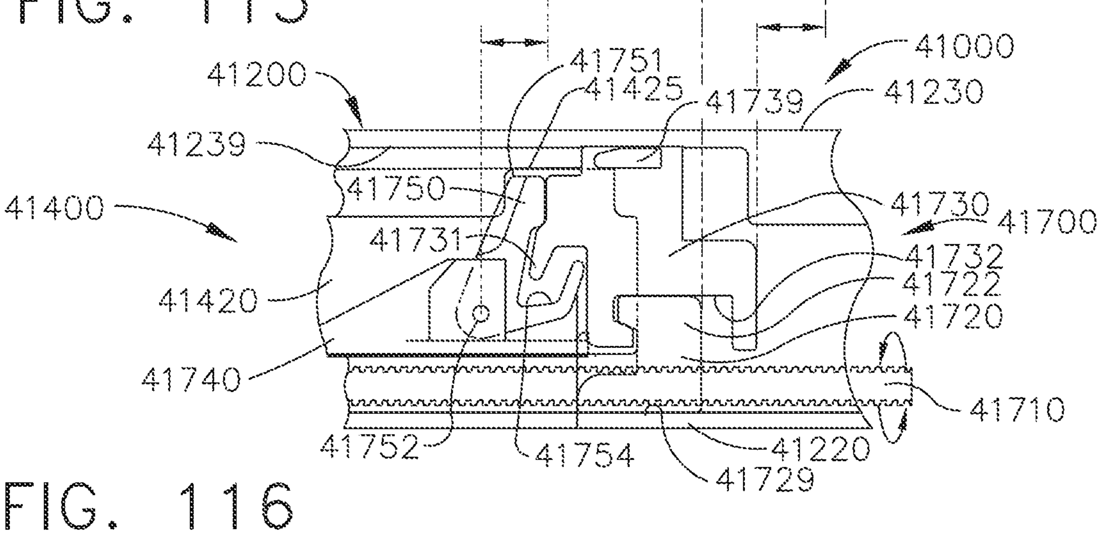
Figure 117:
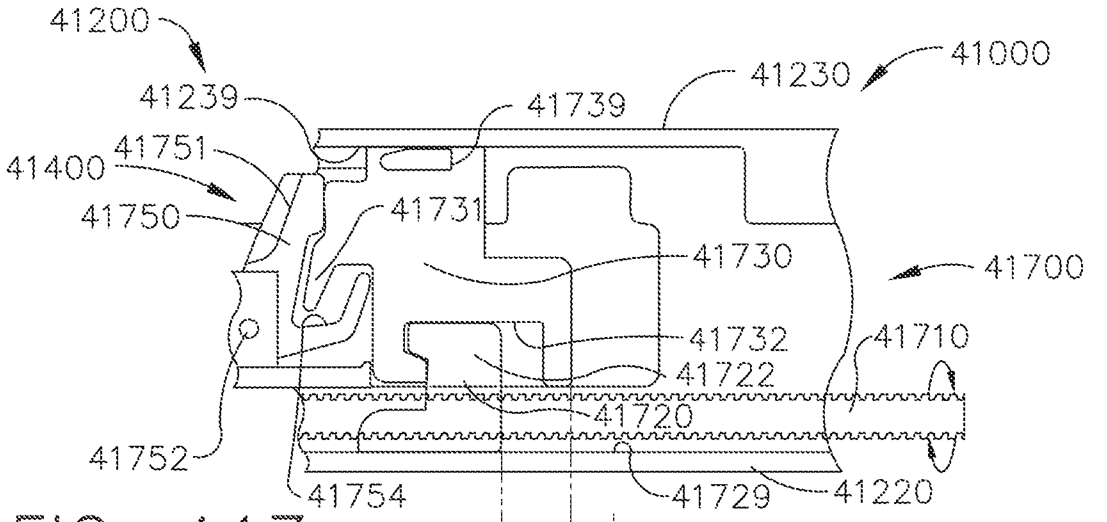
Figure 118:
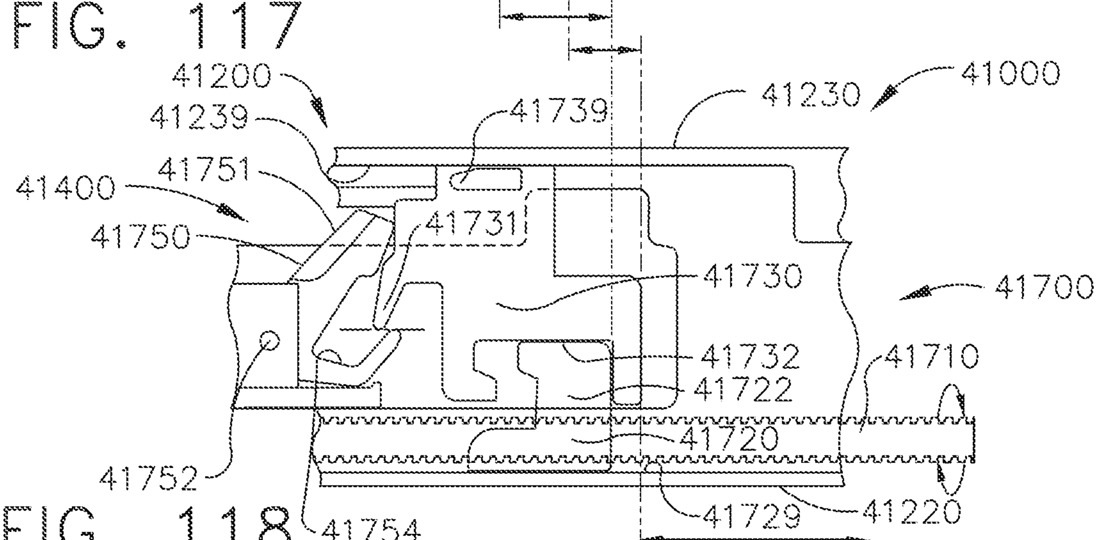
Figure 119:
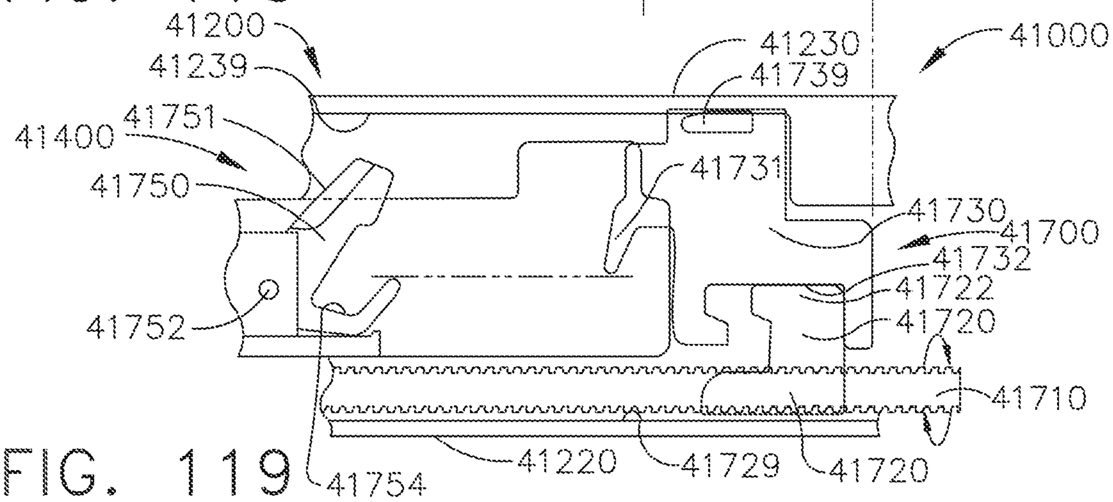
Figure 120:
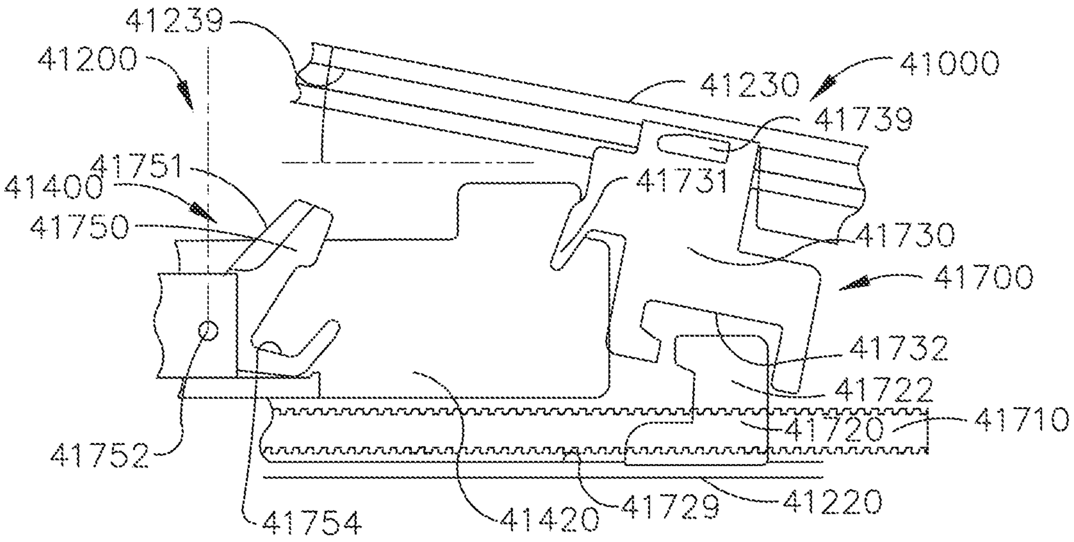

The staple firing system 41700 comprises a rotatable drive shaft 41710 and a firing nut 41720 threadably engaged with a threaded portion of the drive shaft 41710. Similar to the above, the firing nut 41720 is advanced distally when the drive shaft 41710 is rotated in a first direction and retracted proximally when the drive shaft 41710 is rotated in a second, or opposite, direction. The staple firing system 41700 further comprises a clamping member 41730, a sled 41740 movable distally during the staple firing stroke to push the staple drivers and the staples toward staple forming pockets defined in the second jaw 41230, and a tissue cutting knife 41750 rotatably mounted to the sled 41740. Referring primarily to FIG. 114, the clamping member 41730 is retained in the second jaw, or anvil, 41230. More specifically, lateral cams 41739 extending from the clamping member 41730 are contained in the longitudinal slot 41239 defined in the second jaw 41230 such that the clamping member 41730 moves with the second jaw 41230. Thus, when the second jaw 41230 is in an open position, as illustrated in FIG. 114, the clamping member 41730 is in an elevated position and, when the second jaw 41230 is in a closed position as illustrated in FIG. 115, the clamping member 41730 is in a lowered position. When the clamping member 41730 is in its elevated position, the clamping member 41730 is not engaged with the firing nut 41720. When the clamping member 41730 is in its lowered position, however, the clamping member 41730 is engaged with the firing nut 41720. When the clamping member 41730 is in its lowered position, the firing nut 41720 and the clamping member 41730 can be advanced distally to perform a staple firing stroke. The entire disclosures of U.S. Patent Application Publication No. 2016/0249928, entitled SURGICAL APPARATUS, which published on Sep. 1, 2016, and U.S. Patent Publication No. 2018/0168650, entitled CONNECTION PORTIONS FOR DISPOSABLE LOADING UNITS FOR SURGICAL STAPLING INSTRUMENTS, which published on Jun. 21, 2018, are incorporated by reference herein.

Further to the above, the clamping member 41730 comprises a recess 41732 defined therein which is configured to receive a top portion 41722 of the firing nut 41720 when the clamping member 41730 is lowered onto the firing nut 41720, as illustrated in FIG. 115. Moreover, the clamping member 41730 further comprises a hook 41734 which is received in a recess 41754 defined in the tissue cutting knife 41750 when the clamping member 41730 is lowered onto the firing nut 41720. When the firing nut 41720 is advanced distally, referring to FIGS. 116 and 117, the firing nut 41720 pushes the clamping member 41730 distally which abuts the sled 41740 to push the sled 41740 through the staple firing stroke. The clamping member 41730 also abuts the tissue cutting knife 41750 to support the tissue cutting knife 41750 during the staple firing stroke and prevent the tissue cutting knife 41750 from rotating backward, or proximally, when the tissue cutting knife 41750 is cutting the tissue. When the drive shaft 41710 is rotated in the opposite direction, referring to FIG. 118, the firing nut 41720 is driven proximally which pushes the clamping member 41730 proximally. In such instances, the hook 41734 of the clamping member 41730 contacts the proximal end of the tissue cutting knife 41750 which rotates the tissue cutting knife 41750 backwardly so that the clamping member 41730 can decouple from the tissue cutting knife 41750. At such point, referring to FIG. 119, the firing nut 41720 and the clamping member 41730 are returned back to their proximal, unfired positions while the sled 41740 and the tissue cutting knife 41750 remain behind in their fired positions. Notably, the knife edge 41751 of the tissue cutting knife 41750 is extending above the deck, or top, of the cartridge body 41420 when the tissue cutting knife 41750 is left behind; however, in other embodiments, the knife edge 41751 is recessed entirely below the deck of the cartridge body 41420 when the tissue cutting knife 41750 is rotated backwardly. In any event, referring to FIG. 120, the second jaw 41230 can be re-opened once the firing nut 41720 and the clamping member 41730 have been returned to their proximal, unfired position.

Figure 121:
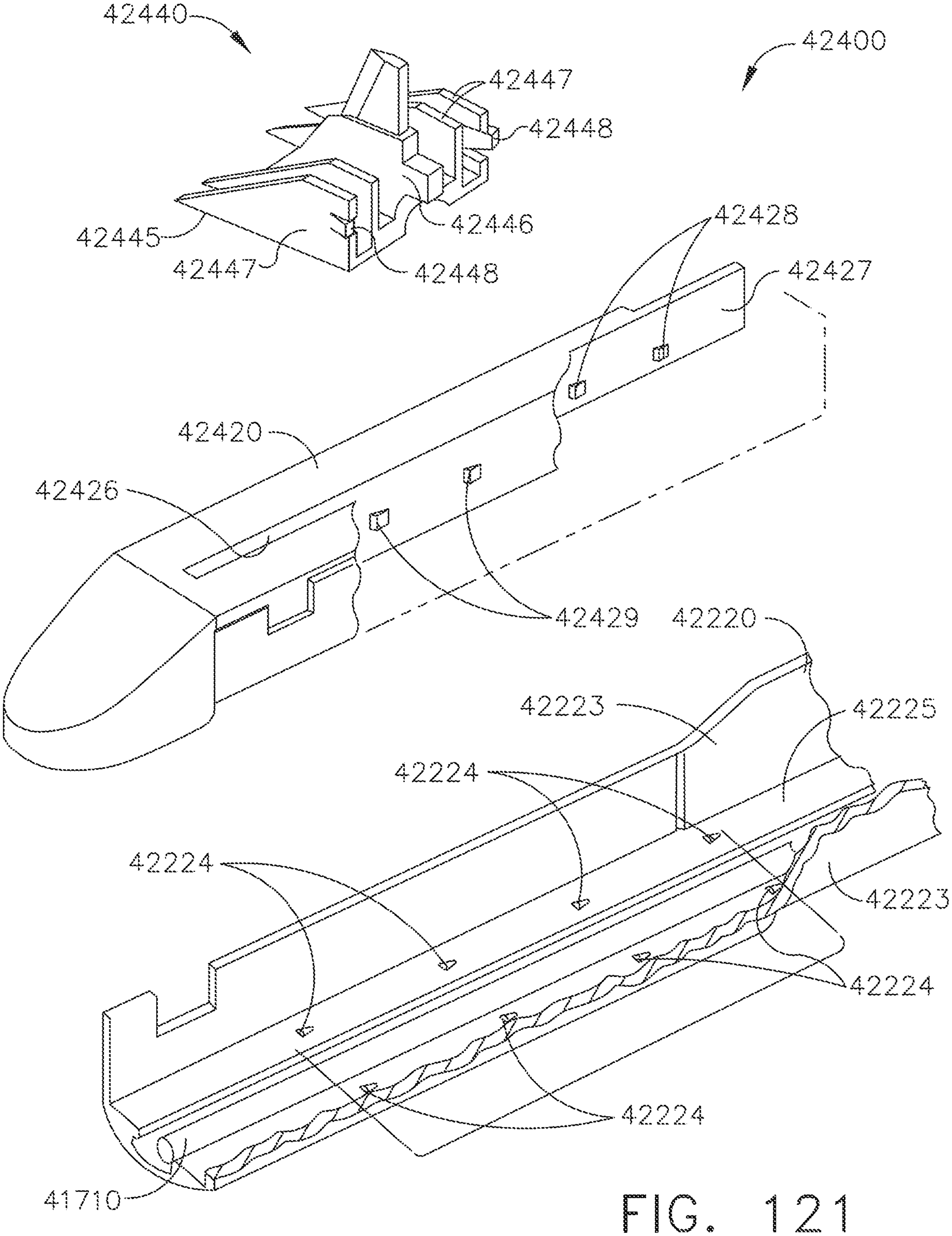

As discussed above, the sled 41740 and the tissue cutting knife 41750 are left behind in their fired positions after the staple firing stroke, or after the staple firing stroke is stopped. In some instances, the tissue cutting knife 41750 may not decouple from the clamping member 41730. FIG. 121 illustrates an embodiment which can assist in holding the sled 41740 and the tissue cutting knife 41750 in their fired positions. FIG. 121 illustrates a staple cartridge 42400 and a jaw 42220 configured to receive the staple cartridge 42400. The jaw 42220 comprises a bottom support 42225 and two lateral up-standing walls 42223. The staple cartridge 42400 comprises a cartridge body 42420 that is positioned between the lateral walls 42223 and, in addition, a sled 42440 translatable within the cartridge body 42420. The cartridge body 42420 comprises staple cavities defined therein with staples removably stored in the staple cavities. The cartridge body 42420 further comprises a longitudinal slot 42426 defined therein which is configured to receive a central portion 42446 of the sled 42440. The cartridge body 42420 further comprises projections 42429 which extend inwardly from the sidewalls of the longitudinal slot 42426 which can inhibit or prevent the proximal movement of the sled 42440. More specifically, each projection 42429 comprises a proximal-facing ramp which permits the sled 42440 to pass thereby during the staple firing stroke and a distal-facing shoulder which stops the proximal movement of the sled 42440. The projections 42429 are arranged longitudinally within the longitudinal slot 42426 such that a projection 42429 can stop the proximal movement of the sled 42440 regardless of where the staple firing stroke is stopped.

Further to the above, referring again to FIG. 121, the cartridge body 42420 also comprises longitudinal slots 42427 defined therein which are configured to receive the lateral staple-deploying ramps 42447 of the sled 42440. Similar to the above, the cartridge body 42420 further comprises projections 42426 which extend inwardly from the sidewalls of the longitudinal slots 42427 which can inhibit or prevent the proximal movement of the sled 42440. More specifically, each projection 42428 comprises a proximal-facing ramp which permits the sled 42440 to pass thereby during the staple firing stroke and a distal-facing shoulder which stops the proximal movement of the sled 42440. The sled 42240 comprises hooks 42248 extending from the rails 42447 which can abut the distal-facing shoulders of the projections 42428 when the sled 42240 is moved proximally. The projections 42428 are arranged longitudinally within the longitudinal slots 42427 such that a projection 42428 can stop the proximal movement of the sled 42440 regardless of where the staple firing stroke is stopped. In addition to or in lieu of the above, the jaw 42220 comprises projections 42224 extending upwardly from the bottom support 42225 which are configured to interact with a bottom portion 42445 of the sled 42440. Each projection 42224 comprises a proximal-facing ramp which permits the sled 42440 to pass thereby during the staple firing stroke and a distal-facing shoulder which stops the proximal movement of the sled 42440.

A surgical stapling instrument 43000 is illustrated in FIGS. 122-128. The surgical instrument 43000 comprises an end effector 43200 including a first jaw 43220 and a second jaw 43230, a replaceable staple cartridge 43400 positioned in the first jaw 43220, and a staple firing drive 43700. The staple cartridge 43400 comprises a cartridge body 43420 and a sled 43440 positioned within the cartridge body 43420 which is slideable from a proximal position (FIG. 122) toward a distal position during a staple firing stroke. The sled 43440 comprises ramps configured to engage staple drivers within the cartridge body 43420 to eject the staples from the staple cartridge 43400. The sled 43440 also comprises a tissue cutting knife 43450 fixedly attached thereto. When the sled 43440 is in its proximal unfired position, referring to FIG. 122, the knife edge of the tissue cutting knife 43450 is positioned between lateral knife guards 43425 extending upwardly from the deck, or top, of the cartridge body 43420. When the sled 43440 is advanced distally during the staple firing stroke, the knife edge of the tissue cutting knife 43450 is exposed to the patient tissue captured between the jaws 43220 and 43230. As described in greater detail below, the sled 43440 is movable distally by a firing bar 43720 of the staple firing system 43700. The entire disclosure of U.S. Pat. No. 8,540,133, entitled STAPLE CARTRIDGE, which issued on Sep. 24, 2013 is incorporated by reference herein.

Figure 123:
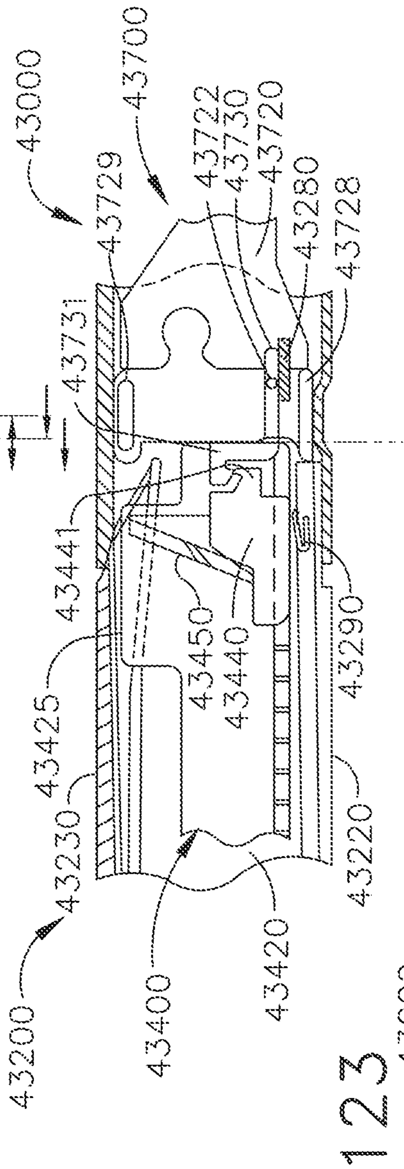
Figure 124:
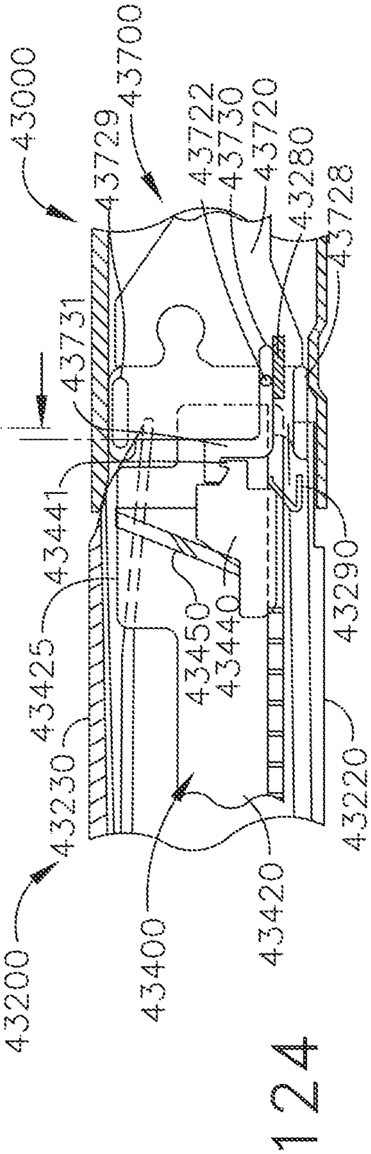

When the second jaw 43230 is in an open position, an unspent staple cartridge 43400 is insertable into the first jaw 43220. When the unspent staple cartridge 43400 is fully seated in the first jaw 43220, the sled 43440 of the unspent staple cartridge 43400 compresses a spent cartridge lockout 43290 mounted to the bottom of the first jaw 43220. The spent cartridge lockout 43290 comprises a folding spring, for example, with one side mounted to the first jaw 43220 and the other side extending upwardly which is contacted by the sled 43220. Once the spent cartridge lockout 43290 has been depressed, or defeated, by the sled 43220, the firing bar 43720 can be advanced distally to couple the firing bar 43720 with the sled 43440, as illustrated in FIGS. 123 and 124. More specifically, the firing bar 43720 comprises a latch 43730 rotatably mounted thereto which becomes latched to the sled 43440 when the firing bar 43720 is advanced distally and the spent cartridge lockout 43290 has been pushed downwardly out of the way by the sled 43440. The latch 43730 comprises a distal latch end 43731 which engages a latch recess 43441 defined in the sled 43440 and, once coupled, the firing bar 43720 is pushed distally to push the sled 43440 through the staple firing stroke. Notably, the firing bar 43720 comprises a first cam 43728 configured to engage the first jaw 43220 and a second cam 43729 configured to engage the second jaw 43230 during the staple firing stroke to hold the jaws 43220 and 43230 in position relative to one another. Also notably, the spent cartridge lockout 43290 is configured to resiliently return to its locked condition after the sled 43440 has been pushed distally off of the spent cartridge lockout 43290—but it does not impede the current staple firing stroke in such instances because the spent cartridge lockout 43290 has already been bypassed by the unspent staple cartridge 43400.

After the staple firing stroke has been completed, or after the staple firing stroke has been stopped, the firing bar 43720 is retracted back into its proximal unfired position. As the firing bar 43720 is being retracted, referring to FIG. 125, the latch 43730 pulls the sled 43440 proximally with the firing bar 43720. As the firing bar 43720 nears its proximal unfired position, the latch 43730 is decoupled from the sled 43740. More specifically, referring to FIG. 126, the latch 43730 contacts the spent cartridge lockout 43290 which lifts the distal latch end 43731 of the latch 43730 out of the latch recess 43441 defined in the sled 43440. At such point, the sled 43440 is no longer retracted with the firing bar 43720. In fact, the sled 43440 is not fully retracted in such circumstances. Instead, referring to FIG. 127, the sled 43440 is left in a partially advanced, or fired, position, in which the sled 43440 is not sitting on the spent cartridge lockout 43290 (but is in a position in which the knife edge of the tissue cutting knife 43750 is protected by the knife guards 43425). As a result, the spent cartridge lockout 43290 remains in its locked position until the spent staple cartridge 43400 is removed from the first jaw 43220 and replaced with an unspent staple cartridge 43400, or another suitable unspent staple cartridge. In the event that the firing bar 43720 were to be advanced distally once again before the spent staple cartridge 43400 is replaced, referring to FIG. 128, the latch 43730 would contact the staple cartridge lockout 43290 and the distal progression of the firing bar 43720 would be stopped. As a result, the spent cartridge lockout 43290 prevents a staple firing stroke of the staple firing system 43700 if an unspent staple cartridge 43400 is not seated in the first jaw 43220.

In addition to or in lieu of the above, any suitable spent cartridge lockout could be used with any of the embodiments disclosed herein. For instance, an electronic spent cartridge lockout could be used. In at least one such embodiment, a stapling instrument comprises an electric motor configured to drive the staple firing system 43700, a controller including a microprocessor configured to control the electric motor, and a sensor in communication with the controller configured to detect the presence of an unspent staple cartridge in the first jaw 43220. The sensor could be configured to detect the presence of the sled 43440 in its proximal unfired position, for example. Notably, the spent cartridge lockout 43290 of the stapling instrument 43000 also serves as a missing cartridge lockout. If a staple cartridge is missing from first jaw 43220 altogether, the staple firing stroke of the staple firing system 43700 would be prevented by the spent cartridge lockout 43290 in the same, or similar, way.

Portions of a stapling instrument 44000 are illustrated in FIGS. 129-133. The stapling instrument 44000 comprises a staple cartridge 44400 and a staple firing drive 44700. The staple cartridge 44400 comprises a cartridge body 44420 including staple cavities 44424 and a longitudinal slot 44426 defined therein, staples removably stored in the staple cavities 44424, and a tissue cutting knife 44450 stored in the proximal end of the cartridge body 44420. The tissue cutting knife 44450 comprises a portion slidably positioned in the longitudinal slot 44426 and a knife edge 44451 that extends above the cartridge body 44420. When the tissue cutting knife 44450 is in a proximal unfired position, referring to FIGS. 129 and 130, the knife edge 44451 is positioned between knife guards 44425 extending upwardly from the cartridge body 44420 such that the knife edge 44451 is not exposed. When the staple cartridge 44400 is loaded into the stapling instrument 44000, the tissue cutting knife 44450 is positioned in front of a firing member 44720 of the staple firing drive 44700. At such point, a gap is present between the firing member 44720 and the tissue cutting knife 44450 and the firing member 44720 is not connected to the tissue cutting knife 44450. When the firing member 44720 is advanced distally, however, the firing member 44720 connects to the tissue cutting knife 44450. More specifically, the tissue cutting knife 44450 comprises proximally-extending latch arms 44452 which are biased inwardly into lock recesses 44722 defined on opposite sides of the firing member 44720 by the sidewalls of the longitudinal slot 44426 when the firing member 44720 contacts the tissue cutting knife 44450 and initially advances the tissue cutting knife 44450 distally. At such point, referring to FIG. 131, the tissue cutting knife 44450 is attached to the firing member 44720 and the tissue cutting knife 44450 and the firing member 44720 are advanced distally together through a staple firing stroke as illustrated in FIG. 132. Advancing the tissue cutting knife 44450 distally moves the knife edge 44451 out from between the knife guards 44425 and exposes the tissue cutting knife 44450 to the tissue. Moreover, the firing member 44720 comprises an integral sled 44740 which is configured to engage staple drivers in the staple cartridge 44400 and eject the staples from the staple cavities 44424 during the staple firing stroke.

After the staple firing stroke has been completed, or after the staple firing stroke has been stopped, the firing member 44720 is retracted back into is proximal unfired position. In such instances, the firing member 44720 pulls the tissue cutting knife 44450 proximally. When the tissue cutting knife 44450 is returned to its proximal unfired position, the knife edge 44451 is positioned between the knife guards 44425. Moreover, referring to FIG. 133, the tissue cutting knife 44450 releases from the firing member 44720 when the tissue cutting knife 44450 is returned to its proximal position. More specifically, referring to FIG. 130, the latch arms 44452 resiliently spring outwardly owing to the clearances provided by recesses 44422 defined in the cartridge body 44420 when the tissue cutting knife 44450 reaches its proximal position. Once the tissue cutting knife 44450 is detached from the firing member 44720, the firing member 44720 is moved proximally into its unfired position. In various instances, the proximal movement of the tissue cutting knife 44450 is stopped when the tissue cutting knife 44450 abuts a proximal shoulder or wall in the cartridge body 44420. In such instances, the firing member 44720 can pull away from the latch arms 44452 if the latch arms 44452 are still partially engaged with the lock recesses 44722 defined in the firing member 44720.

A surgical instrument 45000 is illustrated in FIGS. 134-138. Referring primarily to FIG. 134, the surgical instrument 45000 comprises an end effector 45200 including a first jaw 45220 and a second jaw, or anvil, 45230 rotatable relative to the first jaw 45220 about a pivot pin 45240 between an open, unclamped position and a closed, clamped position. The surgical instrument 45000 further comprises a jaw closure system 45600 configured to close the second jaw 45230. More specifically, the jaw closure system 45600 comprises a closure member 45620 movable proximally to cam the second jaw 45230 downwardly toward its closed position. The surgical instrument 45000 further comprises a staple firing system 45700 including a rotatable drive shaft 45710 and a firing member 45720 threadably engaged with the drive shaft 45710 which is movable distally during a staple firing stroke. The first jaw 45220 is configured to receive a replaceable staple cartridge 45400 therein which comprises a cartridge body 45420, staples removably stored in the cartridge body 45420, and staple drivers configured to support and drive the staples out of the cartridge body 45420 during the staple firing stroke. The staple cartridge 45400 further comprises a sled 45440 movable from a proximal unfired position to a distal fired position by the firing member 45720 to push the staple drivers upwardly within the cartridge body 45420 toward the top, or deck, of the cartridge body 45420 during the staple firing stroke.

Further to the above, the surgical instrument 45000 further comprises a lockout assembly 45900 configured to prevent the second jaw 45230 from being fully closed and prevent the firing member 45720 from being advanced distally through a staple firing stroke if the staple cartridge 45400 is missing from the first jaw 45220 or the staple cartridge 45400 positioned in the first jaw 45220 has been previously fired. Referring primarily to FIGS. 135 and 136, the lockout assembly 45900 comprises a frame 45910, an anvil closure lockout 45920, and a staple firing lockout 45930. The frame 45910 is fixedly mounted to the first jaw 45220 and is positioned underneath the pivot pin 45240, but could be positioned in any suitable location. The anvil closure lockout 45920 is rotatably mounted to the frame 45910 about a pivot 45922 and is rotatable between a locked position (FIG. 135) and an unlocked position (FIGS. 137 and 138) about the pivot 45922. The anvil closure lockout 45920 comprises a proximal end 45924 and a distal end 45926. The proximal end 45924 of the anvil closure lockout 45920 comprises a latch releasably engaged with a latch shoulder 45624 defined on the closure member 45620 when the anvil closure lockout 45920 is in its locked position (FIG. 135). In such instances, the anvil closure lockout 45920 prevents the closure member 45620 from moving proximally to close the second jaw 45230. When a staple cartridge 45400 is inserted into the first jaw 45220, however, the proximal end of the cartridge body 45420 contacts the distal end 45926 of the anvil closure lockout 45920 and rotates the anvil closure lockout 45920 into its unlocked position, as illustrated in FIG. 137. In such instances, the proximal end 45924 of the anvil closure lockout 45920 is disengaged from the closure member 45620 and the closure member 45620 can be moved proximally to close the second jaw 45230. In fact, the anvil closure lockout 45920 remains unlocked so long as the staple cartridge 45400 is seated in the first jaw 45220 and, as a result, the second jaw 45230 can be opened and closed by a clinician, as many times as desirable, so long as the staple cartridge 45400 is seated in the first jaw 45220. Once the staple cartridge 45400 is removed, however, the anvil closure lockout 45920 automatically re-locks. More specifically, the lockout assembly 45900 comprises a biasing spring 45940 positioned intermediate the anvil closure lockout 45920 and the staple firing lockout 45930 which is compressed when the anvil closure lockout 45920 is rotated into its unlocked position and, when the staple cartridge 45400 is removed, the biasing spring 45940 resiliently returns the anvil closure lockout 45920 back into its locked position.

The stapling firing lockout 45930 is rotatably mounted to the frame 45910 about a pivot 45932 and is rotatable between a locked position (FIG. 135) and an unlocked position (FIG. 137) about the pivot 45932. The staple firing lockout 45930 comprises a proximal end 45934 and a distal end 45936. The distal end 45936 of the staple firing lockout 45930 comprises a latch releasably engaged with the firing member 45720 when the staple firing lockout 45930 is in its locked position (FIG. 135). In such instances, the staple firing lockout 45930 prevents the firing member 45720 from moving distally to perform the staple firing stroke. When an unspent staple cartridge 45400 is inserted into the first jaw 45220, however, the sled 45440 of the staple cartridge 45400 contacts the distal end 45936 of the staple firing lockout 45930 and rotates the staple firing lockout 45930 into its unlocked position, as illustrated in FIG. 137. In such instances, the distal end 45936 of the staple firing lockout 45930 is disengaged from the firing member 45720 and the firing member 45720 can be moved distally to perform the staple firing stroke. Once the sled 45440 is advanced distally, however, the staple firing lockout 45930 automatically re-locks. More specifically, the biasing spring 45940 positioned intermediate the anvil closure lockout 45920 and the staple firing lockout 45930 is compressed when the staple firing lockout 45930 is rotated into its unlocked position and, when the sled 45440 is advanced distally, the biasing spring 45940 resiliently returns the staple firing lockout 45930 back into its locked position. As a result, the staple firing lockout 45930 is rotated back into its locked position when the sled 45440 is advanced distally through its staple firing stroke by the firing member 45720. This is immaterial, at this point, because the firing member 45720 has already been advanced distally and the staple firing lockout 45930 can no longer stop the staple firing stroke. Notably, though, the sled 45440 is not returned proximally by the firing member 45720 after the staple firing stroke and, when the firing member 45720 is returned back to its proximal unfired position, the staple firing lockout 45930 is biased in front of the firing member 45720 by the biasing spring 45940 such that a subsequent firing stroke of the firing member 45720 isn't possible until the spent staple cartridge 45400 is replaced with an unspent staple cartridge 45400. The entire disclosure of U.S. patent application Ser. No. 16/458,108, entitled SURGICAL INSTRUMENT SYSTEM COMPRISING AN RFID SYSTEM, filed on Jun. 30, 2019, is incorporated by reference herein.

A staple cartridge 46400 is illustrated in FIGS. 139-143. The staple cartridge 46400 comprises a cartridge body 46420, staples removably stored in the cartridge body 46420, staple drivers configured to support and drive the staples out of the cartridge body 46420, and a sled 46440 configured to push the staple drivers upwardly toward the top, or deck, of the cartridge body 46420 during a staple firing stroke. The sled 46440 comprises ramps, or rails, 46442 configured to engage the staple drivers which are slideably positioned in longitudinal slots 46422 defined in the cartridge body 46420. The sled 46440 further comprises a central portion 46446 which is slideably positioned in a central longitudinal slot 46426 defined in the cartridge body 46420. The sled 46440 is moveable from a proximal unfired position to a distal fired position during the staple firing stroke in which the sled 46440 is pushed distally by a staple firing system. After the staple firing stroke, or after the staple firing stroke has been stopped, the staple firing system is operated in reverse to reset the staple firing system. In such instances, the staple firing system pulls the sled 46440 proximally toward its proximal unfired position; however, the sled 46440 is stopped before it reaches its proximal unfired position, as described in greater detail below. At such point the staple firing system detaches from the sled 46440 such that the sled 46440 remains behind in a partially fired position.

Referring primarily to FIG. 139, further to the above, the staple cartridge 46400 further comprises a spent cartridge lock 46490 rotatably mounted to the cartridge body 46420 about a pin 46425. Referring primarily to FIG. 140, the spent cartridge lock 46490 comprises a trippable portion 46497 extending into an aperture 46447 defined in the sled 46440 when the spent cartridge lock 46490 is in its unlocked position (FIG. 140). When the sled 46440 is advanced distally, as illustrated in FIG. 141, an end wall of the aperture 46447 defined in the sled 46440 contacts the trippable portion 46497 of the spent cartridge lock 46490 and rotates the spent cartridge lock 46490 into a locked position (FIG. 142). In the locked position of the spent cartridge lock 46490, referring to FIG. 142, a lock portion 46495 of the spent cartridge lock 46490 is positioned in a lock aperture 46427 defined in the cartridge body 46420. When the sled 46440 is retracted after the staple firing stroke, further to the above, the proximal motion of the sled 46440 is blocked by the lock portion 46495 which prevents the sled 46440 from being returned to its proximal unfired position. Instead, the sled 46440 remains in a retracted, but spent, position. In co-operation with a staple firing lockout in the surgical instrument, the staple firing system is prevented from advancing the sled 46440 out of its retracted spent position. The entire disclosures of U.S. Pat. No. 7,000,818, entitled SURGICAL STAPLING INSTRUMENT HAVING SEPARATE AND DISTINCT CLOSING AND FIRING SYSTEMS, U.S. Pat. No. 6,988,649, entitled SURGICAL STAPLING INSTRUMENT HAVING A SPENT CARTRIDGE LOCKOUT, U.S. Pat. No. 6,978,921, entitled SURGICAL STAPLING INSTRUMENT INCORPORATING AN E-BEAM FIRING MECHANISM, U.S. Pat. No. 6,959,852, entitled SURGICAL STAPLING INSTRUMENT WITH MULTISTROKE FIRING INCORPORATING AN ANTI-BACKUP MECHANISM, and U.S. Pat. No. 6,905,057, entitled SURGICAL STAPLING INSTRUMENT INCORPORATING A FIRING MECHANISM HAVING A LINKED TRANSMISSION, are incorporated by reference herein.

In such embodiments, the firing bar of the staple firing system must engage the sled 46440 at the outset of the staple firing stroke in order to pass over a staple firing lockout defined in the first jaw 46220 and, if the firing bar does not engage the sled 46440 at the outset of the staple firing stroke, the firing bar abuts the staple firing lockout and the firing bar is blocked from performing the staple firing stroke. As a result of this arrangement, a spent cartridge cannot be accidentally re-used. In order to re-use the stapling instrument, the spent staple cartridge 46400 must be removed and replaced with an unspent staple cartridge 46400, or any other suitable unspent staple cartridge.

Figure 57:
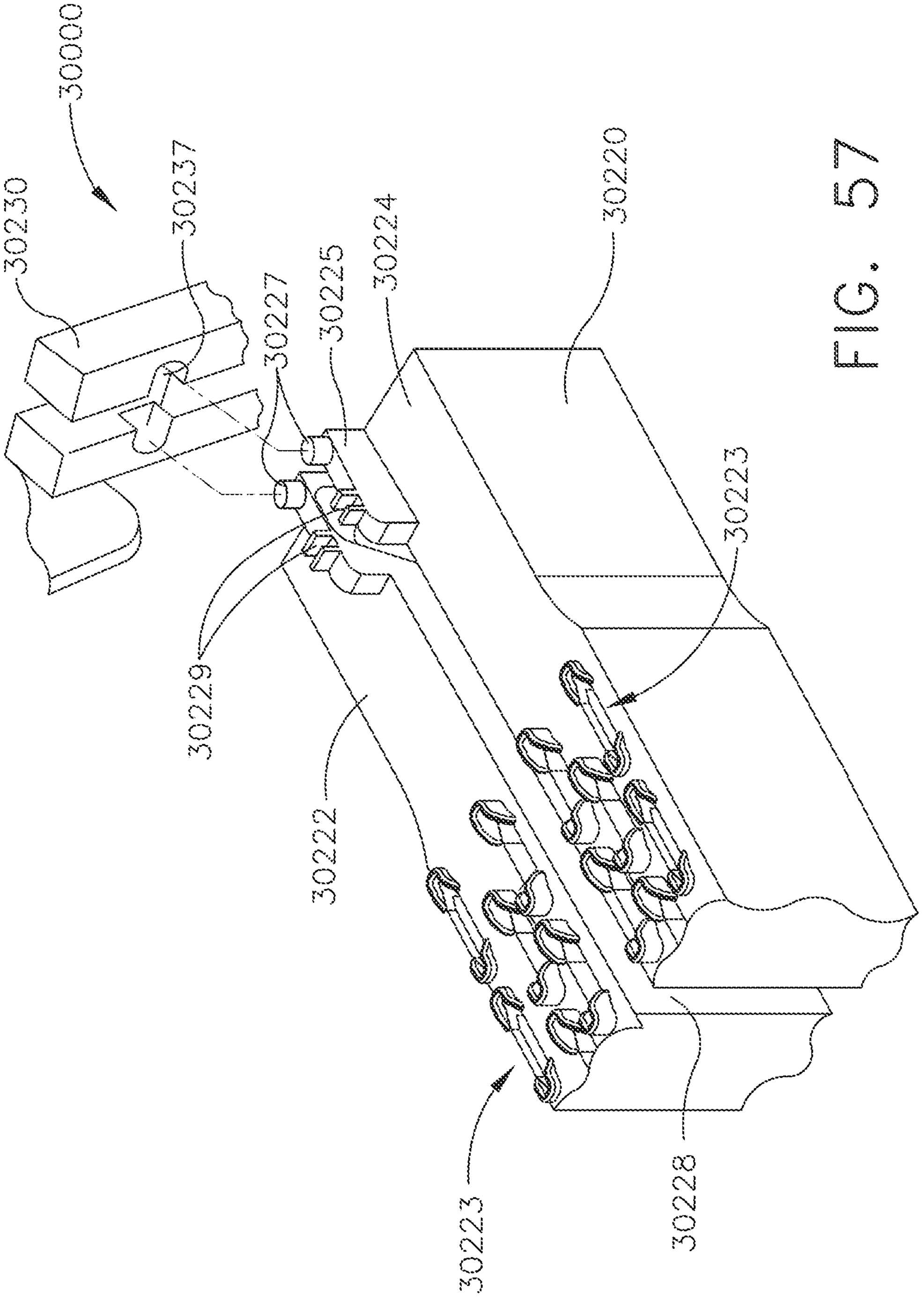
FIG. 57 is a partial perspective view of a staple cartridge and an anvil in accordance with at least one embodiment.

Referring to FIG. 57, an end effector of a stapling instrument comprises a staple cartridge 30220 and an anvil 30230. The anvil 30230 is movable relative to the staple cartridge 30220 between an open, unclamped, position and a closed, clamped, position. The staple cartridge 30220 comprises a cartridge body 30222 including a proximal end 30224, a distal end, and a deck extending between the proximal end 30224 and the distal end. The cartridge body 30222 further comprises a longitudinal slot 30228 extending from the proximal end 30224 toward the distal end and, in addition, staple cavities 30223 arranged in longitudinal rows on opposite sides of the longitudinal slot 30228. A staple, or any other suitable fastener, is removably stored in each staple cavity 30223.

Further to the above, the stapling instrument comprises a cartridge jaw configured to receive the staple cartridge 30220. The cartridge jaw and/or the staple cartridge 30220 comprise features configured to releasably retain the staple cartridge 30220 in the cartridge jaw. In various instances, the staple cartridge 30220 comprises snap-fit features at the proximal end 30224 and at the distal end of the staple cartridge body 30222 which releasably hold the staple cartridge 30220 in the cartridge jaw, for example. In various instances, referring to FIG. 58, the proximal end of the staple cartridge 30220 may not be fully seated, or not snapped into place, within the cartridge jaw when the staple cartridge 30220 is inserted into the cartridge jaw. In such instances, the proximal end 30224 of the cartridge body 30222 may be higher than the distal end resulting in a tilted deck between the proximal end 30224 and the distal end. A clinician can correct this condition by pushing down on the proximal end 30224 of the cartridge body 30222 to fully seat the proximal end 30234—if they notice it. If not, the stapling instrument has a self-correcting feature which fully seats the staple cartridge 30220 in the cartridge jaw, as discussed in greater detail below.

Figure 58:
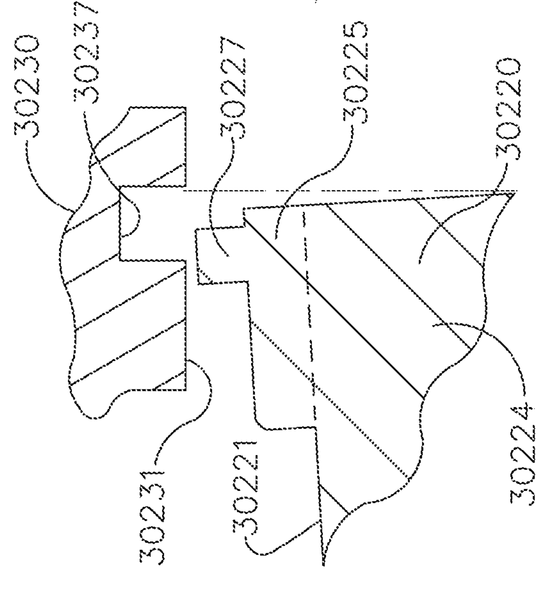
FIG. 58 is a partial cross-sectional view of the staple cartridge and the anvil of FIG. 57 illustrating the staple cartridge in an unseated configuration.

The cartridge body 30222 comprises projections 30225 extending upwardly from the proximal end 30224 of the cartridge body 30222. A first projection 30225 extends upwardly from a first side of the longitudinal slot 30228 and a second projection 30225 extends upwardly from a second side of the longitudinal slot 30228. Each projection 30225 includes an alignment post 30227 extending therefrom which is configured to be received within an alignment slot 30237 defined in the anvil 30230 when the anvil 30230 is moved into its clamped position. If the staple cartridge 30220 is not properly seated in the cartridge jaw when the anvil 30230 is moved into is clamped position, as illustrated in FIG. 58, a push surface at a proximal end of the anvil 30230 will contact the alignment posts 30227 and push downwardly onto the staple cartridge 30220 until the staple cartridge 30220 is seated in the cartridge jaw. On the other hand, if the staple cartridge 30220 is properly seated in the cartridge jaw, the alignment slots 30237 can receive the alignment posts 30227 without pushing down on the staple cartridge 30220. Advantageously, this arrangement assures that tissue support surface 30221 of the staple cartridge 30220 and the tissue support surface 30231 of the anvil 30230 are properly aligned when the anvil 30230 is in its clamped position. Moreover, this arrangement assures that the staples stored within the staple cartridge 30220 are properly aligned with the staple forming pockets defined in the anvil 30230 when the anvil 30230 is in its clamped position.

Figure 60:
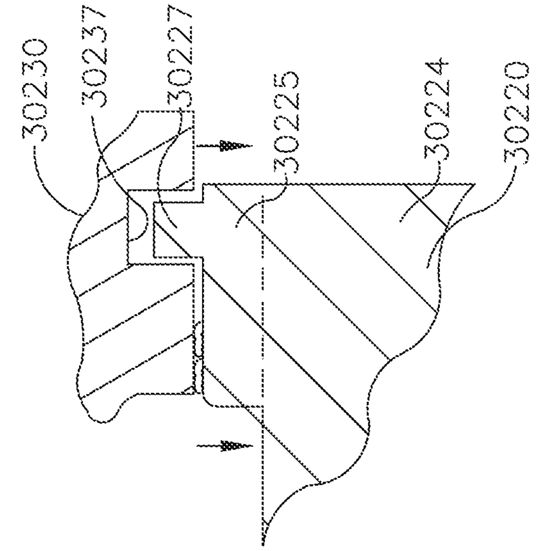
FIG. 60 is a partial cross-sectional view of the staple cartridge and the anvil of FIG. 57 illustrating the anvil in a clamped configuration.
Figure 59:
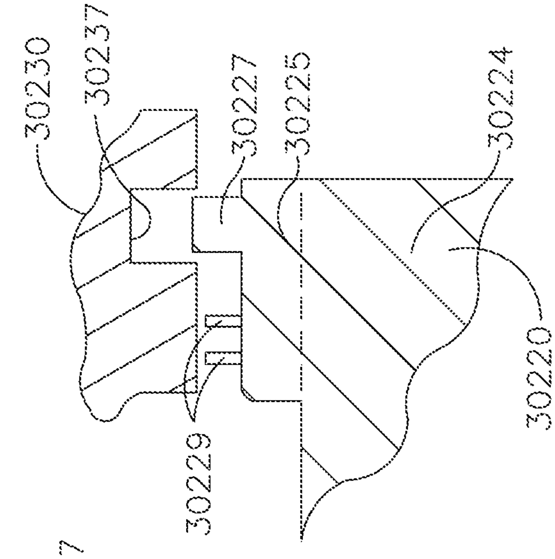
FIG. 59 is a partial cross-sectional view of the staple cartridge and the anvil of FIG. 57 illustrating the staple cartridge in a seated configuration.

Further to the above, referring to FIGS. 59 and 60, the staple cartridge 30220 can further comprise one or more crush ribs 30229 extending from each of the projections 30225. The crush ribs 30229 are sized and configured such that the anvil 30230 contacts the staple cartridge 30220 whether or not the staple cartridge 30220 is properly, or improperly, seated in the cartridge jaw. When the anvil 30230 is moved into its clamped position, the anvil 30230 contacts the crush ribs 30229 and permanently deforms them. In such instances, as a result, a snug interface is created between the staple cartridge 30220 and the anvil 30230. Such an arrangement can account for the various manufacturing tolerances of the staple cartridge 30220 and the anvil 30230, among others. Moreover, the crush ribs 30229 and the alignment posts 30227 can work co-operatively align the anvil 30230 with the staple cartridge 30220. For instance, the alignment posts can provide a gross alignment between the anvil 30230 and the staple cartridge 30220 while the crush ribs 30229 can provide a fine alignment between the anvil 30230 and the staple cartridge 30220.

Further to the above, the staple cartridge 30220 and/or the staple firing drive of the stapling instrument comprises a tissue cutting knife translatable from the proximal end 30224 of the cartridge body 30222 toward the distal end 30226 during a staple firing stroke to eject the staples from the cartridge body 30222. During the staple firing stroke, a knife edge of the tissue cutting knife extends above the top surface 30221 of the cartridge body 30222 to cut the tissue clamped between the staple cartridge 30220 and the anvil 30230. In various instances, absent more, the knife edge would be exposed above the top surface 30221 when the staple cartridge 30220 is not positioned in the cartridge jaw if the tissue cutting knife is part of the staple cartridge 30220 and/or when the staple cartridge 30220 is positioned in the cartridge jaw and the anvil is in an open, or unclamped, position. With this in mind, the projections 30225 are sized and configured to extend above and cover the knife edge when the tissue cutting member is in its proximal, unfired position. Moreover, the projections 30225 are sized and configured to extend longitudinally with respect to the knife edge when the tissue cutting member is in its proximal, unfired position. When the tissue cutting member is moved distally during the staple firing stroke, the knife edge moves distally out from between the projections 30225 and becomes exposed.

Figure 61:
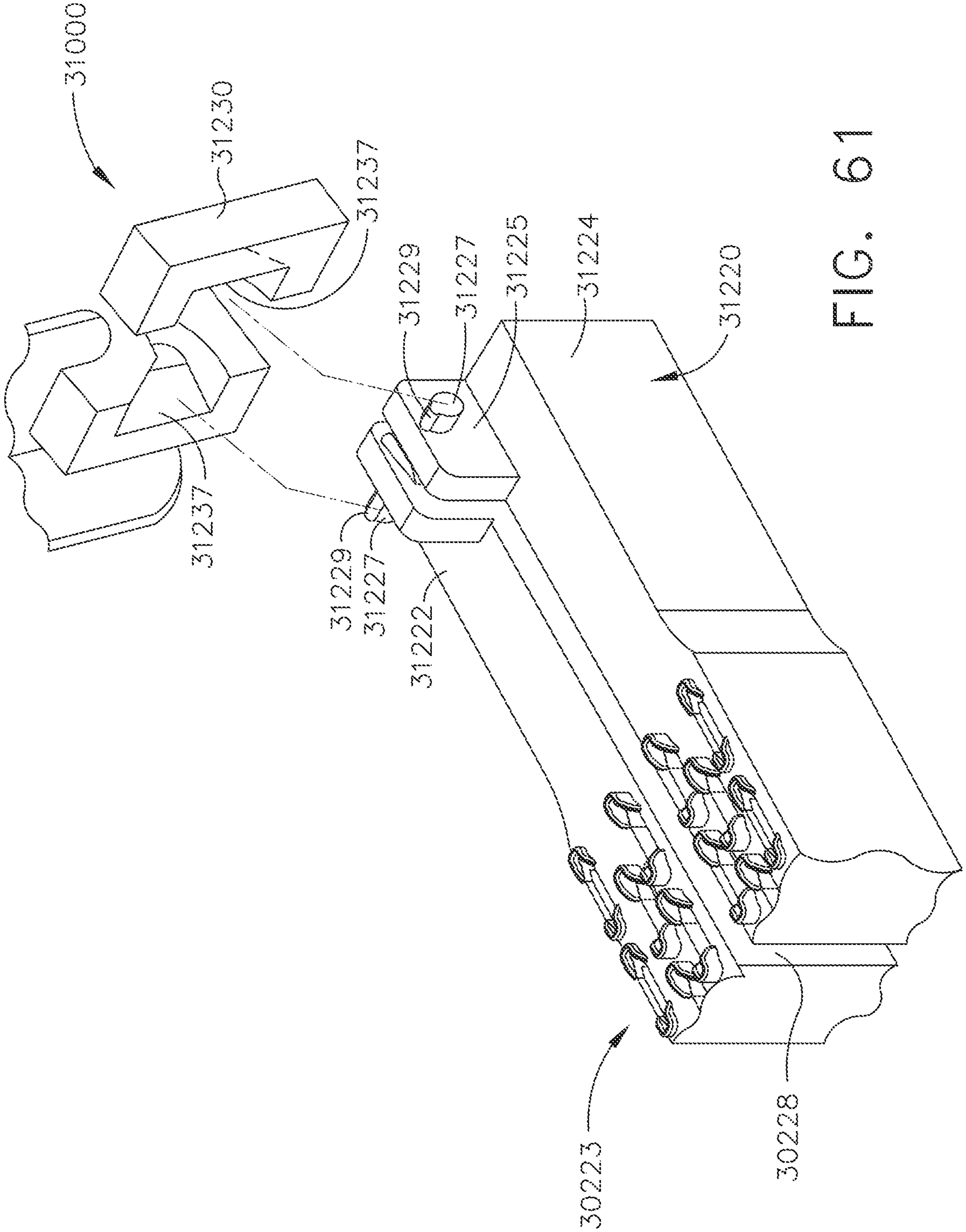
FIG. 61 is a partial perspective view of a staple cartridge and an anvil in accordance with at least one embodiment.
Figure 64:
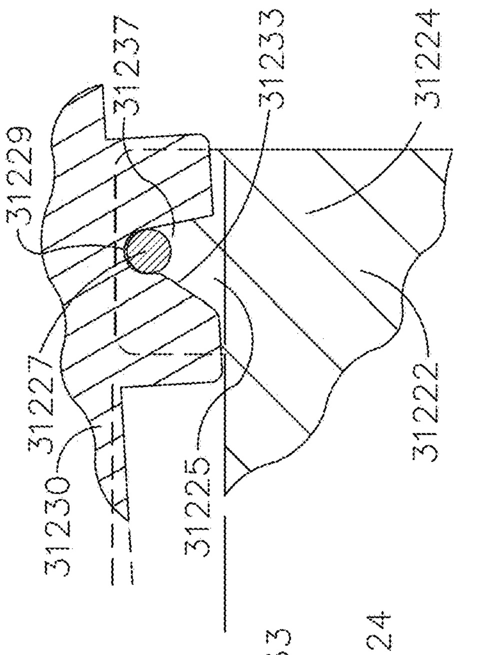
FIG. 64 is a partial cross-sectional view of the staple cartridge and the anvil of FIG. 61 illustrating the anvil in an overclamped configuration.
Figure 63:
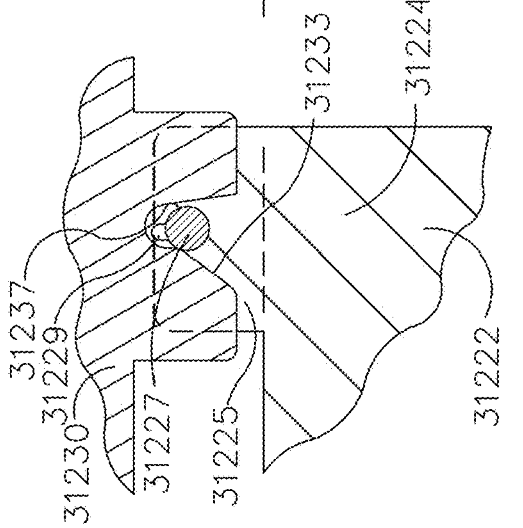
FIG. 63 is a partial cross-sectional view of the staple cartridge and the anvil of FIG. 61 illustrating the anvil in a clamped configuration.
Figure 62:
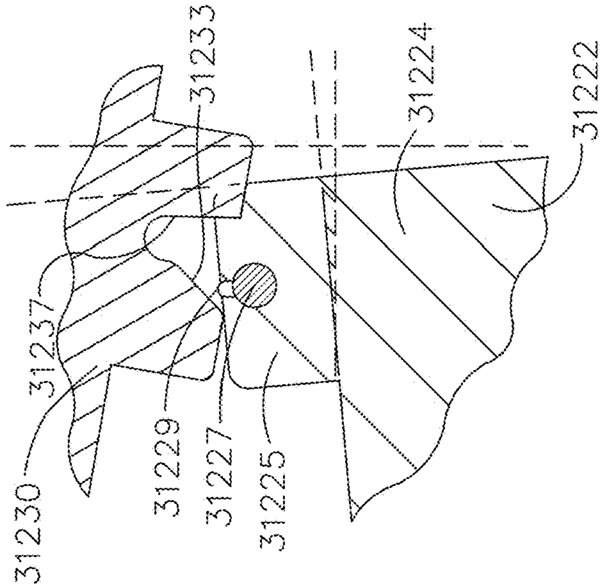
FIG. 62 is a partial cross-sectional view of the staple cartridge and the anvil of FIG. 61 illustrating the staple cartridge in an unseated configuration.
Figure 65:
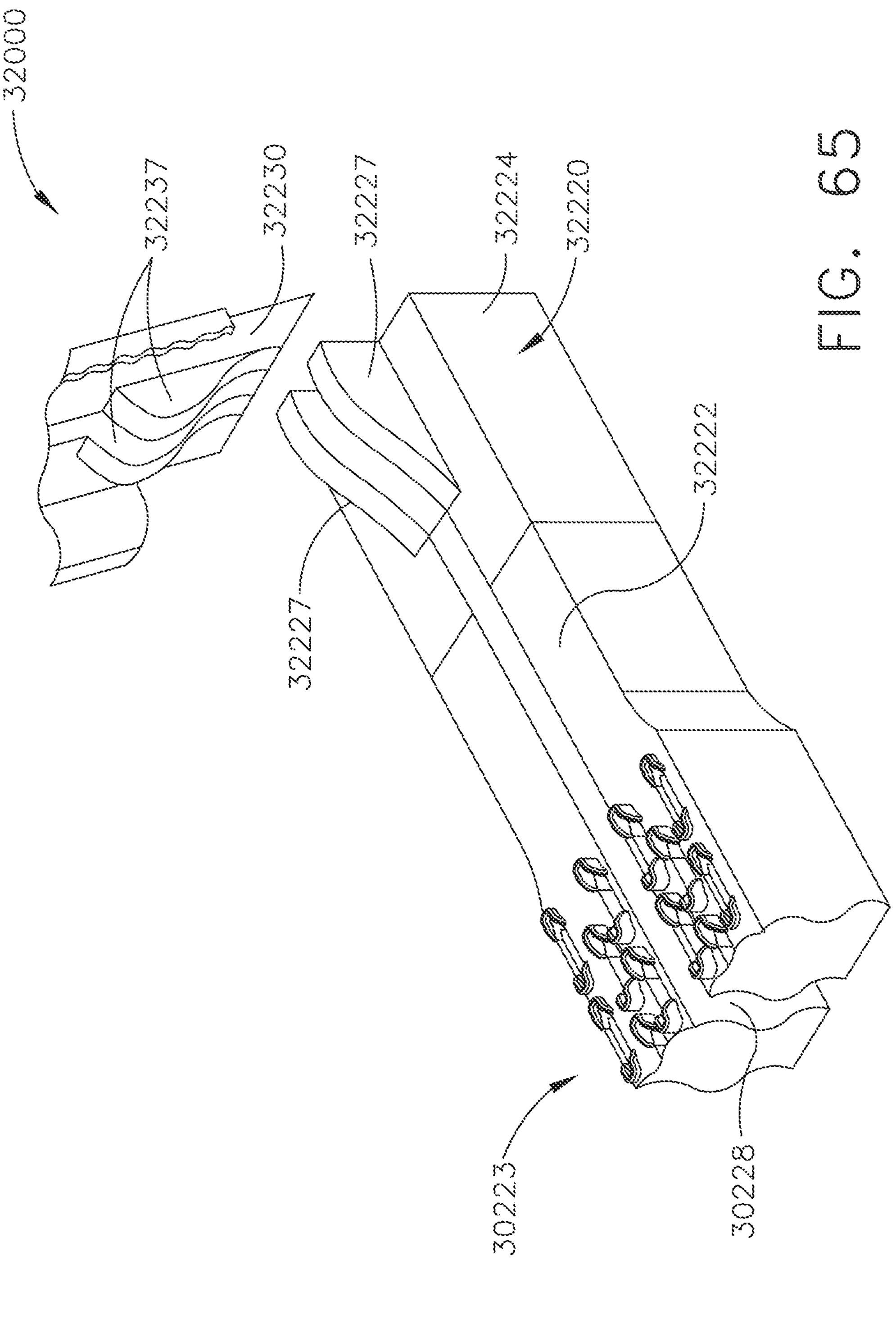
FIG. 65 is a partial perspective view of a staple cartridge and an anvil in accordance with at least one embodiment.
Figure 68:
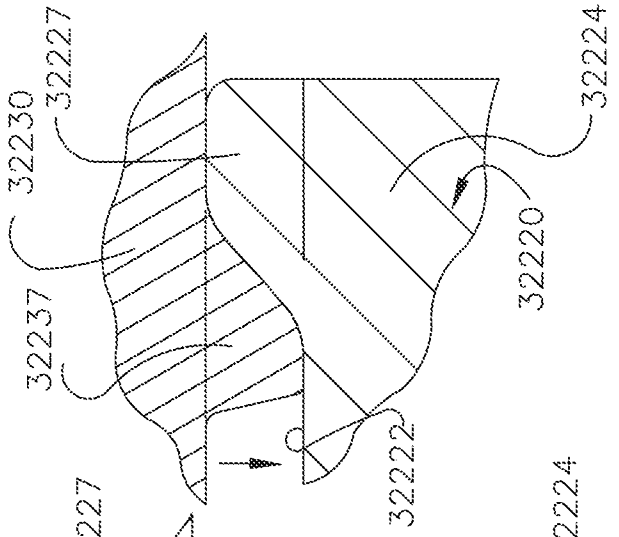
FIG. 68 is a partial cross-sectional view of the staple cartridge and the anvil of FIG. 65 illustrating the staple cartridge in a fully seated configuration.
Figure 67:
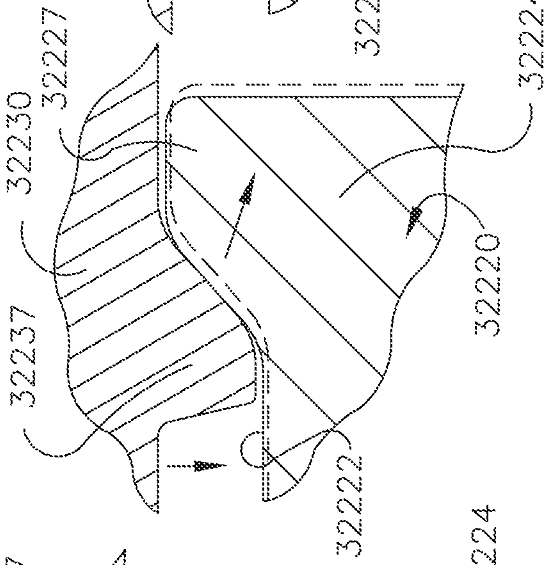
FIG. 67 is a partial cross-sectional view of the staple cartridge and the anvil of FIG. 65 illustrating the staple cartridge in a partially seated configuration.
Figure 66:
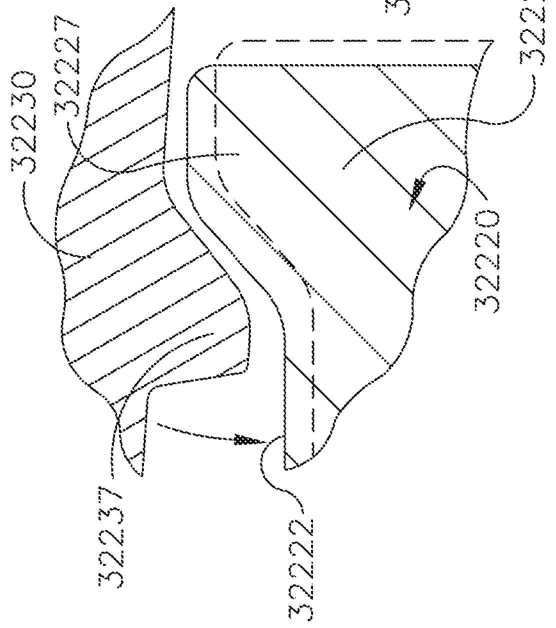
FIG. 66 is a partial cross-sectional view of the staple cartridge and the anvil of FIG. 65 illustrating the staple cartridge in an unseated configuration.

A staple cartridge 31220 and an anvil 31230 are depicted in FIGS. 61-64 which are similar to the staple cartridge 30220 and the anvil 30230 in many respects. The staple cartridge 31220 comprises a cartridge body 31222 comprising a proximal end 31224 which, similar to the above, will be pushed into its fully seated position by the anvil 31230 when the anvil 31230 is moved into its clamped position. The cartridge body 31222 comprises projections 31225 extending upwardly from the proximal end 31224 of the cartridge body 31222. Similar to the above, the projections 31225 flank the longitudinal slot 30228 and each comprise an alignment post 31227 extending therefrom. As shown in FIG. 61, the alignment posts 31227 are cantilevered above a deck of the staple cartridge 30220. The alignment posts 31227 are configured to be received within alignment slots 31237 defined in the anvil 31230 when the anvil 31230 is moved into is clamped position. As shown in FIGS. 62-64, at least one alignment slot 31237 defines at least one cam surface 31233 that is configured to engage the respective alignment post 31227 during movement of the anvil 31230 to the clamped position to thereby seat the staple cartridge 31220. The alignment posts 31227 further comprises crush ribs 31229 extending therefrom which are crushed by the anvil 31230 when the anvil 31230 is overclamped (FIG. 64) past a parallel position (FIG. 63) to seat the staple cartridge 31220 if it has not yet been seated.

A staple cartridge 32220 and an anvil 32230 are depicted in FIGS. 65-68 which are similar to the staple cartridges 30220, 31220 and the anvils 30230, 31230 in many respects. The staple cartridge 32220 comprises a cartridge body 32222 comprising a proximal end 32224 which, similar to the above, will be pushed into its fully seated position by the anvil 32230 when the anvil 32230 is moved into its clamped position. The cartridge body 32222 comprises cams 32227 extending upwardly from the proximal end 32224 of the cartridge body 32222. Similar to the above, the cams 32227 flank the longitudinal slot 30228 and each comprise an arcuate profile. The cams 32227 are configured to be engaged by corresponding cams 32237 extending from the anvil 32230 when the anvil 32230 is moved into is clamped position to seat the staple cartridge 32220 if the staple cartridge 32220 has not yet been seated.

Figure 70:
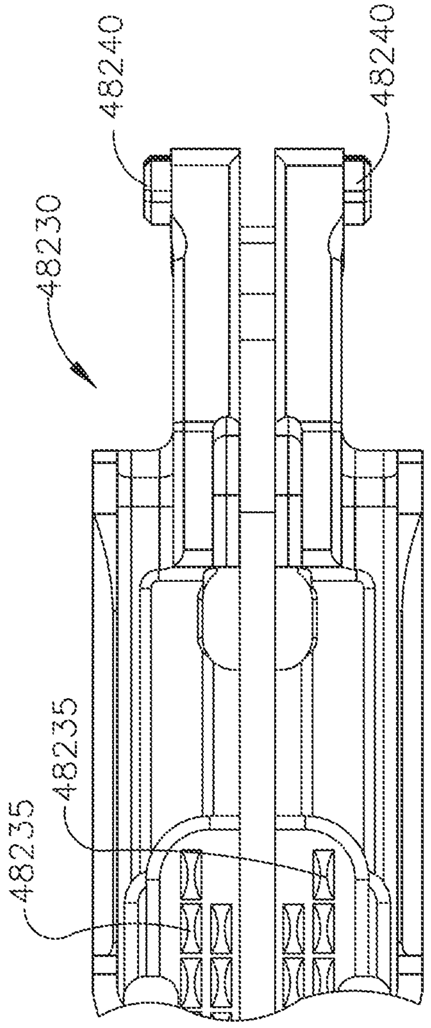
FIG. 70 is a detail view of the anvil of FIG. 69.
Figure 69:
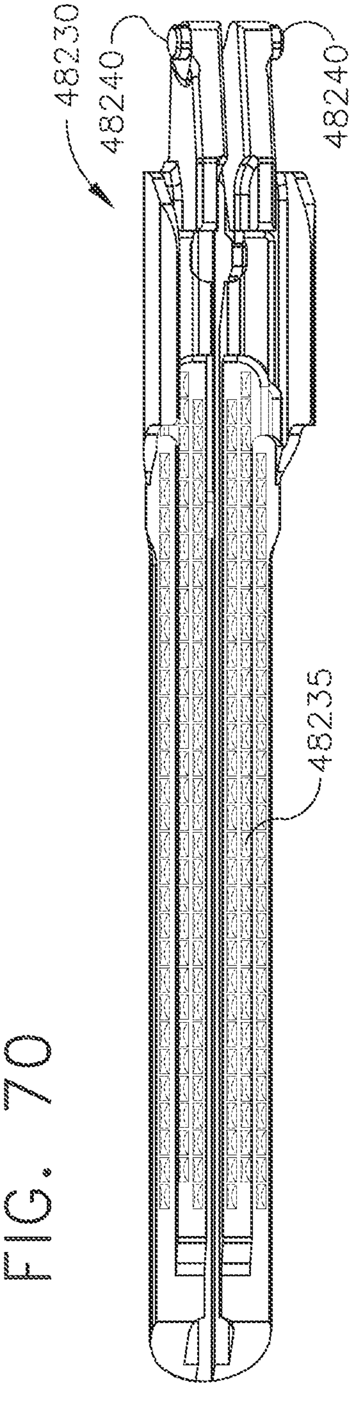
FIG. 69 is a plan view of an anvil in accordance with at least one embodiment.
Figure 71:
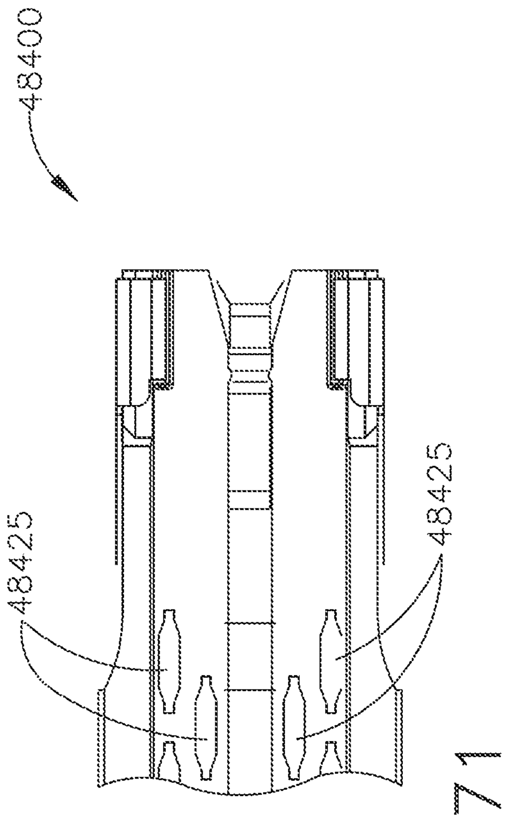
FIG. 71 a partial plan view of a staple cartridge in accordance with at least one embodiment.
Figure 72:
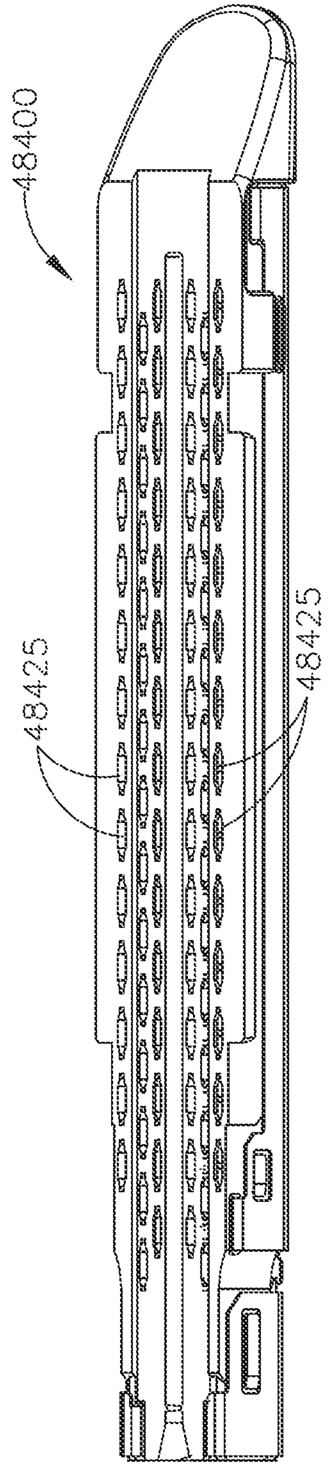
FIG. 72 is a perspective view of the staple cartridge of FIG. 71.

Referring to FIGS. 71 and 72, a staple cartridge 48400 comprises a cartridge body including staple cavities 48425 defined therein. Referring to FIGS. 69 and 70, an anvil 48230 is rotatably mounted to a jaw supporting the staple cartridge 48400 about pivot pins 48240. The anvil 48230 comprises staple forming pockets 48235 defined therein which are aligned with the staple cavities 48245 when the anvil 48230 is closed. More specifically, each staple forming pocket 48235 is aligned with a corresponding staple cavity 48245 such that the staple ejected from the staple cavity 48245 is deformed by its corresponding forming pocket 48235. In at least one instance, each forming pocket 48235 comprises two forming cups, each of which being configured to deform a leg of the staple.

Figure 18:
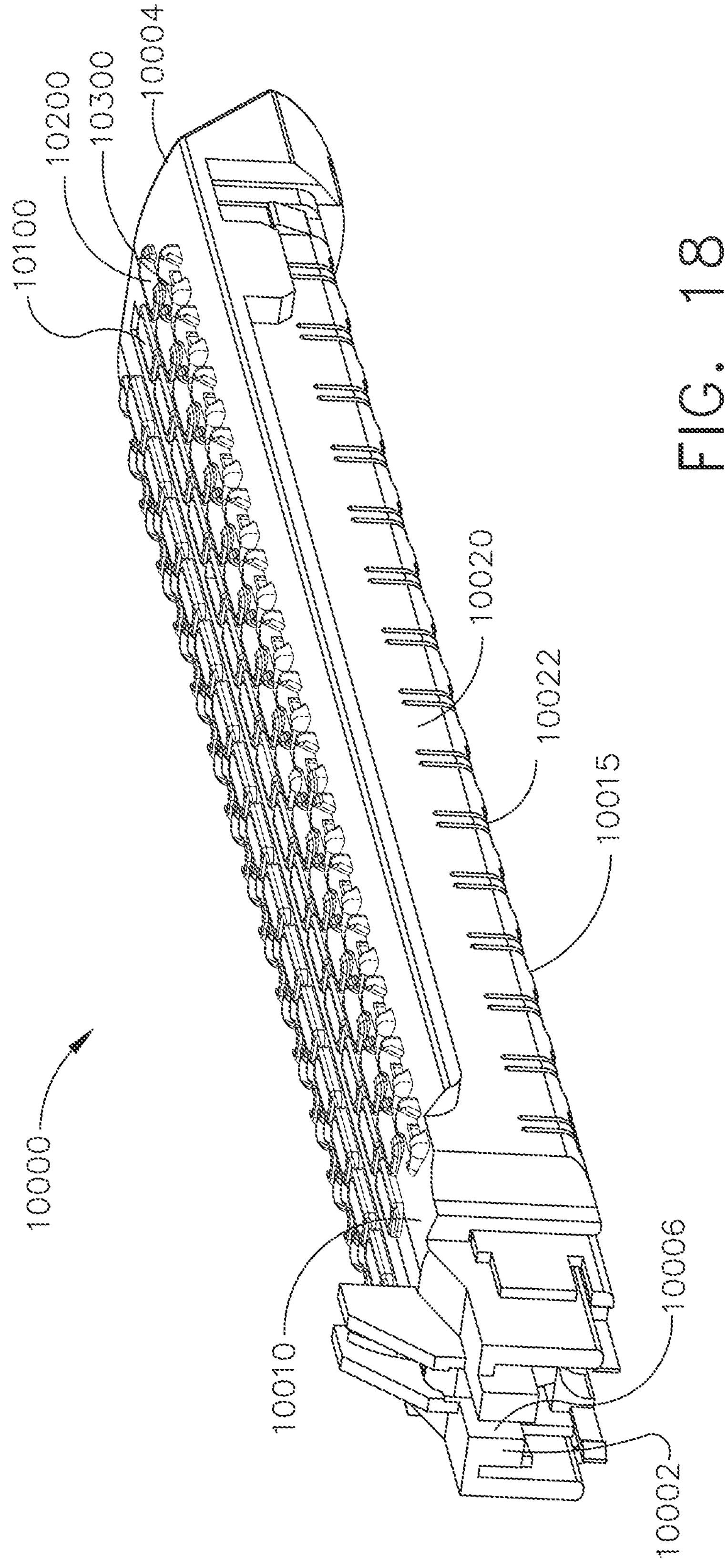
FIG. 18 is a perspective view of a staple cartridge comprising driver retention features in accordance with at least one embodiment.
Figure 20:
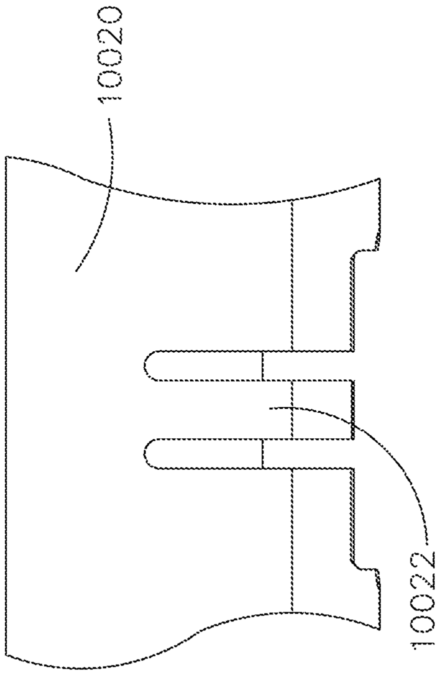
FIG. 20 is a partial elevational view of a sidewall of the staple cartridge of FIG. 18.
Figure 19:
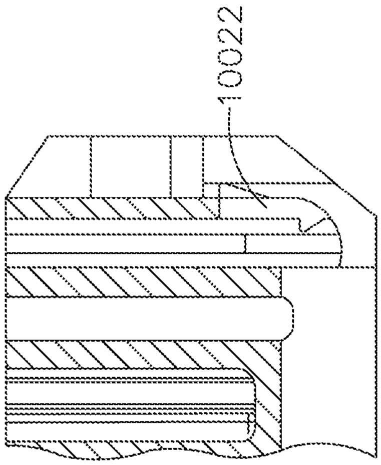
FIG. 19 is a partial cross-sectional view of the staple cartridge of FIG. 18.
Figure 22:
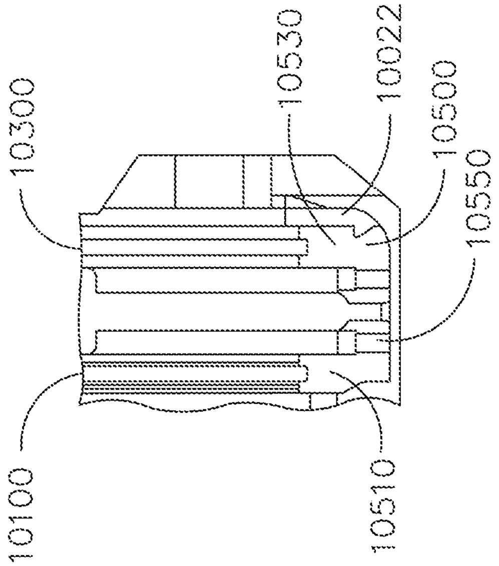
FIG. 22 is a partial cross-sectional view of the staple cartridge of FIGS. 18-21 and an interface between the staple driver and the driver retention feature when the staple driver is in the unfired and/or retention position.
Figure 21:
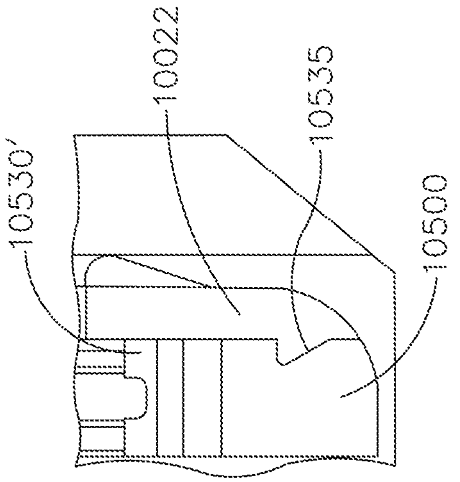
FIG. 21 is a partial cross-sectional view of the staple cartridge of FIG. 18 further comprising a staple driver in an unfired and/or retention position.

A staple cartridge 10000 is illustrated in FIG. 18. The staple cartridge 10000 further comprises a deck surface 10010 and a base 10015. A sidewall 10020 extends between the deck surface 10010 and the base 10015. The staple cartridge 10000 further comprises an elongate slot 10006 extending from a proximal end 10002 toward a distal end 10004. A longitudinal axis is defined along the staple cartridge 10000 by the elongate slot 10006. The staple cartridge 10000 comprises staple cavities defined therein. The staple cavities are arranged in three longitudinal rows. A first row of staple cavities 10100 extends alongside the elongate slot 10006. A second row of staple cavities 10200 extends alongside the first row of staple cavities 10100 on the same side of the elongate slot 10006. A third row of staple cavities 10300 extends alongside the second row of staple cavities 10200.

Staple drivers 10500 are movably positioned within the staple cavities 10100, 10200, 10300. More specifically, the staple drivers 10500 are configured to move from an unfired position to a fired position during a staple firing stroke. Each staple driver 10500 comprises a first staple-supporting portion 10510, a second staple-supporting portion 10520, and a third staple-supporting portion 10530. The first staple-supporting portion 10510 supports a staple in a staple cavity 10100 from the first longitudinal row, the second staple-supporting portion 10520 supports a staple in a staple cavity 10200 from the second longitudinal row, and the third staple-supporting portion 10530 supports a staple in a staple cavity 10300 from the third longitudinal row. A base 10550 connects the three staple-supporting portions 10510, 10520, 10530 to one another.

In various instances, staple cartridges comprise a component, such as a tray, for example, positioned below and/or underneath the base of the staple cartridge to prevent elements, such as, for example, the staple drivers and/or the staples, from disassociating from the staple cartridge during storage and/or handling. In instances where such an additional component is undesirable, staple cartridges can comprise one or more driver retention features as discussed in greater detail herein. In addition to maintaining the staple drivers within the staple cartridge, driver retention features can also serve to maintain the staple drivers in their unfired position prior to the staple firing stroke. Holding the staple drivers in their unfired position prior to the staple firing stroke can facilitate a uniform and/or successful staple firing stroke. In such instances, the driver retention features discussed herein prevent the staple drivers from unwanted movement in any direction within the staple cavities.

Referring now to FIGS. 18-22, the staple cartridge 10000 comprises a plurality of locking arms 10022 that are configured to serve as a driver retention feature. The plurality of locking arms 10022 are defined within the exterior sidewall 10020 of the staple cartridge 10000. The locking arms 10022 are longitudinally spaced apart from one another along a length of the staple cartridge 10000. Each locking arm 10022 comprises a resilient engagement portion that is configured to interface with a staple driver to maintain the staple driver in its unfired position. In the embodiment shown in FIG. 19, each locking arm 10022 comprises a projection that extends into a staple cavity 10300 from the third longitudinal row; however, the locking arms 10022 could extend into any suitable staple cavity. A staple driver 10500 is shown in its unfired position in FIGS. 21 and 22. The staple driver 10500 comprises an indent and/or notch 10535 defined in the third staple-supporting portion 10530. When the staple driver 10500 is in its unfired position, the notch 10535 interfaces with and/or receives the projection from the locking arm 10022 of the staple cartridge 10000. The interface between the staple driver 10500 and the locking arm 10022 provides a driver retention capability to the staple cartridge 10000. Additional driver retention features are described in greater detail herein.

Figure 23:
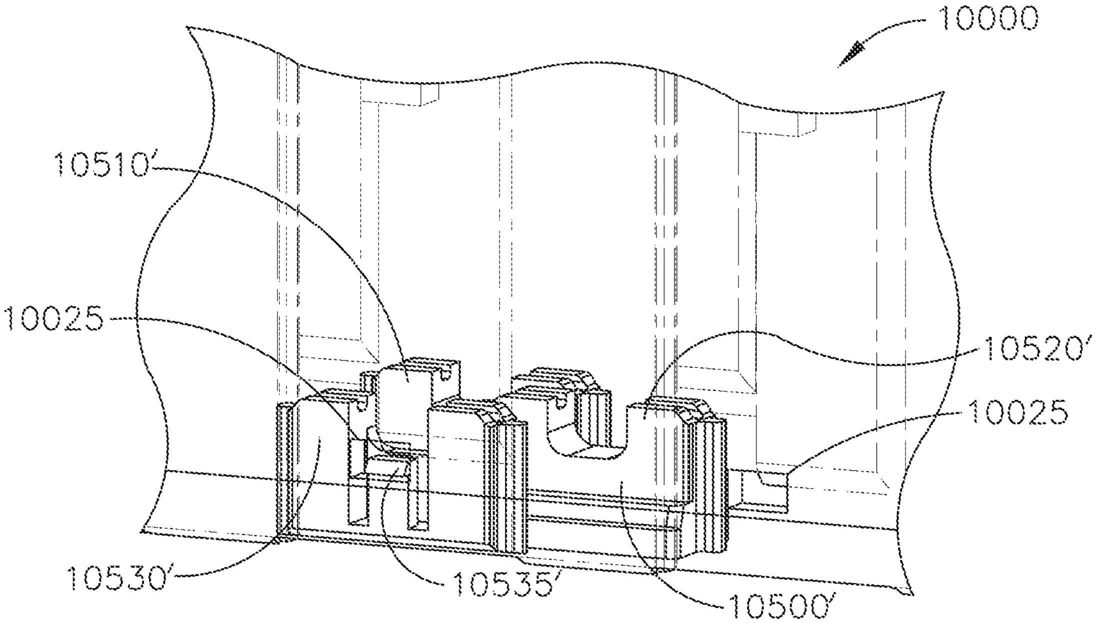
FIG. 23 is a partial cross-sectional view of a staple cartridge comprising windows defined therein and a staple driver in accordance with at least one embodiment.
Figure 24:
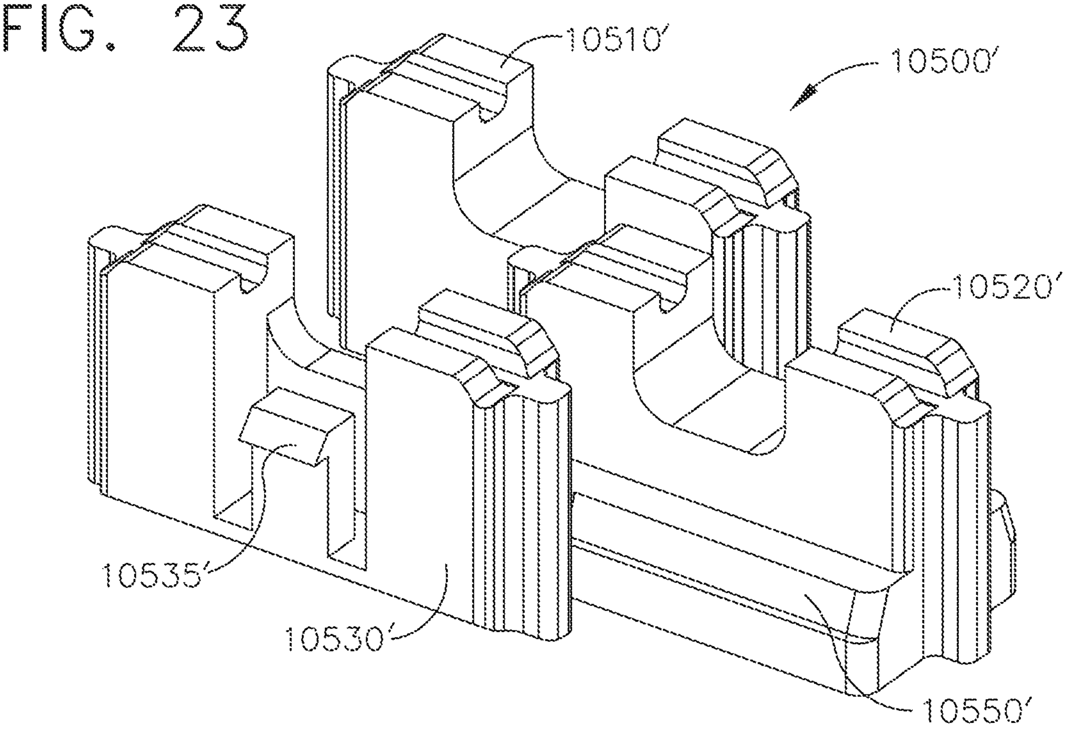
FIG. 24 is a perspective view of the staple driver of FIG. 23.

A staple cartridge 10000', similar in many respects to the staple cartridge 10000, is illustrated in FIG. 23. The staple cartridge 10000' comprises windows 10025 that are defined in the sidewall 10020, wherein the windows 10025 are longitudinally spaced apart from one another. The windows 10025 are positioned at the same height along the staple cartridge 10000 as one another. A staple driver 10500', similarly in many respects to the staple driver 10500 is configured to be movably received within the staple cartridge 10000'. The staple driver 10500', shown in FIG. 24, comprises a driver retention member and/or projection 10535' resiliently extending from a sidewall of the third staple-supporting portion 10530' toward the sidewall 10020 of the staple cartridge 10000'. Stated another way, the portion 10530' of the staple driver 10500' extending into a staple cavity 10300 from the third longitudinal row comprises a driver retention member and/or projection 10535' extending from the third staple-supporting portion 10530' toward the sidewall 10020 of the staple cartridge 10000'.

The driver retention member 10535' is resiliently connected to the base 10550' of the staple driver 10500'. When the staple driver 10500' is in its unfired position, as shown in FIG. 23, the driver retention member 10535' extends through the window 10025 defined in the staple cartridge 10000'. The projection of the driver retention member 10535 through the window 10025 prevents the staple driver 10500' from freely moving in any direction within the staple cavities 10100, 10200, 10300. Stated another way, an external force must be applied to the staple driver 10500' and/or the staple cartridge 10000' in order to bias the projection 10535' out of the window 10025. The driver retention member 10535' comprises a tapered and/or ramped upper surface configured to facilitate the disengagement of the driver retention member 10535' from the window 10025 during the staple firing stroke. As an upward force, such as the force applied by an advancing firing member, is applied to the staple driver 10500', the driver retention member 10535' is biased away from the sidewall 10020 of the staple cartridge 10000'. The driver retention member 10535' then disengages from the window 10025, and the staple driver 10500' is free to translate from the unfired position toward the fired position.

In various instances, the windows 10025 are positioned at different heights along the sidewall 10020 of the staple cartridge 10000'. Such a window arrangement facilitates the ability for the staple drivers to be held at different heights in the staple cartridge 10000'.

Figure 25:
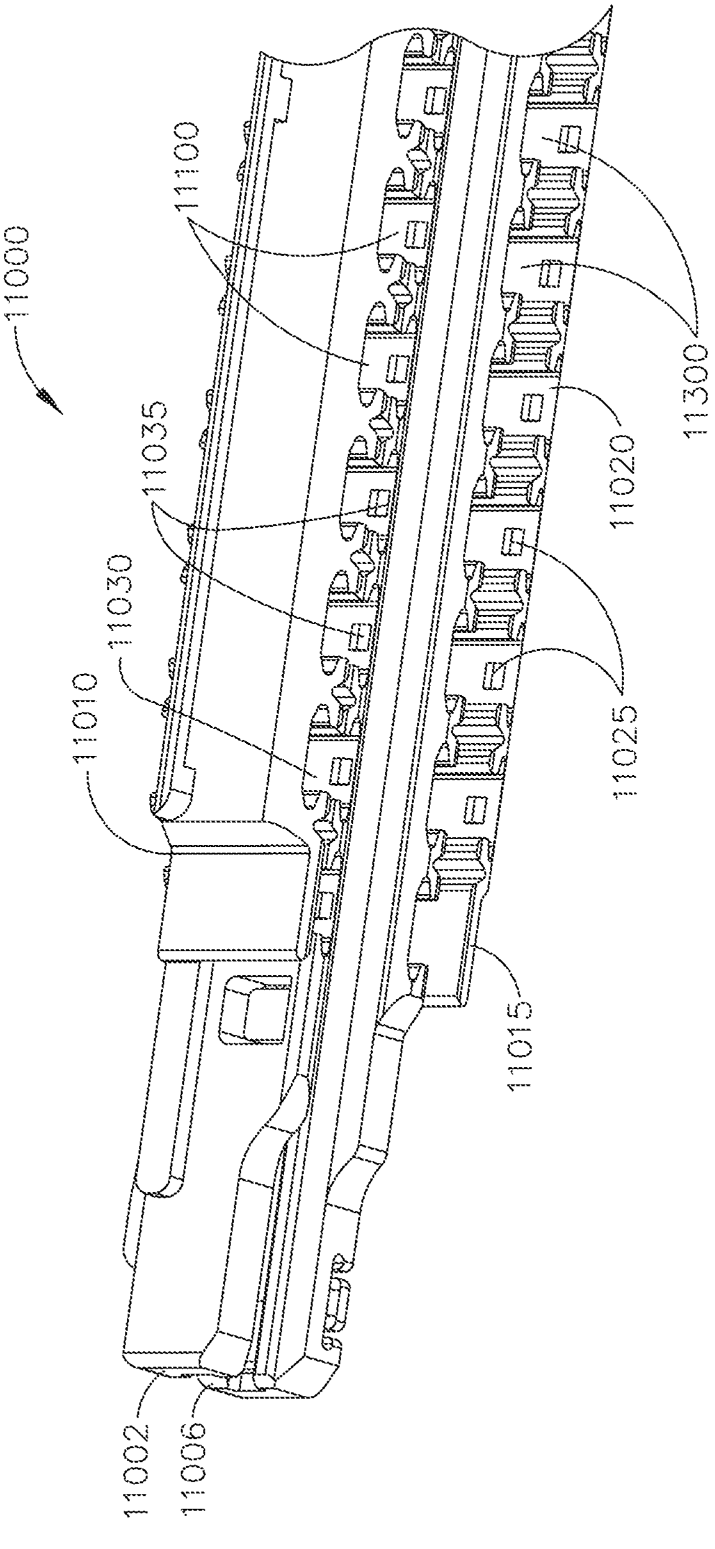
FIG. 25 is a perspective view of a staple cartridge comprising driver retention features in accordance with at least one embodiment.
Figure 26:
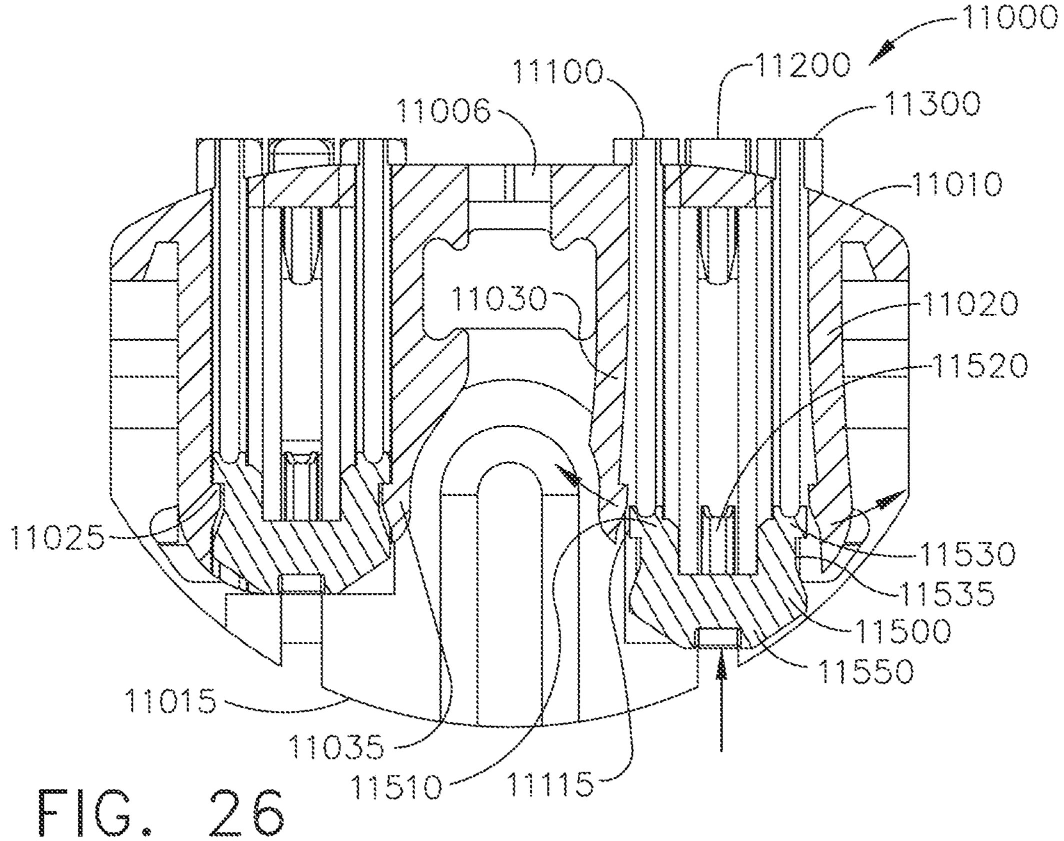
FIG. 26 is a cross-sectional view of the staple cartridge of FIG. 25, wherein the staple cartridge comprises staple drivers.

A staple cartridge 11000 is depicted in FIGS. 25 and 26 that is similar in many respects to the staple cartridge 10000. The staple cartridge 11000 comprises a deck surface 11010 and a base 11015. The staple cartridge 11000 further comprises an elongate slot 11006 extending from a proximal end 11002 toward a distal end 11004. A longitudinal axis is defined along the staple cartridge 11000 by the elongate slot 11006. The staple cartridge 11000 comprises staple cavities defined therein. The staple cavities are arranged in three longitudinal rows. A first row of staple cavities 11100 extends alongside the elongate slot 11006. A second row of staple cavities 11200 extends alongside the first row of staple cavities 11100 on the same side of the elongate slot 11006. A third row of staple cavities 11300 extends alongside the second row of staple cavities 11200.

Figure 27:
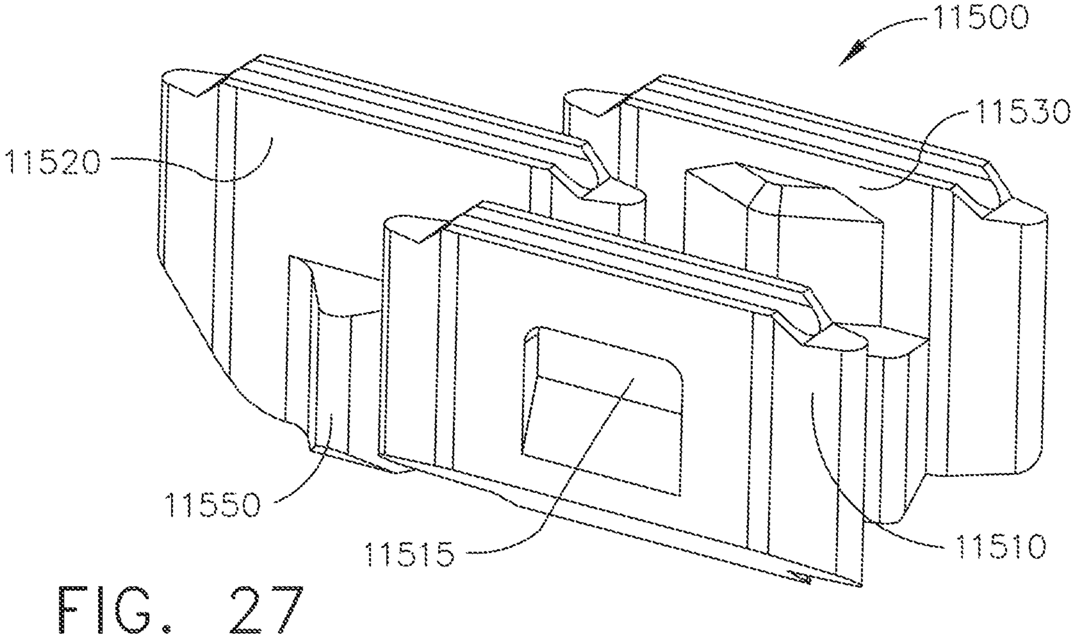
FIG. 27 is a perspective view of one of the staple drivers of FIG. 26.

Staple drivers 11500 are movably positioned in the staple cavities 11100, 11200, 11300. Each staple driver 11500 is configured to move from an unfired position and a fired position during the staple firing stroke. As shown in FIG. 27, the staple driver 11500 comprises a first staple-supporting portion 11510, a second staple-supporting portion 11520, and a third staple-supporting portion 11530. The first staple-supporting portion 11510 supports a staple in a staple cavity 11100 from the first longitudinal row, the second staple-supporting portion 11520 supports a staple in a staple cavity 11200 from the second longitudinal row, and the third staple-supporting portion 11530 supports a staple in a staple cavity 11300 from the third longitudinal row. A base 11550 connects the three staple-supporting portions 11510, 11520, 11530 to one another.

The staple cartridge 11000 comprises an exterior wall 11020 that serves as a sidewall to the staple cavities within the third longitudinal row 11300. The exterior wall 11020 comprises a resilient engagement portion comprising projections 11025 defined thereon. The staple cartridge 11000 further comprises an interior wall 11030 that serves as a sidewall to the staple cavities within the first longitudinal row 11100. The interior wall 11030 comprises a resilient engagement portion comprising projections 11035 defined thereon. The projections 11025, 11035 of the staple cartridge 11000 are configured to engage each staple driver 11500 as the staple drivers 11500 move within the staple cavities. As shown in FIGS. 26 and 27, a detent and/or notch 11515 is defined in the first staple-supporting portion 11510 and the third staple-supporting portion 11530. In various embodiments, the detent and/or notch 11515 can be defined on any suitable portion of the staple driver 11500, such as the second staple-supporting portion 11520, for example.

A staple driver 11500 is shown being inserted into the base 11015 on the right side of the elongate slot 11006 of the staple cartridge 11000 shown in FIG. 26. An insertion path of the staple driver 11500 is blocked by the resilient engagement portions 11025, 11035 of the staple cartridge 11000. Stated another way, the resilient engagement portions 11025, 11035 prevent the staple driver 11500 from being inserted into the staple cartridge 11000 without application of an external force. As an upward force is applied to the staple driver 11500, the first staple-supporting portion 11510 contacts the interior wall 11030 of the staple cartridge 11000. The contact between the first staple-supporting portion 11510 and the interior wall 11030 causes at least a portion of the interior wall 11030 to bias away from the staple driver 11500 and toward the elongate slot 11006. Similarly, the third staple-supporting portion 11530 contacts the exterior wall 11020 of the staple cartridge 11000 as the staple driver 11500 is loaded into the staple cartridge 11000. The contact between the third staple-supporting portion 11530 and the exterior wall 11020 causes at least a portion of the exterior wall 11020 bias away from the staple driver 11500 and away from the elongate slot 11006. When the interior wall 11030 and the exterior wall 11020 are biased away from the staple cavity, the insertion path of the staple driver 11500 is cleared, and the staple driver 11500 is able to be loaded into the staple cartridge 11000 and held in the unfired position.

A staple driver 11500 is shown being held in the unfired position on the left side of the elongate slot 11006 of the staple cartridge 11000 shown in FIG. 26. Notably, the resilient engagement portions of the interior wall 11030 and the exterior wall 11020 are in an unbiased and/or natural configuration. The staple driver 11500 is held in the unfired position, as the projections 11025, 11035 defined on the resilient engagement portions are received by the detents and/or notches 11515 defined in the first staple-supporting portion 11510 and the third staple-supporting portion 11530 of the staple driver 11500. Stated another way, the interface between the projections 11025, 11035 of the staple cartridge 11000 and the notch and/or detent 11515 of the staple driver 11500 prevents the staple driver 11500 from moving in either direction out of the unfired position.

Figure 29:
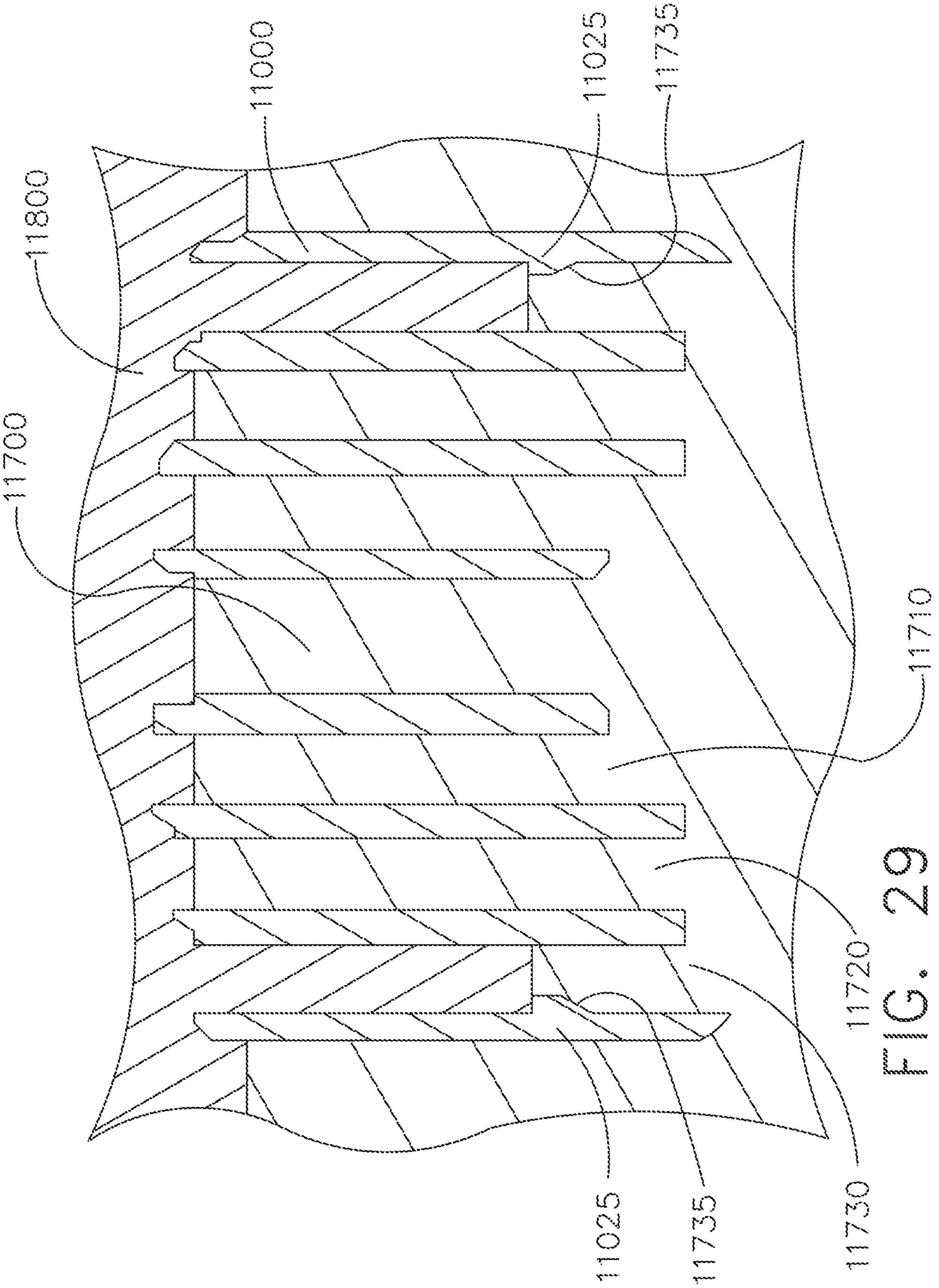
FIG. 29 is a cross-sectional view of a top mold and a bottom mold for forming a staple cartridge configured to movably receive the staple driver of FIG. 28 therein.

As discussed in greater detail herein, driver retention features can be integrally formed within the staple cartridge. Staple cartridges, such as the staple cartridge 11900, can be manufactured through an injection molding process. As shown in FIG. 29, a top mold 11800 and a bottom mold 11700 are positioned in a manner that allows for the injection molding of the staple cartridge 11900 comprising a driver retention feature. Similar to the staple cartridge 11000, the staple cartridge 11900 comprises three longitudinal rows of staple cavities extending along each side of an elongate slot.

Figure 30:
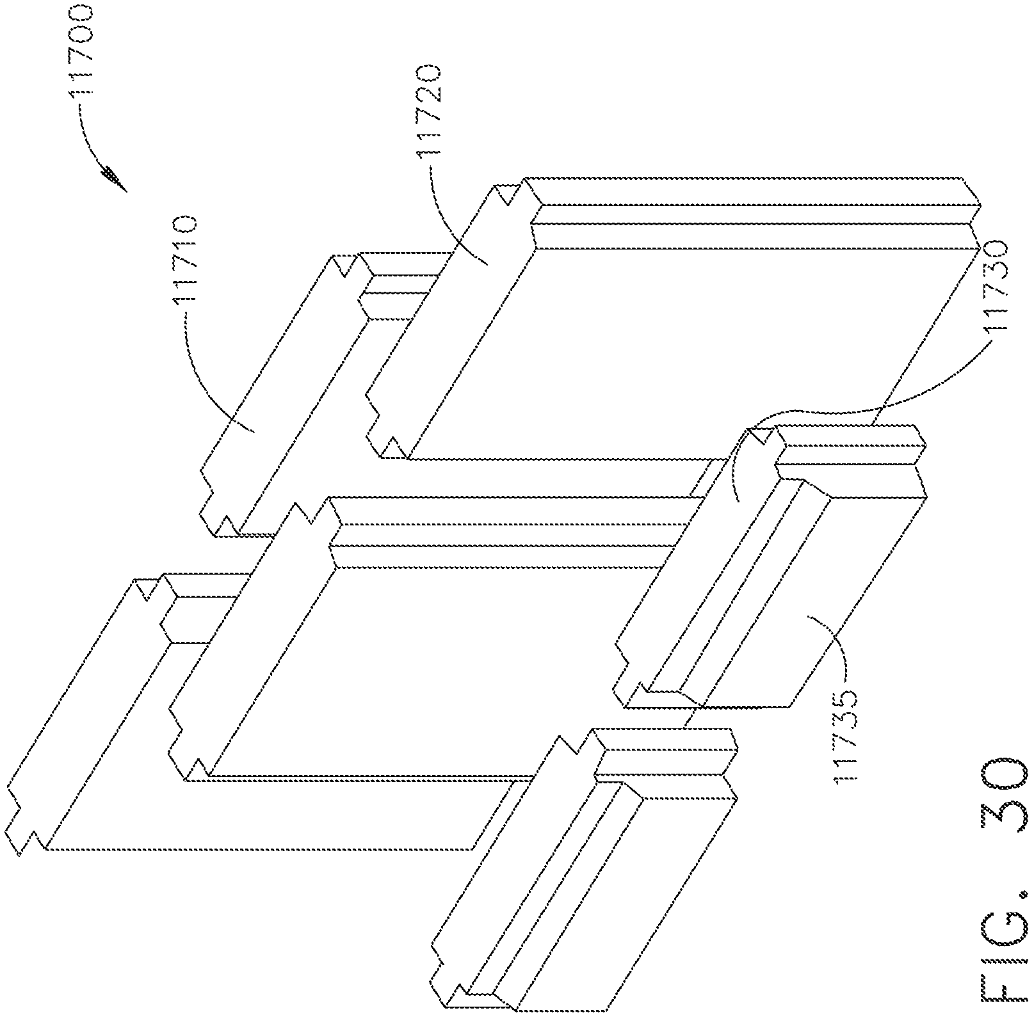
FIG. 30 is a perspective view of the bottom mold of FIG. 29.

As shown in FIGS. 29 and 30, the bottom mold 11700 comprises a central projection 11750 extending from a base, wherein the central projection 11750 is configured to define the elongate slot in the staple cartridge 11900. The bottom mold 11700 further comprises three projections extending from the base along each side of the central projection 11750. A first projection 11710 extends from the base alongside the central projection 11750 a first distance and is configured to define the staple cavities within a first longitudinal row. A second projection 11720 extends from the base alongside the first projection 11710 to a second distance and is configured to define the staple cavities within a second longitudinal row. A third projection 11730 extends from the base alongside the second projection 11720 to a third distance and is configured to define the staple cavities within a third longitudinal row. The third distance is shorter than the first distance and the second distance.

The top mold 11800 comprises a central projection 11850 extending from a base, wherein the central projection 11850 is configured to be aligned with the central projection 11750 of the bottom mold 11700 in order to define the elongate slot in the staple cartridge 19000. The top mold 11800 further comprises three projections extending from the base along each side of the central projection 11850. A first projection 11810 extends a first distance from the base alongside the central projection 11850. The first projection 11810 is aligned with and/or cooperates with the first projection 11710 of the bottom mold 11700 to define the first longitudinal row of staple cavities. A second projection 11820 extends a second distance from the base alongside the first projection 11810. The second projection 11820 is aligned with and/or cooperates with the second projection 11720 of the bottom mold 11700 to define the second longitudinal row of staple cavities. A third projection 11830 extends a third distance from the base alongside the second projection 11820. The third projection 11830 is aligned with and/or cooperates with the third projection 11730 of the bottom mold 11700 to define the third row of staple cavities and the driver retention feature. The third distance is greater than the first distance and the second distance. Stated another way, the first and second projections 11710, 11720 of the bottom mold 11700 define a majority of the first and second longitudinal rows of staple cavities as the first and second projections 11710, 11720 are taller than the third projection 11730 of the bottom mold 11700. Conversely, the third projection 11830 of the top mold 11800 defines a majority of the third longitudinal row of staple cavities as the third projection 11830 is taller than the first and second projections 11820, 11830 of the top mold 11800.

The third projection 11730 extends a shorter distance from the base of the bottom mold 11700 in order to form a driver retention feature within the staple cartridge 11900. While the ends of the first projections 11710, 11810 and the second projections 11720, 11820 comprise a rectangular profile, the ends of the third projections 11730, 11830 comprise a tapered and/or ramped profile. The tapered and/or ramped profile of the third projection 11730 of the bottom mold 11700 complements the tapered and/or ramped profile of the third projection 11830 of the top mold 11800. The tapered profiles allow for the definition of a resilient engagement portion comprising locking projections 11925 on an exterior wall of the staple cartridge 11900, wherein the locking projections 11925 extend into the staple cavities. In the depicted embodiment, the locking projections 11925 extend into the staple cavities from the third longitudinal row. The locking projections 11925 are positioned in such a manner to interface with the staple drivers to maintain the staple driver in their unfired position. The locking projections 11925 are configured to prevent unwanted movement of the staple drivers within the staple cavities, such as movement of the staple drivers from their unfired position toward the fired position and/or disassociation from the staple cartridge 19000.

Figure 28:
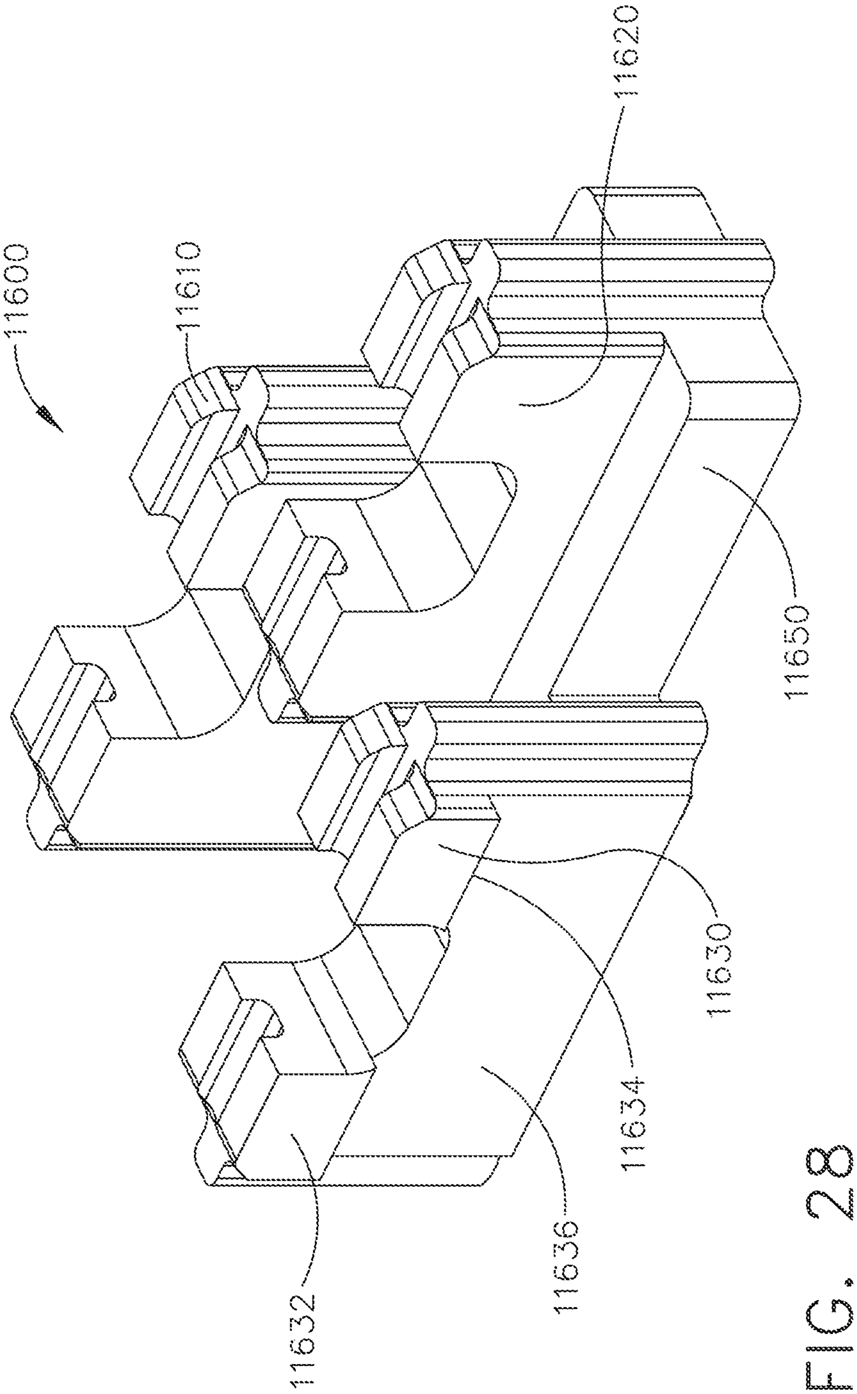
FIG. 28 is a perspective view of a staple driver comprising a retention ledge in accordance with at least one embodiment.

FIG. 28 illustrates a staple driver 11600 for use with the staple cartridge 11900. The staple driver 11600 comprises a first staple-supporting portion 11610 configured to be positioned in a staple cavity from the first longitudinal row, a second staple-supporting portion 11620 configured to be positioned in a staple cavity from the second longitudinal row, and a third staple-supporting portion 11630 configured to be positioned in a staple cavity from the third longitudinal row. The third staple-supporting portion 11630 comprises a ledge 11634. In various instances, a bottom section 11636 of the third staple-supporting portion 11630 is removed in order to form the ledge 11634. The ledge 11634 comprises a flat surface that directly abuts a flat surface formed on each locking projection 11925 of the staple cartridge 11900 when the staple driver 11600 is in the unfired position. Such an interface prevents the staple drivers 11600 from disassociating from the staple cartridge 11900 through the base of the staple cartridge 11900. Each locking projection 11925 further comprises a ramped surface to facilitate translation of the staple drivers 11600 from their unfired position toward their fired position upon being contacted by a firing member during the staple firing stroke. In the depicted embodiment, a smaller force is required to move the staple drivers 11600 from their unfired position toward their fired position than the force required to move the staple drivers 11600 from their unfired position toward the base of the staple cartridge 11900.

FIGS. 31A-32B illustrate various elements of a staple cartridge 12000 during a staple firing stroke. The staple cartridge 12000 comprises a cartridge body 12005 including a deck surface 12010. Staple cavities 12020 are defined within the cartridge body 12005. Staples are removably positioned within the staple cavities 12020. Staple drivers 12200 are positioned within the staple cavities 12020 to support the staples, which are configured drive the staples toward an anvil positioned opposite the staple cartridge 12000 during a staple firing stroke. Each of the staple drivers 12200 are configured to support a staple on a staple-supporting surface 12230 defined thereon. Each staple driver 12200 comprises a proximal end 12202 and a distal end 12204. The proximal end 12202 of each staple driver 12200 comprises a tapered engagement surface, or ramp, 12210. FIGS. 31A-32B depict a relationship between a firing member 12100 and a staple driver 12200 of the staple cartridge 12000 as the firing member 12100 moves from a proximal position to a distal position during the staple firing stroke. The firing member 12100 is proximal to the staple driver 12200 when the firing member 12100 is in the proximal position, and the firing member 12100 is distal to the staple driver 12200 when the firing member 12100 is in the distal position.

Figure 31A:
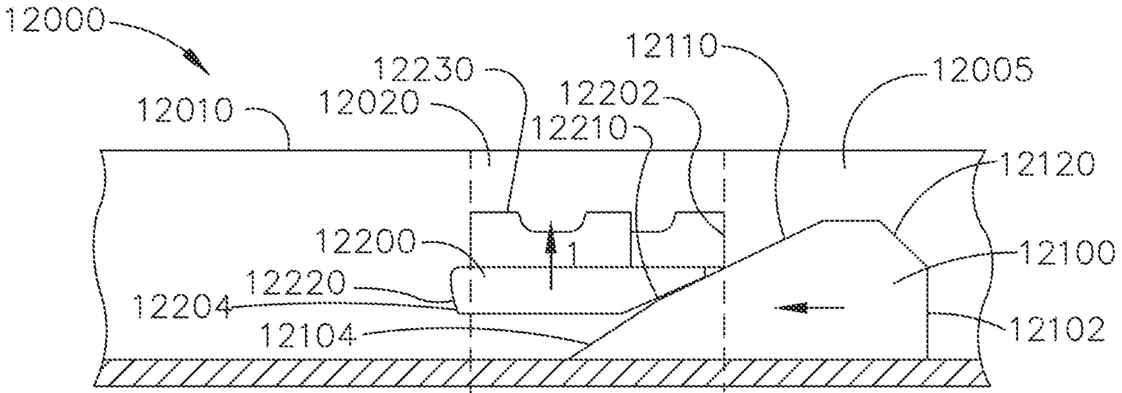
FIG. 31A is a partial cross-sectional view of a staple cartridge including a firing member contacting a staple driver as the firing member translates distally during a staple firing stroke in accordance with at least one embodiment.

The staple drivers 12200 are configured to translate upwardly within the staple cavities 12020 during the staple firing stroke. As discussed in greater detail herein, the staple drivers 12200 are in an unfired position, or configuration, prior to being contacted by the firing member 12100 during the staple firing stroke. FIG. 31A illustrates the firing member 12100 advancing from its proximal position toward its distal position. A distal end 12104 of the firing member 12100 contacts the tapered engagement surface 12210 of the staple driver 12200 as a result of the distal movement of the firing member 12100. The contact between the tapered engagement surface 12210 and the distal end 12104 of the firing member 12100 causes the staple driver 12200 to begin driving upward in a first direction 1. The firing member 12100 comprises a ramped surface 12210 configured to facilitate the upward translation of the staple driver 12200 as the firing member 12100 advances distally through the staple cartridge 12000.

Figure 31B:
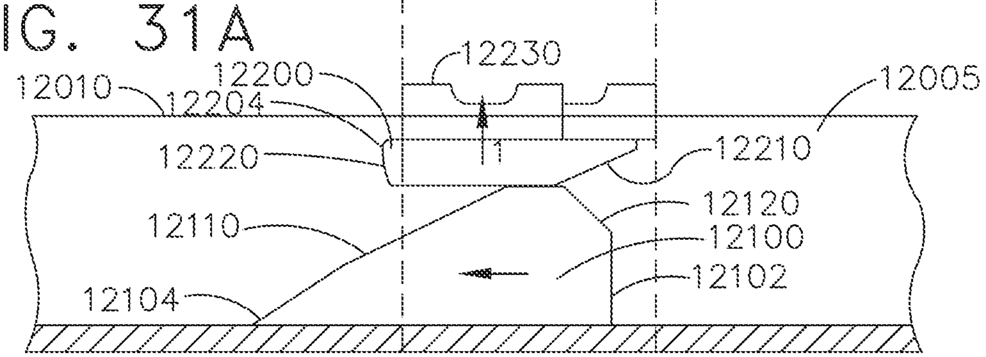
FIG. 31B is a partial cross-sectional view of the staple driver of FIG. 31A in a fully-fired position.

The staple drivers 12200 ultimately reach a fully-fired position as the staple drivers 12200 are driven upwardly by the firing member 12100. The staple driver 12200 is shown in the fully-fired position in FIG. 31B. In the fully-fired position, at least a portion of the staple driver 12200 extends above, or is over-driven relative to, the deck surface 12010 of the staple cartridge 12000. As shown in FIG. 31B, the firing member 12100 is capable of translating proximally and distally with little to no contact with the staple driver 12200 when the staple driver 12200 is in the fully-fired position. As such, the staple driver 12200 does not prevent the firing member 12100 from translating along a firing path and/or a retraction path when the staple driver 12200 is maintained in its fully-fired position.

Once a staple driver 12200 reaches its fully-fired position, the firing member 12100 continues to translate distally until the firing member 12100 is past the staple driver 12200. As the firing member 12100 translates distally past the staple driver 12200, the staple driver 12200 may, in some instances, fall downwards in a second direction 2 from its fully-fired position to a position somewhere between its unfired position and its fully-fired position, i.e., a raised position. The staple driver 12200 is shown in the raised position in FIG. 32A. When the staple driver 12200 is in the raised and/or retention position, the staple driver 12200 is positioned higher than the staple driver 12200 in its unfired position but lower than the staple driver 12200 in its fully-fired position. In various instances, for example, the staple driver 12200 does not extend above the deck surface 12010 of the staple cartridge 12000 when the staple driver 12200 is in the raised position.

In many embodiments, the firing member 12100 is retracted proximally from its distal position after the staple firing stroke has been completed or is otherwise stopped. However, if one or more staple drivers 12200 have fallen downwardly toward the unfired position, the firing member 12100 is blocked from being retracted past the fallen staple drivers 12200. As discussed in greater detail herein, the firing member 12100 is not prevented from being retracted proximally when the staple drivers 12200 are in their raised position and/or their fully-fired position.

Figure 32A:
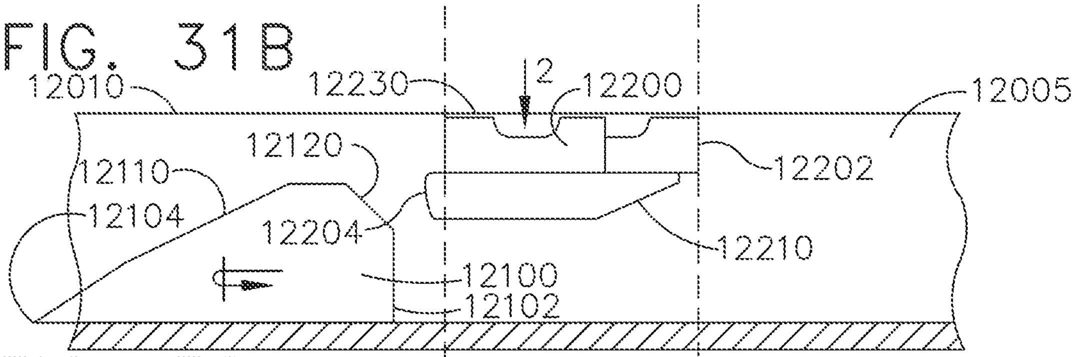
FIG. 32A is a partial cross-sectional view of the firing member and the staple driver of FIG. 31A after the firing member translates distally past the staple driver.
Figure 32B:
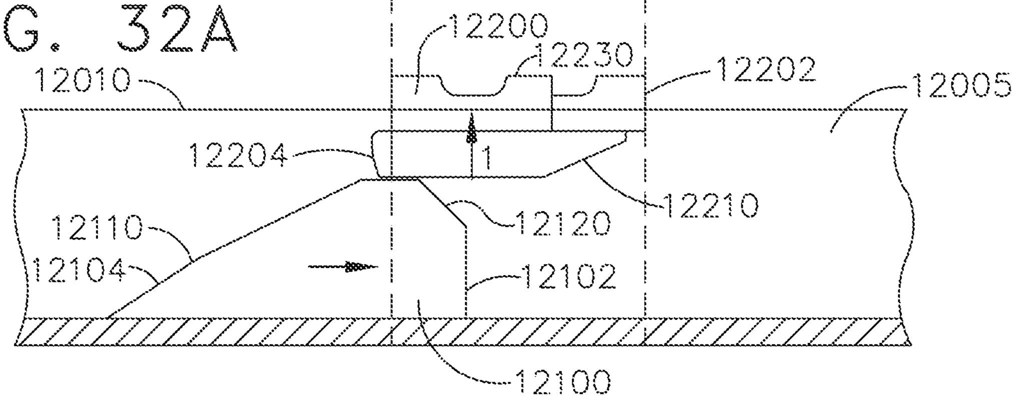
FIG. 32B is a partial cross-sectional view of the firing member of FIG. 31A contacting the staple driver as the firing member translates proximally after the staple firing stroke.

As shown in FIG. 32B, a proximal end 12102 of the firing member 12100 comprises as angled engagement surface or ramp 12120. As the firing member 12100 is retracted proximally, the angled engagement surface 12120 of the firing member 12100 contacts the distal end 12204 of the staple driver 12200. The contact made between the angled engagement surface 12120 of the firing member 12100 and the distal end 12204 of the staple driver 12200 causes the staple driver 12200 to once again drive upward in the first direction 1. The staple driver 12200 is driven to the fully-fired position or to any suitable position that allows the firing member 12100 to retract proximally past the staple driver 12200. In the depicted embodiment, a portion of the staple driver 12200 moves above the deck surface 12010 of the staple cartridge 12000 to allow the firing member 12100 to retract. The staple driver 12200 may fall back toward the unfired position once the firing member 12100 is retracted past the staple driver 12200. Various manners to keep the staple driver in the fully-fired position and/or the raised position are discussed in greater detail herein.

Figure 33:
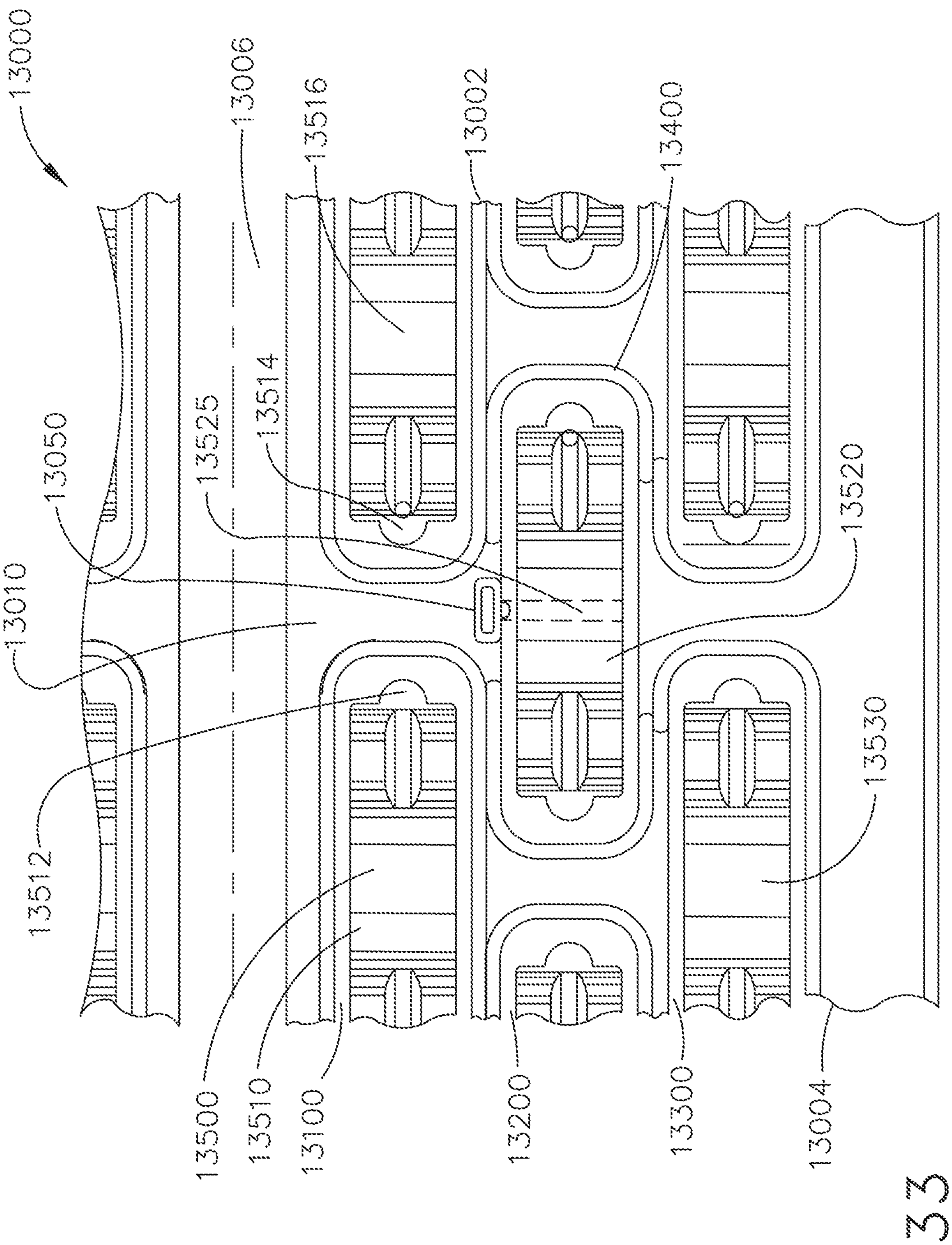
FIG. 33 is a partial plan view of a staple cartridge comprising staple drivers and a driver retention member in accordance with at least one embodiment.

A staple cartridge 13000 is depicted in FIG. 33. The staple cartridge 13000 comprises an elongate slot 13006 extending from a proximal end 13002 toward a distal end 13004. The elongate slot 13006 defines a longitudinal axis of the staple cartridge 13000. Staple cavities are defined in the staple cartridge 13000, and the staple cavities are arranged in longitudinal rows. A first longitudinal row of staple cavities 13100 extends alongside the elongate slot 13006. A second longitudinal row of staple cavities 13200 extends alongside the first longitudinal row of staple cavities 13100 on the same side of the elongate slot 13006. A third longitudinal row of staple cavities 13300 extends alongside the second longitudinal row of staple cavities 13200. The staple cavities 13100 within the first longitudinal row are laterally aligned with the staple cavities 13300 within the third longitudinal row. The staple cavities 13200 within the second longitudinal row are laterally offset from the staple cavities 13100, 13300 within the first and third longitudinal rows, respectively.

As discussed in greater detail herein, the staple cartridge 13000 comprises projections 13400 extending upward and/or toward an anvil from a deck surface 13010. The projections 13400 surround at least a portion of the staple cavities 13100, 13200, 13300 and serve to, for example, prevent tissue from moving relative to the deck surface 13010 and/or support the staples as they are being ejected during a staple firing stroke.

Figure 34:
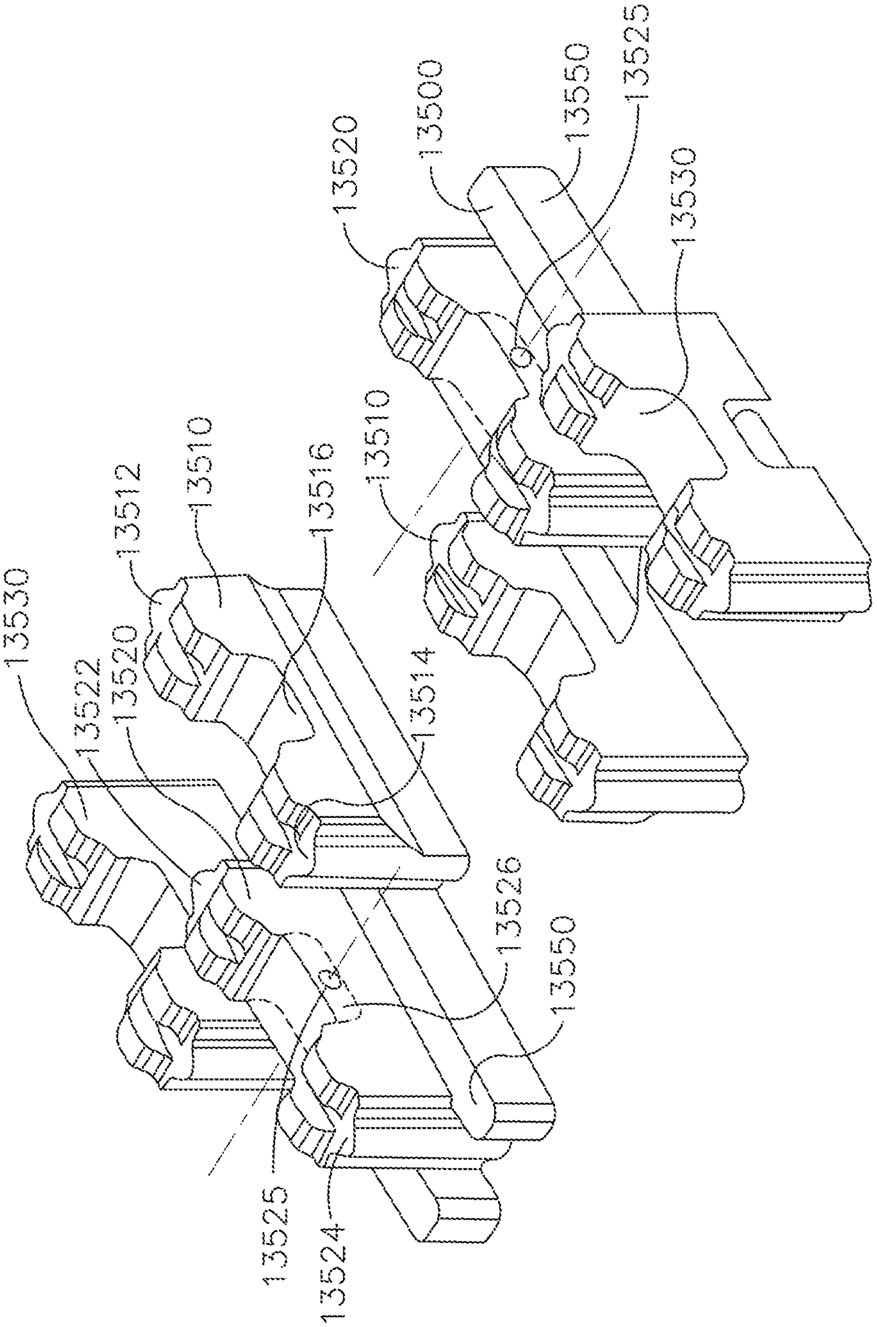
FIG. 34 is a perspective view of the staple drivers of FIG. 33, wherein an aperture is defined in the staple drivers, and wherein the aperture is configured to receive the driver retention member when the staple driver is in a raised, or retention, position.

Staple drivers 13500 are movably positioned within the staple cavities and are configured to support and drive the staples toward an anvil positioned opposite the staple cartridge 13000 during a staple firing stroke. As shown in FIG. 34, each staple driver 13500 comprises a first staple-supporting portion 13510, a second staple-supporting portion 13520, and a third staple-supporting portion 13530. The first staple-supporting portion 13510 is positioned within a staple cavity 13100 to support and drive a staple within the first longitudinal row, the second staple-supporting portion 13520 is positioned within a staple cavity 13200 to support and drive a staple within the second longitudinal row, and the third staple-supporting portion 13530 is positioned within a staple cavity 13300 to support and drive a staple within the third longitudinal row. The three staple-supporting portions 13510, 13520, 13530 are connected together through a base 13550 of the staple driver 13500. While the depicted staple drivers 13500 comprise three staple-supporting portions, a staple driver can comprise any suitable number of staple-supporting portions such as one staple-supporting portion or two staple-supporting portions, for example.

Staple drivers 13500 are configured to translate within the staple cavity during the staple firing stroke. As discussed in greater detail herein, the staple drivers 13500 are in an unfired position prior to being contacted by the firing member during the staple firing stroke. The staple drivers 13500 ultimately reach a fully-fired position as the staple drivers 13500 are driven upwardly by the firing member. Once a staple driver 13500 reaches its fully-fired position, the firing member continues to translate distally until the firing member is no longer in contact with the staple driver 13500. As the firing member translates distally past the staple driver 13500, the staple driver 13500 may fall to a raised position in between the unfired position and the fully-fired position.

Figure 35:
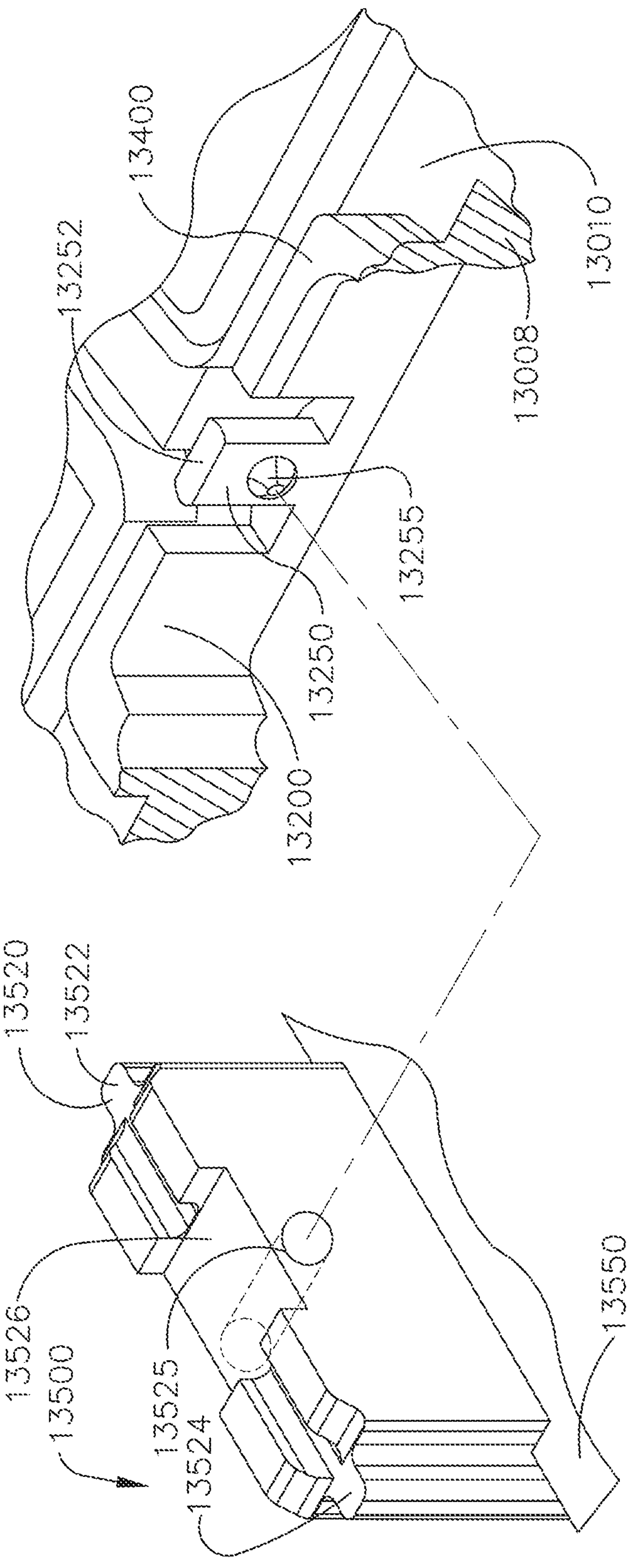
FIG. 35 is a partial cross-sectional view of the interaction between the driver retention member and the aperture of the staple driver of FIG. 34 when the staple driver is in the raised position.

To maintain the staple drivers at least in their raised position after the firing member is no longer in contact with the staple drivers, the staple cartridge 13000 comprises driver retention members 13050 that extend into and/or over the staple cavities to engage the staple driver 13500 and hold the staple drivers 13500 in their raised position and/or fully-fired position. Each driver retention member 13050 extends into an individual staple cavity 13200 within the second longitudinal row of staple cavities from the cartridge body 13008. In the embodiment depicted in FIG. 35, the driver retention member 13050 is positioned in between the projections 13400 surrounding a portion of the staple cavity 13200. An aperture 13525 is defined in a portion of the staple driver 13500 which is configured to receive the driver retention member 13050. As the depicted driver retention member 13050 extends into the staple cavity 13200 from the second longitudinal row, the aperture 13525 is defined in the second staple-supporting portion 13520.

The aperture 13525 can be located on any suitable portion of the staple driver 13500. In various instances, a staple driver 13500 can have more than one aperture 13525 defined therein. The aperture 13525 can be formed within the staple driver 13500 in any suitable manner. In various instances, the aperture 13525 is created by an injection molded pin.

In various instances, the second staple-supporting portion 13520 comprises additional material than the first and third staple-supporting portions 13510, 13530 to account for the aperture 13525 defined therein. For example, referring to FIG. 34, the first staple-supporting portion 13510 comprises a first end 13512 and a second end 13514. The first end 13512 is configured to support a first leg of a staple, and the second end 13514 is configured to support a second leg of the staple. The first end 13512 and the second end 13514 are connected to one another by a middle portion 13516. The middle portion 13516 is positioned a first distance below the first end 13512 and the second end 13514. The middle portion 13516 does not contact the staple when the staple is supported by first staple-supporting portion 13510. The second staple-supporting portion 13520 comprises a first end 13522 and a second end 13524. The first end 13522 is configured to support a first leg of a staple, and the second end 13524 is configured to support a second leg of the staple. The first end 13522 and the second end 13524 are connected to one another by a middle portion 13526. The middle portion 13526 is positioned a second distance below the first end 13522 and the second end 13524. The second distance is less than the first distance. In other words, the middle portion 13526 of the second staple-supporting portion 13520 is larger to accommodate for the aperture 13525 defined therein.

The driver retention member 13050 comprises a flexible tab 13252 and a projection 13255 extending from the tab 13252. As the firing member drives the staple driver 13500 from the unfired position toward the fully-fired position, the staple driver 13500 causes the tab 13252 of the driver retention member 13050 to resiliently bend out of the drive path of the staple driver 13500. Stated another way, the upward force applied to the staple driver 13500 by the firing member is strong enough to bias the driver retention member 13050 out of the drive path of the staple driver 13500 to allow the staple driver 13500 to reach the fully-fired position. The projection 13255 is configured to be received by the aperture 13525 of the staple driver 13500 when the staple driver 13500 is at and/or near its fully-fired position. In the depicted embodiment, the aperture 13525 is positioned above the projection 13255 of the driver retention member 13050 when the staple driver 13500 is in the fully-fired position. As the firing member translates distally past the staple driver 13500, the staple driver 13500 may begin to fall back toward the unfired position. In such instances, the tab 13252 of the driver retention member 13050 springs back into the drive path of the staple driver 13500 such that the projection 13255 of the driver retention member 13050 is caught by and/or otherwise is engaged with the aperture 13525 of the staple driver 13500. The driver retention member 13050 maintains the staple driver 13500 in its raised position when the projection 13255 is received by the aperture 13525. As described in greater detail with respect to FIGS. 31A-32B, the staple driver 13500 does not prevent the firing member from retracting proximally past the staple driver 13500 when the staple driver 13500 is locked in this position. The projection 13255 and the aperture 13525 can be configured and/or arranged to hold the staple driver 13500 in its fully-fired position or, alternatively, the projection 13255 and the aperture 13525 can be configured and/or arranged to hold the staple driver 13500 in its raised position between the unfired position and its fully-fired position.

Figure 36A:
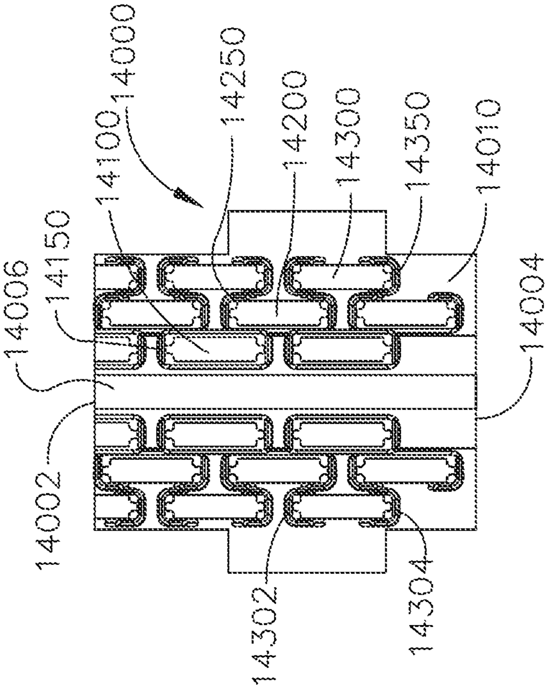
FIG. 36A is a partial elevational view of a staple cartridge comprising a curved deck surface and projections extending from the deck surface in accordance with at least one embodiment.
Figure 36B:
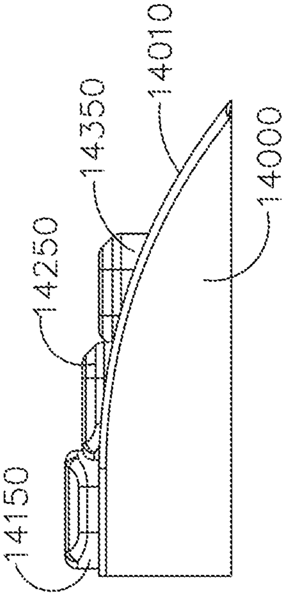
FIG. 36B is a partial plan view of the projections extending from the curved deck surface of FIG. 36A.

Turning now to FIGS. 36A and 36B, a staple cartridge 14000 comprising a deck surface 14010 and an elongate slot 14006 extending from a proximal end 14002 toward a distal end 14004 is depicted. The deck surface 14010 of the staple cartridge 14000 is rounded and/or curved. Stated another way, the deck surface 14010 varies laterally with respect to a longitudinal axis defined by the elongate slot 14006. The highest point of the illustrated deck surface 14010 is adjacent to the elongate slot 14006. The staple cartridge 14000 further comprises staple cavities arranged in three longitudinal rows. A first longitudinal row of staple cavities 14100 extends alongside the elongate slot 14006. A second longitudinal row of staple cavities 14200 extends alongside the first longitudinal row of staple cavities 14100, and a third longitudinal row of staple cavities 14300 extends alongside the second longitudinal row of staple cavities 14200. The staple cartridge 14000 further comprises projections that extend above the deck surface 14010. The projections depicted on the staple cartridge 14000 are in the form of pocket extenders. A pocket extender supports the legs of the staple above the deck of the staple cartridge. Embodiments are envisioned in which the projections are not pocket extenders. A first projection 14150 surrounds a portion of each of the staple cavities 14100 within the first longitudinal row, a second projection 14250 surrounds a portion of each of the staple cavities 14200 within the second longitudinal row, and a third projection 14350 surrounds a portion of each of the staple cavities 14300 within the third longitudinal row. The projections are connected to one another. For example, the first projections 14150 connect to the second projections 14250 and/or the second projections 14250 connect to the third projections 14350. In other instances, the projections are separate and distinct from one another and are not connected to one another except by the deck surface 14010.

The projections 14150, 14250, 14350 comprise a square or substantially square geometry. Stated another way, the projections 14150, 14250, 14350 surround portions of the staple cavities in a manner that mimics the geometry of a square. Among other things, the curves and/or edges of the projections 14150, 14250, 14350 are not severe. In the depicted embodiment, the first projection 14150 surrounds a staple cavity 14100 from within the first longitudinal row in its entirety. The second projection 14250 surrounds approximately three-quarters of a staple cavity 14200 from within the second longitudinal row. The third projection 14350 is comprised of two projections that surround a proximal end 14302 and a distal end 14304 of a staple cavity 14300 from within the third longitudinal row, wherein the two projections are not connected. Overall, the third projection 14350 encompasses approximately half of the staple cavity 14300. In various instances, the first projection 14150 surrounds a staple cavity to a greater amount than the second projection 14250 and the third projection 14350. As shown in the depicted embodiment, the degree to which the projections 14150, 14250, 14350 encompass a particular staple cavity varies based on the lateral position of the staple cavity with respect to the elongate slot 14006. While the depicted projections within a particular longitudinal row of staple cavities are all the same, it is envisioned that the projections within the same longitudinal row can vary based on the position of a particular staple cavity with respect to the proximal end 14002 and/or the distal end 14004 of the staple cartridge 14000.

The projections 14150, 14250, 14350 shown in FIGS. 36A and 36B extend from the deck surface 14010 to different heights. More specifically, the height of each projection 14150, 14250, 14350 varies based on the location of the projection 14150, 14250, 14350 and/or the staple cavity 14100, 14200, 14300 with respect to the elongate slot 14006. In various instances, each projection 14150, 14250, 14350 comprises a distinct height; however, any suitable height is envisioned to achieve a particular tissue effect. In the depicted embodiment, the height of the first projection 14150 is greater than the height of the second projection 14250, and the height of the second projection 14250 is less than the height of the third projection 14350.

Figure 37A:
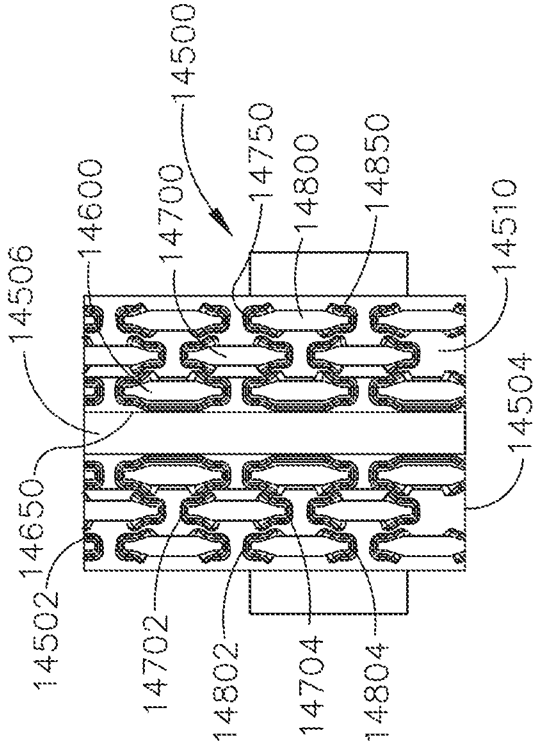
FIG. 37A is a partial elevational view of a staple cartridge comprising a curved deck surface in accordance with at least one embodiment.
Figure 37B:
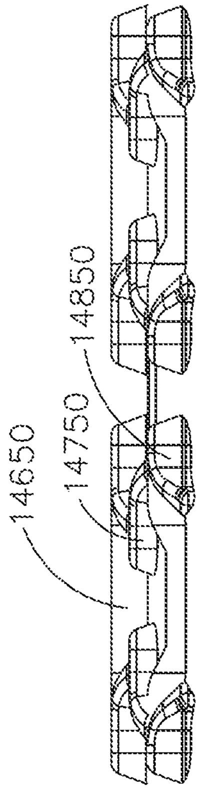
FIG. 37B is a partial plan view of the projections extending from the curved deck surface of FIG. 37A.

A staple cartridge 14500 comprising a deck surface 14510 and an elongate slot 14506 extending from a proximal end 14502 toward a distal end 14504 is depicted in FIGS. 37A and 37B. The height of the deck surface 14510 of the staple cartridge 14500 is rounded and/or curved. Stated another way, the deck surface 14510 varies laterally with respect to a longitudinal axis defined by the elongate slot 14506. The highest point of the illustrated deck surface 14510 is adjacent to the elongate slot 14506. The staple cartridge 14500 further comprises staple cavities arranged in three longitudinal rows. A first longitudinal row of staple cavities 14600 extends alongside the elongate slot 14506. A second longitudinal row of staple cavities 14700 extends alongside the first longitudinal row of staple cavities 14600, and a third longitudinal row of staple cavities 14800 extends alongside the second longitudinal row of staple cavities 14700. The staple cartridge 14500 further comprises projections that extend above the deck surface 14510. The projections depicted on the staple cartridge 14500 are in the form of pocket extenders. A pocket extender supports the legs of the staple above the deck of the staple cartridge. Embodiments are envisioned in which the projections are not pocket extenders. A first projection 14650 surrounds a first portion of each of the staple cavities 14600 within the first longitudinal row, a second projection 14750 surrounds a second portion of each of the staple cavities 14700 within the second longitudinal row, and a third projection 14850 surrounds a third portion of each of the staple cavities 14800 within the third longitudinal row. In various instances, the projections are connected to one another. However, in the embodiment depicted in FIGS. 37A and 37B, the projections are separate and distinct from one another.

The projections 14650, 14750, 14850 each comprise an elongate, or diamond-like geometry. The projections 14650, 14750, 14850 surround portions of the staple cavities in a manner that closely conforms to the borders of the staple cavities, which are also elongate and diamond-like in shape. Among other things, the curves and/or edges of the projections 14650, 14750, 14850 form acute and/or obtuse angles. In the depicted embodiment, the first projection 14650 surrounds approximately three-quarters of a staple cavity 14600 from within the first longitudinal row. The second projection 14750 is comprised of two projections that surround a proximal end 14702 and a distal end 14704 of a staple cavity 14700 from within the second longitudinal row, wherein the two projections are not connected. Overall, the second projection 14750 encompasses approximately half of the staple cavity 14700. Similarly, the third projection 14850 is comprised of two projections that surround a proximal end 14802 and a distal end 14804 of a staple cavity 14800 from within the third longitudinal row, wherein the two projections are not connected. Overall, the third projection 14850 encompasses approximately half of the staple cavity 14800. In various instances, the first projection 14650 surrounds a staple cavity to a greater degree than the second projection 14750 and the third projection 14850. In various instances, the second projections 14750 and the third projections 14850 surround staple cavities to the same and/or similar degree. As shown in the depicted embodiment, the degree to which the projections 14650, 14750, 14850 encompass a particular staple cavity can vary based on the lateral position of the staple cavity with respect to the elongate slot 14506. While the depicted projections within a particular longitudinal row of staple cavities are all the same, it is envisioned that the projections within the same longitudinal row can vary based on the position of a particular staple cavity with respect to the proximal end 14502 and/or the distal end 14504 of the staple cartridge 14500.

The projections 14650, 14750, 14850 shown in FIGS. 37A and 37B extend from the deck surface 14510 to the same and/or similar heights. More specifically, the height of each projection 14650, 14750, 14850 is substantially the same regardless of the location of the projection 14650, 14750, 14850 and/or the staple cavity 14600, 14700, 14800 with respect to the elongate slot 14506; however, any suitable height is envisioned to achieve a particular tissue effect.

Figure 38A:
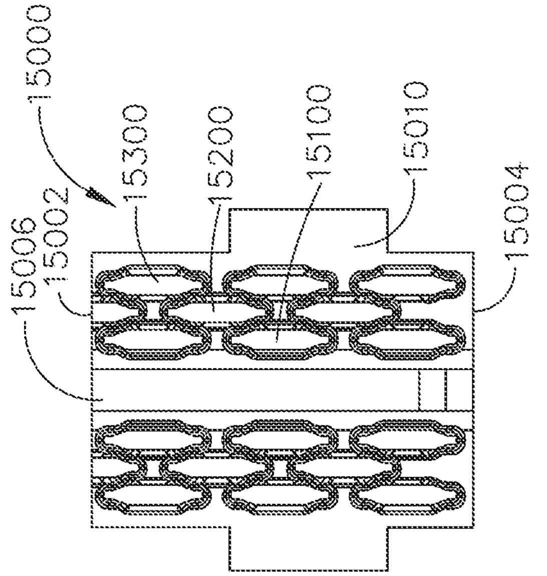
FIG. 38A is a partial elevational view of a staple cartridge comprising a curved deck surface in accordance with at least one embodiment.
Figure 38B:
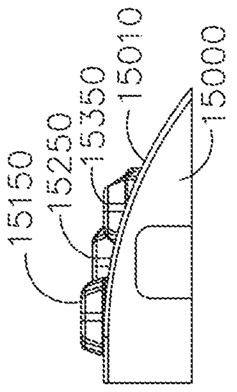
FIG. 38B is a partial plan view of the projections extending from the curved deck surface of FIG. 38B.

Turning now to FIGS. 38A and 38B, a staple cartridge 15000 comprising a deck surface 15010 and an elongate slot 15006 extending from a proximal end 15002 toward a distal end 15004 is depicted. The deck surface 15010 of the staple cartridge 15000 is rounded and/or curved. Stated another way, the height of the deck surface 15010 varies laterally with respect to a longitudinal axis defined by the elongate slot 15006. The highest point of the illustrated deck surface 15010 is adjacent to the elongate slot 15006. The staple cartridge 15000 further comprises staple cavities arranged in three longitudinal rows. A first longitudinal row of staple cavities 15100 extends alongside the elongate slot 15006. A second longitudinal row of staple cavities 15200 extends alongside the first longitudinal row of staple cavities 15100, and a third longitudinal row of staple cavities 15300 extends alongside the second longitudinal row of staple cavities 15200. The staple cartridge 15000 further comprises projections that extend above the deck surface 15010. The projections depicted on the staple cartridge 15000 are in the form of pocket extenders. A pocket extender supports the legs of the staple above the deck of the staple cartridge. Embodiments are envisioned in which the projections are not pocket extenders. A first projection 15150 surrounds a first portion of each of the staple cavities 15100 within the first longitudinal row, a second projection 15250 surrounds a second portion of each of the staple cavities 15200 within the second longitudinal row, and a third projection 15350 surrounds a third portion of each of the staple cavities 15300 within the third longitudinal row. In the depicted embodiment, the projections are connected to one another. More specifically, a first projection 15150 is connected to a second projection 15250, and a second projection 15250 is connected to a third projection 15350.

The projections 15150, 15250, 15350 comprise an elongate, or diamond-like geometry. Stated another way, the projections 15150, 15250, 15350 surround portions of the staple cavities in a manner that closely conforms to the borders of the staple cavities. In the depicted embodiment, the first projection 15150 surrounds a staple cavity 15100 from within the first longitudinal row in its entirety. The second projection 15250 surrounds a staple cavity 15200 from within the second longitudinal row in its entirety. The third projection 15350 surrounds a staple cavity 15300 from within the third longitudinal row in its entirety. As shown in the depicted embodiment, the degree to which the projections 15150, 15250, 15350 encompass a particular staple cavity is the same regardless of the lateral position of the staple cavity with respect to the elongate slot 15006.

The projections 15150, 15250, 15350 shown in FIGS. 38A and 38B extend from the deck surface 15010 to different heights. Not only can the projections 15150, 15250, 15350 vary based on the location of the staple cavity 15100, 15200, 15300 with respect to the elongate slot 15006, but the height of the projection can vary across each individual staple cavity. Stated another way, the height of a particular projection is not uniform across the entire projection. In the depicted embodiment, the height of the projection increases as the projection is spaced further away from the lateral slot 15006 to account for the curved nature of the deck surface 15010. More specifically, portions of a projection located closer to the elongate slot 15006 are shorter than portions of a projection located further from the elongate slot 15006.

Figure 39A:
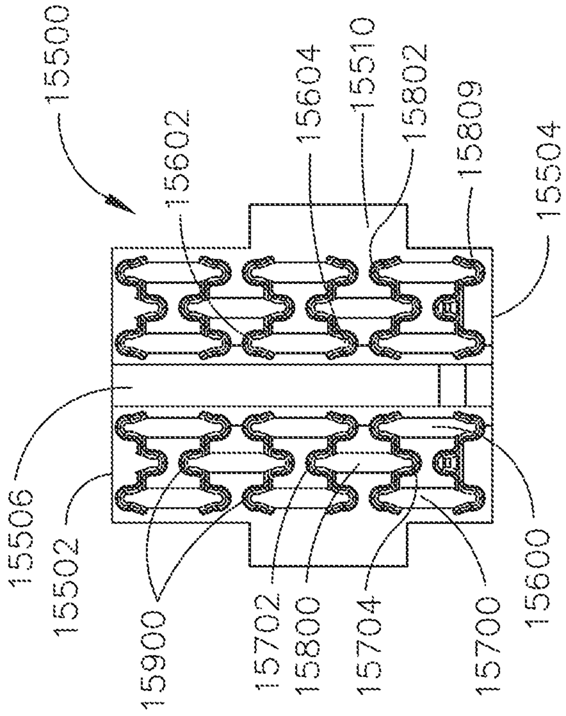
FIG. 39A is a partial elevational view of a staple cartridge comprising a curved deck surface in accordance with at least one embodiment.
Figure 39B:
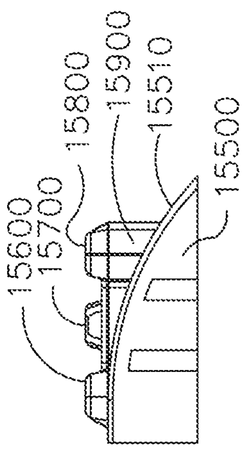
FIG. 39B is a partial plan view of the projections extending from the curved deck surface of FIG. 39A.

A staple cartridge 15500 comprising a deck surface 15510 and an elongate slot 15506 extending from a proximal end 15502 toward a distal end 15504 is depicted in FIGS. 39A and 39B. The deck surface 15510 of the staple cartridge 15500 is rounded and/or curved. Stated another way, the height of the deck surface 15510 varies laterally with respect to a longitudinal axis defined by the elongate slot 15506. The highest point of the illustrated deck surface 15510 is adjacent to the elongate slot 15506. The staple cartridge 15500 further comprises staple cavities arranged in three longitudinal rows. A first longitudinal row of staple cavities 15600 extends alongside the elongate slot 15506. A second longitudinal row of staple cavities 15700 extends alongside the first longitudinal row of staple cavities 15600, and a third longitudinal row of staple cavities 15800 extends alongside the second longitudinal row of staple cavities 15700. The staple cartridge 15500 further comprises projections 15900 that extend above the deck surface 15510. The projections 15900 depicted on the staple cartridge 15000 are in the form of pocket extenders. A pocket extender supports the legs of the staple above the deck of the staple cartridge. Embodiments are envisioned in which the projections are not pocket extenders. The projections 15900 span across the three longitudinal rows of staple cavities. For example, a projection 15900 encompasses a proximal end 15602 of a staple cavity 15600 from the first longitudinal row, a distal end 15704 of a staple cavity 15700 from the second longitudinal row, and a proximal end 15802 of a staple cavity 15800 from the third longitudinal row. Another projection 15900 encompasses a distal end 15604 of a staple cavity 15600 from the first longitudinal row, a proximal end 15702 of a staple cavity 15700 from the second longitudinal row, and a distal end 15804 of a staple cavity 15800 from the third longitudinal row.

The projections 15900 comprise a diamond-like geometry. The projections 15900 surround portions of the staple cavities in a manner that closely conforms to the borders of the staple cavities. The height of each projection 15900 varies as the projection 15900 extends laterally away from the elongate slot 15506. As shown in FIGS. 39A and 39B, an overall height of the staple cartridge 15500 including the projections 15900 is the same across each projection 15900. In order to achieve a level surface across the projection 15900 with the curved deck surface 15506, the height of the projection 15900 must vary as the projection 15900 extends away from the elongate slot 15606. For example, in the depicted embodiment, the portion of the projection 15900 spaced furthest away from the elongate slot 15506 extends a larger distance away from the deck surface 15510 than the portion of the projection 15900 spaced closest to the elongate slot 15506.

Figure 40:
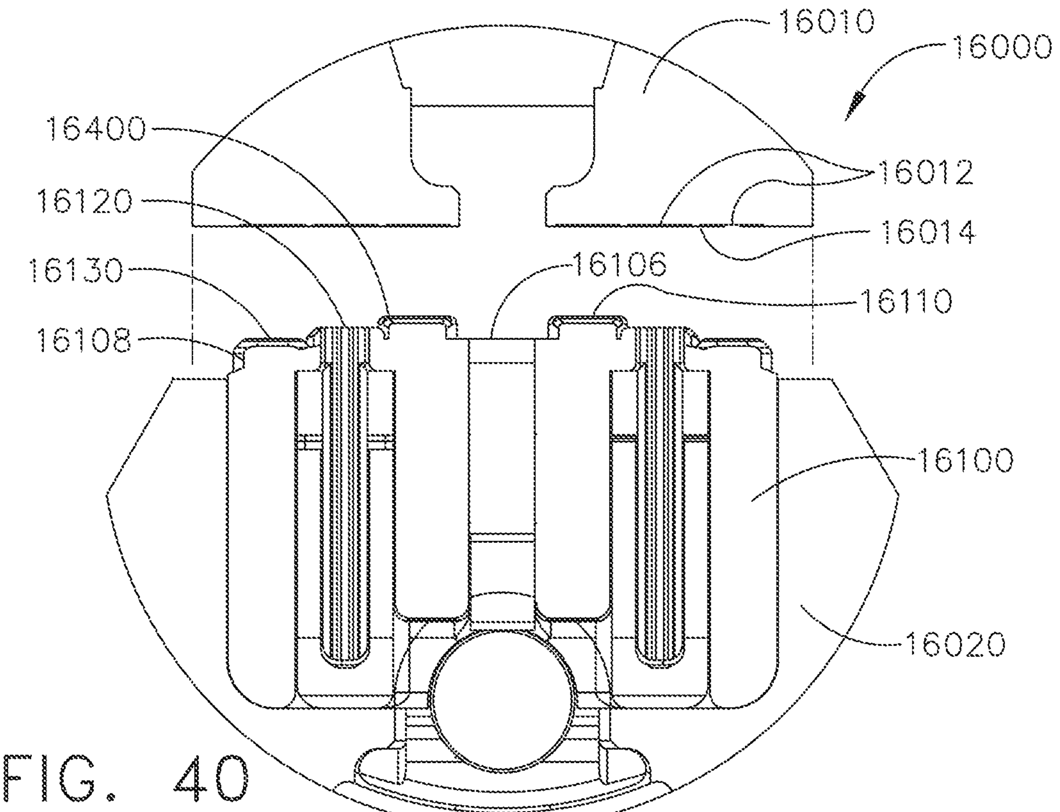
FIG. 40 is a partial cross-sectional view of a staple cartridge seated in an end effector, wherein the staple cartridge comprises a curved deck surface and projections extending from the curved deck surface in accordance with at least one embodiment.

FIG. 40 illustrates an end effector 16000 for use with a surgical stapling instrument. The end effector 16000 comprises an anvil 16010 and a staple cartridge jaw 16020. At least one of the anvil 16010 and the staple cartridge jaw 16020 are movable with respect to one another between an open configuration and a closed configuration. The end effector 16000 shown in FIG. 40 is in the closed configuration. The anvil 16010 comprises a planar tissue-supporting surface 16014, wherein the tissue-supporting surface 16014 comprises a plurality of staple forming pockets 16012 defined therein.

A staple cartridge 16100 is configured to be replaceably seated in the staple cartridge jaw 16020. The staple cartridge 16100 comprises an elongate slot 16106 that extends from a proximal end toward a distal end. A longitudinal axis of the staple cartridge 16100 is defined along the elongate slot 16106. The staple cartridge 16100 further comprises a deck surface 16108 that is rounded and/or curved. In various instances, the staple cartridge 16100 comprises a sloped deck surface. A tissue gap is defined between the deck surface 16108 and the tissue-supporting surface 16014 of the anvil 16010. The tissue gap varies laterally with respect to the elongate slot 16106. In the depicted embodiment, the tissue gap is the smallest at a point adjacent to the elongate slot 16106. The tissue gap becomes larger at points spaced laterally away from the elongate slot 16106.

The staple cartridge 16100 comprises staple cavities defined therein. A first longitudinal row of staple cavities 16100 extends alongside the elongate slot 16106. A second longitudinal row of staple cavities 16200 extends alongside the first longitudinal row of staple cavities 16100 on the same side of the elongate slot 16106. A third longitudinal row of staple cavities 16300 extends alongside the second longitudinal row of staple cavities 16200. As the longitudinal rows of staple cavities are spaced apart laterally, the tissue gap varies between the longitudinal rows. The tissue gap is the smallest between a staple cavity 16110 within the first longitudinal row and the tissue-supporting surface 16014 of the anvil 16010, while the tissue gap is the largest between a staple cavity 16130 within the third longitudinal row and the tissue-supporting surface 16014 of the anvil 16010.

The staple cartridge 16100 comprises projections 16400 extending upward and/or toward the anvil 16010 from the curved deck surface 16108. The projections 16400 surround at least a portion of the staple cavities 16110, 16120, 16130 and serve to, for example, prevent tissue supported between the deck surface 16108 and the tissue-supporting surface 16014 of the anvil 16010 from moving out of a desired position and/or provide stability to a staple driver and/or a staple during a staple firing stroke. The degree to which the projections 16400 surround a particular staple cavity can vary based on the position of the staple cavity in the staple cartridge 16100. The projections 16400 can vary based on the location of the particular staple cavity with respect to the elongate slot 16106. For example, projections 16400 surrounding the staple cavities 16110 within the first longitudinal row can all be the same. However, the projections 16400 surrounding the staple cavities 16110 within the first longitudinal row can be different from the projections 16400 surrounding the staple cavities 16120, 16130 within the second and third longitudinal rows. The projections 16400 can also vary based on the location of the particular staple cavity with respect to the proximal end and/or the distal end of the staple cartridge 16100. The projections 16400 can vary in height, length, and/or geometry, for example. Manners in which the projections 16400 can vary are discussed in greater detail herein.

In the depicted embodiment, a first projection **16400*a* surrounds a first portion of a staple cavity 16110 within the first longitudinal row of staple cavities. The first projection 16400*a* extends a first distance above the deck surface 16108. A second projection 16400*b* surrounds a second portion of a staple cavity 16120 within the second longitudinal row of staple cavities. The second projections 16400*b* extends a second distance above the deck surface 16108. A third projection 16400*c* surrounds a third portion of a staple cavity 16130 within the third longitudinal row of staple cavities. The third projection 16400*c* extends a third distance above the deck surface 16108. In various instances, the first distance is different than the second distance and the third distance. In the embodiment depicted in FIGS. 40 and 41, the third distance is greater than the first distance, and the first distance is greater than the second distance; however, the projections 16400 can extend from the deck surface 16108** to any distance to achieve a desired tissue-gripping effect.

Figure 41:
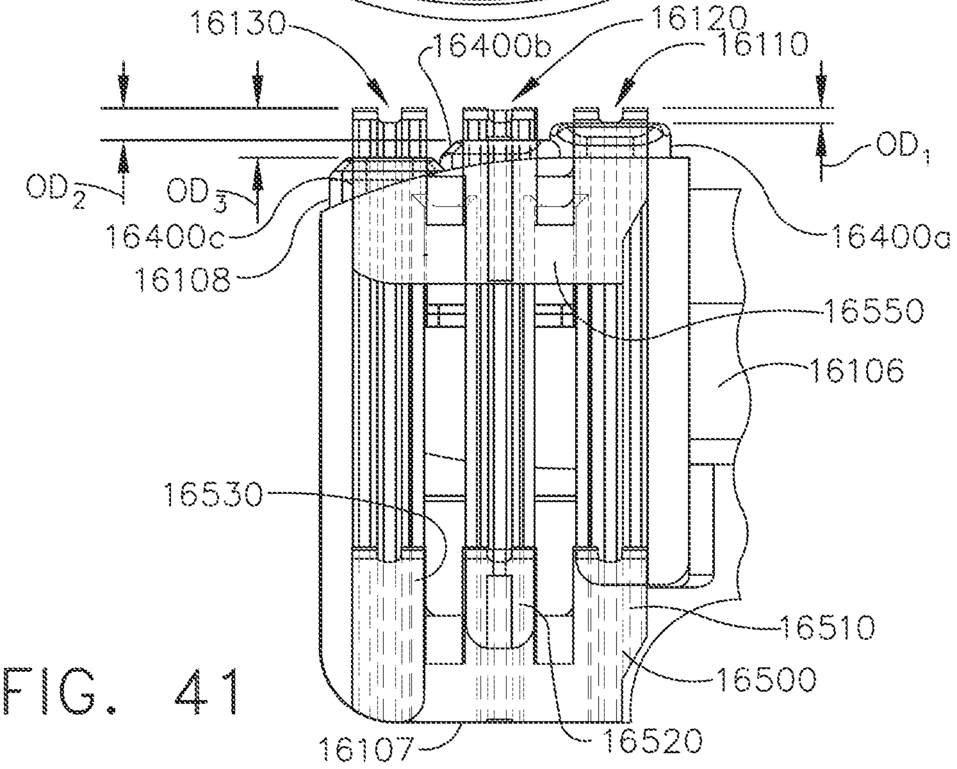
FIG. 41 is a partial cross-sectional view of a staple driver of the staple cartridge of FIG. 40 in an unfired position and a fully-fired position, wherein a portion of the staple driver extends above the projections and the curved deck surface when the staple driver is in the fully-fired position.

Turning now to FIG. 41, the staple cartridge 16100 further comprises a staple driver 16500. The staple driver 16500 comprises a first staple-supporting portion 16510, a second staple supporting portion 16520, and a third staple-supporting portion 16530. The first staple-supporting portion 16510 extends within a staple cavity 16110 from the first longitudinal row of staple cavities. The second staple-supporting portion 16520 extends within a staple cavity 16120 from the second longitudinal row of staple cavities. The third staple-supporting portion 16530 extends within a staple cavity 16130 from the third longitudinal row of staple cavities. The staple-supporting portions 16510, 16520, 16530 are connected together through a base 16550. The staple-supporting portions 16510, 16520, 16530 all extend a distance away from the base 16550 of the staple driver 16500. A top surface of each staple-supporting portion 16510, 16520, 16530 is aligned with the top surfaces of the other staple-supporting portions 16510, 16520, 16530 of the staple drivers 16500 in the staple cartridge 16100.

The staple-supporting portions 16510, 16520, 16530 are configured to translate within the respective staple cavities 16110, 16120, 16130 during a staple firing stroke. As discussed in greater detail herein, the staple driver 16500 is moved between an unfired position and a fully-fired position during the staple firing stroke. The staple driver 16500 is shown in the unfired position near a base 16107 of the staple cartridge 16100 in FIG. 41. In the depicted embodiment, the base 16550 of the staple driver 16500 aligns with and/or is flush with the base 16107 of the staple cartridge 16100 when the staple driver 16500 is in its unfired position.

The staple driver 16500 is also shown in the fully-fired position near the deck surface 16108 of the staple cartridge 16100 in FIG. 41. In the fully-fired position, a portion of the staple driver 16500 is "overdriven" and extends above the deck surface 16108 of the staple cartridge 16100. As discussed in greater detail herein, the staple cartridge 16100 comprises projections 16400 extending from the deck surface 16108 toward the anvil 16010. The projections 16400 surrounding at least a portion of each staple cavity serve to, for example, further compress tissue while also providing support for the overdriven staple drivers 16500. As discussed above, all of the projections 16400 extend from the deck surface 16108 to the different heights. The projections 16400 serve to guide the legs of a staple during formation and/or provide additional stability to the staple driver 16500 during the staple firing stroke. The first projection 16400*a* reduces the tissue gap between the first staple cavity 16110 and the tissue-supporting surface 16014 of the anvil 16010 by the height of the first projection 16400*a*. Likewise, the second projection 16400*b* reduces the tissue gap between the second staple cavity 16120 and the tissue-supporting surface 16014 of the anvil 16010 by the height of the second projection 16400*b*. The third projection 16400*c* reduces the tissue gap between the third staple cavity 16130 and the tissue-supporting surface 16014 of the anvil 16010 by the height of the third projection 16400*c*.

In the fully-fired position, the first staple-supporting surface 16510 of the staple driver 16500 extends a first distance $OD_1$ above the projection 16400*a*, the second staple-supporting surface 16520 extends a second distance $OD_2$ above the projection 16400*b*, and the third staple-supporting surface extends a third distance $OD_3$ above the projection 16400*c*. Due to the curved nature of the deck surface 16108 and the varied heights of the projections 16400, the first distance $OD_1$ is different than the second distance $OD_2$ and the third distance $OD_3$. In the depicted embodiment, the third distance $OD_3$ is larger than the second distance $OD_2$, and the second distance $OD_2$ is larger than the first distance $OD_1$.

A staple is removably positioned within each staple cavity. In at least one instance, the staples are deformed to the same, or at least substantially the same, height. Uniform staple formation is achieved as the overdrive distances $OD_1$, $OD_2$, $OD_3$ of the staple driver 16500 account for the variation in tissue gap along the deck surface 16108. As shown in FIG. 41, the distance between the first staple-supporting portion 16510 of the staple driver 19150 and a corresponding staple forming pocket 16012 of the anvil 16010 is the same as the distance between the second staple-supporting portion 16520 and a corresponding staple forming pocket 16012 when the staple driver 16500 is in the fully-fired position. Likewise, the distances between the first and second staple-supporting surfaces 16510, 16520 and the corresponding staple forming pockets 16012 are the same as the distance between the third staple-supporting surface 16530 and a corresponding staple forming pocket 16012 when the staple driver 16500 is in the fully-fired position. Thus, the staples positioned within all three longitudinal rows of staple cavities are configured to be formed and/or bent to the same height.

As outlined above, a surgical end effector comprises an anvil and a staple cartridge jaw. In some embodiments, the staple cartridge jaw is movable relative to the anvil while in other embodiments, the anvil is movable relative to the staple cartridge jaw. When the anvil is in an open position, the staple cartridge jaw is positioned on one side of the tissue that is to be stapled, and the anvil jaw is positioned on the opposite side. In such instances, the end effector is moved relative to the tissue until the tissue is suitably positioned between the staple cartridge jaw and the anvil. To avoid the target tissue from being positioned proximal to the proximal-most staple cavities, the anvil may comprise downwardly extending projections commonly referred to as "tissue stops" which serve to block the target tissue from being positioned too far proximal between the anvil and the staple cartridge. The tissue stops extend downward past the deck surface of the staple cartridge to prevent the tissue from being positioned too far proximal between the anvil and the staple cartridge. Stated another way, the tissue stops make sure that the tissue positioned between the jaws of the end effector is not accurately cut by a cutting member without being stapled. The tissue stops are sized and configured such that tissue does not become accidentally pinched between the tissue stops and the lateral sides of the staple cartridge jaw. Tissue stops are discussed in greater detail in U.S. patent application Ser. No. 16/105,140, entitled SURGICAL STAPLER ANVILS WITH TISSUE STOP FEATURES CONFIGURED TO AVOID TISSUE PINCH, the entirety of which is incorporated by reference herein. In various instances, a staple cartridge comprises a tissue stop that works in cooperation with the tissue stops of the anvil.

Figure 42:
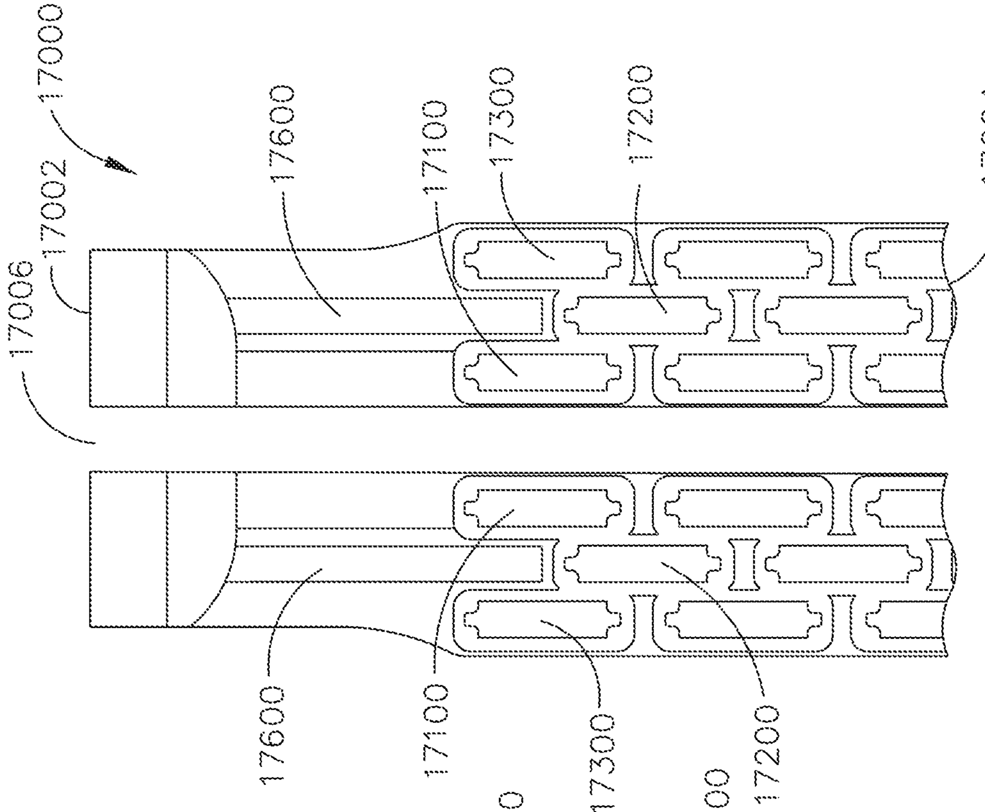
FIG. 42 is a partial plan view of a staple cartridge comprising three longitudinal rows of staple cavities, wherein the proximal-most staple cavity is located in a middle row in accordance with at least one embodiment.

FIG. 42 illustrates a staple cartridge 17000 comprising an elongate slot 17006 extending from a proximal end 17002 toward a distal end 17004. A longitudinal axis is defined by the elongate slot 17006. The staple cartridge 17000 comprises three longitudinal rows of staple cavities defined on each side of the elongate slot 17006. A first longitudinal row of staple cavities 17100 extends alongside the elongate slot 17006. A second longitudinal row of staple cavities 17200 extends alongside the first longitudinal row of staple cavities 17100. A third longitudinal row of staple cavities 17300 extends alongside the second longitudinal row of staple cavities 17200. The staple cavities 17100 within the first longitudinal row are aligned with the staple cavities 17300 within the third longitudinal row, whereas the staple cavities 17200 within the second longitudinal row are offset from the staple cavities 17100, 17300 within the first and third longitudinal rows. The proximal-most staple cavity 17100, 17300 within the first and third longitudinal rows, respectively, are proximal to the proximal-most staple cavity 17200 within the second longitudinal row. The staple cartridge 17000 further comprises a pair of tissue stops, or walls, 17600 that extend in between the proximal-most staple cavities 17100, 17300 from the first and third longitudinal rows. A dashed line extends laterally though the staple cartridge 17000 to represent the location of the tissue stops of an opposing anvil. As shown in FIG. 42, a proximal half of both proximal-most staple cavities 17100, 17300 from the first and third longitudinal rows is proximal to the dashed line and, owing to the tissue stops 17600, tissue is prevented from moving proximal respect to these staple cavities. Due to the of proximal-most staple cavities being located in the first longitudinal row, a tight seal is formed by a staple line as a cutting member cuts through the tissue positioned between the jaws of the end effector.

Figure 43:
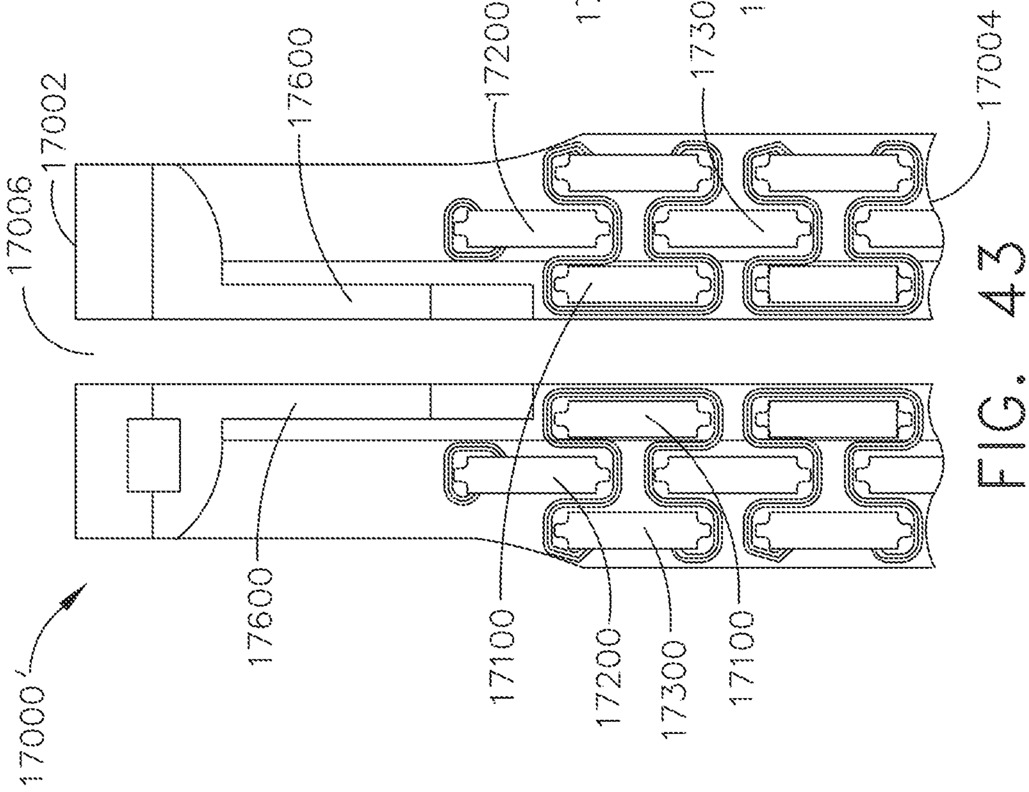
FIG. 43 is a partial plan view of a staple cartridge comprising three longitudinal rows of staple cavities, wherein the proximal-most staple cavity is not located in a middle row in accordance with at least one embodiment.

FIG. 43 illustrates a staple cartridge 17000' comprising an elongate slot 17006 extending from a proximal end 17002 toward a distal end 17004. A longitudinal axis is defined by the elongate slot 17006. The staple cartridge 17000 comprises three longitudinal rows of staple cavities defined on each side of the elongate slot 17006. A first longitudinal row of staple cavities 17100 extends alongside the elongate slot 17006. A second longitudinal row of staple cavities 17200 extends alongside the first longitudinal row of staple cavities 17100. A third longitudinal row of staple cavities 17300 extends alongside the second longitudinal row of staple cavities 17200. The staple cavities 17100 within the first longitudinal row are aligned with the staple cavities 17300 within the third longitudinal row, whereas the staple cavities 17200 within the second longitudinal row are offset from the staple cavities 17100, 17300 within the first and third longitudinal rows. The proximal-most staple cavity 17100, 17300 within the first and third longitudinal rows, respectively, are distal to the proximal-most staple cavity 17200 within the second longitudinal row. A dashed line extends laterally through the staple cartridge 17000' to represent the location of the tissue stops of an opposing anvil. Notably, the tissue stops that interact with the staple cartridge 17000' are positioned distal to the tissue stops that interact with the staple cartridge 17000. Such a difference in the tissue stop location is due, at least in part, to the location of the proximal-most staple cavity 17100 within the first longitudinal row with respect to the proximal-most staple cavities from other longitudinal rows.

Figure 44:
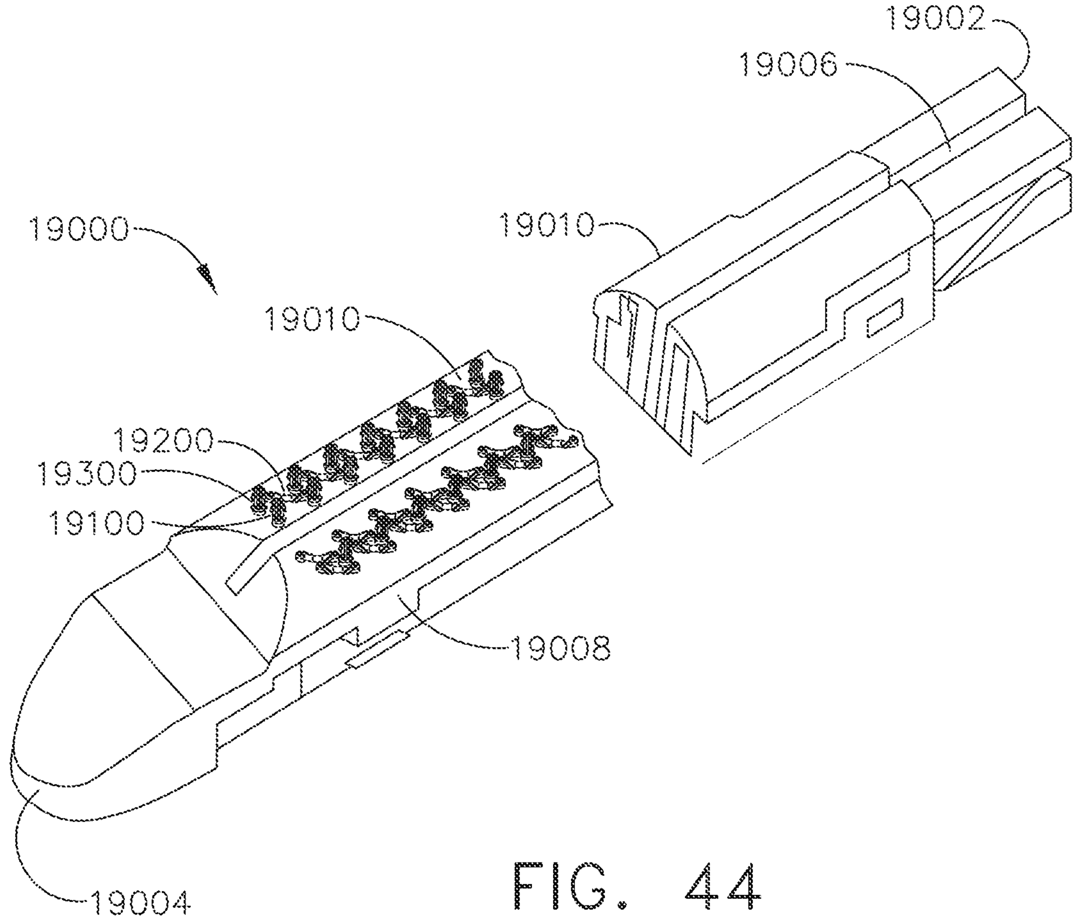
FIG. 44 is a partial perspective view of a staple cartridge comprising projections extending from a curved deck surface, in accordance with at least one embodiment.

A staple cartridge 19000 is depicted in FIG. 44. The staple cartridge 19000 is configured to be seated in a channel of a cartridge jaw of a surgical end effector. The end effector comprises an anvil jaw 19050, which opposes the cartridge jaw when the end effector is in a closed configuration. At least one of the anvil jaw 19050 and the cartridge jaw are movable with respect to one another between an open configuration and the closed configuration. The anvil 19050 comprises a plurality of staple forming pockets defined therein which are configured to deform the staples ejected from the staple cartridge 19000.

The staple cartridge 19000 comprises a cartridge body 19008 including an elongate slot 19006 extending from a proximal end 19002 toward a distal end 19004 of the cartridge body 19008. The cartridge body 19008 further comprises a deck surface 19010. Staple cavities 19100, 19200, 19300 are defined within the cartridge body 19008. The staple cavities 19100, 19200, 19300 are arranged in three rows, wherein the three rows extend along the same side of the elongate slot 19006. The first row of staple cavities 19100 extends adjacent to and/or alongside the elongate slot 19006. The third row of staple cavities 19300 is positioned furthest away from the elongate slot 19006, and the second row of staple cavities 19200 extends in between the first row of staple cavities 19100 and the third row of staple cavities 19300.

A longitudinal axis is defined along the elongate slot 19006 of the staple cartridge 19000. As shown in FIG. 44, none of the staple cavities 19100, 19200, 19300 within the three rows are oriented parallel to the longitudinal axis. In other words, the axes defined by the staple cavities 19100, 19200, 19300 are not parallel to the longitudinal axis defined by the elongate slot 19006. Each staple cavity 19100 within the first row defines an axis that is substantially parallel to the axis defined by each staple cavity 19300 within the third row. Each staple cavity 19200 within the second row is oriented substantially perpendicular to the staple cavities 19100, 19300 within the first and third rows.

The deck surface 19010 of the staple cartridge 19000 is rounded and/or curved. Stated another way, the height of the deck surface 19010 varies laterally with respect to the longitudinal axis defined by the elongate slot 19006. The tallest point of the illustrated deck surface 19010 is adjacent to the elongate slot 19006 which extends down the central portion of the cartridge body 19008. A portion of the staple cartridge 19000 in FIG. 44 is shown without staple cavities to more clearly illustrate the rounded nature and/or curvature of the deck surface 19010.

Figure 45:
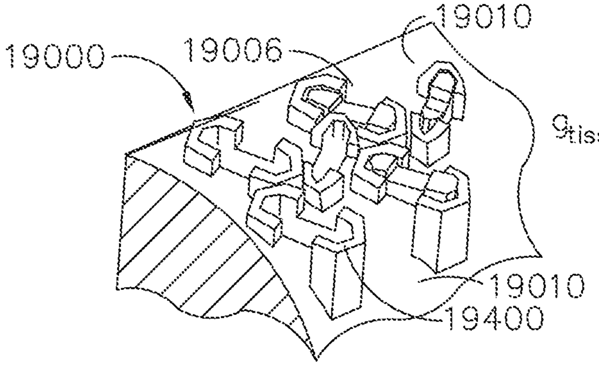
FIG. 45 is a partial cross-sectional view of the staple cartridge of FIG. 44, wherein the projections extend a first distance from the curved deck surface.
Figure 46:
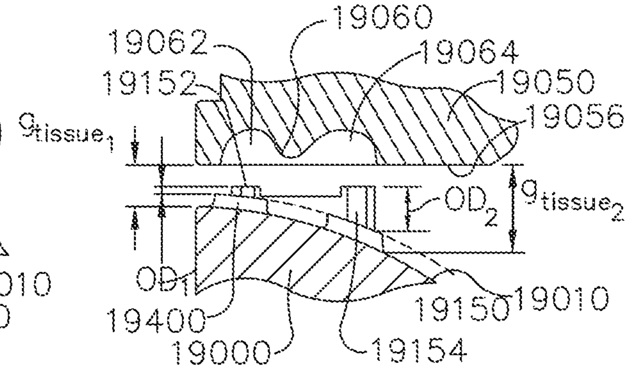
FIG. 46 is a partial cross-sectional view of an end effector in a closed configuration, wherein the end effector comprises the staple cartridge of FIG. 45 seated in a cartridge jaw.

Turning now to FIGS. 45 and 46, the staple cartridge 19000 is shown in greater detail. The staple cartridge 19000 comprises projections 19400 that extend above the deck surface 19010. Among other things, the projections 19400 are configured to grip the tissue clamped between the jaws of the end effector and/or prevent the tissue from sliding relative to the staple cartridge 19000. The projections 19400 depicted on the staple cartridge 19000 are in the form of pocket extenders. The depicted pocket extenders provide support to the staples and/or the staple drivers as the staples are driven out of the staple cartridge 19000 toward the anvil 19050. A first projection 19400*a* surrounds a first end 19102 of the staple cavity 19100 and a second projection 19400*b* surrounds a second end 19104 of the staple cavity 19100. While the projections 19400 are shown as surrounding only a portion of each staple cavity, it is envisioned that the projections 19400 can surround any desired amount of a staple cavity, such as the entire staple cavity, for example.

Figure 52:
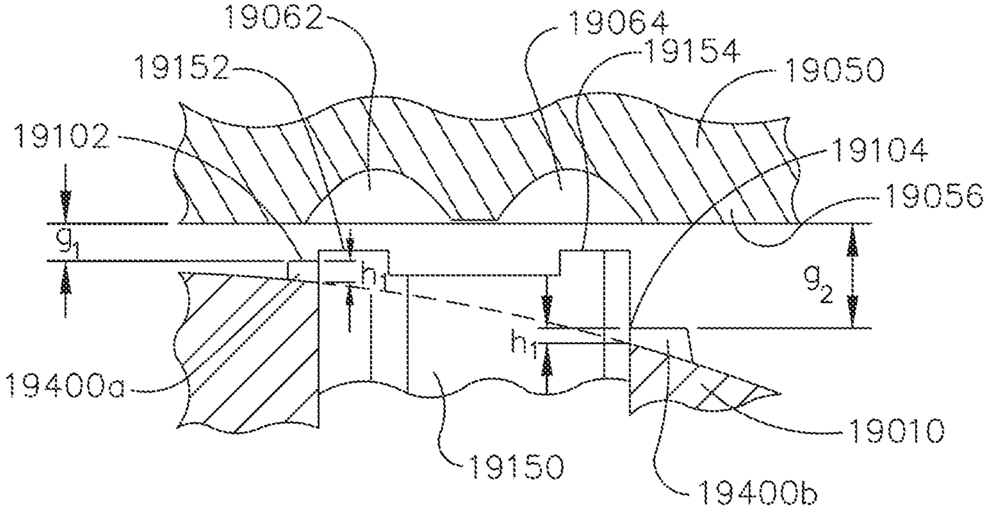
FIG. 52 is a partial cross-sectional view of an end effector in a closed configuration, wherein the end effector comprises a staple cartridge comprising projections extending a uniform distance from a curved deck surface, in accordance with at least one embodiment.

The projections 19400 shown in FIGS. 45, 46, and 52 are uniform in height. In other words, all of the projections 19400 extend the same distance from the deck surface 19010 of the staple cartridge 19000. FIGS. 46 and 52 illustrate an end effector in the closed configuration. In the closed configuration, a tissue gap is defined between the deck surface 19010 of the staple cartridge 19000 and the tissue-compression surface 19056 of the anvil 19050. Due to the curved nature of the deck surface 19010, the tissue gap varies laterally across the cartridge deck 19010 with respect to the elongate slot 19006.

The anvil 19050 further comprises a plurality of staple forming pockets 19060 defined in the tissue-compression surface 19056. Each staple forming pocket 19060 corresponds to an individual staple cavity 19100, 19200, 19300 of the staple cartridge 19000. As shown in FIG. 46, each staple forming pocket 19060 comprises a first pocket 19062 and a second pocket 19064. The first pocket 19062 is aligned with a first end 19152 of a staple driver, and the second pocket 19064 is aligned with the second end 19154 of the staple driver. The first leg of the staple is configured to contact the first pocket 19062 as the staple is being formed while the second leg of the staple is configured to contact the second pocket 19064 is configured to contact the second leg of the staple as the staple is being formed.

As shown in FIG. 46, a first tissue gap $g_{tissue1}$ is defined between the deck surface 19010 of the staple cartridge 19000 and the tissue-supporting surface 19056 of the anvil 19050. The first tissue gap $g_{tissue1}$ is measured at a point adjacent to the elongate slot 19006. A second tissue gap $g_{tissue2}$ is defined between the deck surface 19010 of the staple cartridge 19000 and the tissue-supporting surface 19056 of the anvil 19050. The second tissue gap $g_{tissue2}$ is measured at a point spaced laterally away from the elongate slot 19006. The second tissue gap $g_{tissue2}$ is larger than the first tissue gap $g_{tissue1}$. The presence of a smaller tissue gap adjacent to the elongate slot 19006 causes the tissue alongside the elongate slot 19006 to be compressed to a greater degree than tissue spaced laterally away from the elongate slot 19006. This is especially the case when the tissue clamped between the jaws of the end effector is substantially uniform in thickness. Such a greater compression causes bodily fluids to disperse away from the elongate slot 19006 which, among other things, promotes a uniform cut line and/or a secure staple line.

A staple driver 19150 from a first row of staple cavities 19100 is shown in FIGS. 46 and 52 in a fully-fired position. In the fully-fired position, a portion of the staple driver 19150 is "overdriven" and extends above the deck surface 19010 of the staple cartridge 19000. As discussed in greater detail herein, the staple cartridge 19000 comprises projections 19400 extending from the deck surface 19010 toward the anvil 19050 that surround at least a portion of the staple cavities. The projections 19400 serve to, for example, further compress tissue while also providing support for the overdriven staple drivers 19150 and/or the staples driven by the staple drivers 19150. As discussed above, all of the projections 19400 extend from the deck surface 19010 to the same ultimate height $h_1$. As shown in FIG. 52, the first projection 19400*a* reduces the tissue gap $g_1$ by the height $h_1$ over the first projection 19400*a* at the point where the first staple leg of the staple is being formed. Likewise, the second projection 19400*b* reduces the tissue gap $g_2$ by the height $h_1$ over the second projection 19400*b* at the point where the second staple leg of the staple is being formed.

In the fully-fired position of the staple driver 19150, the first end 19152 of the staple driver 19150 extends a first distance $OD_1$ above the projection 19400*a* while the second end 19154 of the staple driver 19150 extends a second distance $OD_2$ above the projection 19400*b*. Due to the curved nature of the deck surface 19010, the uniform height $h_1$ of the projections 19400, and the orientation of the staple cavity 19100 with respect to the longitudinal axis, the first distance $OD_1$ is different than the second distance $OD_2$. In the depicted embodiment, the second distance $OD_2$ is larger than the first distance $OD_1$.

The legs of the staple within the staple cavity 19100 are configured to be formed to the same height, or at least substantially the same height, as one another. Uniform staple leg formation is achieved as the overdrive distances $OD_1$, $OD_2$ of the staple driver 19150 account for the variation in tissue gap along the staple cavity 19100. As shown in FIG. 46, the distance between the first end 19152 of the staple driver 19150 and the first pocket 19062 of the forming pocket 19060 is the same as the distance between the second end 19154 of the staple driver 19150 and the second pocket 19064 of the forming pocket 19060. Thus, the legs of the staple are formed and/or bent to the same degree.

Figure 47:
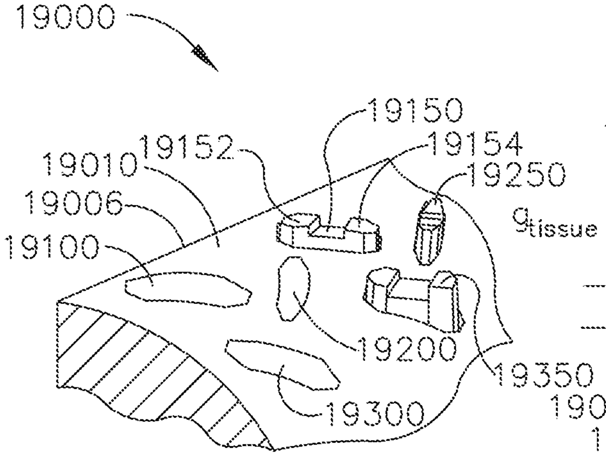
FIG. 47 is a partial cross-sectional view of a staple cartridge comprising a projection-free, curved deck surface, in accordance with at least one embodiment.
Figure 48:
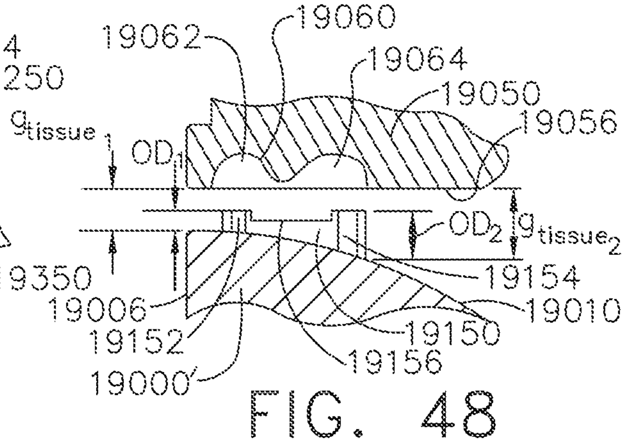
FIG. 48 is a partial cross-sectional view of an end effector in a closed configuration, wherein the end effector comprises the staple cartridge of FIG. 47 seated in a cartridge jaw.

Unlike the projections 19400 that extend above the deck surface 19010 of the staple cartridge 19000, the staple cartridge 19000' shown in FIGS. 47 and 48 comprises a smooth deck surface 19010. Stated another way, nothing projects and/or extends above the deck surface 19010. Staple drivers 19150, 19250, 19350 are movably positioned within the staple cavities 19100, 19200, 19300. Each staple driver, such as staple driver 19150, comprises a cradle 19156 configured to support a base of a staple. The cradle 19156 comprises a first end 19152 and a second end 19154. The first end 19152 is configured to support the staple near where the base of the staple meets a first leg of the staple. The second end 19154 is configured to support the staple near where the base of the staple meets a second leg of the staple.

FIG. 48 illustrates an end effector comprising the staple cartridge 19000' seated in the staple cartridge jaw. The end effector is in the closed configuration. In the closed configuration, a tissue gap is defined between the deck surface 19010 of the staple cartridge 19000' and the tissue-compression surface 19056 of the anvil 19050. Due to the curved nature of the deck surface 19010, the tissue gap varies laterally across the cartridge deck 19010 with respect to the elongate slot 19006. In the depicted embodiment, the tissue gap is smallest at the point adjacent to the elongate slot 19006. The tissue gap becomes larger at points spaced laterally away from the elongate slot 19006.

More specifically, a first tissue gap $g_{tissue1}$ is defined between the deck surface 19010 of the staple cartridge 19000' and the tissue-supporting surface 19056 of the anvil 19050. The first tissue gap $g_{tissue1}$ is measured at a point adjacent to the elongate slot 19006. A second tissue gap $g_{tissue2}$ is defined between the deck surface 19010 of the staple cartridge 19000' and the tissue-supporting surface 19056 of the anvil 19050. The second tissue gap $g_{tissue2}$ is measured at a point spaced laterally apart from the elongate slot 19006. The second tissue gap $g_{tissue2}$ is larger than the first tissue gap $g_{tissue1}$. The presence of a smaller tissue gap adjacent to the elongate slot 19006 results in the tissue alongside the elongate slot 19006 being compressed to a greater degree than the tissue spaced laterally away from the elongate slot 19006. This is especially true when the tissue clamped between the jaws of the end effector is substantially uniform in thickness. Such a greater compression causes bodily fluids to disperse away from the elongate slot 19006 which, among other things, promotes a uniform cut line and/or a secure staple line.

A staple driver 19150 from a first row of staple cavities 19100 is shown in FIG. 48 in a fully-fired position. In the fully-fired position, a portion of the staple driver 19150 is "overdriven" and extends above the deck surface 19010 of the staple cartridge 19000'. The first end 19152 of the staple driver 19150 extends a first distance $OD_1$ above the deck surface 19006 while the second end 19154 of the staple driver 19150 extends a second distance $OD_2$ above the deck surface. Due to the curved nature of the deck surface 19010 and the orientation of the staple cavity 19100 with respect to the longitudinal axis, the first distance $OD_1$ is different than the second distance $OD_2$. In the depicted embodiment, the second distance $OD_2$ is larger than the first distance $OD_1$. Notably, the overdrive distances of the staple cartridge 19000' comprising a smooth and/or projection-free deck surface 19010 are greater than the overdrive distances of the staple cartridge 19000 comprising projections extending from the deck surface.

The legs of the staple within the staple cavity 19100 are configured to be formed to the same height, or at least substantially the same height, as one another. Uniform staple leg formation is achieved as the overdrive distances $OD_1$, $OD_2$ of the staple driver 19150 account for the variation in tissue gap along the staple cavity 19100. As shown in FIG. 48, the distance between the first end 19152 of the staple driver 19150 and the first pocket 19062 of the staple-forming pocket 19060 is the same as the distance between the second end 19154 of the staple driver 19150 and the second pocket 19064 of the staple-forming pocket 19060. Thus, the legs of the staple are formed and/or bent to the same degree.

Figure 49:
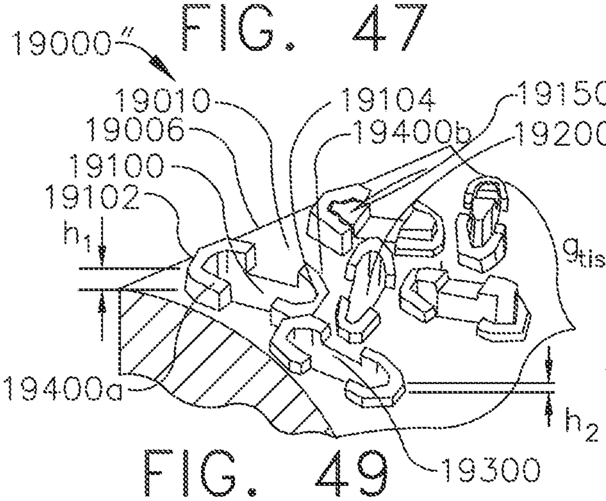
FIG. 49 is a partial cross-sectional view of a staple cartridge comprising projections extending varying distances from a curved deck surface, in accordance with at least one embodiment.
Figure 50:
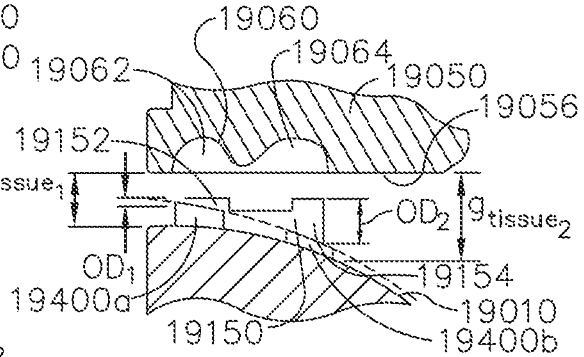
FIG. 50 is a partial cross-sectional view of an end effector in a closed configuration, wherein the end effector comprises the staple cartridge of FIG. 49 seated in a cartridge jaw.

FIGS. 49 and 50 depict a staple cartridge 19000" that is similar in many aspects to the staple cartridge 19000. For example, both staple cartridges 19000, 19000" comprise a curved and/or rounded deck surface 19010 profile with projections 19400 that extend above the deck surface. Moreover, the projections 19400 on the staple cartridge 19000" are also in the form of pocket extenders. A first projection 19400*a* surrounds a first end 19102 of the staple cavity 19100 and a second projection 19400*b* surrounds a second end 19104 of the staple cavity 19100. While the projections 19400 are shown as surrounding only a portion of each staple cavity, it is envisioned that the projections 19400 can surround any suitable amount of a staple cavity, such as the entire staple cavity, for example.

The projections 19400 shown in FIGS. 49 and 50 extend from the deck surface 19010 to different heights. More specifically, the height of each projection 19400 varies based on the location of the projection 19400 with respect to the elongate slot 19006. In various instances, the height of the projection 19400 decreases as the projection 19400 is positioned further away from the elongate slot 19006. As shown in FIG. 49, a first projection 19400*a* surrounding a first end 19102 of a staple cavity 19100 extends from the deck surface 19010 to a first height $h_1$. A second projection 19400*a* surrounding a second end 19104 of the same staple cavity 19100 extends from the deck surface 19010 to a second height $h_2$. The first height $h_1$ is different than the second height $h_2$. In the depicted embodiment, the second height $h_2$ is shorter than the first height $h_1$. Having a projection with a greater height closer to the knife slot 19006 can, among other things, facilitate the flow of fluids away from the cut line.

FIG. 50 illustrates an end effector comprising the staple cartridge 19000" seated in the staple cartridge jaw. The end effector is in the closed configuration. In the closed configuration, a tissue gap is defined between the deck surface 19010 of the staple cartridge 19000" and the tissue-supporting surface 19056 of the anvil 19050. Due to the curved nature of the deck surface 19010, the tissue gap varies laterally across the cartridge deck 19010 with respect to the elongate slot 19006. As shown in FIG. 50, a first tissue gap $g_{tissue1}$ is defined between the deck surface 19010 of the staple cartridge 19000" and the tissue-compression surface 19056 of the anvil 19050. The first tissue gap $g_{tissue1}$ is measured at a point adjacent to the elongate slot 19006. A second tissue gap $g_{tissue2}$ is defined between the deck surface 19010 of the staple cartridge 19000" and the tissue-compression surface 19056 of the anvil 19050. The second tissue gap $g_{tissue2}$ is measured at a point spaced laterally away from the elongate slot 19006. The second tissue gap $g_{tissue2}$ is larger than the first tissue gap $g_{tissue1}$. The presence of a smaller tissue gap adjacent to the elongate slot 19006 causes the tissue alongside the elongate slot 19006 to be compressed to a greater degree than tissue spaced laterally away from the elongate slot 19006. This is especially the case when the tissue clamped between the jaws of the end effector is substantially uniform in thickness. Such a greater compression causes bodily fluids to disperse away from the elongate slot 19006 which, among other things, promotes a uniform cut line and/or a secure staple line.

A staple driver 19150 from a first row of staple cavities 19100 is shown in FIG. 50 in a fully-fired position. In the fully-fired position, a portion of the staple driver 19150 is "overdriven" and extends above the deck surface 19010 of the staple cartridge 19000". As discussed in greater detail above, the staple cartridge 19000" comprises projections 19400 extending from the deck surface 19010 toward the anvil 19050 that surround at least a portion of the staple cavities. The projections 19400 serve to, for example, further compress tissue while also providing support for the overdriven staple drivers 19150 and/or the staples driven by the staple drivers 19150. The projections 19400 extend from the deck surface 19010 of the staple cartridge 19000" to different ultimate heights.

In the fully-driven position of a staple driver 19150, the first end 19152 of the staple driver 19150 extends a first distance $OD_1$ above the projection 19400*a* while the second end 19154 of the staple driver 19150 extends a second distance $OD_2$ above the projection 19400*b*. Notably, the overdrive distances of the staple cartridge 19000" are less than the overdrive distances of the staple cartridge 19000' comprising a smooth deck surface 19010. Due to the curved nature of the deck surface 19010 and the orientation of the staple cavity 19100 with respect to the longitudinal axis, the first distance $OD_1$ is different than the second distance $OD_2$. In the depicted embodiment, the second distance $OD_2$ is larger than the first distance $OD_1$.

The legs of the staple within the staple cavity 19100 are configured to be formed to the same height, or at least substantially the same height, as one another. Uniform staple leg formation is achieved as the overdrive distances $OD_1$, $OD_2$ of the staple driver 19150 account for the variation in the tissue gap along the staple cavity 19100. As shown in FIG. 50, the distance between the first end 19152 of the staple driver 19150 and the first pocket 19062 of the forming pocket 19060 is the same as the distance between the second end 19154 of the staple driver 19150 and the second pocket 19064 of the forming pocket 19060. Thus, the legs of the staple are evenly formed.

Figure 51:
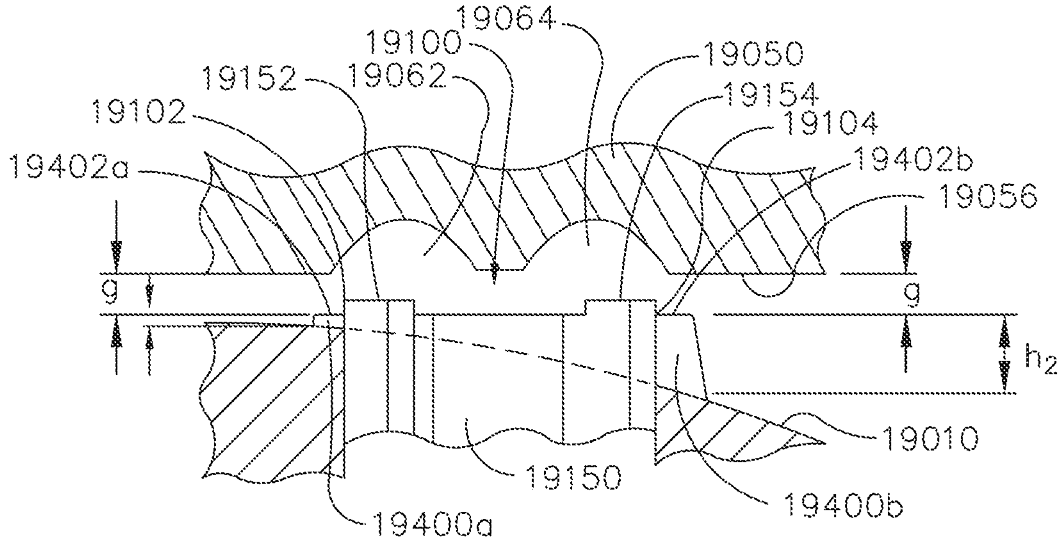
FIG. 51 is a partial cross-sectional view of an end effector in a closed configuration, wherein the end effector comprises a staple cartridge comprising projections extending varying distances from a curved deck surface, in accordance with at least one embodiment.

FIG. 51 illustrates a portion of an end effector comprising a staple cartridge with projections 19400 having different heights. A first projection 19400*a* extends from a first side 19102 of a staple cavity 19100 to a first height $h_1$. A second projection 19400*b* extends from a second side 19104 of the staple cavity 19100 to a second height $h_2$. The second height $h_2$ is different than the first height $h_1$. In the depicted embodiment, the second height $h_2$ is taller than the first height $h_1$; however, any suitable arrangement is envisioned. While the second projection 19400*b* is taller than the first projection 19400*a*, a top surface 19402*a* of the first projection 19400*a* and a top surface 19402*b* of the second projection 19400*b* are the same distance from a tissue-supporting surface 19056 of the anvil 19050 when the end effector is in the closed configuration. Stated another way, a tissue gap comprises a uniform gap distance "g" across the staple cavity 19100.

As discussed above in greater detail, projections 19400 can provide support to the staple and/or the staple driver as the staple driver and the staple are driven toward the anvil. The greater height $h_2$ of the second projection 19400*b* minimizes the overdrive of the second end 19154 of the staple driver 19150. Minimizing the portion of the staple driver 19150 that is exposed above the deck surface 19010 makes the staple driver 19150 less susceptible to becoming dislodged and/or misaligned during the staple firing stroke. The projections 19400 serve to, for example, enhance stability of the staple driver, maintain alignment of the staple driver as the staple firing stroke is performed, and/or prevent the staple driver from becoming dislodged.

Figure 53:
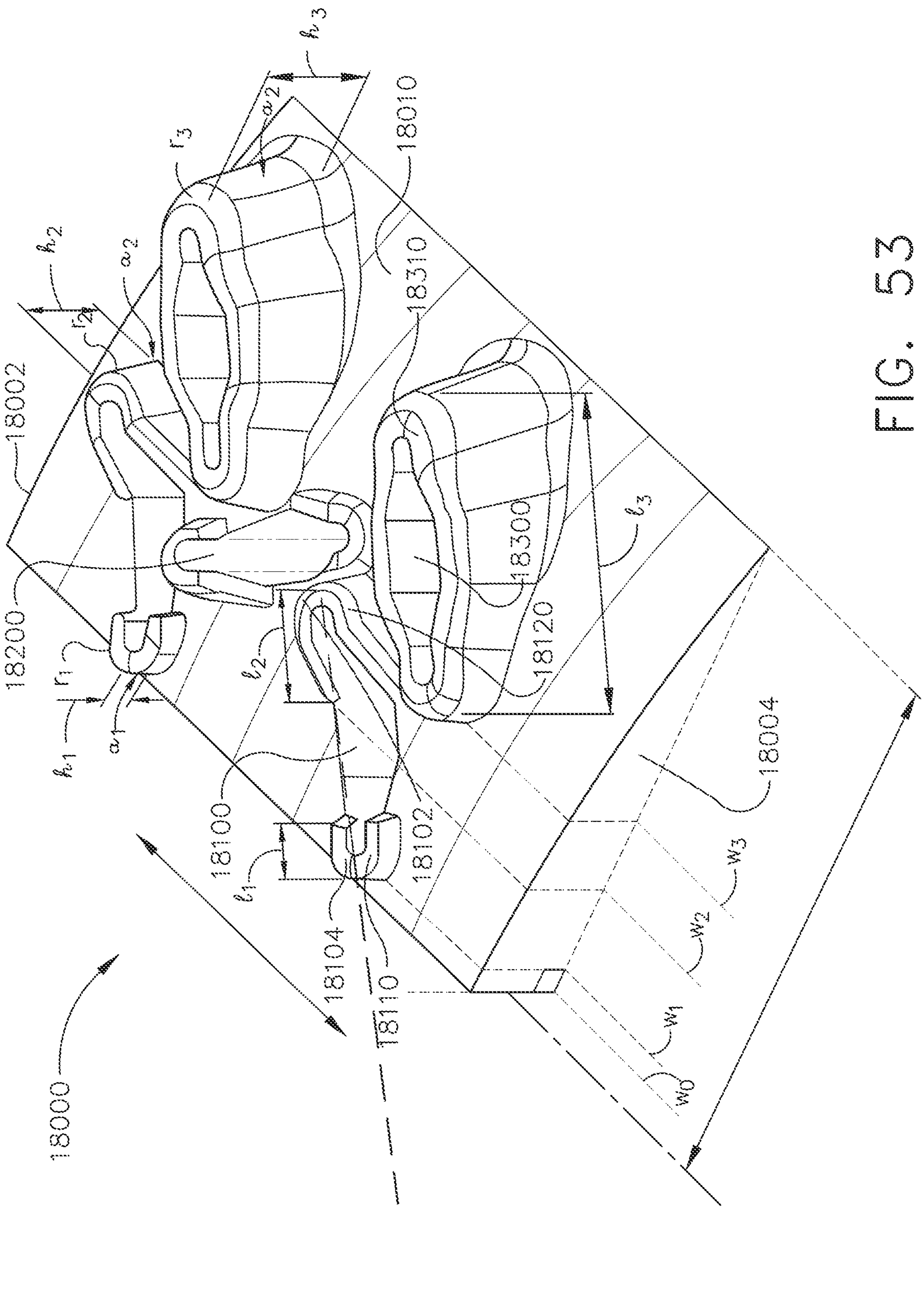
FIG. 53 is a partial cross-sectional view of a staple cartridge comprising variable projections extending from a curved deck surface, in accordance with at least one embodiment.

FIGS. 53-56 illustrate the variability of tissue gripping features and/or projections across an individual staple cavity. As described in greater detail herein, the staple cavity is defined within a cartridge body. The cartridge body comprises a deck surface with a curved and/or rounded profile. Various parameters of the tissue gripping features and/or projections can be varied along the deck surface of a staple cartridge to achieve a desired tissue effect. Such parameters include, for example, the angle at which the projection extends from the deck surface, the height to which the projection extends, the length of the staple cavity that the projection surrounds, and/or the radius the projection curves around an end of the staple cavity. FIG. 53 illustrates a portion of a staple cartridge 18000 comprising a plurality of tissue gripping features. The staple cartridge 18000 comprises an elongate slot 18006 extending from a proximal end 18002 toward a distal end 18004. Similarly to the staple cartridge 19000, the staple cartridge 18000 comprises a rounded and/or curved deck surface 18010. Stated another way, the height of the deck surface 18010 varies laterally with respect to the elongate slot 18006. The tallest point of the illustrated deck surface 18010 is adjacent to the elongate slot 18006.

Staple cavities 18100, 18200, 18300 are defined within a cartridge body 18008. The staple cavities 18100, 18200, 18300 are arranged in three rows, wherein the three rows extend along the same side of the elongate slot 18006. The first row of staple cavities 18100 extends adjacent to and/or alongside the elongate slot 18006. The third row of staple cavities 18300 is positioned furthest away from the elongate slot 18006, and the second row of staple cavities 18200 extends in between the first row of staple cavities 18100 and the third row of staple cavities 18300.

A longitudinal axis is defined by the elongate slot 18006. As shown in FIG. 53, none of the staple cavities 18100, 18200, 18300 are oriented parallel to the longitudinal axis. In other words, the axes defined by the staple cavities 18100, 18200, 18300 are not parallel to the longitudinal axis defined by the elongate slot 18006. Each staple cavity 18100 within the first row defines a first cavity axis. Each staple cavity 18200 within the second row defines a second cavity axis. Each staple cavity 18300 within the third row defines a third cavity axis. As depicted in FIG. 53, the first cavity axis is oriented in a different direction than the second cavity axis. The first cavity axis is substantially parallel to the third cavity axis.

The staple cartridge 18000 comprises various projections 18400 extending from the deck surface 18010. The projections 18400 surround a portion of each staple cavity to varying degrees. Similar to the above, the projections 18400 can vary in size and/or geometry based on the position and/or orientation on the cartridge body 18008. In various instances, and as depicted in FIG. 53, all of the projections 18400 surrounding the staple cavities within a particular row are the same. In other instances, the projections 18400 surrounding the staple cavities within a particular row vary from one another. For example, the size and/or geometry of the projections 18400 may vary based on the longitudinal position of the individual staple cavity with respect to other staple cavities. The height of each projection can be different across the staple cartridge, and even between the projections surrounding an individual staple cavity.

Further to the above, a staple cavity 18100 comprises a proximal end 18102 and a distal end 18104, wherein the distal end 18104 is closer to the elongate slot 18006 than the proximal end 18102. A first projection 18110 is aligned with the distal end 18104 and extends away from the deck surface 18010 to a first height $h_1$. A second projection 18120 is aligned with the proximal end 18102 and extends away from the deck surface 18010 to a second height $h_2$. In the depicted embodiment, the first height $h_1$ is shorter than the second height $h_2$. In various instances, the projections positioned closer to the elongate slot 18006 have a shorter height than projections positioned further away laterally from the elongate slot 18006. For example, the projection 18310 of the staple cavity 18300 within the third row extends a height $h_3$, which is taller than either heights $h_1$, $h_2$ of the projections 18110, 18120 from the staple cavity 18100 of the first row.

The angle that the projections extend away from the deck surface can also be different. For example, the first projection 18110 of the staple cavity 18100 extends away from the deck surface 18010 at a first angle $a_1$, while the second projection 18120 extends away from the deck surface 18010 at a second angle $a_2$. In the depicted embodiment, the first angle $a_1$ is perpendicular to the deck surface 18010, and the first angle $a_1$ is not perpendicular to the deck surface 18010. The second projection 18120 extends at a more sloped angle with respect to the deck surface 18010, while the first projection 18110 extends at a steeper and/or harsher angle with respect to the deck surface 18010. In various instances, the projections positioned closer to the elongate slot 18006 extend away from the deck surface of the staple cartridge at sharper angles than projections positioned further away laterally from the elongate slot 18006. For example, the projection 18310 of the staple cavity 18300 within the third row extends from the deck surface at an angle $a_3$, which is smaller than either angle $a_1$, $a_2$ of the projections 18110, 18120 from the staple cavity 18100 of the first row. Other arrangements are possible.

An overall length of the staple cavity that each projection covers can also be a varied parameter. In various instances, the projection can surround the entire length of the staple cavity. In other instances, the projection can only surround a fraction of the length of the staple cavity. For example, the first projection 18110 of the staple cavity 18100 surrounds a small portion of the staple cavity 18100, such as 10%, for example. The first projection 18110 covers a first length $l_1$ of the staple cavity 18100. The second projection 18120, however, surrounds a larger portion of the staple cavity 18100, such as 30%, for example. The second projection 18120 covers a second length $l_2$ of the staple cavity 18100. Thus, the second length $l_2$ is larger than the first length $l_1$. In various instances, the projections positioned closer to the elongate slot 18006 surround a smaller portion of the staple cavity than projections positioned further away laterally from the elongate slot 18006. For example, the projection 18310 of the staple cavity 18300 within the third row surrounds a third length $l_3$, which happens to be the entire length of the staple cavity 18300. The third length $l_3$ is larger than either length $l_1$, $l_2$ covered by the projections 18110, 18120 from the staple cavity 18100 of the first row. Other arrangements are possible.

The radius that a projection curves around an end of a staple cavity can be varied across the staple cartridge. In various instances, the projection can form a sharp curve around an end of the staple cavity. In other instances, the projection can form a blunt curve around the end of the staple cavity. For example, the first projection 18110 of the staple cavity 18100 forms a curve with a first radius $r_1$ around the distal end 18104 of the staple cavity 18100. The second projection 18120 of the staple cavity 18100 forms a curve with a second radius $r_2$ around the proximal end 18102 of the staple cavity 18100. The first radius $r_1$ is smaller than the second radius $r_2$, resulting in the formation of a sharper curve by the first projection 18110 surrounding the distal end 18104 of the staple cavity 18100 than the curve formed by the second projection 18120 surrounding the proximal end 18102 of the staple cavity 18100. In various instances, the projections positioned laterally closer to the elongate slot surround an end of a staple cavity with a sharper curve than the projections positioned further away laterally from the elongate slot 18006. For example, the projection 18310 of the staple cavity 18300 within the third row forms a curve with a third radius $r_3$ around the edges of the staple cavity 18300. The third radius $r_3$ is less than either radii $r_1$, $r_2$ formed by the projections 18110, 18120 from the staple cavity 18100 of the first row. Thus, the third radius $r_3$ is duller and/or less severe than either radii $r_1$, $r_2$. Other arrangements are possible.

Other parameters, such as the geometry of the top surface of the projections 19400, can be different to achieve a desired tissue effect. In various instances, the projections 19400 comprise rounded outer edges to prevent and/or minimize trauma to the tissue supported between the jaws of the end effector. In other instances, the projections 19400 comprise sharp outer edges to facilitate the grip between the projections 19400 and the tissue supported between the jaws of the end effector.

Figure 54:
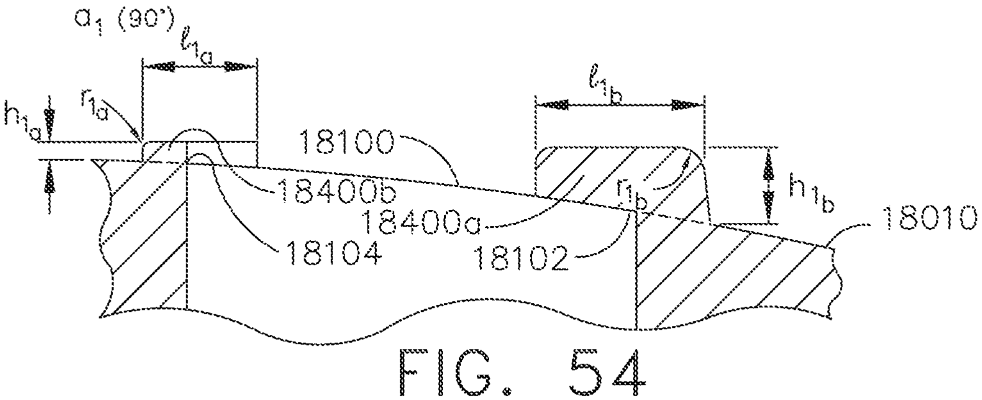
FIG. 54 is a partial cross-sectional view of a staple cavity from a first longitudinal row of staple cavities defined in the curved deck surface of the staple cartridge of FIG. 53, wherein the first longitudinal row extends alongside an elongate slot.

FIG. 54 illustrates projections surrounding portions of a staple cavity 18100 from the first longitudinal row of staple cavities defined in the staple cartridge 18000. As discussed in greater detail above, the first longitudinal row extends alongside and/or adjacent to the elongate slot 18006. A first projection **18400*a* extends across a first length $l_{1b}$ of a proximal end 18102 of the staple cavity 18100, while a second projection 18400*b* extends across a second length $l_{1a}$ of the distal end 18104 of the staple cavity 18100. The first length $l_{1b}$ is longer than the second length $l_{1a}$. As a result, the first projection 18400***a* surrounds a larger portion of the staple cavity 18100 than the second projection 18400*b*. The projections 18400*a*, 18400*b* extend from the deck surface 18010 at a first angle $a_1$. In the depicted embodiment, the projections 18400*a*, 18400*b* extend from the deck surface 18010 at the same angle; however, it is envisioned that the projections 18400*a*, 18400*b* can extend from the deck surface 18010 at any suitable angle to control the flow of tissue. The first projection 18400*a* comprises a tissue-supporting edge that comprises a first radius of curvature rib, and the second projection 18400*b* comprises a tissue-supporting edge that comprises a second radius of curvature $r_{1a}$. In various instances, the first radius of curvature $r_{1b}$ is different than the second radius of curvature $r_{1a}$, but they could be the same in other embodiments. In the depicted embodiment, the first radius of curvature $r_{1b}$ is larger than the second radius of curvature $r_{1a}$. Stated another way, a sharper edge is formed by the second projection 18400*b*. As the second projection 18400*b* is positioned closest to the elongate slot 18006, and thus, the cut line, a sharper edge may provide a stronger grip on the tissue positioned between the jaws of the end effector and prevent the tissue from moving out of a desired position, for example. As shown in FIG. 53, due to the orientation of the staple cavity 18100, a proximal end 18102 of the staple cavity 18100 is further away from the elongate slot 18006 of the staple cartridge 18000 than the distal end 18104 of the staple cavity 18100. For example, a portion of the projection 18400*b* surrounding the proximal end 18102 of the staple cavity 18100 extends a first height $h_{1b}$ above the deck surface 18010. A portion of the projection 18400*a* surrounding the distal end 18104 of the staple cavity 18100 extends a second height $h_{1a}$ above the deck surface 18010. The first height $h_{1b}$ is different than the second height $h_{1a}$, but could be the same in other embodiments. In the depicted embodiment, the portion of the projection 18400*b* surrounding the proximal end 18102 of the staple cavity 18100 extends further above the deck surface 18010 than the portion of the projection 18400*a* surrounding the distal end 18104 of the staple cavity 18100. The difference in height allows for the top surfaces of the projection 18400 to be substantially level across the staple cavity 18100, as the deck surface 18010 is curved.

Figure 55:
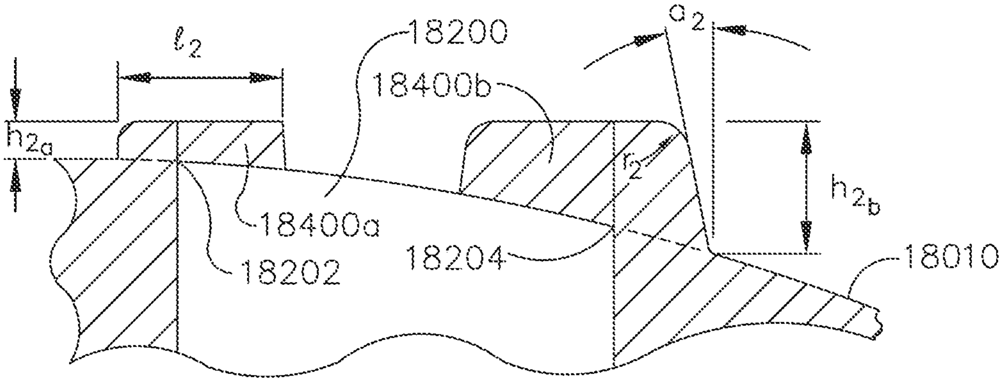
FIG. 55 is a partial cross-sectional view of a staple cavity from a second longitudinal row of staple cavities defined in the curved deck surface of the staple cartridge of FIGS. 53 and 54, wherein the second longitudinal row extends alongside the first longitudinal row.

FIG. 55 illustrates projections surrounding portions of a staple cavity 18200 from the second longitudinal row of staple cavities defined in the staple cartridge 18000. As discussed in greater detail above, the second longitudinal row extends alongside and/or adjacent to the first longitudinal row of staple cavities 18100. The second longitudinal row is spaced further laterally from the elongate slot 18006 than the first longitudinal row. A first projection 18400*a* extends across a length $l_2$ of a proximal end 18202 of the staple cavity 18200, and a second projection 18400*b* extends across a length $l_2$ of the distal end 18204 of the staple cavity 18200. In the depicted embodiment, the first length $l_2$ and the second length $l_2$ are the same; however, any suitable length is envisioned to achieve the desired result. As a result, the first projection 18400*a* surrounds the same dimension of the staple cavity 18200 as the second projection 18400*b*. The projections 18400*a*, 18400*b* extend from the deck surface 18010 at a second angle $a_2$. In the depicted embodiment, the projections 18400*a*, 18400*b* extend from the deck surface 18010 at the same angle; however, it is envisioned that the projections 18400*a*, 18400*b* can extend from the deck surface 18010 at any suitable angle to control the flow of tissue. The second angle $a_2$ with which the projections of the second staple cavity 18200 extend from the deck surface 18010 is larger than the first angle $a_1$ with which the projections of the first staple cavity 18100 extend from the deck surface 18010. Stated another way, the angle with which the projections extend from the deck surface 18010 become larger and/or less harsh as the staple cavity is positioned laterally away from the elongate slot 18006. The first projection 18400*a* and the second projection 18400*b* comprise a tissue-supporting edge that comprises a second radius of curvature $r_2$. In the depicted embodiment, the radii of curvature $r_2$ is the same for both projections 18400*a*, 18400*b*, but they could be different in other embodiments. In various instances, the radii of curvature $r_2$ of the projections from the second staple cavity 18200 are larger than the radii of curvature $r_{1a}$, $r_{1b}$ of the projections from the first staple cavity 18100. Stated another way, a sharper edge is formed by the projections from the first staple cavity 18100. As the first staple cavity 18100 is positioned closest to the elongate slot 18006, and thus, the cut line, a sharper edge may provide a stronger grip on the tissue positioned between the jaws of the end effector and prevent the tissue from moving out of a desired position, for example. As shown in FIG. 53 the orientation of the staple cavity 18200 is opposite that of the staple cavity 18100. More specifically, a distal end 18204 of the staple cavity 18200 is further away from the elongate slot 18006 of the staple cartridge 18000 than the proximal end 18202 of the staple cavity 18200. For example, a portion of the projection 18400*a* surrounding the proximal end 18202 of the staple cavity 18200 extends a first height $h_2a$ above the deck surface 18010. A portion of the projection 18400*b* surrounding the distal end 18204 of the staple cavity 18200 extends a second height $h_2$ b above the deck surface 18010. The first height $h_2a$ is different than the second height $h_2$ b, but could be the same in other embodiments. In the depicted embodiment, the portion of the projection 18400*b* surrounding the distal end 18204 of the staple cavity 18200 extends further above the deck surface 18010 than the portion of the projection 18400*a* surrounding the proximal end 18202 of the staple cavity 18200. The difference in height allows for the top surfaces of the projection 18400 to be substantially level across the staple cavity 18200, as the deck surface 18010 is curved.

Figure 56:
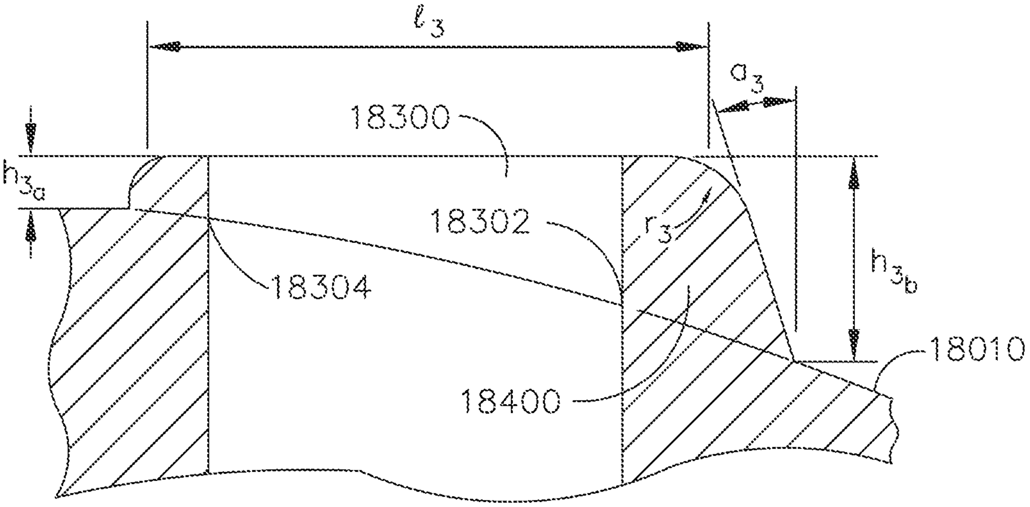
FIG. 56 is a partial cross-sectional view of a staple cavity from a third longitudinal row of staple cavities defined in the curved deck surface of the staple cartridge of FIGS. 53-55, wherein the third longitudinal row extends alongside the second longitudinal row.

FIG. 56 illustrates a projection 18400 surrounding a staple cavity 18300 from the third longitudinal row of staple cavities defined in the staple cartridge 18000. As discussed in greater detail above, the third longitudinal row is laterally spaced the furthest from the elongate slot 18006. The projection 18400 extends across a third length $l_3$ of the staple cavity 18300. The third length $l_3$ is greater than any of the lengths $l_1$, $l_2$ of the projections 18400 surrounding portions of the staple cavities from the first longitudinal row 18100 and the second longitudinal row 18200. In the depicted embodiment, the third length $l_3$ is the entire circumference, and thus, the entire length of the staple cavity 18300. The projection 18400 extends from the deck surface 18010 at a third angle $a_3$. The third angle $a_3$ with which the projection of the third staple cavity 18300 extends from the deck surface 18010 is larger than the first angle $a_1$ and the second angle $a_2$ with which the projections of the first staple cavity 18100 extend from the deck surface 18010, respectively. Stated another way, the angle with which the projection extends from the deck surface 18010 become larger and/or less harsh as the staple cavity is positioned laterally away from the elongate slot 18006. The projection 18400 comprises a tissue-supporting edge that comprises a third radius of curvature $r_3$. In various instances, the radii of curvature $r_3$ of the projection from the third staple cavity 18300 is larger than the radii of curvature $r_{1a}$, $r_{1b}$, $r_2$ of the projections from the first staple cavity 18100 and the second staple cavity 18200. As a result, a sharper edge is formed by the projections from the first staple cavity 18100. As the first staple cavity 18100 is positioned closest to the elongate slot 18006, and thus, the cut line, a sharper edge may provide a stronger grip on the tissue positioned between the jaws of the end effector. Such a stronger grip may prevent the tissue from moving out of a desired position, for example. As shown in FIG. 53, due to the orientation of the staple cavity 18300, a proximal end 18302 of the staple cavity 18300 is further away from the elongate slot 18006 of the staple cartridge 18000 than the distal end 18304 of the staple cavity 18300. The height of the projection 18400 across the staple cavity 18300 is non-uniform. A portion of the projection 18400 surrounding the proximal end 18302 of the staple cavity 18300 extends a first height $h_3$ b above the deck surface 18010. A portion of the projection 18400 surrounding the distal end 18304 of the staple cavity 18300 extends a second height $h_3a$ above the deck surface 18010. The first height $h_3$ b is different than the second height $h_3a$, but they could be the same in other embodiments. In the depicted embodiment, the portion of the projection 18400 surrounding the proximal end 18302 of the staple cavity 18300 extends further above the deck surface 18010 than the portion of the projection 18400 surrounding the distal end 18304 of the staple cavity 18300. The difference in height allows for the top surface of the projection 18400 to be substantially level across the staple cavity 18300, as the deck surface 18010 is curved.

The entire disclosures of U.S. Patent Application Publication No. 2015/0297222, entitled FASTENER CARTRIDGE INCLUDING EXTENSIONS HAVING DIFFERENT CONFIGURATIONS, which published on Oct. 25, 2015, U.S. Patent Application Publication No. 2012/0074198, entitled STAPLE CARTRIDGE, which published on Mar. 29, 2012, and U.S. Patent Application Publication No. 2013/0256379, entitled SURGICAL STAPLING CARTRIDGE WITH LAYER RETENTION FEATURES, which published on Oct. 3, 2013, are incorporated by reference herein.

Notably, the above-described arrangements with could also be adapted for use with embodiments in which the staple cartridge jaw is rotated relative to the anvil.

A surgical instrument 50000 comprising a powered articulation system 50100 is illustrated in FIGS. 154-156. The surgical instrument 50000 further comprises a housing, a shaft 50200 extending from the housing, and an end effector extending from the shaft 50200. In at least one embodiment, the end effector comprises a staple cartridge. The shaft 50200 defines a longitudinal shaft axis SA and comprises a longitudinal shaft portion 50210, a first articulatable shaft portion 50220 extending from the longitudinal shaft portion 50210, and a second articulatable shaft portion 50240 extending from the first articulatable shaft portion 50220. The end effector extends from the second articulatable shaft portion 50240. The first articulatable shaft portion 50220 is rotatably connected to the longitudinal shaft portion 50210 by a first articulation joint 50230 defining a first articulation axis $AA_1$ that is orthogonal to the longitudinal shaft axis SA. In at least one embodiment, the first articulatable shaft portion 50220 is rotatably connected to the longitudinal shaft portion 50210 by a pin or pins, for example. The second articulatable shaft portion 50240 is rotatably connected to the first articulatable shaft portion 50220 by a second articulation joint 50250 defining a second articulation axis $AA_2$ that is orthogonal to the first articulation axis $AA_1$ and the shaft axis SA. In at least one embodiment, the second articulatable shaft portion 50240 is rotatably connected to the first articulatable shaft portion 50220 by a pin or pins, for example.

Further to the above, the first articulatable shaft portion 50220 comprises a first hypoid drive gear 50222 defined thereon. The first drive gear 50222 is centered about the first articulation axis $AA_1$ and comprises a first set of radial teeth 50224. At least a portion of the first set of radial teeth 50224 are positioned distal to the first articulation axis $AA_1$. However, other embodiments are envisioned where the entire first set of radial teeth 50224 are positioned distal to the first articulation axis $AA_1$. In any event, the surgical instrument 50000 further comprises a first rotary drive shaft 50300 including a first bevel gear 50310 at its distal end. The first bevel gear 50310 is engaged with the first set of radial teeth 50224 of the first drive gear 50222 such that when the first rotary drive shaft 50300 is rotated, the first drive gear 50222 and the first articulatable shaft portion 50220 are rotated about the first articulation axis $AA_1$. The first rotary drive shaft 50300 is parallel to the longitudinal shaft axis SA and orthogonal to the first articulation axis $AA_1$.

Further to the above, the second articulatable shaft portion 50240 comprises a second hypoid drive gear 50242 defined thereon. The second drive gear 50242 is centered about the second articulation axis $AA_2$ and comprises a second set of radial teeth 50244 (see FIG. 154). At least a portion of the second set of radial teeth 50244 are positioned distal to the second articulation axis $AA_2$. However, other embodiments are envisioned where the entire second set of radial teeth 50244 are positioned distal to the second articulation axis $AA_2$. In any event, the surgical instrument 50000 further comprises a second rotary drive shaft 50400 including a second bevel gear 50410 at its distal end. The second bevel gear 50410 is engaged with the second set of radial teeth 50244 of the second drive gear 50242 such that when the second rotary drive shaft 50400 is rotated, the second drive gear 50242 and the second articulatable shaft portion 50240 are rotated about the second articulation axis $AA_2$. When the first articulatable shaft portion 50220 has not been rotated about the first articulation axis $AA_1$, the second rotary drive shaft 50400 is parallel to the longitudinal shaft axis SA and orthogonal to the first articulation axis $AA_1$ and the second articulation axis $AA_2$.

Further to the above, the first rotary drive shaft 50300 and the second rotary drive shaft 50400 are operable independently of one another. The first rotary drive shaft 50300 is driven by a first electric motor and the second rotary drive shaft 50400 is driven by a second electric motor. The first and second electric motors are positioned in the housing of the surgical instrument 50000, but could be positioned in any suitable location. Because the first rotary drive shaft 50300 and the second rotary drive shaft 50400 are operable independently of one another, the end effector is articulatable relative to the shaft 50200 about multiple axes (i.e., the first articulation axis $AA_1$ and the second articulation axis $AA_2$) simultaneously or independently. Further, the arrangement between the first and second rotary drive shafts 50300, 50400 and the first and second drive gears 50222, 50242 does not allow the powered articulation system 50100 to be back driven. In other words, when the first and second rotary drive shafts 50300, 50400 are rotated a specified amount, the first and second articulation joints 50230, 50250 will remain locked in position regardless of the external forces applied to first or second articulatable shaft portions 50220, 50240.

FIG. 157 illustrates another powered articulation system 50100' that is similar to the powered articulation system

50100 depicted in FIGS. 154-156 in many respects. The powered articulation system 50100' comprises a first worm gear 50310' at the distal end of the first rotary drive shaft 50300. In at least one embodiment, the powered articulation system 50100' further comprises a universal joint to couple the first worm gear 50310' and the first rotary drive shaft 50300, for example. In any event, the first worm gear 50310' is engaged with the first set of radial teeth 50224 on the first hypoid drive gear 50222. Thus, rotation of the first rotary drive shaft 50300 will result in rotation of the first articulatable shaft portion 50220 about the first articulation axis $AA_1$. The powered articulation system 50100' further comprises a second worm gear 50410' that is rotatable by the second rotary drive shaft 50400. The second worm gear 50410' is angled transverse to the longitudinal shaft axis SA. In at least one instance, the angle is approximately 45 degrees, for example. In at least one embodiment, a universal joint is utilized to couple the second worm gear 50410' and the second rotary drive shaft 50400, for example. In any event, the second set of radial teeth 50244 of the second hypoid drive gear 50242 are engaged with the second worm gear 50410', and, thus, rotation of the second rotary drive shaft 50400 will result in the rotation of the second articulatable shaft portion 50240 about the second articulation axis $AA_2$.

Further to the above, the first worm gear 50310' engages more of the first set of radial teeth 50224 of the first hypoid drive gear 50222 than the first bevel gear 50310 depicted in FIGS. 154-156. Further, the second worm gear 50410' engages more of the second set of radial teeth 50244 of the second hypoid drive gear 50242 than the second bevel gear 50410 depicted in FIGS. 154-156. The additional thread engagement of the first worm gear 50310' and the second worm gear 50410' with their respective hypoid drive gears 50222, 50242 aids in preventing the hypoid drive gears 50222, 50242 from being back driven when external forces are applied to the end effector.

FIG. 158 illustrates another powered articulation system 50100" that is similar to the powered articulation systems 50100 and 50100' depicted in FIGS. 154-157 in many respects. The powered articulation system 50100" comprises a second worm gear 50410" that is rotatable by the second rotary drive shaft 50400. The second worm gear 50410" is perpendicular to the longitudinal shaft axis SA. In at least one embodiment, a universal joint is utilized to couple the second worm gear 50410" and the second rotary drive shaft 50400, for example. In any event, the second set of radial teeth 50244 of the second hypoid drive gear 50242 are engaged with the second worm gear 50410", and, thus, rotation of the second rotary drive shaft 50400 will result in the rotation of the second articulatable shaft portion 50240 about the second articulation axis $AA_2$.

Further to the above, the second worm gear 50410" engages more of the second set of radial teeth 50244 of the second hypoid drive gear 50242 than the second bevel gear 50410 depicted in FIGS. 154-156 and the second worm gear 50410' depicted in FIG. 157. The additional thread engagement of the second worm gear 50410" with the hypoid drive gear 50242 aids in preventing the hypoid drive gear 50242 from being back driven when external forces are applied to the end effector.

A surgical instrument 51000 comprising a powered articulation system 51100 is illustrated in FIGS. 159-161. The surgical instrument 51000 further comprises a housing, a shaft 51200 extending from the housing, and an end effector 51300 extending from the shaft 51200. In at least one embodiment, the end effector 51300 comprises a staple cartridge. The shaft 51200 defines a longitudinal shaft axis SA and comprises a distal shaft portion 51210 at its distal end. The surgical instrument further comprises a first articulation joint 51400 and a second articulation joint 51500 configured to rotatably connect the end effector 51300 to the shaft 51200 such that the end effector 51300 is rotatable relative to the shaft 51200 about two axes. More specifically, an articulatable shaft portion 51600 is rotatably connected to the distal shaft portion 51210 to define the first articulation joint 51400 and the end effector 51300 is rotatably connected to the articulatable shaft portion 51600 to define the second articulation joint 51500. The articulatable shaft portion 51600 is rotatable relative to the shaft 51200 about a first articulation axis $AA_1$ that is orthogonal to the shaft axis SA. The end effector 51300 is rotatable relative to the articulatable shaft portion 51600 about a second articulation axis $AA_2$ that is orthogonal to the first articulation axis $AA_1$ and the shaft axis SA. In at least one embodiment, the articulatable shaft portion 51600 is rotatably connected to the distal shaft portion 51210 by a pin and the articulatable shaft portion 51600 is rotatably connected to the end effector 51300 by a pin, for example.

Further to the above, the surgical instrument 51000 further comprises a first cable actuator 51700 and a second cable actuator 51800. A first pair of articulation cables 51710 extends from the first cable actuator 51700 on either side of the first cable actuator 51700. The first pair of articulation cables 51710 extend beyond the first articulation axis $AA_1$ and are operably engaged with the articulatable shaft portion 51600. The first pair of articulation cables 51710 are configured to translate together when the first cable actuator 51700 is translated proximally and distally.

Further to the above, the second cable actuator 51800 comprises a driving portion 51820 and a fixed portion on opposite sides of the shaft 51200. The surgical instrument 51000 further comprises a second articulation cable 51810 comprising a first end 51812 that is attached to the driving portion 51820 of the cable actuator 51800 and a second end that is attached to the fixed portion of the second cable actuator 51800 to form a continuous loop. More specifically, the second articulation cable 51810 defines a loop which extends from the driving portion 51820 of the second cable actuator 51800, through the first articulation joint 51400, beyond the second articulation axis $AA_2$, around the distal end of the articulatable shaft portion 51600, back through the first articulation joint 51400 and into the fixed portion of the second cable actuator 51800. The fixed portion of the second cable actuator 51800 acts as a spring or plunger when the driving portion 51820 of the second cable actuator 51800 is translated such that movement of the driving portion 51820 is resisted, but not prevented. To articulate the end effector 51300, the second articulation cable 51810 is pushed or pulled through the continuous loop discussed above. Other embodiments are envisioned where the second cable actuator 51800 comprises a push actuator and a pull actuator on either side of the shaft 51200. In such an embodiment, the push and pull actuators are actuated in opposite directions to push or pull the second articulation cable 51810 through the continuous loop.

The first and second cable actuators 51700, 51800 are configured to be independently translated relative to the shaft 51200 in response to actuations within the housing. In at least one embodiment, the housing comprises a motor configured to output rotary motions and the first and second cable actuators 51700, 51800 are operably responsive to the rotary motions. However, other embodiments are envisioned with two motors in the housing which generate separate rotary motions for translating the first and second cable actuators 51700, 51800.

In use, further to the above, the articulatable shaft portion 51600 and the end effector 51300 extending therefrom are rotated about the first articulation axis $AA_1$ when the first pair of articulation cables 51710 are actuated by the first cable actuator 51700. More specifically, actuation of the first cable actuator 51700 in a proximal direction will rotate the articulatable shaft portion 51600 and the end effector 51300 about the first articulation axis $AA_1$ in a clockwise CW direction and actuation of the first cable actuator 51700 in a distal direction will rotate the articulatable shaft portion 51600 and the end effector 51300 about the first articulation axis $AA_1$ in a counter-clockwise CCW direction. The end effector 51300 is rotated about the second articulation axis $AA_2$ when the second articulation cable 51810 is actuated by the driving portion 51820 of the second cable actuator 51800. More specifically, the end effector 51300 comprises a boss portion 51310 operably engaged with the second articulation cable 51810. When the second articulation cable 51810 is actuated the boss portion 51310 is rotated about the second articulation axis $AA_2$ which results in rotation of the end effector 51300 about the second articulation axis $AA_2$.

Further to the above, the boss portion 51310 of the end effector 51300 further comprises a set of radial teeth 51312 defined on the proximal end thereof. The surgical instrument 51000 further comprises a distal articulation lock member 51314 configured to engage the set of radial teeth 51312 to prevent articulation of the end effector 51300 about the second articulation axis $AA_2$ when the distal articulation lock 51314 is engaged with the set of radial teeth 51312. The distal articulation lock member 51314 is translatable via an electric motor 51316, but could comprises any suitable motivator. The distal articulation lock member and the electric motor are positioned distally with respect to the first articulation axis $AA_1$. In use, the end effector 51300 cannot be rotated about the second articulation axis $AA_2$ when the distal articulation lock member 51314 is engaged with the radial teeth 51312, and the end effector 51300 can be rotated about the second articulation axis $AA_2$ when the distal articulation lock member 51314 is not engaged with the set of radial teeth 51312.

Further to the above, the articulatable shaft portion 51600 comprises a second set of radial teeth on the proximal end of the articulatable shaft portion 51600. At least a portion of the second set of radial teeth are positioned proximal to the first articulation axis $AA_1$. The surgical instrument 51000 further comprises a proximal articulation lock member configured to selectively engage the second set of radial teeth on the articulatable shaft portion 51600 to prevent rotation of the articulatable shaft portion 51600 and end effector 51300 about the first articulation axis $AA_1$. The proximal articulation lock member is translatable via an electric motor. The proximal articulation lock member and the electric motor are positioned proximally with respect to the first articulation axis $AA_1$.

Further to the above, the surgical instrument 51000 further comprises a flexible firing actuator 51900 extending from the housing, through the shaft 51200, through the first and second articulation joints 51400, 51500 and into the end effector 51300. The flexible firing actuator 51900 is configured to perform an end effector function in response to an actuation from the housing of the surgical instrument 51000. As illustrated in FIGS. 159 and 160, the first pair of articulation cables 51710 and the second articulation cable 51810 are positioned on the outer perimeter of the surgical instrument 51000 leaving space along the shaft axis SA of the surgical instrument for the flexible firing actuator 51900 to extend through. Such an arrangement allows the flexible firing actuator 51900 to be employed with an end effector that is rotatable about two different axis (i.e., the first and second articulation axis $AA_1$ and $AA_2$) for example.

A surgical instrument 52000 comprising a powered articulation system 52100 is illustrated in FIG. 162. The surgical instrument 52000 further comprises a housing, a shaft 52200 defining a shaft axis SA and extending from the housing, an articulatable shaft portion 52300 extending from the shaft 52200, and an end effector 52400 extending from the articulatable shaft portion 52300. A first articulation joint 52500 is between the shaft 52200 and the articulatable shaft portion 52300 and a second articulation joint 52600 is between the articulatable shaft portion 52300 and the end effector 52400. The first articulation joint 52500 defines a first articulation axis $AA_1$ that is orthogonal to the shaft axis SA. The second articulation joint 52600 defines a second articulation axis $AA_2$ that is orthogonal to the first articulation axis $AA_1$ and the shaft axis SA.

The surgical instrument 52000 further comprises a first pair of articulation cables 52210 extending from the shaft 52200 and operably engaged with the articulatable shaft portion 52300. The articulatable shaft portion 52300 comprises a rotary disc 52310 defined on its proximal end and one of the first pair of articulation cables 52210 is attached to one side of the rotary disc 52310 and the other of the first pair of articulation cables 52210 is attached to the other side the rotary disc 52310. The first pair of articulations cables 52210 are configured to rotate the articulatable shaft portion 52300 about the first articulation axis $AA_1$ when actuated. In other words, one of the first pair of articulation cables 52210 is driven distally and/or the other of the first pair of articulation cables 52210 is driven proximally to rotate the rotary disc 52310 and therefore rotate the articulatable shaft portion 52300 about the first articulation axis $AA_1$. The first pair of articulation cables 52210 are operably responsive to an electric motor positioned within the housing, for example.

Further to the above, the articulatable shaft portion 52300 comprises a set of radial teeth 52320 defined on the proximal end of the rotary disc 52310. At least a portion of the set of radial teeth 52320 are positioned proximal to the first articulation axis $AA_1$. The surgical instrument 52000 further comprises a proximal articulation lock member 52330 configured to selectively engage the set of radial teeth 52320 on the articulatable shaft portion 52300 to prevent rotation of the articulatable shaft portion 52300 about the first articulation axis $AA_1$ when the proximal articulation lock member 52330 is engaged with the set of radial teeth 52320. The proximal articulation lock member 52330 is translatable via an electric motor 52340, or any suitable motivator. The proximal articulation lock member 52330 and the electric motor 52340 are positioned proximally with respect to the first articulation axis $AA_1$. When the first pair of articulation cables 52210 are actuated to rotate the articulatable shaft portion 52300 about the first articulation axis $AA_1$, the proximal articulation lock member 52330 is automatically disengaged with the set of radial teeth 52320 to permit articulation of the articulatable shaft portion 52300 about the first articulation axis $AA_1$.

The surgical instrument 52000 further comprises a second pair of articulation cables 52410 extending from the shaft 52200 and operably engaged with the end effector 52400. More specifically, one of the second pair of articulation cables 52410 is attached to the end effector 52400 on one side of the second articulation axis $AA_2$ and the other one of the second pair of articulation cables 52410 is attached to the end effector 52400 on the other side of the second articulation axis $AA_2$. The second pair of articulations cables 52410 are configured to rotate the end effector 52400 about the second articulation axis $AA_2$ when actuated. In other words, one of the second pair of articulation cables 52410 is driven distally and/or the other of the second pair of articulation cables 52410 is driven proximally to rotate the end effector 52400 relative to the articulatable shaft portion 52300 about the second articulation axis $AA_2$. The second pair of articulation cables 52410 are operably responsive to an electric motor positioned within the housing.

Further to the above, the end effector 52400 comprises a set of radial teeth 52420 defined on the proximal end of the end effector 52400. At least a portion of the set of radial teeth 52420 are positioned proximal to the second articulation axis $AA_2$. The surgical instrument 52000 further comprises a distal articulation lock member 52430 configured to engage the set of radial teeth 52420 on the end effector 52400 to prevent rotation of the end effector 52400 about the second articulation axis $AA_2$ when the distal articulation lock member 52430 is engaged with the set of radial teeth 52420. The distal articulation lock member 52430 is translatable via an electric motor 52440, or any suitable motivator. When the second pair of articulation cables 52410 are actuated to rotate the end effector 52400 about the second articulation axis $AA_2$, the distal articulation lock member 52430 is automatically disengaged with the set of radial teeth 52420 to permit articulation.

A surgical instrument 53000 comprising a powered articulation system 53100 is illustrated in FIGS. 163-167. The surgical instrument 53000 comprises a housing, a shaft 53200 defining a shaft axis SA and extending from the housing, an articulatable shaft portion 53300 extending from the shaft 52200, and an end effector 53400 extending from the articulatable shaft portion 53300. A first articulation joint 53500 is between the shaft 53200 and the articulatable shaft portion 53300 and a second articulation joint 53600 is between the articulatable shaft portion 53300 and the end effector 53400. The first articulation joint 53500 defines a first articulation axis $AA_1$ that is orthogonal to the shaft axis SA. The second articulation joint 53600 defines a second articulation axis $AA_2$ that is orthogonal to the first articulation axis $AA_1$ and the shaft axis SA.

The powered articulation system 53100 comprises a first set of articulation cables comprising a right articulation cable 53210 and a left articulation cable 53212. The right articulation cable 53210 is operably engaged with a first outer articulation gear 53310*a* that is rotatably mounted to the distal end of the shaft 53200 and rotatable about the first articulation axis $AA_1$. The left articulation cable 53212 is operably engaged with a second outer articulation gear 53310*b* that is mounted to the distal end of the shaft 53200 and rotatable about the first articulation axis $AA_1$. When the right and left articulation cables 53210, 53212 are actuated, the first and second outer articulation gears 53310*a*, 53310*b* are rotated.

Further to the above, the first outer articulation gear 53310*a* comprises a first gear slot 53312 and the second outer articulation gears 53310*a* comprises a second gear slot 53314. A first pin 53900 extends through a first opening in the proximal end of a first slider member 53700, through a first slot 53240*a* defined in the shaft 53200 and through the first gear slot 53312 of the first outer articulation gear 53310*a*. A second pin 53910 extends through a second opening 53810 in the proximal end of a second slider member 53800, through a second slot 53240*b* defined in the shaft 53200 and through the second gear slot 53314 of the second outer articulation gear 53310*b*. The distal ends of the first slider member 53700 and the second slider member 53800 are slidably fixed to either side of the end effector 53400 within a groove 53410 defined in the top surface of the end effector 53400. More specifically, the first slider member 53700 is attached to the groove 53410 by a first pin 53420 and the second slider member 53800 is attached to the groove 53410 by a second pin 53430. The first slider member 53700 is fixed to the end effector 53400 on one side of the second articulation axis $AA_2$ and the second slider member 53800 is fixed to the end effector 53400 on the other side of the second articulation axis $AA_2$ Other embodiments are envisioned with different pin and groove arrangements between the slider members 53700, 53800 and the end effector 53400 to accommodate predetermined ranges of articulation for the end effector 53400 about the second articulation axis $AA_2$.

In use, when the right and left articulation cables 53210, 53212 are actuated in opposite directions, the first outer articulation gear 53310*a* will rotate in a first direction and the second outer articulation gear 53310*b* will rotate in a second direction opposite the first direction. Further, when the first outer articulation gear 53310*a* and the second outer articulation gear 53310*b* are rotated in opposite directions, the first slider member 53700 and the second slider member 53800 translate in opposite directions and the end effector 53400 is rotated about the second articulation axis $AA_2$, as discussed in greater detail below.

Further to the above, when the first outer gear 53310*a* engaged with the right articulation cable 53210 is rotated in the counter-clockwise direction CCW, the first gear slot 53312 of the first outer gear 53310*a* applies a camming force to the first pin 53900 forcing the first pin 53900 to move radially outward within the first gear slot 53312. As discussed above, the first pin 53900 is positioned through the first slot 53240*a* in the shaft 53200 and is therefore limited to proximal and distal translation within the first slot 53240*a*. Thus, when the first outer gear 53310*a* is rotated in the counter-clockwise direction CCW, the first pin 53900 translates proximally within the first slot 53240*a* of the shaft 53200 and the first slider member 53700 translates proximally as illustrated in FIG. 165. When the second outer gear 53310*b* engaged with the left articulation cable 53212 is rotated in the clockwise direction CW, the second gear slot 53314 of the second outer gear 53310*b* applies a camming force to the second pin 53910 forcing the second pin 53910 to move radially outward within the second gear slot 53312 of the second outer gear 53310*b*. As discussed above, the second pin 53910 is positioned through the second slot 53240*b* in the shaft 53200 and is therefore limited to proximal and distal translation within the second slot 53240*b*. Thus, when the second outer gear 53310*b* is rotate in the clockwise direction CW, the second pin 53910 translates distally within the second slot 53240*b* and the second slider member 53800 is translated distally as illustrated in FIG. 165. Similarly, when the first outer gear 53310*a* engaged with the right articulation cable 53210 is rotated in the clockwise direction CW and the second outer gear 53310*b* engaged with the left articulation cable 53212 is rotated in the counter-clockwise direction CCW, the first slider member 53700 is translated distally and the second slider member 53800 is translated proximally.

As discussed above, the distal ends of the first and second slider members 53700, 53800 are attached to the end effector 53400 on either side of the second articulation axis $AA_2$. Thus, when the first slider member 53700 and the second slider member 53800 are translated in opposite directions by the right articulation cable 53210 and the left articulation cable 53212, respectively, the end effector 53400 is rotated about the second articulation axis $AA_2$. Other embodiments are envisioned where only one half of the powered articulation system 53100 is utilized to rotate the end effector about the second articulation axis $AA_2$. In one such arrangement, only the right articulation cable 53210, the first outer articulation gear 53310*a*, the first pin 53900, and the first slider 53700 are utilized to rotate the end effector 53400 about the second articulation axis $AA_2$, for example.

Further to the above, a first inner articulation gear 53320*a* and a second inner articulation gear 53320*b* (see FIG. 166) are mounted to the proximal end of the articulatable shaft portion 53300 and rotatably mounted to the distal end of the shaft 53200 such that the first and second inner articulation gears 53320*a*, 53320*b* are rotatable about the first articulation axis $AA_1$. A second right articulation cable 53214 and a second left articulation cable 53216 are operably engaged with the first inner articulation gear 53320*a* and the second inner articulation gear 53320*b*, respectively. In use, when the second set of articulation cables 53214, 53216 are actuated, the first inner articulation gear 53320*a* and the second inner articulation gear 53320*b* are rotated about the first articulation axis $AA_1$. Thus, when the second set of articulation cables are actuated, the articulatable shaft portion 53300 and the end effector 53400 extending therefrom are rotated about the first articulation axis $AA_1$.

Further to the above, the surgical instrument 53000 comprises a first articulation lock member 53950 and a second articulation lock member 53960 positioned within the shaft 53200 of the surgical instrument 53000. The first articulation lock member 53950 and the second articulation lock member 53960 are configured to operably engage radial sets of teeth on the articulation gears 53310*a*, 53310*b*, 53320*a*, 53320*b* to prevent rotation of the articulatable shaft portion 53300 about the first articulation axis $AA_1$ and to prevent rotation of the end effector 53400 about the second articulation axis $AA_2$. The surgical instrument 53000 further comprises a first lock actuator 53955 configured to actuate the first articulation lock member 53950 and a second lock actuator 53965 configured to actuate the second articulation lock member 53960. In at least one embodiment, the first lock actuator 53955 and the second lock actuator 53965 comprise solenoids, electric motors, or any suitable motivator, and/or combinations thereof. Other embodiments are envisioned where the first and second lock actuators 53955, 53965 are actuatable due to rotary motions produced in the housing of the surgical instrument 53000. In at least one embodiment, the first and second articulation lock members 53950, 53960 are configured to automatically disengage the articulation gears 53310*a*, 53310*b*, 53320*a*, 53320*b* when the first and second sets of articulation cables are actuated.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Any of the systems disclosed herein can be used with a handled surgical instrument. Moreover, any of the systems disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail and is incorporated by reference herein in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Patent Application Publication No. 2011/0226837, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Patent Application Publication No. 2012/0074198, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. U.S. Pat. No. 8,393,514, entitled SELECTIVELY ORIENTABLE IMPLANTABLE FASTENER CARTRIDGE, which issued on Mar. 12, 2013, is also hereby incorporated by reference in its entirety.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical stapling instrument comprising:

(a) an end effector including:

(i) a first jaw having an anvil, wherein the anvil includes:

(A) a plurality of staple forming surfaces, and (B) at least one alignment slot, wherein the at least one alignment slot defines at least one cam surface, and (ii) a second jaw configured to cooperate with the first jaw to clamp tissue; and (b) a staple cartridge configured to be supported by the second jaw, wherein the staple cartridge includes:

(i) a cartridge body having a deck, (ii) a plurality of staple cavities extending through the deck and configured to receive respective staples, and (iii) at least one alignment post extending above the deck and configured to be received within the at least one alignment slot of the anvil, wherein the at least one cam surface is configured to engage the at least one alignment post during movement of the anvil relative to the second jaw from an unclamped configuration to a clamped configuration to thereby move the staple cartridge relative to the second jaw from an unseated state in which the plurality of staple cavities are misaligned relative to the plurality of staple forming surfaces, to a seated state in which the plurality of staple cavities are aligned with the plurality of staple forming surfaces.

2. The surgical stapling instrument of claim 1, wherein the anvil includes a tissue compression surface.

3. The surgical stapling instrument of claim 2, wherein the deck is oriented substantially obliquely relative to the tissue compression surface when the staple cartridge is in the unseated state.

4. The surgical stapling instrument of claim 2, wherein the deck is oriented substantially parallel relative to the tissue compression surface when the anvil is in the clamped configuration with the staple cartridge in the seated state.

5. The surgical stapling instrument of claim 2, wherein the at least one cam surface is oriented substantially obliquely relative to the tissue compression surface.

6. The surgical stapling instrument of claim 1, wherein the staple cartridge further includes at least one crush rib, wherein the anvil is configured to crush the at least one crush rib during movement of the anvil relative to the second jaw from the clamped configuration to an overclamped configuration.

7. The surgical stapling instrument of claim 6, wherein the deck is oriented substantially obliquely relative to a tissue compression surface of the anvil when the anvil is in the overclamped configuration with the staple cartridge in the seated state.

8. The surgical stapling instrument of claim 1, wherein the at least one cam surface is ramped downwardly in a distal direction.

9. The surgical stapling instrument of claim 1, wherein the staple cartridge further includes at least one projection extending upwardly from the deck, wherein the at least one alignment post extends laterally outwardly above the deck from the at least one projection.

10. The surgical stapling instrument of claim 9, wherein the at least one alignment post is cantilevered above the deck from the at least one projection.

11. The surgical stapling instrument of claim 9, wherein the staple cartridge further includes at least one crush rib extending upwardly from the at least one alignment post.

12. The surgical stapling instrument of claim 1, wherein the staple cartridge further includes a longitudinal slot extending through the deck, wherein the at least one alignment post includes a pair of alignment posts flanking the longitudinal slot.

13. The surgical stapling instrument of claim 1, further comprising a shaft extending along a longitudinal axis, wherein the end effector is operatively coupled with the shaft.

14. The surgical stapling instrument of claim 1, wherein the staple cartridge further includes a plurality of staple drivers, wherein each staple driver of the plurality of staple drivers is movably positioned within a corresponding staple cavity of the plurality of staple cavities.

15. The surgical stapling instrument of claim 14, wherein the staple cartridge further includes a sled translatable distally through the staple cartridge, wherein the sled is configured to engage the plurality of staple drivers during distal translation of the sled to drive respective staples into contact with the anvil of the first jaw.

16. A staple cartridge for a surgical stapling instrument, the staple cartridge comprising:

(a) a cartridge body having a deck;

(b) a longitudinal slot extending through the deck;

(c) a plurality of staple cavities extending through the deck and configured to receive respective staples;

(d) a pair of projections extending upwardly from the deck and flanking the longitudinal slot;

(e) a pair of alignment posts, wherein each alignment post of the pair of alignment posts extends laterally outwardly from a respective projection of the pair of projections relative to the longitudinal slot such that each alignment post of the pair of alignment posts is cantilevered above the deck from the respective projection of the pair of projections; and (f) a pair of crush ribs configured to be crushed by an anvil of the surgical stapling instrument, wherein each crush rib of the pair of crush ribs extends upwardly from a respective alignment post of the pair of alignment posts.

17. The staple cartridge of claim 16, wherein the pair of projections are proximal of the plurality of staple cavities.

18. The staple cartridge of claim 17, wherein the pair of projections extend upwardly from a proximal end of the deck.

19. The staple cartridge of claim 16, wherein each alignment post of the pair of alignment posts has a circular cross-sectional shape.

20. A method of operating a surgical stapling instrument including (i) an end effector having first and second jaws configured to cooperate with each other to clamp tissue, and (ii) a staple cartridge having (A) a cartridge body including a deck, and (B) a plurality of staple cavities extending through the deck and configured to receive respective staples, the method comprising:

(a) positioning the staple cartridge in the second jaw such that the staple cartridge is in an unseated state, (b) pivoting an anvil of the first jaw relative to the second jaw from an unclamped configuration to a clamped configuration, such that at least one alignment post of the staple cartridge is received within at least one alignment slot of the anvil, and such that the anvil engages the at least one alignment post to thereby move the staple cartridge relative to the second jaw from the unseated state to a seated state in which an upper surface of the deck is oriented substantially parallel relative to a lower surface of the anvil; and (c) pivoting the anvil relative to the second jaw from the clamped configuration to an overclamped configuration in which the lower surface of the anvil is oriented substantially obliquely relative to the upper surface of the deck, such that the anvil crushes at least one crush rib of the staple cartridge.

* * * * *